US012503455B2

(12) United States Patent
Kumaravel et al.

(10) Patent No.: US 12,503,455 B2
(45) Date of Patent: Dec. 23, 2025

(54) NUCLEIC ACID-BINDING PHOTOPROBES AND USES THEREOF

(71) Applicant: Arrakis Therapeutics, Inc., Waltham, MA (US)

(72) Inventors: Gnanasambandam Kumaravel, Lexington, MA (US); Jennifer C. Petter, Stow, MA (US); Jonathan Craig Blain, Melrose, MA (US); Donovan Noel Chin, Lexington, MA (US); Chao Fang, Lexington, MA (US); Herschel Mukherjee, Somerville, MA (US); Neil Kubica, Swampscott, MA (US)

(73) Assignee: Arrakis Therapeutics, Inc., Waltham, MA (US)

(*) Notice: Subject to any disclaimer, the term of this patent is extended or adjusted under 35 U.S.C. 154(b) by 542 days.

(21) Appl. No.: 18/155,528

(22) Filed: Jan. 17, 2023

(65) Prior Publication Data

US 2023/0312520 A1    Oct. 5, 2023

Related U.S. Application Data

(62) Division of application No. 16/207,062, filed on Nov. 30, 2018, now Pat. No. 11,807,623.

(Continued)

(51) Int. Cl.

*C12Q 1/6816* (2018.01)
*A61K 9/00* (2006.01)

(Continued)

(52) U.S. Cl.

CPC .......... *C07D 401/14* (2013.01); *A61K 9/0019* (2013.01); *A61K 9/0053* (2013.01);

(Continued)

(58) Field of Classification Search

CPC .. C07D 401/14; C07D 217/26; C07D 401/12; C07D 495/04; C07D 401/04;

(Continued)

(56) References Cited

U.S. PATENT DOCUMENTS

| | | | |
|---|---|---|---|
| 4,835,263 | A | 5/1989 | Nguyen et al. |
| 5,514,786 | A | 5/1996 | Cook et al. |

(Continued)

FOREIGN PATENT DOCUMENTS

| | | | |
|---|---|---|---|
| CA | 2836266 | A1 | 11/2012 |
| EP | 2688093 | A1 | 1/2014 |

(Continued)

OTHER PUBLICATIONS

Dubinsky et al. Diazirine based photoaffinity labeling. Bioorg. Med. Chem. 20 (2012) 554-570. (Year: 2012).*

(Continued)

*Primary Examiner* — Shafiqul Haq
(74) *Attorney, Agent, or Firm* — Dechert LLP; Andrea L.C. Reid; Joseph W. Arico

(57) ABSTRACT

The present invention relates to photoactivatable compounds and methods of use thereof for determining binding site and other structural information about RNA transcripts. The invention also provides methods of identifying RNA transcripts that bind compounds and are thus druggable, methods of screening drug candidates, and methods of determining drug binding sites and/or accessible or reactive sites on a target RNA.

16 Claims, 75 Drawing Sheets

Specification includes a Sequence Listing.

Related U.S. Application Data

(60) Provisional application No. 62/593,175, filed on Nov. 30, 2017.

(51) Int. Cl.

| | |
|---|---|
| ***A61K 31/522*** | (2006.01) |
| ***A61K 31/65*** | (2006.01) |
| ***A61K 39/395*** | (2006.01) |
| ***A61K 47/54*** | (2017.01) |
| ***A61K 47/68*** | (2017.01) |
| ***A61P 25/28*** | (2006.01) |
| ***A61P 43/00*** | (2006.01) |
| ***C07D 217/26*** | (2006.01) |
| ***C07D 401/12*** | (2006.01) |
| ***C07D 401/14*** | (2006.01) |
| ***C07D 495/04*** | (2006.01) |
| ***C12N 15/115*** | (2010.01) |
| ***G01N 33/50*** | (2006.01) |

(52) U.S. Cl.
CPC ............ *A61K 31/522* (2013.01); *A61K 31/65* (2013.01); *A61K 39/395* (2013.01); *A61K 47/545* (2017.08); *A61K 47/6809* (2017.08); *A61P 25/28* (2018.01); *A61P 43/00* (2018.01); *C07D 217/26* (2013.01); *C07D 401/12* (2013.01); *C07D 495/04* (2013.01); *C12N 15/115* (2013.01); *C12Q 1/6816* (2013.01); *G01N 33/5008* (2013.01)

(58) Field of Classification Search
CPC .. C07D 487/04; A61K 9/0019; A61K 9/0053; A61K 31/522; A61K 31/65; A61K 39/395; A61K 47/545; A61K 47/6809; A61P 25/28; A61P 43/00; C12N 15/115; C12Q 1/6816; C12Q 2523/101; C12Q 2525/205; C12Q 2525/30; C12Q 2563/107; G01N 33/5008; C07C 237/32; C07C 247/18; C07C 271/16
See application file for complete search history.

(56) References Cited

U.S. PATENT DOCUMENTS

| | | | |
|---|---|---|---|
| 5,534,408 | A | 7/1996 | Green et al. |
| 5,585,069 | A | 12/1996 | Zanzucchi et al. |
| 5,639,600 | A | 6/1997 | McGrath et al. |
| 5,935,776 | A | 8/1999 | Green et al. |
| 6,150,414 | A | 11/2000 | Meruelo et al. |
| 6,794,140 | B1 | 9/2004 | Goldsborough |
| 6,828,450 | B2 | 12/2004 | Hua et al. |
| 6,867,290 | B2 | 3/2005 | Goldsborough |
| 7,074,801 | B1 | 7/2006 | Yoshida et al. |
| 7,087,648 | B1 | 8/2006 | McGrath |
| 7,244,568 | B2 | 7/2007 | Goldsborough |
| 7,381,531 | B2 | 6/2008 | Stojanovic et al. |
| 7,687,146 | B1 | 3/2010 | Freitas, Jr. |
| 7,745,614 | B2 | 6/2010 | Kool et al. |
| 7,928,211 | B2 | 4/2011 | Hansen et al. |
| 8,084,204 | B2 | 12/2011 | Stojanovic et al. |
| 8,202,823 | B2 | 6/2012 | Hansen et al. |
| 8,313,424 | B2 | 11/2012 | Gabrielidis |
| 8,318,424 | B2 | 11/2012 | Weeks et al. |
| 8,481,513 | B2 | 7/2013 | Bandarage et al. |
| 8,541,448 | B2 | 9/2013 | Charmot et al. |
| 8,617,819 | B2 | 12/2013 | Swager et al. |
| 9,150,612 | B2 | 10/2015 | Disney |
| 10,731,202 | B2 | 8/2020 | Lindemann et al. |
| 2002/0091163 | A1 | 7/2002 | Hua et al. |
| 2002/0177548 | A1 | 11/2002 | Schwendner et al. |
| 2003/0170650 | A1 | 9/2003 | Karube et al. |
| 2003/0198966 | A1 | 10/2003 | Stojanovic et al. |
| 2004/0043046 | A1 | 3/2004 | Vic et al. |
| 2004/0121337 | A1 | 6/2004 | Deans et al. |
| 2005/0196775 | A1 | 9/2005 | Swager et al. |
| 2005/0205434 | A1 | 9/2005 | Sen et al. |
| 2005/0211978 | A1 | 9/2005 | Bu et al. |
| 2005/0282190 | A1 | 12/2005 | Shi et al. |
| 2006/0051782 | A1 | 3/2006 | Wood et al. |
| 2006/0073607 | A1 | 4/2006 | Rose et al. |
| 2006/0127929 | A1 | 6/2006 | Swager et al. |
| 2006/0185161 | A1 | 8/2006 | Rauscher |
| 2007/0009201 | A1 | 1/2007 | Chandross et al. |
| 2008/0188377 | A1 | 8/2008 | Disney et al. |
| 2008/0227213 | A1 | 9/2008 | Disney |
| 2009/0233277 | A1 | 9/2009 | Murakami |
| 2009/0234109 | A1 | 9/2009 | Han et al. |
| 2010/0016208 | A1 | 1/2010 | Hasan et al. |
| 2010/0016610 | A1 | 1/2010 | Keinan |
| 2010/0170796 | A1 | 7/2010 | Bhatia et al. |
| 2011/0008304 | A1 | 1/2011 | Troyer et al. |
| 2011/0077394 | A1 | 3/2011 | Bell et al. |
| 2011/0092381 | A1 | 4/2011 | Sood et al. |
| 2011/0144083 | A1 | 6/2011 | Himmelsbach et al. |
| 2012/0060935 | A1 | 3/2012 | Carter et al. |
| 2012/0177578 | A1 | 7/2012 | Swager et al. |
| 2012/0252876 | A1 | 10/2012 | Tenenbaum et al. |
| 2012/0263648 | A1 | 10/2012 | Shapiro et al. |
| 2013/0253179 | A1 | 9/2013 | Burr et al. |
| 2013/0338178 | A1 | 12/2013 | Shenk et al. |
| 2014/0145673 | A1 | 5/2014 | Heilbrun |
| 2014/0161685 | A1 | 6/2014 | Lee et al. |
| 2014/0212869 | A1 | 7/2014 | Sampas et al. |
| 2014/0212945 | A1 | 7/2014 | Disney |
| 2015/0020944 | A1 | 1/2015 | Till et al. |
| 2015/0031754 | A1 | 1/2015 | Shi et al. |
| 2015/0203442 | A1 | 7/2015 | Wang et al. |
| 2015/0209441 | A1 | 7/2015 | Carell |
| 2015/0210732 | A1 | 7/2015 | Cailly et al. |
| 2015/0219652 | A1 | 8/2015 | Le et al. |
| 2015/0307487 | A1 | 10/2015 | Disney et al. |
| 2015/0357142 | A1 | 12/2015 | Bulovic et al. |
| 2016/0069922 | A1 | 3/2016 | Horiuchi et al. |
| 2016/0083783 | A1 | 3/2016 | Blainey et al. |
| 2016/0177514 | A1 | 6/2016 | Meroz et al. |
| 2017/0217974 | A1 | 8/2017 | Or et al. |
| 2017/0226121 | A1 | 8/2017 | Zlotnick et al. |
| 2017/0233726 | A1 | 8/2017 | Hansen et al. |
| 2017/0253876 | A1 | 9/2017 | Eberwine et al. |
| 2018/0265911 | A1 | 9/2018 | Chenoweth et al. |
| 2019/0194150 | A1 | 6/2019 | Petter et al. |

FOREIGN PATENT DOCUMENTS

| | | | |
|---|---|---|---|
| GB | 288885 | A | 4/1928 |
| GB | 1205706 | A | 9/1970 |
| JP | 63-054363 | | 3/1988 |
| JP | 2009263435 | A | 11/2009 |
| WO | WO-1996038579 | A1 | 12/1996 |
| WO | WO-1999031119 | A1 | 6/1999 |
| WO | WO-2001007657 | A1 | 2/2001 |
| WO | WO-2001068640 | A1 | 9/2001 |
| WO | WO-2002028808 | A1 | 4/2002 |
| WO | WO-2006047756 | A2 | 5/2006 |
| WO | WO-2006071776 | A2 | 7/2006 |
| WO | WO-2007105023 | A1 | 9/2007 |
| WO | WO-2009077173 | A2 | 6/2009 |
| WO | WO-2009157938 | A1 | 12/2009 |
| WO | WO-2011030349 | A1 | 3/2011 |
| WO | WO-2011048184 | A1 | 4/2011 |
| WO | WO-2014028459 | A1 | 2/2014 |
| WO | WO-2014029193 | A1 | 2/2014 |
| WO | WO-2014074906 | A1 | 5/2014 |
| WO | WO-2014100473 | A1 | 6/2014 |
| WO | WO-2014153459 | A2 | 9/2014 |
| WO | WO-2014162148 | A2 | 10/2014 |
| WO | WO-2015009678 | A2 | 1/2015 |
| WO | WO-2015021415 | A1 | 2/2015 |
| WO | WO-2015021990 | A1 | 2/2015 |
| WO | WO-2015031819 | A1 | 3/2015 |
| WO | WO-2015035243 | A1 | 3/2015 |

(56) References Cited

FOREIGN PATENT DOCUMENTS

| | | | |
|---|---|---|---|
| WO | WO-2015042184 | A2 | 3/2015 |
| WO | WO-2015043156 | A1 | 4/2015 |
| WO | WO-2015045247 | A1 | 4/2015 |
| WO | WO-2015054247 | A1 | 4/2015 |
| WO | WO-2015063952 | A1 | 5/2015 |
| WO | WO-2015094958 | A1 | 6/2015 |
| WO | WO-2015121336 | A1 | 8/2015 |
| WO | WO-2015180901 | A1 | 12/2015 |
| WO | WO-2016011348 | A1 | 1/2016 |
| WO | WO-2016028649 | A1 | 2/2016 |
| WO | WO-2016069922 | A1 | 5/2016 |
| WO | WO-2017053982 | A1 | 3/2017 |
| WO | WO-2017064156 | A1 | 4/2017 |
| WO | WO-2017136450 | A2 | 8/2017 |
| WO | WO-2017147557 | A1 | 8/2017 |
| WO | WO-2018160636 | A1 | 9/2018 |
| WO | WO-2019109046 | A1 | 6/2019 |

OTHER PUBLICATIONS

Aberlin and Bunton, "Spontaneous hydrolysis of sulfonyl fluorides," J Org Chem . . . 1970;35(6):1825-1828.

Aires-De-Sousa, et al., "Prediction of 1H NMR Chemical Shifts Using Neural Networks," Anal Chem. 2002;74(1):80-90.

Bachellerie et al., "The expanding snoRNA world," Biochimie. 2002;84(8):775-790.

Baffy, "MicroRNAs in Nonalcoholic Fatty Liver Disease," J Clin Med. 2015;4(12):1977-1988.

Banez-Coronel et al., "A Pathogenic Mechanism in Hunting's Disease involves Small CAG-Repeated RNA with Neurotoxic Activity," PLoS Genet. 2012;8(2):e1002481.

Banfi et al., "Resurrecting and processing NMR spectra on-line," Chimia. 2008;62(4);280-281.

Barbosa et al., "Gene Expression Regulation by Upstream Open Reading Frames and Human Disease," PLOS Genetics. 2013;9(8):1-12.

Barros et al., "Bridgehead-Substituted Triptycenes for Discovery of Nucleic Acid Junction Binders," Org. Lett., 2016, vol. 18, pp. 2423-2426.

Barros et al., "Modulation of the *E. coli* rpoH Temperature Sensor with Triptycene-Based Small Molecules," Angew Chem In Ed Engl. 2016;55(29):8258-8261.

Barros et al., "Recognition of Nucleic Acid Junctions Using Triptycene-Based Molecules," Angew Chem Int Ed Engl. 2014;53(50):13746-13750.

Barros et al., "Triptycene-based small molecules modulate (CAG) (CTG) repeat junctions," Chem Sci. 2015;6(8):4752-5744.

Barros, "Targeting Nucleic Acid Junctions Using Triptycene-Based Molecules," Publicly Accessible Penn Dissertations, vol. 1603, http://repository.upenn.edu/edissertations/1603, 2015.

Belyanskaya et al., "Discovering Drugs with DNA-Encoded Library Technology: From Concept to Clinic with an Inhibitor of Soluble Epoxide Hydrolase,", Chembiochem. 2017;18(9):837-842.

Bennett and Swayze, "RNA Targeting Therapeutics: Molecular Mechanisms of Antisense Oligonucleotides as a Therapeutic Platform," Annu Rev Pharmacol and Toxicol. 2010;50:259-93.

Berg et al., "Desulfonylation of 2-hydroxy-3,5-dinitro-alpha-toluenesulfonyl-alpha-chymotrypsin", Journal of the American Chemical Society, 1975, vol. 97, No. 14 (pp. 4121-4126).

Bevilacqua, "Genome-Wide Analysis of RNA Secondary Structure," Annu. Rev. Genet. 2016, 50, pp. 235-266.

Binshtein et al., "Cryo-electron microscopy and the amazing race to atomic resolution", Biochemistry 2015, vol. 54, No. 20 (pp. 3133-3141).

Blackwood et al., "Some Transformations of Tetracycline at the 4-Position", Canadian Journal of Chemistry, 1965, vol. 43, No. 5 (pp. 1382-1388).

Blakskjaer et al., "Fidelity by design: Yoctoreactor and binder trap enrichment for small-molecule DNA-encoded libraries and drug discovery", Curr Opin Chem Biol., 2015, vol. 26 (pp. 62-71).

Bodner et al., "Pharmacological promotion of inclusion formation: A therapeutic approach for Huntington's and Parkinson's diseases," PNAS, vol. 103, No. 11, Mar. 14, 2006 (pp. 4246-4251).

Boer et al., "Self-assembly of functionalizable two-component 3D DNA arrays through the induced formation of DNA three-way-junction branch points by supramolecular cylinders", 2010, vol. 122, issue 13 (pp. 2386-2389).

Boer et al., "Self-assembly of functionalizable two-component 3D DNA arrays through the induced formation of DNA three-way-junction branch points by supramolecular cylinders", 2010, vol. 49, issue 13 (pp. 2336-2339).

Boucle et al., "Synthesis and antiviral evaluation of novel heteroarylpyrimidines analogs as HBV capsid effectors," Bioorg Med Chem Lett. 2017; 27(4):904-910.

Bourne et al., "Small-Molecule Effectors of Hepatitis B Virus Capsid Assembly Give Insight into Virus Life Cycle," J Virol. 2008; 82(20):10262-10270.

Brodersen et al., "The Structural Basis for the Action of the Antibiotics Tetracycline, Pactamycin, and Hygromycin B on the 30S Ribosomal Subunit," Cell Press, vol. 103, Dec. 22, 2000, (pp. 1143-1154).

Brown et al., "Structural insights into the stabilization of MALAT1 noncoding RNA by a bipartite triple helix," Nature Structural & Molecular Biology, vol. 21, No. 7, Jul. 2014 (pp. 633-640).

Budworth et al., "A brief history of triplet repeat diseases," Methods Molecular Biology, vol. 1010, 2013 (pp. 3-17).

Busan et al., "Role of Context in RNA Structure: Flanking Sequences Reconfigure CAG Motif Folding in Huntingtin Exon 1 Transcripts," Biochemistry, vol. 52, No. 46, Nov. 19, 2013 (pp. 8219-8225).

Calvo et al., "Upstream open reading frames cause widespread reduction of protein expression and are polymorphic among humans," Proceedings of the National Academy of Sciences, vol. 106, No. May 5, 18, 2009 (pp. 7507-7512).

Cao, "Recent developments in ligase-mediated amplification and detection", Trends in Biotechnology, 2004, vol. 22, No. 1, 38-44.

Carninci et al., "The transcriptional landscape of the mammalian genome," Science, vol. 309, Sep. 2, 2005 (pp. 1559-1563).

Castillo et al., "Fast and Accurate Algorithm for the Simulation of NMR spectra of Large Spin Systems," Journal of Magnetic Resonance, vol. 209, issue 2, Apr. 2011 (pp. 123-130).

Cerasino et al., "DNA Three-Way Junction with a Dinuclear Iron(II) Supramolecular Helicate at the Center: A NMR Structural Study," Inorganic Chemistry, vol. 46, No. 16, 2007 (pp. 6245-6251).

Chan et al., "Novel selection methods for DNA-encoded chemical libraries", Current Opinion in Chemical Biology, 2015, vol. 26 (pp. 55-61).

Chillon et al., "Native Purification and Analysis of Long RNAs," Methods Enzymol., vol. 558, 2015 (pp. 3-37).

Clark et al., "Design, synthesis and selection of DNA-encoded small-molecule libraries", Nature Chemical Biology, 2009, vol. 5 (pp. 647-654).

Codelli et al., "Second-Generation Difluorinated Cyclooctynes for Copper-Free Click Chemistry," Journal of the American Chemical Society, vol. 130, 2008 (pp. 11486-11493).

Colca et al., "Cross-linking in the living cell locates the site of action of oxazolidinone antibiotics," J Biol Chem. 2003; 278(24):21972-9.

Cox et al., "Therapeutic genome editing: prospects and challenges," Nature Medicine, vol. 21, Feb. 2015 (pp. 121-131).

Croce, "Causes and consequences of microRNA dysregulation in cancer," Nature Rev. Genet., vol. 10, No. 10, Oct. 2009 (pp. 704-714).

De La Pena et al., "Three-way RNA junctions with remote tertiary contacts: a recurrent and highly versatile fold," RNA Society, vol. 15, No. 11, Nov. 2009, (pp. 1949-1964).

Deng et al., "Prognostic Value of Long Non-Coding RNA HOTAIR in Various Cancers", PLOS One, 2014, vol. 9, No. 10, (9 pages).

Diamond et al., "Thermodynamics of Three-Way Multibranch Loops in RNA," American Chemical Society, vol. 40, No. 23, May 18, 2001 (pp. 6971-6981).

Dommerholt et al., "Readily Accessible Bicyclononynes for Bioorthogonal Labeling and Three-Dimensional Imaging of Living Cells", Angew Chem Int Ed, 2010, 49, 9422-9425.

(56) References Cited

OTHER PUBLICATIONS

Doyle et al, "Trans-regulation of RNA-binding protein motifs by microRNA," Frontiers in Genetics, vol. 5, article 79, Apr. 15, 2014, (pp. 1-10).
Duskova et al., "Identification of Three-Way DNA Junction Ligands through Screening of Chemical Libraries and Validation by Complementary in Vitro Assays", J. Med. Chem., 2019, vol. 62, No. 9 (pp. 4456-4466).
Dykxhoorn "MicroRNAs and Metastasis: Little RNAs Go a Long Way," Cancer Research, vol. 70, Jul. 27, 2010 (pp. 6401-6406).
Esse et al., "Tetracycloxides. I. A New Class of Tetracycline Derivatives", J. Am. Chem. Soc., 1964, vol. 86, No. 18 (3874-3875).
Evans et al., "Addition of Lithiated 9-Deazapurine Derivatives to a Carbohydrate Cyclic Imine:? Convergent Synthesis of the Aza-C-nucleoside Immucillins", J. Org. Chem., 2001, vol. 66, issue 17, (pp. 5723-5730).
Fairclough et al., "Therapy for Duchenne muscular dystrophy: renewed optimism from genetic approaches," Nature Reviews Genetics, 2013, 14, 373-378.
Fourmy et al., "Structure of the A site of *Escherichia coli* 16S ribosomal RNA complexed with an aminoglycoside antibiotic", Science, 1996, vol. 274, No. 5291 (pp. 1367-1371).
Franzini et al., "Chemical Space of DNA-Encoded Libraries", J. Med. Chem., 2016, vol. 59, No. 14 (pp. 6629-6644).
Friedman et al., "Most mammalian mRNAs are conserved targets of microRNAs", Genome Res., 2009, vol. 19, No. 1 (pp. 92-105).
Garcia et al., "New Photoactivatable Structural and Affinity Probes of RNAs," Nucleic Acids Research, vol. 18 (1); 1990, pp. 89-95.
Gatchel & Zoghbi, "Diseases of unstable repeat expansion: mechanisms and common principles," Nature Reviews Genetics, vol. 6, 2005(pp. 743-755).
Geiseler et al., "Synthesis of the altertoxin III framework", Tetrahedron, 2013, vol. 69, No. 18 (pp. 3683-3689).
Gering et al., "Kinetics of inactivation of .alpha.-chymotrypsin with substituted benzenesulfonyl fluorides", J. Am. Chem. Soc., 1974, vol. 96, No. 1 (pp. 233-238).
Ghildiyal et al., "Small silencing RNAs: an expanding universe", Nat. Rev. Genet., 2009, vol. 10, No. 2 (pp. 94-108).
Goodnow Jr. et al., "DNA-encoded chemistry: enabling the deeper sampling of chemical space", Nature Reviews Drug Discovery, 2017, vol. 16 (pp. 131-147).
Gregory et al., "Clickable Photoaffinity Ligands for Metabotropic Glutamate Receptor 5 Based on Select Acetylenic Negative Allosteric Modulators," ACS Chem. Biol., vol. 11(7), 2016, pp. 1870-1879.
Guan & Disney, "Recent Advances in Developing Small Molecules Targeting Rna," Acs Chemistry Biology, vol. 7, No. 1, 2012 (pp. 73-86).
Guan et al., "Covalent Small-Molecule-RNA Complex Formation Enables Cellular Profiling of Small-Molecule-RNA Interactions," Angewandte Chemie 52, 2013 (pp. 10010-10013).
Guan, "Covalent Small-Molecule-RNA Complex Formation Enables Cellular Profiling of Small-Molecule-RNA Interactions," Angew. Chem. Int. Ed. 2013, 52, pp. 10010-10013.
Guild and Esteller, "Cis-acting noncoding RNAs: friends and foes," Nature Structural & Molecular Biology, 2012, vol. 19 (pp. 1068-1075).
Gura, "DNA helps build molecular libraries for drug testing", Science, 2015, vol. 350, No. 6265 (pp. 1139-1140).
Gutschner et al., "The hallmarks of cancer: a long non-coding RNA point of view", RNA Biology, 2012 , vol. 9, No. 6 (pp. 703-719).
Gutschner et al., "The Noncoding Rna MALAT1 Is a Critical Regulator of the Metastasis Phenotype of Lung Cancer Cells," Cancer Research, vol. 73, No. 3, Feb. 1, 2013 (pp. 1180-1189).
Haeusler et al., "C9orf72 Nucleotide Repeat Structures Initiate Molecular Cascades of Disease," Nature Structural & Molecular Biology, Mar. 13, 2014, vol. 507 (pp. 195-200).
Hall et al., "Structure determination of an intercalating ruthenium dipyridophenazine complex which kinks DNA by semiintercalation of a tetraazaphenanthrene ligand", Proc Natl Acad Sci U S A., 2011, vol. 108, No. 43 (pp. 17610-4).
Hanif, "Selective Small Molecule Recognition of RNA Base Pairs," ACS Comb. Sci. 2018, 20, pp. 482-491.
Hart et al., "Iptycenes: Extended triptycenes", Tetrahedron, 1986, vol. 42, No. 6 (pp. 1641-1654).
Heemstra, "Learning from the unexpected in life and DNA self-assembly," Beilstein Journal of Organic Chemistry, vol. 11, 2015 (pp. 2713-2720).
Heidema et al., "The reactions of sultones with chymotrypsin. The pH dependence of sulfonylation and desulfonylation", Journal of the American Chemical Society, 1968, vol. 90, No. 7 (pp. 1860-1866).
Holoch and Moazed, "RNA-mediated epigenetic regulation of gene expression", Nature Reviews Genetics, vol. 16, No. 2, Feb. 2015 (pp. 71-84).
Howell et al., "Targeting Higher-Order DNA: Beyond the G-Quadruplex," ChemBioChem, vol. 10, 2009, (pp. 2139-2143).
Ipsaro et al., "From guide to target: molecular insights into eukaryotic RNA-interference machinery", Nat. Struct. Mol. Biol., 2015, vol. 22, No. 1 (pp. 20-28).
Iyer et al., "Barcoded oligonucleotides ligated on RNA amplified for multiplex and parallel in-situ analyses," BioRxiv, Mar. 13, 2018 (pp. 1-49).
Iyer et al., "The Landscape of Long Noncoding RNAs in the Human Transcriptome," Nature Genetics, vol. 47, Mar. 2015 (pp. 199-208).
Izaurralde, "Gene Regulation. Breakers and blockers-miRNAs at work", Science, 2015, vol. 349, No. 6246 (pp. 380-382).
Izbicka et al., "Interactions of five-and six-membered cyclic esters with chymotrypsin: Kinetic evidence for covalent enzyme intermediates", Bioorganic Chemistry, 1981, vol. 10, No. 2 (pp. 118-132).
James, "Inactivation of the protease inhibitor phenylmethylsulfonyl fluoride in buffers," Analytical Biochemistry, vol. 86, No. 2, Jun. 1, 1978, (pp. 574-579).
Jenison et al., "High-resolution molecular discrimination by RNA", Science, 1994, vol. 263, No. 5152 (pp. 1425-1429).
Jewett et al., "Rapid Cu-Free Click Chemistry with Readily Synthesized Biarylazacyclooctynones," J. Am Chem. Soc. 2010, 132, 3688.
Jin et al., "Molecule-binding depending assembly of split aptamer and y-cyclodextrin: A sensitive excimer signaling approach for aptamer biosensors," Analytical Chimica Acta, 2013 (pp. 44-50).
Johnson, "Long non-coding RNAs in Huntington's disease neurodegeneration," Neurobiology of Disease, vol. 46, issue 2, (pp. 245-254).
Jorjani et al., "An updated human snoRNAome", Nucleic Acids Res., 2016, vol. 44, No. 11 (pp. 5068-5082).
Kent et al., "General Approach for Engineering Small-Molecule-Binding DNA Split Aptamers," Analytical Chemistry, vol. 85, 2013 (pp. 9916-9923).
Klattenhoff et al., "Biogenesis and germline functions of piRNAs", Development, 2008, vol. 135, No. 1 (pp. 3-9).
Klumpp et al., "High-resolution crystal structure of a hepatitis B virus replication inhibitor bound to the viral core protein", Proc Natl Acad Sci USA, 2015, vol. 112, No. 49, (pp. 15196-15201).
Komar et al., "Exploring Internal Ribosome Entry Sites as Therapeutic Targets," Frontiers Oncol., vol. 5, article 233, Oct. 2015 (pp. 1-10).
Krzyzosiak et al., "Triplet repeat RNA structure and its role as pathogenic agent and therapeutic target," Nucleic Acids Research, 2012, vol. 40, No. 1 (pp. 11-26).
Kumar et al., "Human Disease-Associated Genetic Variation Impacts Large Intergenic Non-Coding RNA Expression", PLOS Genetics, 2013, vol. 9, No. 1 (9 pages).
Larman et al., "Sensitive, multiplex and direct quantification of RNA sequences using a modified RASL assay", Nucleic Acids Res., 2014, vol. 42, No. 14 (pp. 9146-9157).
Lau et al., "Evolution and protein packaging of small-molecule RNA aptamers", ACS Nano., 2011, vol. 5, No. 10 (pp. 7722-7729).

(56) References Cited

OTHER PUBLICATIONS

Lavender et al., "Structure-Based Alignment and Consensus Secondary Structures for Three HIV-Related RNA Genomes," PLoS Computational Biology, May 20, 2015 (pp. 1-19).
Le Quesne et al., "Dysregulation of protein synthesis and disease," The Journal of Pathology, vol. 220, Oct. 13, 2009 (pp. 140-151).
Leach et al., "The site of action of oxazolidinone antibiotics in living bacteria and in human mitochondria", Mol. Cell, 2007, vol. 26, No. 3 (pp. 393-402).
Lee et al., "Highly efficient ligation of small RNA molecules for microRNA quantitation by high-throughput sequencing", J Vis Exp., 2014, vol. 18, No. 93 (e52095).
Li et al., "Design, Synthesis, and Evaluation of Tetrahydropyrrolo[1,2-c]pyrimidines as Capsid Assembly Inhibitors for HBV Treatment", ACS Med Chem Lett., 2017, vol. 8, No. 9 (pp. 969-974).
Li et al., "Long Non-Coding RNAs and Complex Human Diseases," International Journal of Molecular Sciences, vol. 14, No. 9, Sep. 2013 (pp. 18790-18808).
Li et al., "RASL-seq for massively parallel and quantitative analysis of gene expression", Curr Protoc Mol Biol., 2012, Chapter 4, Unit 4.13 (pp. 1-9).
Ling et al., "Converging mechanisms in ALS and FTD: disrupted RNA and protein homeostasis," Neuron., vol. 79, No. 3 Aug. 7, 2013 (pp. 416-438).
Lipinski et al., "Experimental and computational approaches to estimate solubility and permeability in drug discovery and development settings," Advanced Drug Delivery Reviews, vol. 46, issues 1-3, Mar. 1, 2001 (pp. 3-26).
Lorzano et al., "Fragile X spectrum disorders," Intractable Rare Diseases Research, vol. 3, No. 4, 2014 (pp. 134-146).
Macconnell et al., "An Integrated Microfluidic Processor for DNA-Encoded Combinatorial Library Functional Screening", ACS Comb. Sci., 2017, vol. 19, No. 3 (pp. 181-192).
Machuca-Tzili et al., "Clinical and molecular aspects of the myotonic dystrophies: A review," Muscle & Nerve, vol. 32, issue 1, Mar. 15, 2015 (pp. 1-18).
Martin et al., "Structural effects of linkage disequilibrium on the transcriptome," RNA, vol. 18, 2012 (pp. 77-87).
Matassova et al., "Ribosomal RNA is the target for oxazolidinones, a novel class of translational inhibitors," RNA. 1999; 5(7):939-46.
Mattick et al., "Discovery and annotation of long noncoding RNAs," Nature Structural & Molecular Biology, vol. 22 2012 (pp. 5-7).
Maurano et al., "Systematic Localization of Common Disease-Associated Variation in Regulatory DNA," Science, vol. 337, No. 6099, Sep. 7, 2012 (pp. 1190-1195).
McGinnis et al., "In-cell SHAPE reveals that free 30S ribosome subunits are in the inactive state", Proc. Natl. Acad. Sci. USA, 2015, vol. 112, No. 8 (pp. 2425-2430).
McGinnis et al., "The Mechanisms of Rna Shape Chemistry", J. Am. Chem. Soc., 2012, vol. 134, No. 15 (pp. 6617-6624).
McKeague et al., "Challenges and Opportunities for Small Molecule Aptamer Development", Journal of Nucleic Acids, 2012, vol. 2012, Article ID 748913, 20 pages.
Minikel "How to do a DNA-encoded Library Selection," Cureffi.org, Nov. 17, 2016 (pp. 1-15) retrieved from the internet <http://www.cureffi.org/2016/11/17/how-to-do-a-dna-encoded-library-selection/>.
Morris and Mattick, "The rise of regulatory RNA," Nature Reviews Genetics, vol. 15; Jun. 214 (pp. 423-437).
Moumne, "Tether Influence on the Binding Properties of tRNALys3 Ligands Designed by a Fragment-Based Approach," Organic & Biomolecular Chemistry, 2010, 8(5), pp. 1154-1159.
Nakao et al., "Tetrahydropyridine derivatives with inhibitory activity on the production of proinflammatory cytokines: part 1", Bioorganic & Medicinal Chemistry Letters, 2009, vol. 19, issue 16 (pp. 4607-4610).
Naldini, "Gene therapy returns to center stage," Nature vol. 526, Oct. 4, 2015 (pp. 351-360).
Ning et al., "Visualizing metabolically labeled glycoconjugates of living cells by copper-free and fast huisgen cycloadditions", Angew Chem Int. Ed, 2008, vol. 47, No. 12 (pp. 2253-2255).
Ohashi et al., "Nickel-Catalyzed Dehydrogenative [4+2] Cycloaddition of 1,3-Dienes with Nitriles", J. Am. Chem. Soc., 2011, vol. 133 No. 45 (pp. 18018-18021).
Oleksi, et al., "Molecular Recognition of a Three-Way DNA Junction by a Metallosupramolecular Helicate", vol. 45, 2006 (pp. 1227-1231).
Olson, "MicroRNAs as Therapeutic Targets and Biomarkers of Cardiovascular Disease," Science Trans. Med., vol. 6, No. 239, (pp. 1-10).
Palacino et al., "SMN2 splice modulators enhance U1-pre-mRNA association and rescue SMA mice", Nature Chemical Biology, vol. 11, 2015 (pp. 511-517).
Palazzolo et al., "B2 Attenuates Polyglutamine-Expanded Androgen Receptor Toxicity in Cell and Fly Models of Spinal and Bulbar Muscular Atrophy," Journal of Neuroscience Research, vol. 88, 2010 (pp. 2207-2216).
Palumbo et al., "Kinetics effects and modeling of mRNA turnover", Wiley Interdiscip. Rev. RNA, 2015, vol. 6, No. 3 (pp. 327-336).
Perchellet et al., "Among subsuted 9,10-dihydro-9, 10-[1,2] benzeoanthracene-1,4,5,8-tetraones, the lead antitumor triptycene bisquinone TT24 blocks nucleoside transport, induces apoptotic DNA fragmentation and decreases the viability of L1210 leukemic cells in the nanomolar range of daunorubicin in vitro," Anticancer Drug, vol. 13, No. 9; Jul. 2002 (abstract) 567-81.
Perchellet et al., Tripytcenes; a novel synthetic class of bifunctional anticancer drugs that inhibit nucleoside transport, induce, DNA cleavage and decrease the viability of leukemic cells in the nanomolar range in vitros, Anticancer Drugs, vol. 10, No. 8, Sep. 1999 (abstract) 749-66.
Phongtongpasuk et al., "Binding of a Designed Anti-Cancer Drug to the Central Cavity of an RNA Three-Way Junction," Angewandte Chemie, vol. 52, 2013 (pp. 11513-11516).
Pirakitikulr et al., "The Coding Region of the HCV Genome Contains a Network of Regulatory RNA Structures", Mol. Cell, 2016, vol. 62, No. 1 (pp. 111-120).
Presner and Chinnaiyan, "The emergence of IncRNAs in cancer biology," Cancer Discovery, vol. 1, Oct. 2011 (pp. 391-407).
PubChem-CID-60112986, create date: Aug. 20, 2012 (12 pages).
Qiu et al., "Design and Synthesis of Orally Bioavailable 4-Methyl Heteroaryldihydropyrimidine Based Hepatitis B Virus (HBV) Capsid Inhibitors", J Med Chem., 2016, vol. 59, No. 16 (pp. 7651-7666).
Qiu et al., "Discovery and Pre-Clinical Characterization of Third-Generation 4-H Heteroaryldihydropyrimidine (HAP) Analogues as Hepatitis B Virus (HBV) Capsid Inhibitors", J. Med. Chem., 2017, vol. 60, No. 8 (pp. 3352-3371).
Quiant and Olson, "MicroRNAs in cardiovascular disease: from pathogenesis to prevention and treatment," Journal of Clinical Investigation, vol. 123, No. 1, Jan. 2013 (pp. 11-18).
Ren et al., "Discovery of hepatitis B virus capsid assembly inhibitors leading to a heteroaryldihydropyrimidine based clinical candidate (GLS4)", Bioorg Med Chem., 2017, vol. 25, No. 3, (pp. 1042-1056).
Rinn & Chang, "Genome regulation by long noncoding RNAs," Annual Reviews Biochemistry, vol. 81, 2012 (pp. 145-166).
Rossi et al., "Selective Formation of Secondary Amides via the Copper-Catalyzed Cross-Coupling of Alkylboronic Acids with Primary Amides", Org. Lett., 2013, vol. 15, issue 9 (pp. 2314-2317).
Roy etal., "The intimate relationships of mRNA decay and translation", Trends Genet., 2013, vol. 29, No. 12 (pp. 691-699).
Rudnicki et al., "Diced Triplets Expose Neurons to RISC," PloS Genetics, vol. 8, issue 2, Feb. 2012.
Salamon et al., "Chemical Biology Probes from Advanced DNA-encoded Libraries", ACS Chem. Biol., 2016, vol. 11, No. 2 (pp. 296-307).
Schirle et al., "Structural basis for microRNA targeting", Science, 2014, vol. 346, No. 6209 (pp. 608-613).
Sendoel et al., "Translation from unconventional 5' start sites drives tumour initiation", Nature, 2017, vol. 541, No. 7638 (pp. 494-499).

(56) References Cited

OTHER PUBLICATIONS

Seok et al., “MicroRNA Target Recognition: Insights from Transcriptome-Wide Non-Canonical Interactions”, Mol. Cell, 2016, vol. 39, No. 5 (pp. 375-381).
Seto et al., “The coming of age for Piwi proteins”, Molecular Cell, 2007, vol. 26, No. 5 (pp. 603-609).
Sharma et al., “Enzyme-Linked Small-Molecule Detection Using Split Aptamer Ligation,” Analytical Chemistry, vol. 84, 2012 (pp. 6104-6109).
Sharma et al., “Small-Molecule-Dependent Split Aptamer Ligation,” Journal of the American Chemical Society, vol. 133, 2011 (pp. 12426-12429).
Shi et al., “Recent advances on the encoding and selection methods of DNA-encoded chemical library”, Bioorganic & Medicinal Chemistry Letters, 2017, vol. 27, No. 3 (pp. 361-369).
Siegfried et al., “RNA motif discovery by SHAPE and mutational profiling (SHAPE-MaP),” Nature Methods, vol. 11, 2014 (pp. 959-965).
Smola et al, “Selective 2'-hydroxyl acylation analyzed by primer extension and mutational profiling (SHAPE-MAP) for direct, versatile and accurate RNA structure analysis,” Nature Protocols, vol. 10, No. 11, 2015 (pp. 1643-1669).
Stahlhut & Slack, “MicroRNAs and the cancer phenotype: profiling, signatures and clinical implications,” Genome Medicine, vol. 5, 2013 (pp. 1-12).
Stray et al., “A heteroaryldihydropyrimidine activates and can misdirect hepatitis B virus capsid assembly”, Proc Natl Acad Sci USA, 2005, vol. 102, No. 23 (pp. 8138-8143).
Thomas, “Targeting RNA with Small Molecules,” Chemical Reviews, 2008, 108(4); pp. 1172-1224.
Tius et al., “A bifunctional anthraquinone synthon”, Tetrahedron Letters, 1988, vol. 29, No. 52 (pp. 6909-6912).
Tran, “Identifying the Preferred RNA Motifs and Chemotypes that Interact by Probing Millions of Combinations,” Nature Communiations, 2012, 3, p. 1125.
Tsai et al., “Long noncoding RNA as modular scaffold of histone modification complexes,” Science, vol. 329, No. 5992 Aug. 6, 2010 (pp. 689-693).
Van de Vondervoort et al., “Long non-coding RNAs In Neuro Developmental Disorders,” Frontiers in Molecular Neuroscience, vol. 6, article 53, Dec. 2013 (pp. 1-9).
Vasa et al., “ShapeFinder: a software system for high-throughput quantitative analysis of nucleic acid reactivity information resolved by capillary electrophoresis”, RNA, vol. 14, 2008 (pp. 1979-1990).
Vasudevan et al., “Switching from repression to activation: microRNAs can up-regulate translation”, Science, 2007, vol. 318, No. 5858 (pp. 1931-1934).
Venkatakrishnan et al., “Hepatitis B Virus Capsids Have Diverse Structural Responses to Small-Molecule Ligands Bound to the Heteroaryldihydropyrimidine Pocket,” J Virol. 2016; 90(8):3994-4004.
Wahlestedt, “Targeting long non-coding RNA to therapeutically upregulate gene expression,” Nature Reviews Drug Discovery, vol. 12, No. 6, Jun. 2013 (pp. 433-446).
Wang et al. “Induction of poly (ADP-ribose) polymerase-1 cleavage by antitumor triptycene bisquinones in wild-type and daunorubicin-resistant HL-60 cell lines”, Cancer Letters, vol. 188, issues 1-2, Dec. 15, 2002, (pp. 73-83).
Weeks et al., “Single-molecule correlated chemical probing of RNA,” PNAS vol. 111, No. 38, Sep. 23, 2014, 111 (pp. 13858-13863).
Weingarten-Gabbay et al., “Comparative genetics. Systematic discovery of cap-independent translation sequences in human and viral genomes,” Science, vol. 351, Jan. 15, 2016.
Werner et al., “Nuclear Fractionation Reveals Thousands of Chromatin-Tethered Noncoding RNAs Adjacent to Active Genes”, Cell Reports, 2015, vol. 12, No. 7 (pp. 1-10).
Wheeler et al., “Reversal of RNA-dominance by displacement of protein sequestered on triplet repeat RNA,” Science, vol. 325, No. 5938 Jul. 17, 2009 (pp. 336-339).
Wolbers et al., “Viability study of HL60 cells in contact with commonly used microchip materials”, Electrophoresis, 2006, 27 (pp. 5073-5080).
Wyrick et al., “Synthesis of active site-directed organometallic irreversible protease inhibitors”, Biochim Biophys Acta, 1979, vol. 568, No. 1 (pp. 11-18).
Xiao et al., “Structural basis for specific, high-affinity tetracycline binding by an in vitro evolved aptamer and artificial riboswitch”, Chemistry & biology, 2008, vol. 15, No. 10 (pp. 1125-1137).
Yao et al., “Large intervening non-coding RNA HOTAIR is an indicator of poor prognosis and a therapeutic target in human cancers,” International Journal of Molecular Sciences, vol. 15, Oct. 15, 2014 (pp. 18985-18999).
Yoon et al., “Pd-Catalyzed Spirocyclization via C—H Activation and Benzyne Insertion”, Org. Lett., 2016, vol. 18, No. 24 (pp. 6324-6327).
Yoon et al., “Synthesis of 9-Substituted Triptycene Building Blocks for Solid-Phase Diversification and Nucleic Acid Junction Targeting,” Organic Letters, US, vol. 18, No. 5, pp. 1096-1099.
Yoshimura et al., “Specificity and reactivity of human leukocyte elastase, porcine pancreatic elastase, human granulocyte cathepsin G, and bovine pancreatic chymotrypsin with arylsulfonyl fluorides. Discovery of a new series of potent and specific irreversible elastase inhibitors”, J. Biol. Chem. 1982, vol. 257, No. 9 (pp. 5077-5084).
Zhang et al., “The C9orf72 repeat expansion disrupts nucleocytoplasmic transport,” Nature, vol. 525, No. 7567, Sep. 3, 2015 (pp. 56-61).
Zhou et al., “Heteroaryldihydropyrimidine (HAP) and Sulfamoylbenzamide (SBA) Inhibit Hepatitis B Virus Replication by Different Molecular Mechanisms”, Sci Rep., 2017, vol. 7, No. 42374 (12 pages).
Zu et al., “Non-ATG-initiated translation directed by microsatellite expansions,” PNAS, vol. 108, Dec. 20, 2010 (pp. 260-265).
Zuccato et al., “Molecular mechanisms and potential therapeutical targets in Huntington’s disease,” Physiol Rev. 90:905-981, 2010.
Agami and Couty, “The reactivity of the N-Boc protecting group: an underrated feature,” Tetrahedron. 2002. 58;2701-24.
Barros et al., “Bridgehead-Substituted Triptycenes for Discovery of Nucleic Acid Junction Binders,” Org Lett. 2016;18(10):2423-2426.
Barros et al., “Recongination of Nucleic Acid Junctions Using Triptycene-Based Molecules,” Angew Chem Int Ed Eng. Dec. 8, 2014;53(50):13746-50.
Chaulk et al., “Studies of RNA cleavage by photolysis of N-hydroxypyridine-2(1H)-thione. A new photochemical footprinting method,” Biochemistry. Aug. 29, 2000;39(34):10448-53.
Childs-Disney and Disney, “Approaches to Validate and Manipulate RNA Targets with Small Molecules in Cells,” Annu Rev Pharmacol Toxicol. 2016;56:123-40.
Feng et al., “Light-activated chemical probing of nucleobase solvent accessibility inside cells,” Nat Chem Biol. Mar. 2018; 14(3):276-283.
Ghildiyal and Zamore, “Small silencing RNAs: an expanding universe,” Nat Rev Genet. Feb. 2009;10(2):94-108.
Guan and Disney, “Small-molecule-mediated cleavage of RNA in living cells,” Angew Chem Int Ed Engl. Jan. 28, 2013;52(5):1462-5.
Guan et al., “Small molecule alteration of RNA sequence in cells and animals,” Bioorg Med Chem Lett. Sep. 1, 2018;28(16):2794-6.
Heidema and Kaiser, “The reactions of sultones with chymotrypsin. The pH dependence of sulfonylation and desulfonylation,” J Am Chem Soc. Mar. 27, 1968;90(7):1860-6.
Helming et al., “Vulnerabilities of mutant SWI/SNF complexes in cancer,” Cancer Cell. Sep. 8, 2014;26(3):309-317.
Hoffman et al., “Functional epigenetics approach identifies BRM/SMARCA2 as a critical synthetic lethal target in BRG1-deficient cancers,” Proc Natl Acad Sci U S A. Feb. 25, 2014;111(8):3128-33.
Inoue et al., “N-Alkylation of Imides with O-Alkylisourea under Neutral Conditions,” Synthesis. 1986;4:332-4.
International Preliminary Report on Patentability for International Application No. PCT/US2017/040514, mailed on Jan. 10, 2019.
Izbicka and Bolen, “Isolation and partial characterization of a covalent intermediate between (alpha)-chymotrypsin and (omicron)-hydroxy-(alpha)-toluenesulfonic acid sultone,” Bioorg Chem. Jun. 1981;10(2):133-43.

(56) References Cited

OTHER PUBLICATIONS

Kaelin Jr, "The concept of synthetic lethality in the context of anticancer therapy," Nat Rev Cancer. Sep. 2005;5(9):689-98.
Kaewsapsak et al., "Live-cell mapping of organelle-associated RNAs via proximity biotinylation combined with protein-RNA crosslinking," Elife. Dec. 14, 2017;6:e29224.
Lipinski et al., "Experimental and computational approaches to estimate solubility and permeability in drug discovery and development settings," Adv Drug Deliv Rev. Dec. 2012;64(suppl):4-17.
Lu et al., "Identification of small molecule inhibitors targeting the SMARCA2 bromodomain from a high-throughput screening assay," Acta Pharmacol Sin. Sep. 2018;39(9):1544-1552.
McDonald III et al., "Project DRIVE: A Compendium of Cancer Dependencies and Synthetic Lethal Relationships Uncovered by Large-Scale, Deep RNAi Screening," Cell. Jul. 27, 2017;170(3):577-92.
Meister and Tuschl, "Mechanisms of gene silencing by double-stranded RNA," Nature. Sep. 16, 2004;431(7006):343-9.
Mello and Conte Jr, "Revealing the world of RNA interference," Nature. Sep. 16, 2004;431(7006):338-42.
PCT International Search Report and Written Opinion from PCT/US2017/016065, dated Jun. 27, 2017.
PCT International Search Report and Written Opinion from PCT/US2017/040514, dated Nov. 20, 2017.
PCT International Search Report and Written Opinion from PCT/US2018/063490, dated Jan. 17, 2019.
PCT International Search Report and Written Opinion from PCT/US2019/035481, dated Aug. 13, 2019.
Perchellet et al., "Among substituted 9,10-dihydro-9,10-[1,2]benzenoanthracene-1,4,5,8-tetraones, the lead antitumor triptycene bisquinone TT24 blocks nucleoside transport, induces apoptotic DNA fragmentation and decreases the viability of L1210 leukemic cells in the nanomolar range of daunorubicin in vitro," Anticancer Drugs. Jul. 2002;13(6):567-81.
Pirakitikulr et al., "The Coding Region of the HCV Genome Contains a Network of Regulatory RNA Structures," Mol Cell. Apr. 7, 2016;62(1):111-20.
Qiu et al., "Discovery and Pre-Clinical Characterization of Third-Generation 4-H Heteroaryldihydropyrimidine (HAP) Analogues as Hepatitis B Virus (HBV) Capsid Inhibitors," J Med Chem. Apr. 27, 2017;60(8):3352-3371.
Rinn and Chang, "Genome regulation by long noncoding RNAs," Annu Rev Biochem. 2012;81:145-66.
Roth et al., "A riboswitch selective for the queuosine precursor preQ1 contains an unusually small aptamer domain," Nat Struct Mol Biol. Apr. 2007;14(4):308-17.
Roy and Jacobson, "The intimate relationships of mRNA decay and translation," Trends Genet. Dec. 2013;29(12):691-9.
Sannes-Lowery et al., "Fourier transform ion cyclotron resonance mass spectrometry as a high throughput affinity screen to identify RNA binding ligands", Trends Analyt Chemistry. Aug. 2000;19(8):481-91.
Seok et al., "MicroRNA Target Recognition: Insights from Transcriptome-Wide Non-Canonical Interactions," Mol Cells. May 31, 2016;39(5):375-381.
Sharma and Heemstra, "Small-molecule-dependent split aptamer ligation," J Am Chem Soc. Aug. 17, 2011;133(32):12426-9.
Sharma et al., "Enzyme-linked small-molecule detection using split aptamer ligation," Anal Chem. Jul. 17, 2012;84(14):6104-9.
Shi et al., "Recent advances on the encoding and selection methods of DNA-encoded chemical library," Bioorg Med Chem Lett. Feb. 1, 2017;27(3):361-369.
Su et al., "Discovery of a biomarker and lead small molecules to target r(GGGGCC)-associated defects in c9FTD/ALS," Neuron. Sep. 3, 2014;83(5):1043-50.
Sutherell et al., "Identification and Development of 2,3-Dihydropyrrolo[1,2-a]quinazolin-5(1H)-one Inhibitors Targeting Bromodomains within the Switch/Sucrose Nonfermenting Complex," J Med Chem. May 26, 2016;59(10):5095-101.
Tius et al., "A bifunctional anthraquinone synthon," Tetrahedron Lett. 1988;29(52):6909-12.
Tsai et al., "Long noncoding RNA as modular scaffold of histone modification complexes," Science. Aug. 6, 2010;329(5992):689-93.
Van de Vondervoort et al., "Long non-coding RNAs in neurodevelopmental disorders," Front Mol Neurosci. Dec. 30, 2013;6:53.
Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. Sep. 15, 2015;75(18):3865-3878.
Velema and Kool, "The chemistry and applications of RNA 2'-OH acylation," Nat Rev Chem. 2020;4(1)22-37.
Wang et al., "Induction of poly(ADP-ribose) polymerase-1 cleavage by antitumor triptycene bisquinones in wild-type and daunorubicin-resistant HL-60 cell lines," Cancer Lett. Dec. 15, 2002;188(1-2):73-83.
Wang et al., "Mechanistic studies of a small-molecule modulator of SMN2 splicing," Proc Natl Acad Sci U S A. May 15, 2018;115(20):E4604-E4612.
Werner and Ruthenburg, "Nuclear Fractionation Reveals Thousands of Chromatin-Tethered Noncoding RNAs Adjacent to Active Genes," Cell Rep. Aug. 18, 2015;12(7):1089-98.
Wilson and Doudna, "Molecular mechanisms of RNA interference," Annu Rev Biophys. 2013;42:217-39.
Yoon et al., "Synthesis of 9-Substituted Triptycene Building Blocks for Solid-Phase Diversification and Nucleic Acid Junction Targeting," Org Lett. Feb. 17, 2016;18(5):1096-9.
Zhang et al., "Targeting folded RNA: a branched peptide boronic acid that binds to a large surface area of HIV-1 RRE RNA," Org Biomol Chem. Oct. 7, 2013;11(37):6263-71.
Zhang et al., "The C9orf72 repeat expansion disrupts nucleocytoplasmic transport," Nature. Sep. 3, 2015;525(7567):56-61.
Zhou et al., "Expanding APEX2 Substrates for Proximity-Dependent Labeling of Nucleic Acids and Proteins in Living Cells," Angew Chem Int Ed Engl. Aug. 19, 2019;58(34):11763-11767.
Zhang, Shuo; Design, synthesis and activity evaluation of novel dihydropyrimidine hepatitis B virus inhibitors; Chinese master's dissertation full text database; 2021.
Qvit et al., "Development of bifunctional photoactivatable benzophenone probes and their application to glycoside substrates," Peptide Science, 2008; 90(4):526-36.
Peng et al., "Development of bifunctional photoactivatable benzophenone probes and their application to glycoside substrates," Tetrahedron Letters, 2005;46(35):5893-97.

* cited by examiner

Figure 2
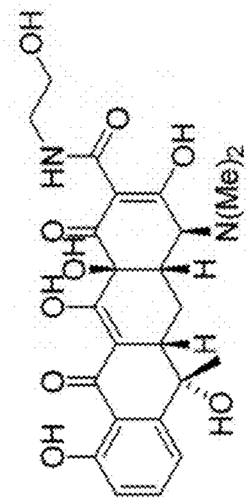
TET-1
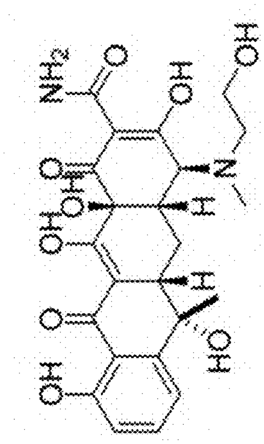
TET-4
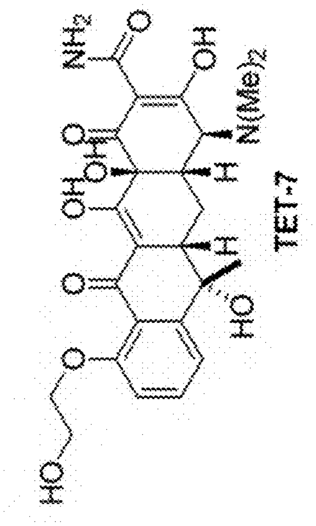
TET-7
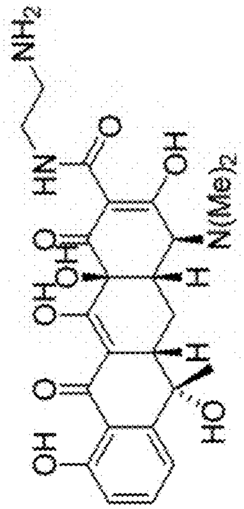
TET-2
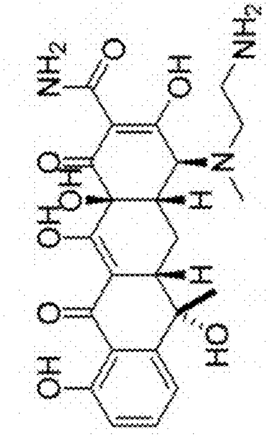
TET-5
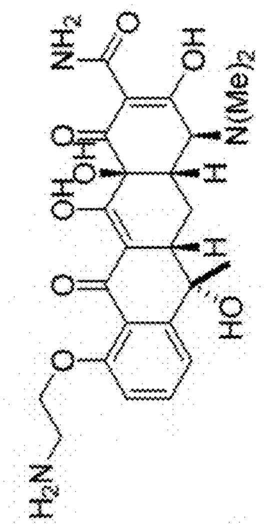
TET-8
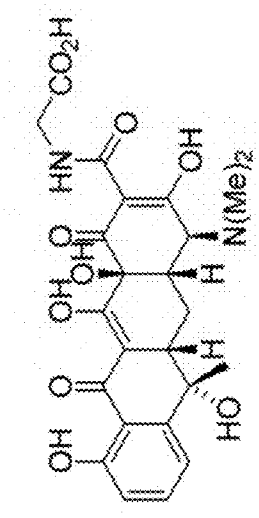
TET-3
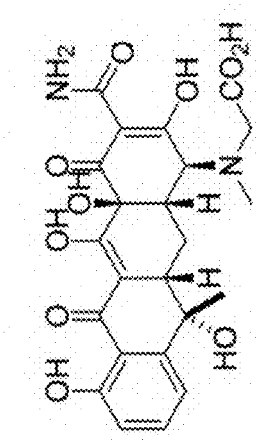
TET-6
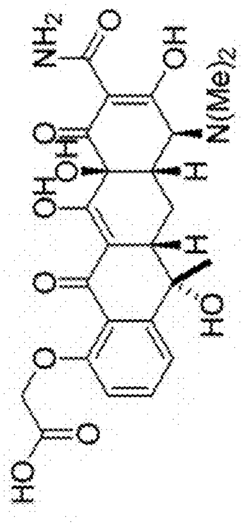
TET-9

X = CH, N, or C-OH;
Y = CH or N;
R1, R2, R3 = each independently selected from halo, -OH, -OMe, $-NH_2$, -NH-(optionally substituted $C_{1-10}$ aliphatic), optionally substituted $C_{1-10}$ aliphatic, or other described tethering groups. The modifier moiety may be attached at any position on R1, R2, or R3, or at the other functional groups on the above structures.

Figure 5

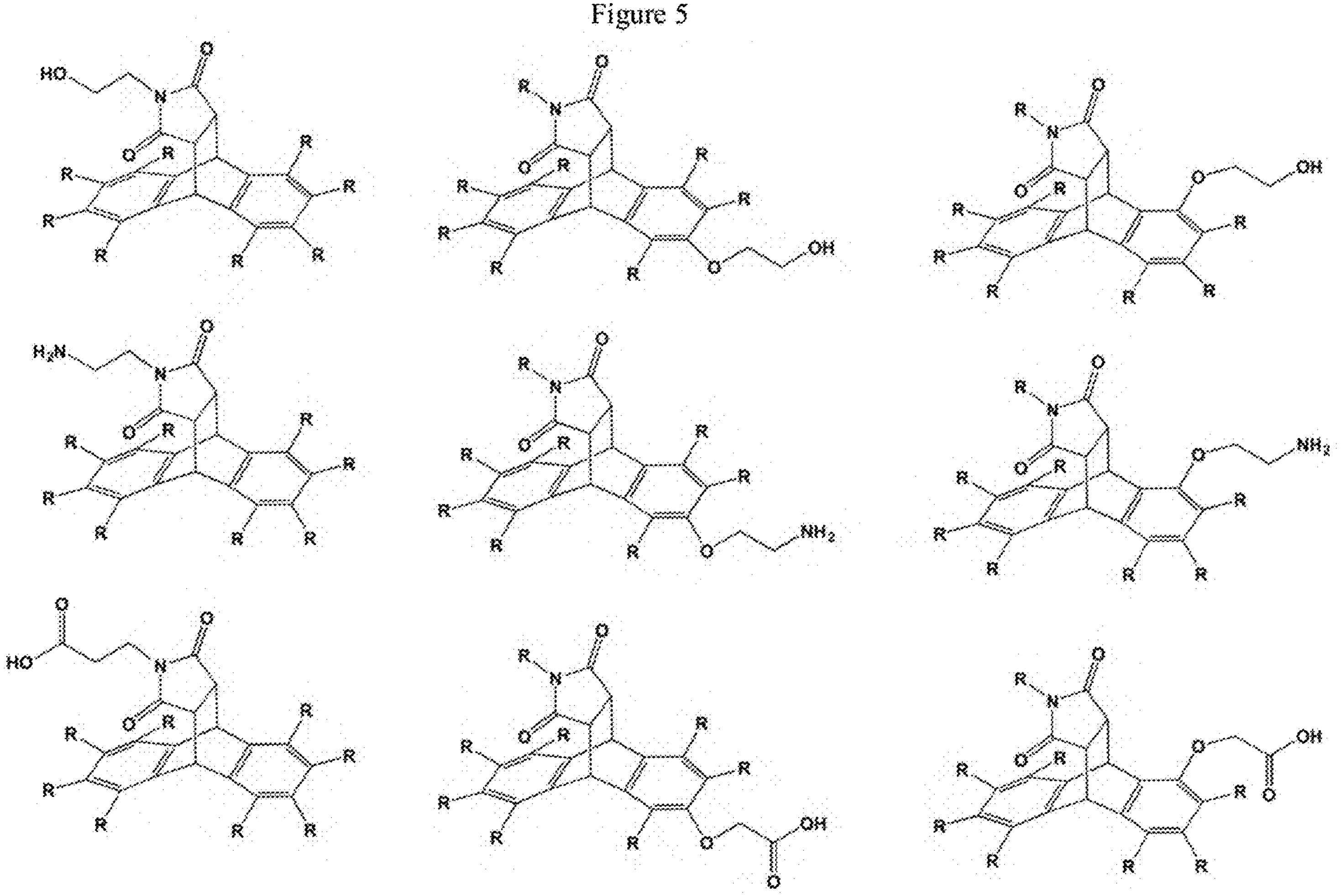

*Note: The corresponding structures having the succinimido group in the opposite stereochemical orientation may also be prepared.*

Each R is independently selected from halo, -OH, -OMe, $-NH_2$, -NH-(optionally substituted $C_{1-10}$ aliphatic), optionally substituted $C_{1-10}$ aliphatic, or other described tethering groups. The modifier moiety may be attached at any position on R, or at the other functional groups on the above structures.

R = tethering group

Figure 9
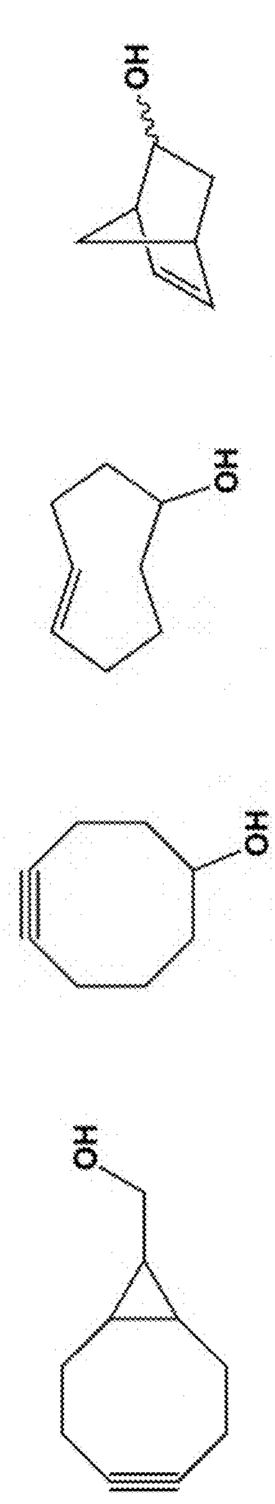
alcohols - connect to tether or warhead via ether or carbamate linkage
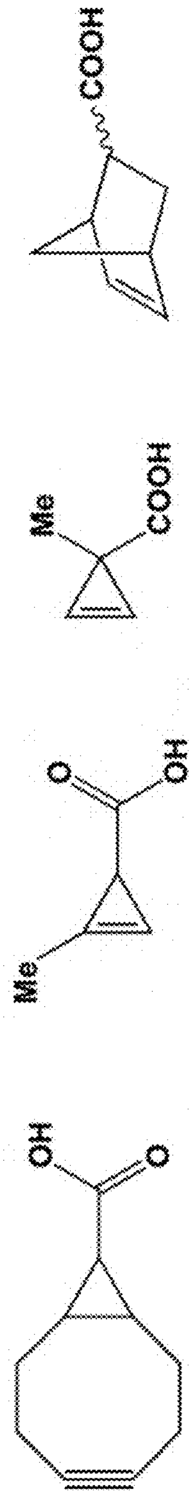
carboxylates - connect to tether or warhead via amide linkage
azides and simple alkynes - connect to tether or warhead directly or via alkyl linkage

| | |
|---|---|
| RNA Ligand | = described elsewhere |
| X | = -CO-, $-SO_2-$, -NH-, -N(alkyl)-, -S-, -O-, -triazole-, -arylene-, -heteroarylene-, etc. |
| n | = 1, 2, 3, 4, 5; n can = 0 when X = CO or $SO_2$ or aryl |
| Y | = a bond, -O-, -S-, -SO-, $-SO_2-$, -NH-, -N(alkyl)-, $-CH_2-$, -arylene-, -heteroarylene-, etc. |
| p | = 0, 1, 2, 3, 4, 5, 6, 7, 8, 9, 10, 11, or 12 |
| m | = 1, 2, 3, 4, 5; m can = 0 when X = -CO- or $-SO_2-$ or -arylene- or -heteroarylene- |
| Warhead | = described elsewhere |

R = Asp, Glu, Lys, Orn, Ser, Tyr, Cys
m = 0, 1, 2
n = 0, 1, 2

R = Asp, Glu, Lys, Orn, Ser, Tyr, Cys
m = 0, 1, 2
n = 0, 1, 2

R = OH, SH, NH2
m = 0, 1, 2
n = 0, 1, 2

R = OH, SH, NH2
m = 0, 1, 2
n = 0, 1, 2

R = Asp, Glu, Lys, Orn, Ser, Tyr, Cys

R = OH, SH, NH2

R = Asp, Glu, Lys, Orn, Ser, Tyr, Cys

R = OH, SH, NH2

Figure 17
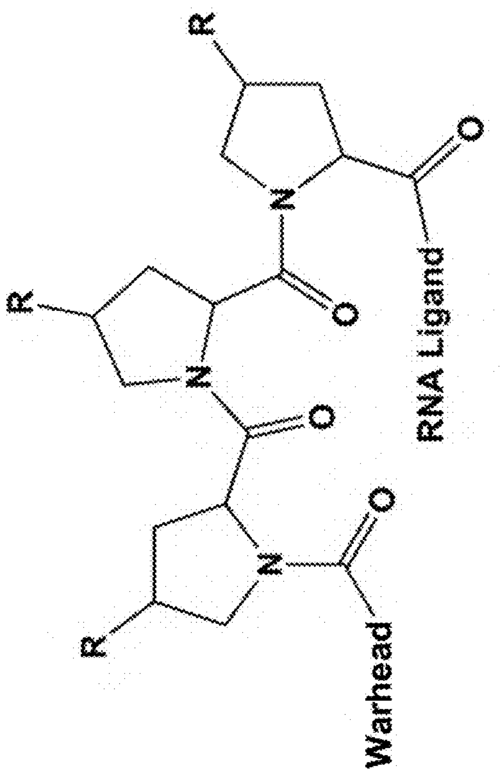
R = H, OH
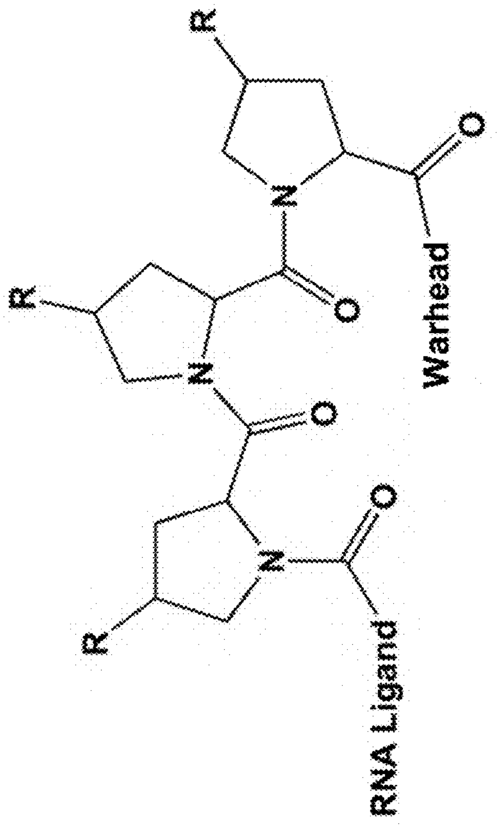
R = H, OH

Commercially available or can be synthesized via:
Journal of Medicinal Chemistry, 49(12), 3682-3692; 2006

Theophylline 5

Theophylline 6

Theophylline 4

Theophylline 8

Theophylline 9

Theophylline 7

Figure 22
*Org Lett 2013, 15, 2314-2317*
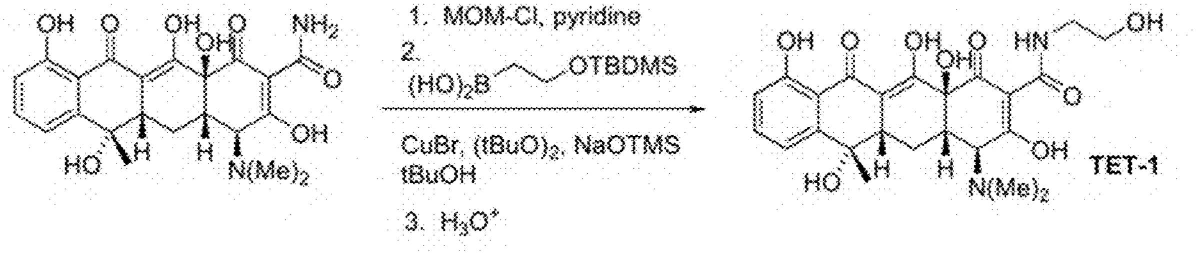
TET-1
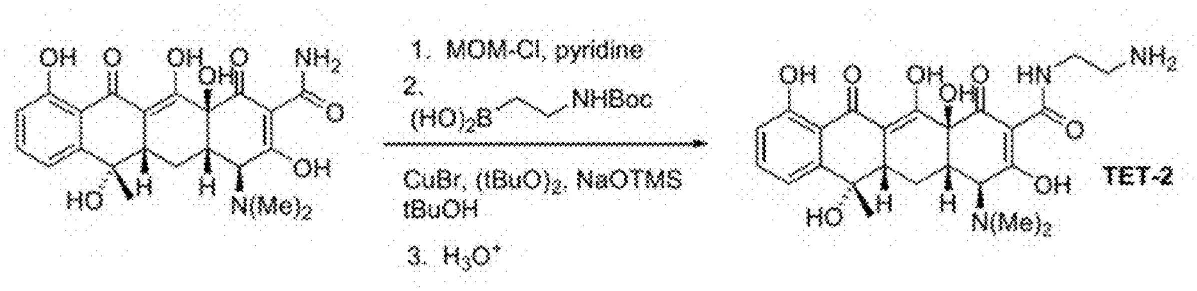
TET-2
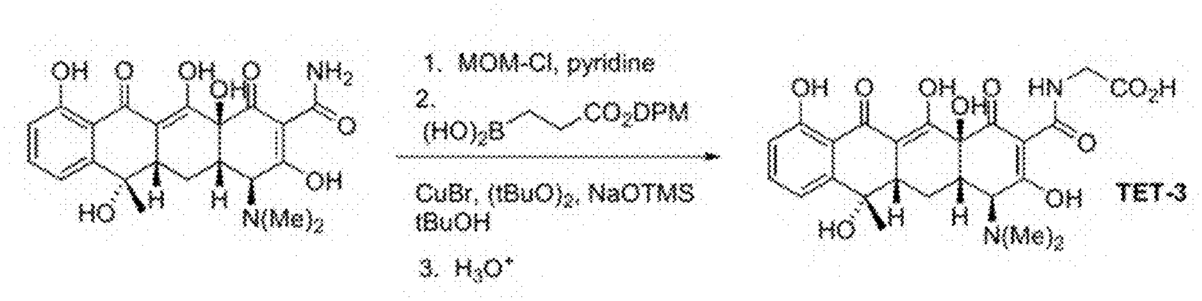
TET-3
*DPM= diphenylmethyl*

Alternative Scheme for TET1, TET-2 and TET-3

* *It may be necessary to persilylate the phenols via TMS-Cl or another acid labile protecting group such as a MOM-Cl with pyridine before the acylation to ensure a selective Mitsunobu, but both routes can be tried*

Figure 24
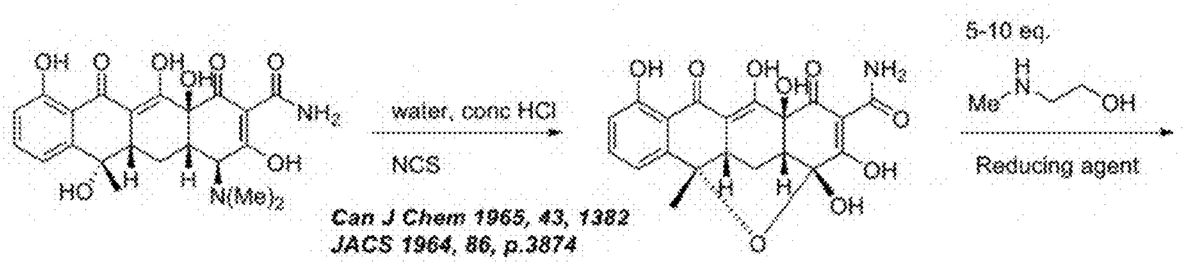
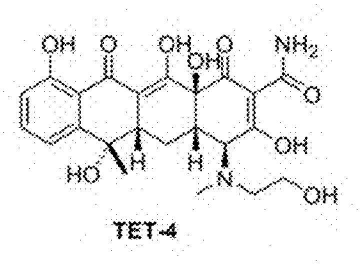
TET-4
*Reducing agents can include: $Na(OAc)_3BH$, $NaBH_3CN$, $NaBH_4$ with or without the addition of mild acid (AcOH)*
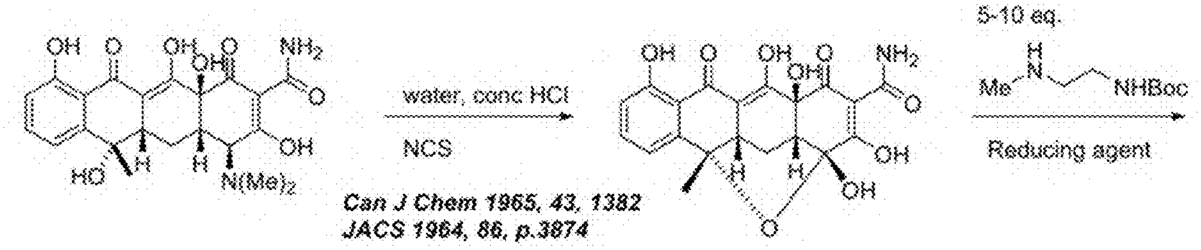
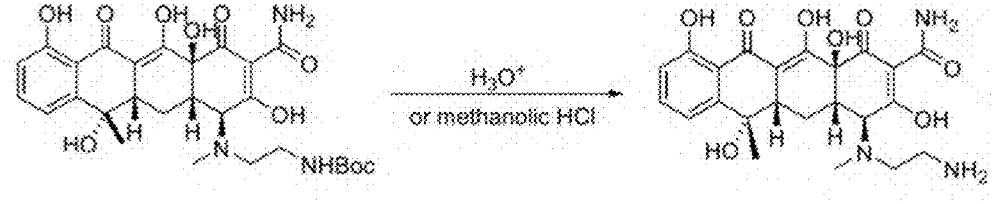
TET-5
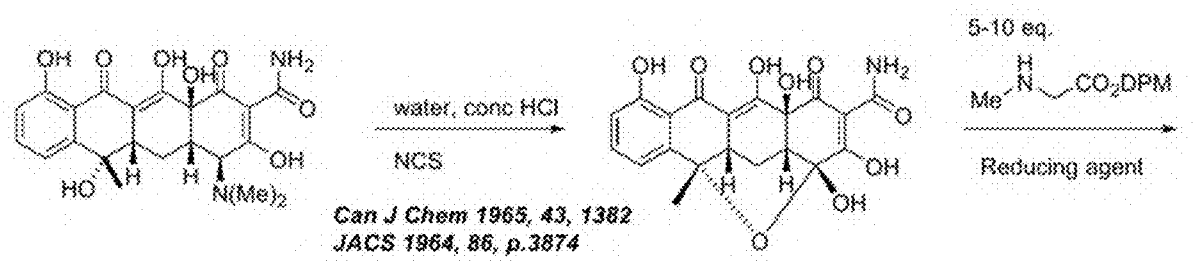
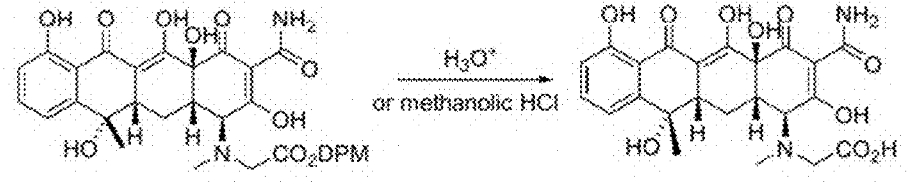
TET-6

Figure 25
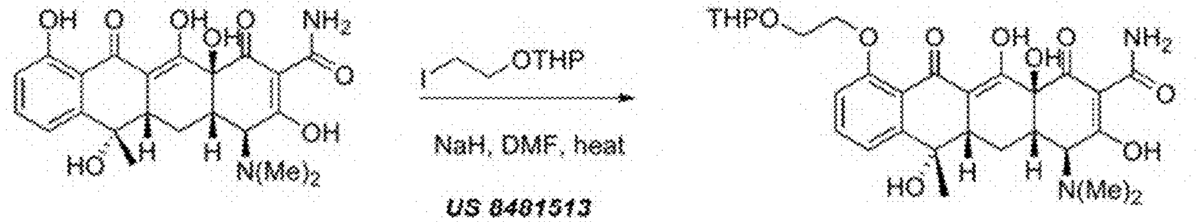
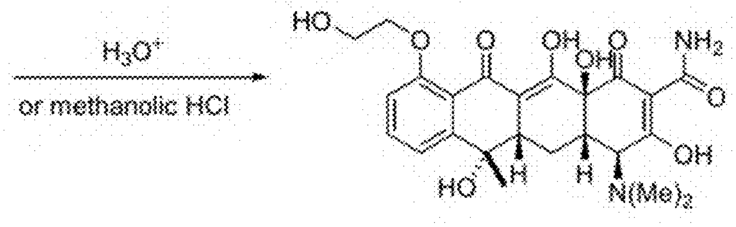
TET-7
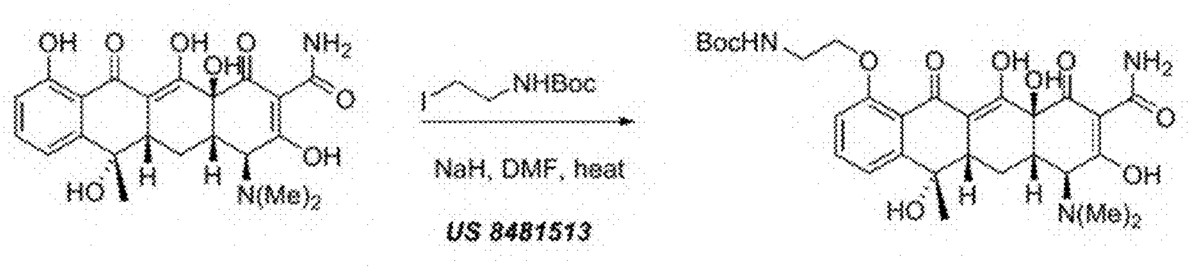
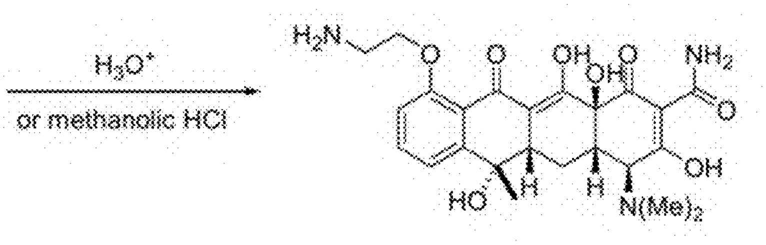
TET-8
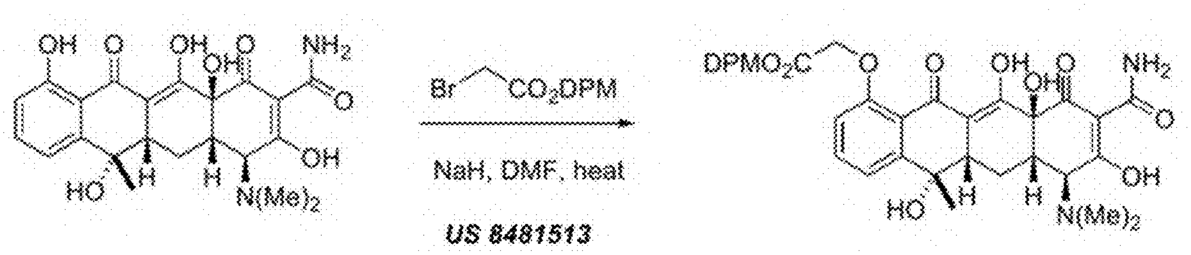
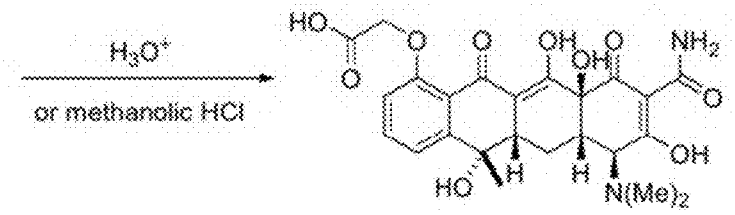
TET-9

Figure 27
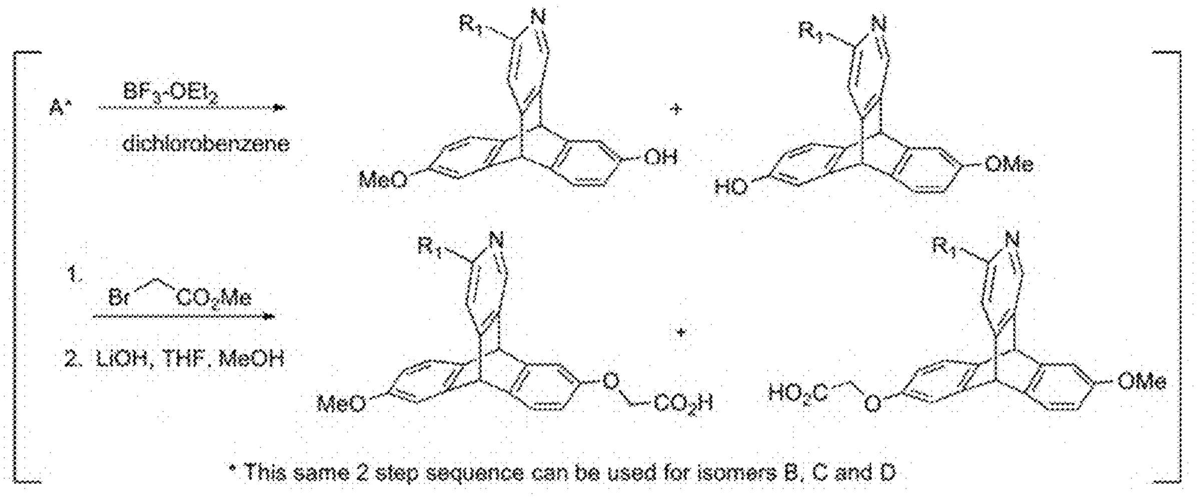
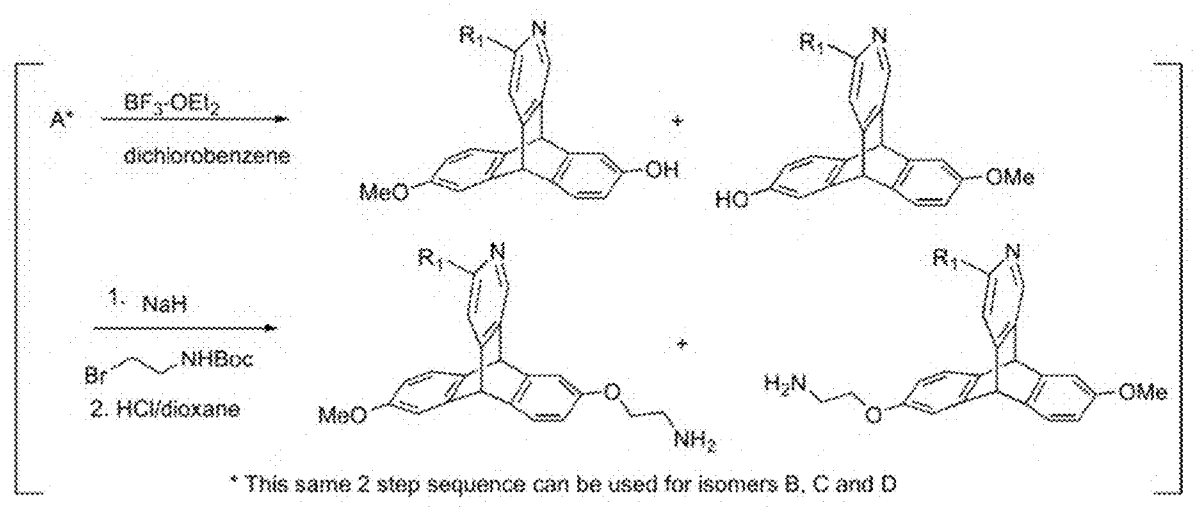

Figure 29
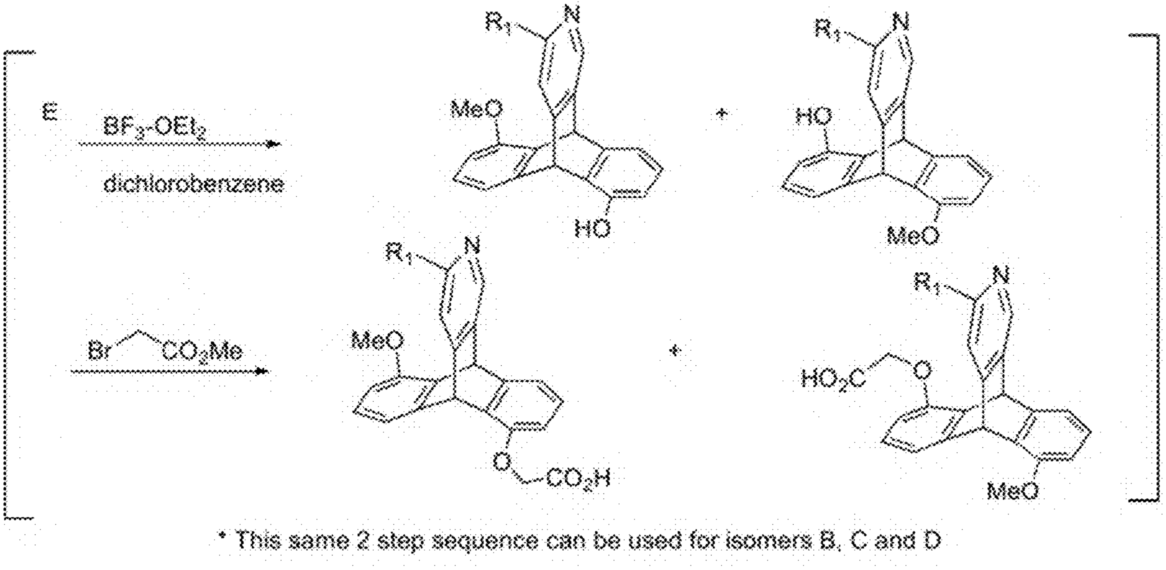
* This same 2 step sequence can be used for isomers B, C and D
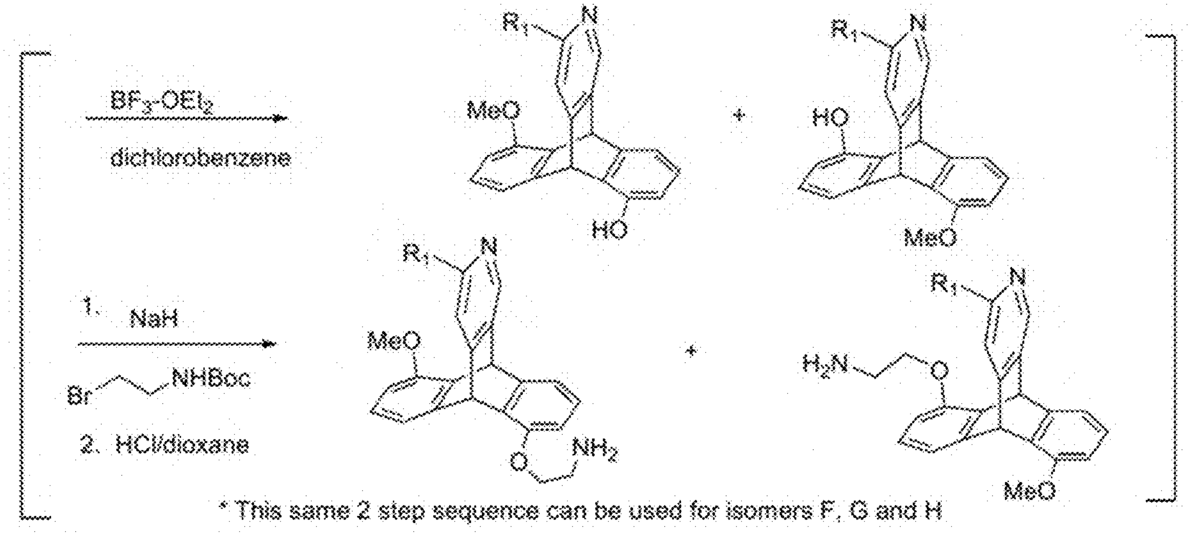
* This same 2 step sequence can be used for isomers F, G and H Figure 30
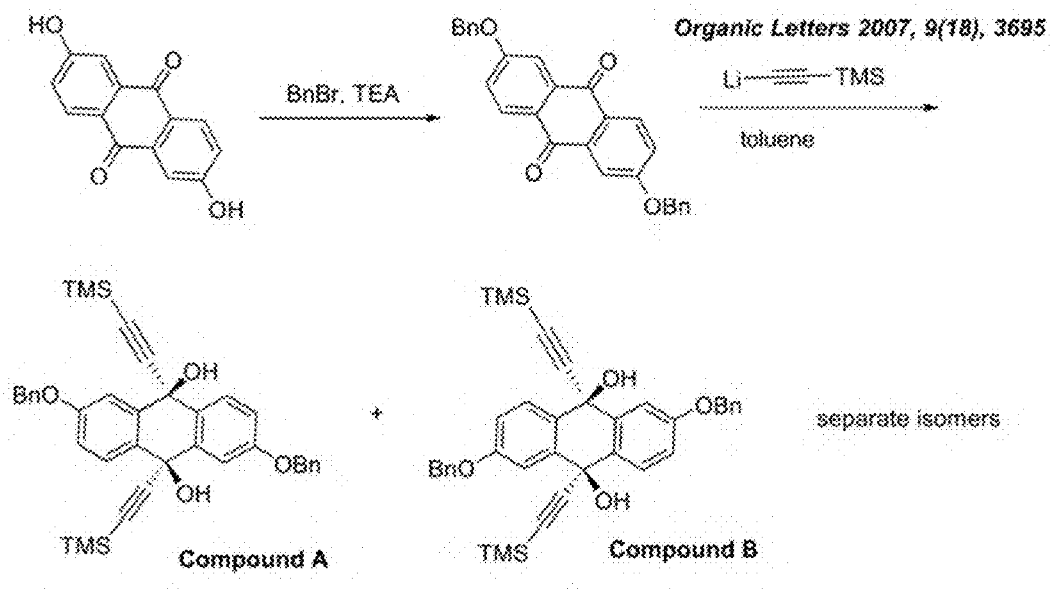
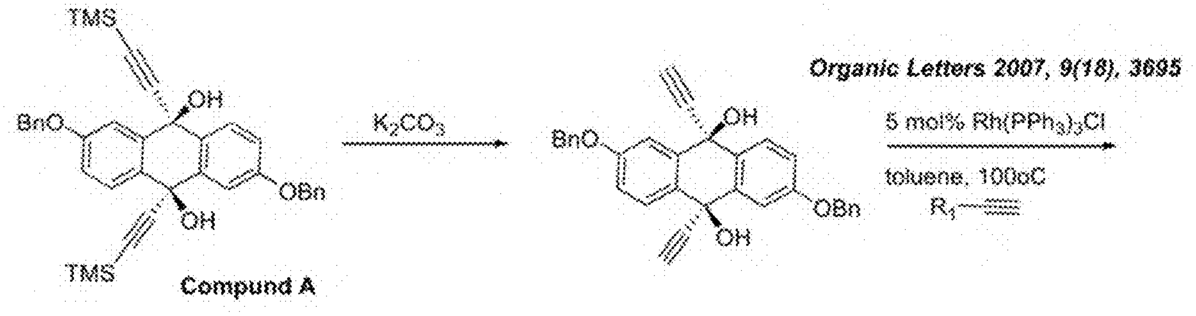
The following Sequence A can also be run on Compound B
Sequence A
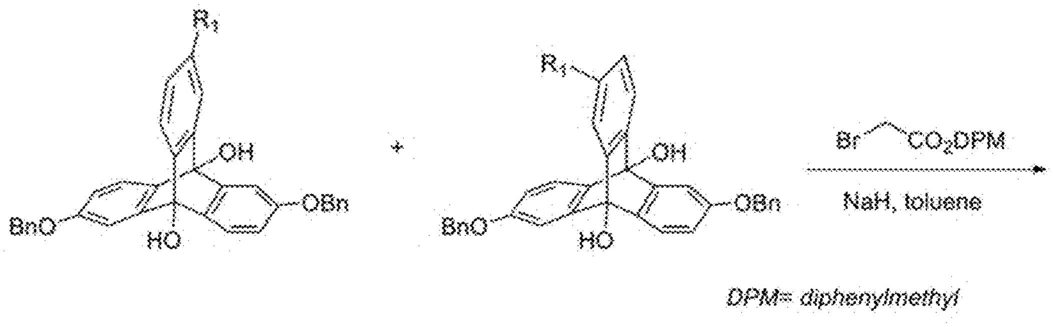
*DPM= diphenylmethyl*

Figure 31
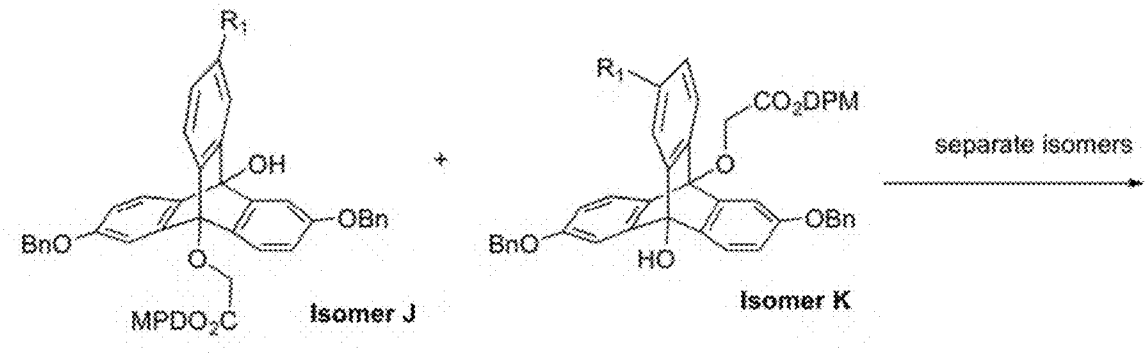
*The following Sequence B also can be run on all generated isomers*
Sequence B
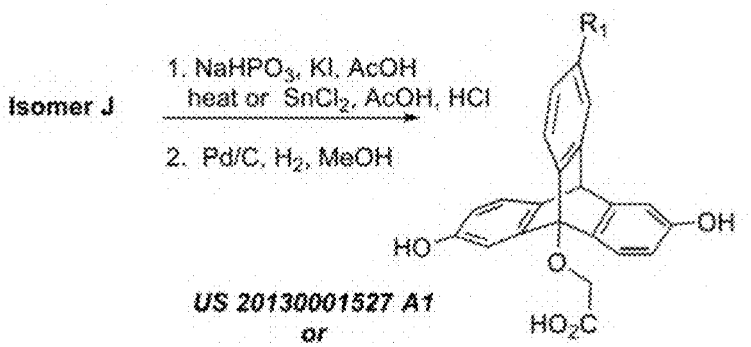
*US 20130001527 A1*
*or*
*Journal of Organic Chemistry, 72(19), 7229-7236; 2007*
*The following Sequence C can be run on Compound B*
Sequence C
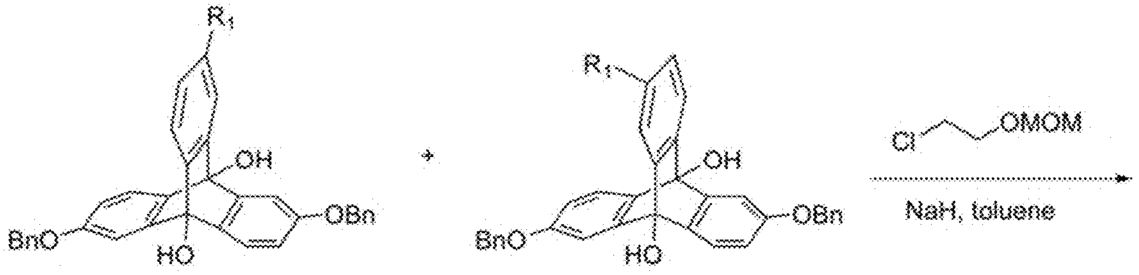

Figure 32
Isomer L + Isomer M
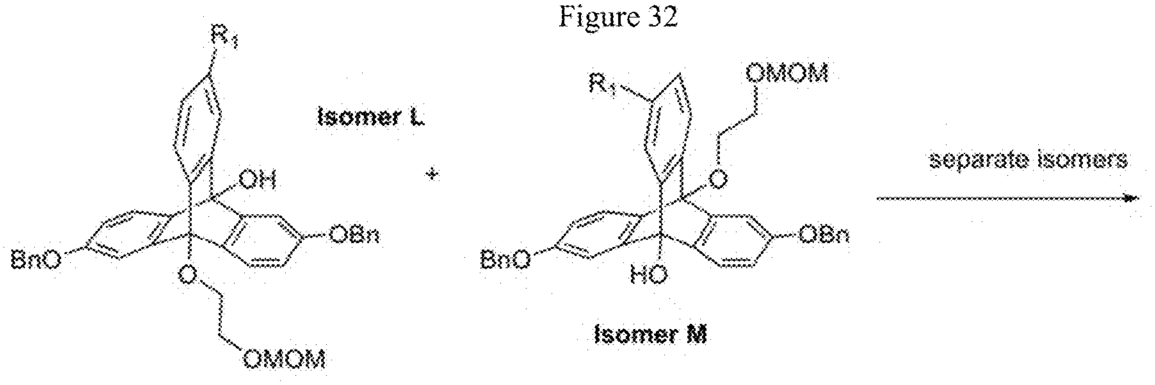
*The following Sequence D can also be run on all generated isomers*
Sequence D
Isomer L
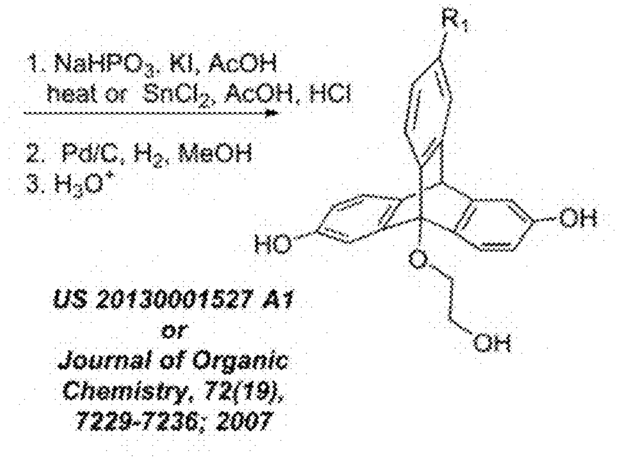
*The following Sequence E can also be run on Compound B*
Sequence E
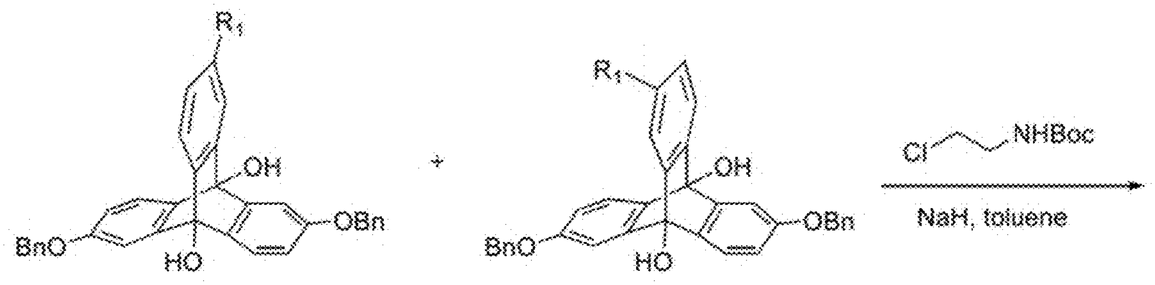

Figure 33
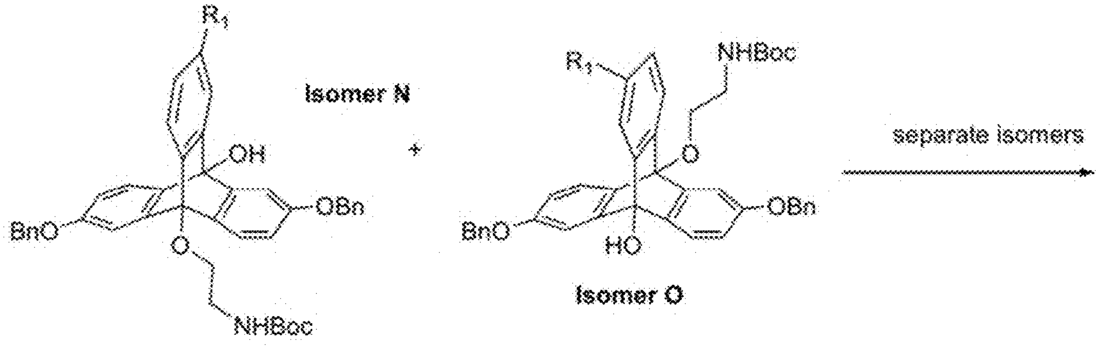
*The following Sequence F can also be run on all generated isomers*
Sequence F
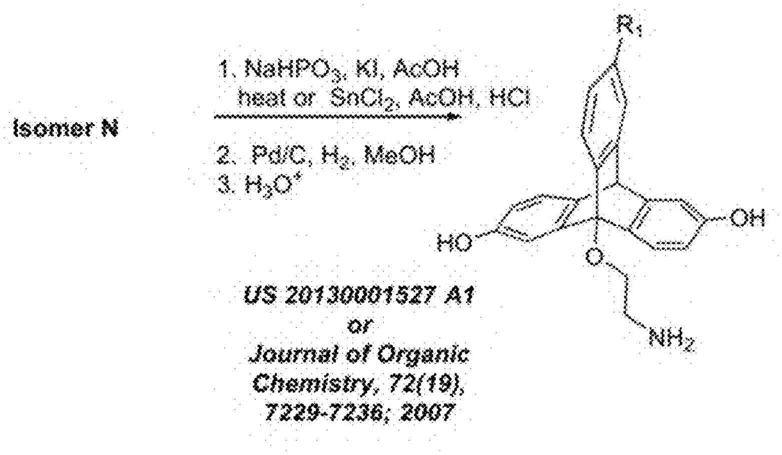
All of these reaction in this Scheme can also be performed starting from this alternative starting material:
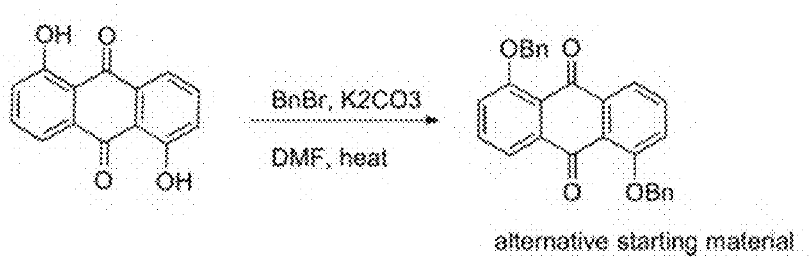
alternative starting material n = 1-30, 1-20, 1-10, or 1-5 n = 1-30, 1-20, 1-10, or 1-5
R1, R2 = nitrogen-linked functional groups described elsewhere

ARK-132: Synthetic Route

ARK-134 Synthetic Route

ARK-135 and 136 Synthetic Route

ARK-188 Synthetic Route

ARK-190 Synthetic Route

ARK-191 Synthetic Route

ARK-195 Synthetic Route

ARK-197 Synthetic Route

Synthetic Route for Ribocil-Based Ligands

Figure 46
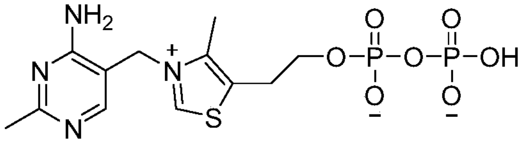
PreQ1 ligand
TPP ligand
Aptamer 21 and Aptamer 21-E
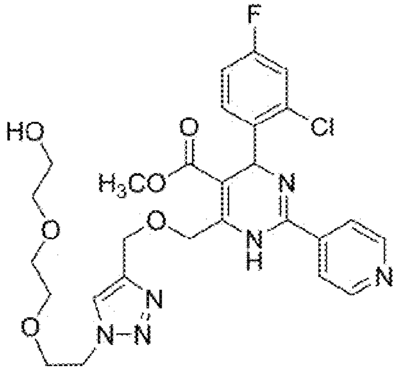
Compound 1b
(Aptamer 21 ligand)

Figure 51
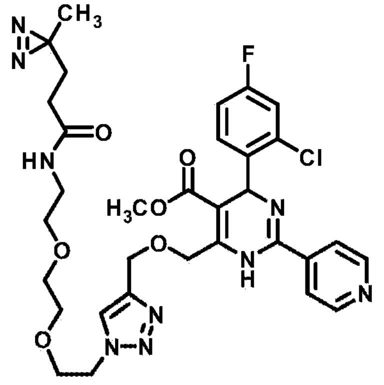
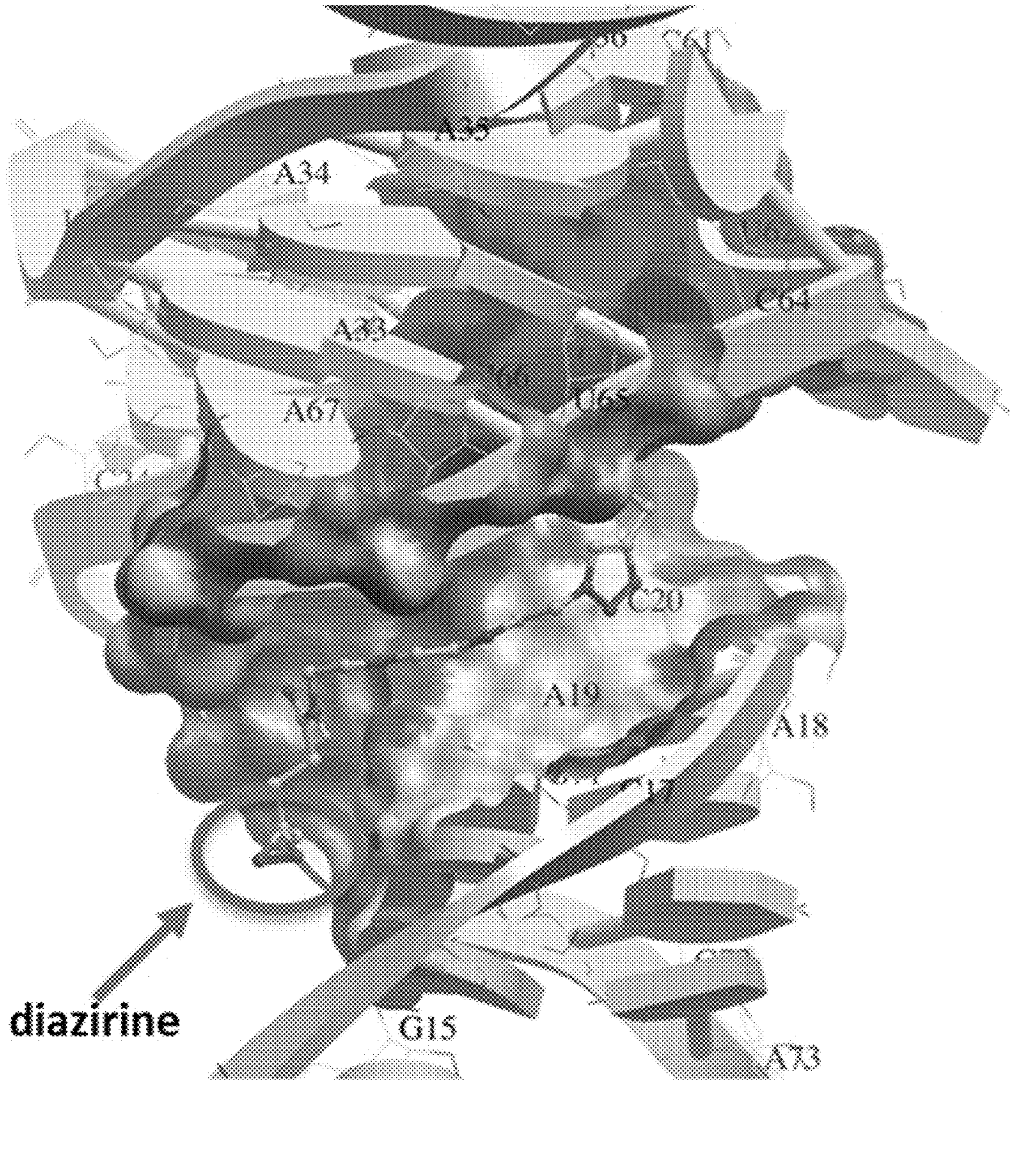

Figure 52
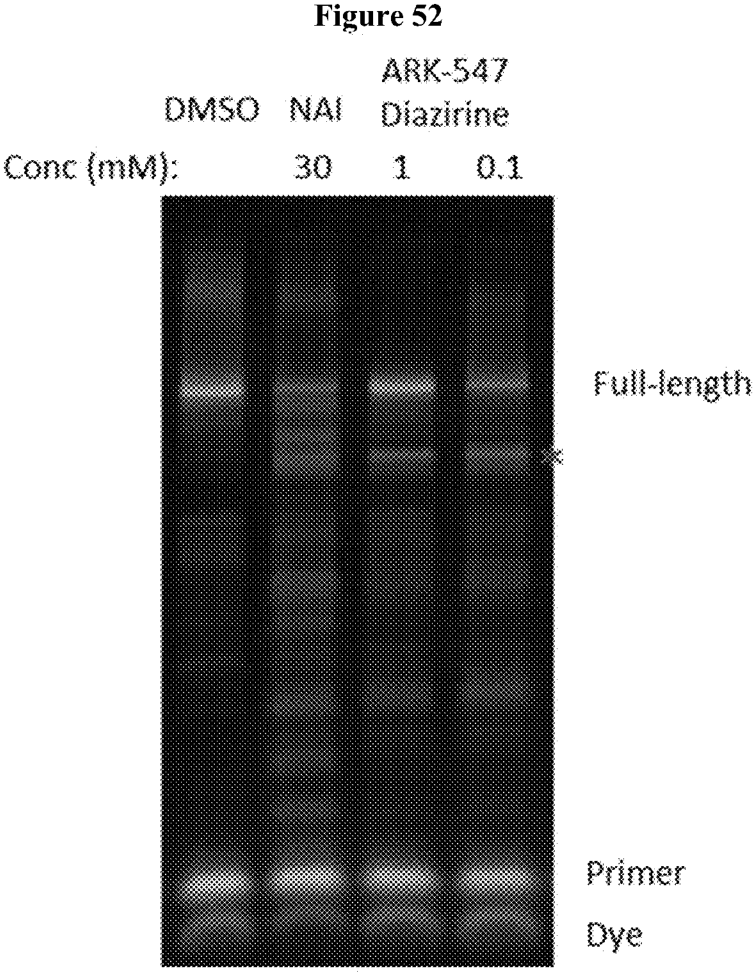
NAI = 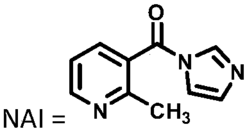
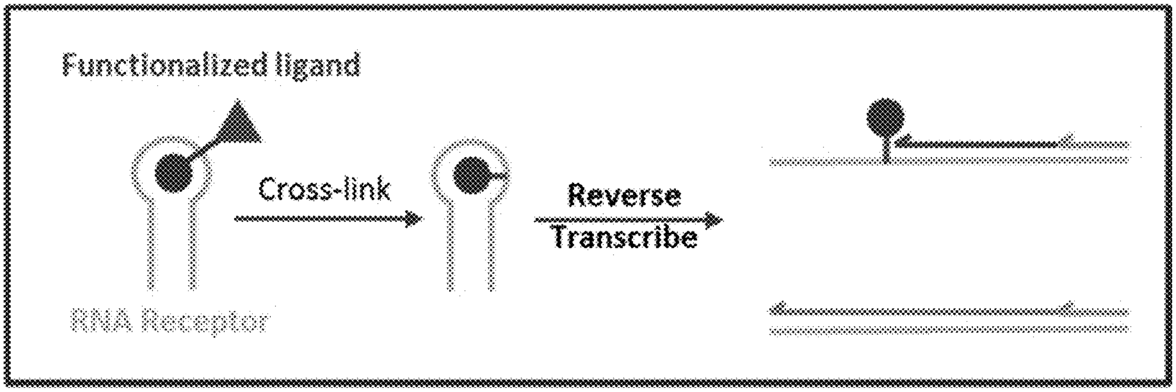

Figure 53
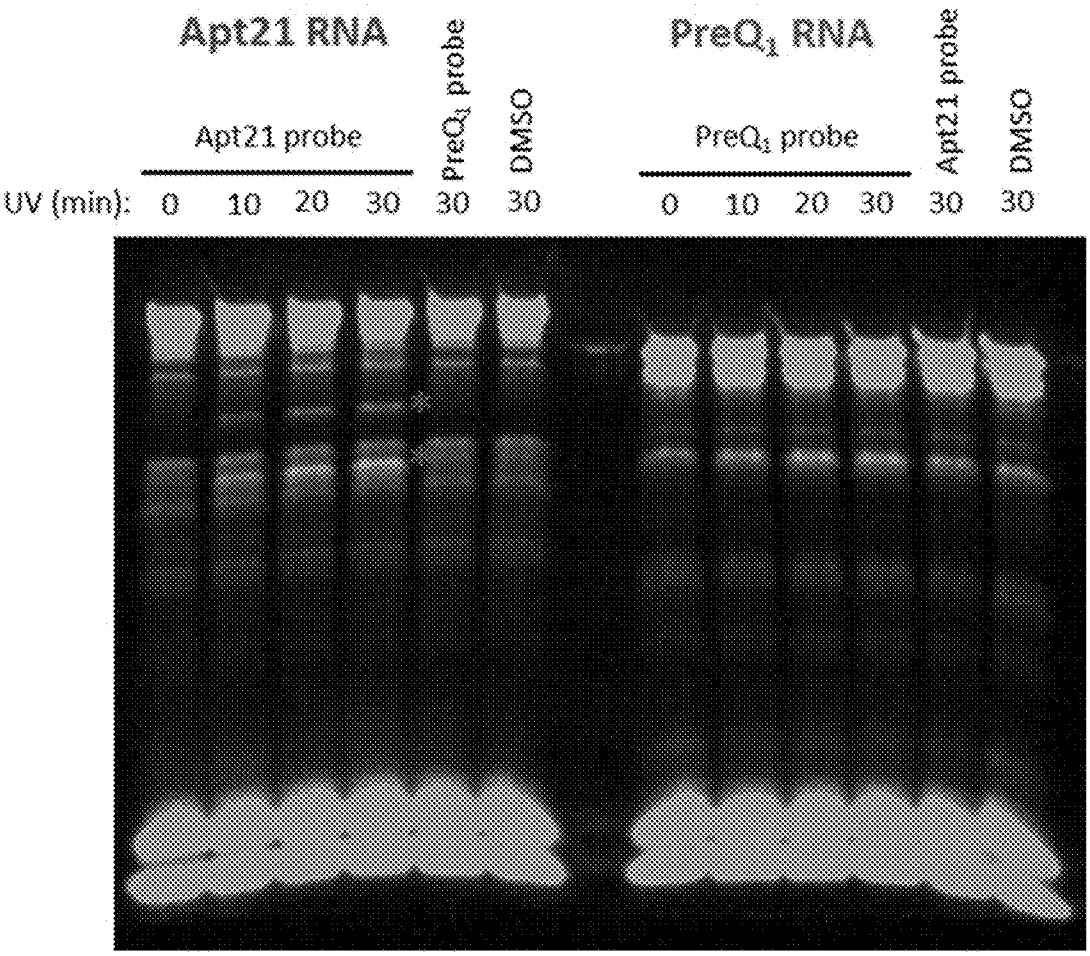
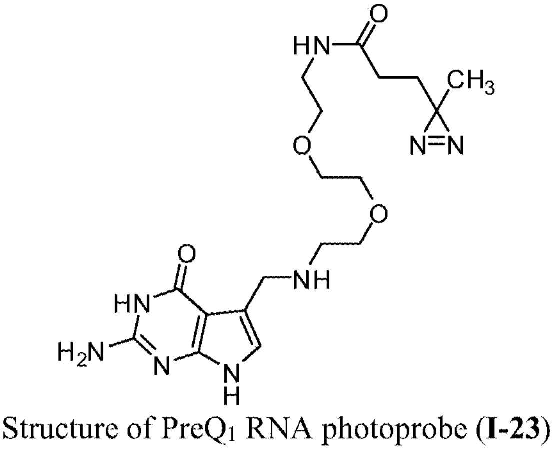
Structure of $PreQ_1$ RNA photoprobe (I-23)

| Lane | Compound | Warhead |
|---|---|---|
| 1 | ARK-139 (Cpd 1b) | None |
| 2 | ARK-547 | Diazirine |
| 3 | **ARK-547 + 100 μM ARK-**139 | |
| 4 | ARK-546 | Bio-diazirine |
| 5 | ARK-579 | Bio-diazirine |
| 6 | ARK-580 | Bio-diazirine |
| 7 | ARK-548 | $CF_3$-diazirine |
| 8 | ARK-544 | Benzophenone |
| 9 | ARK-581 | Phenyl-$N_3$ |
| 10 | ATN-5-36 ($PreQ_1$; compound **I-23**) | Diazirine |

Figure 62
5'-$N_3$-Aptamer 21 / No probe
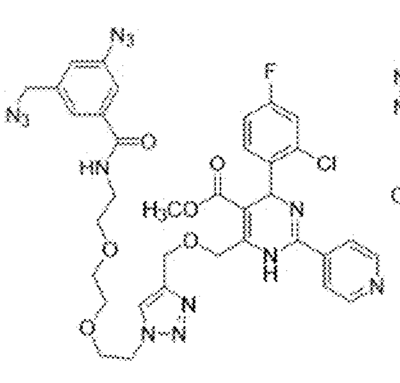
ARK-729
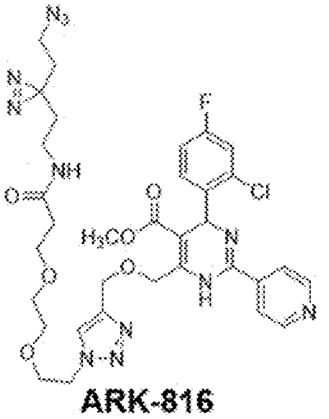
ARK-816
1 2 3 4 5 1 2 3 4 5
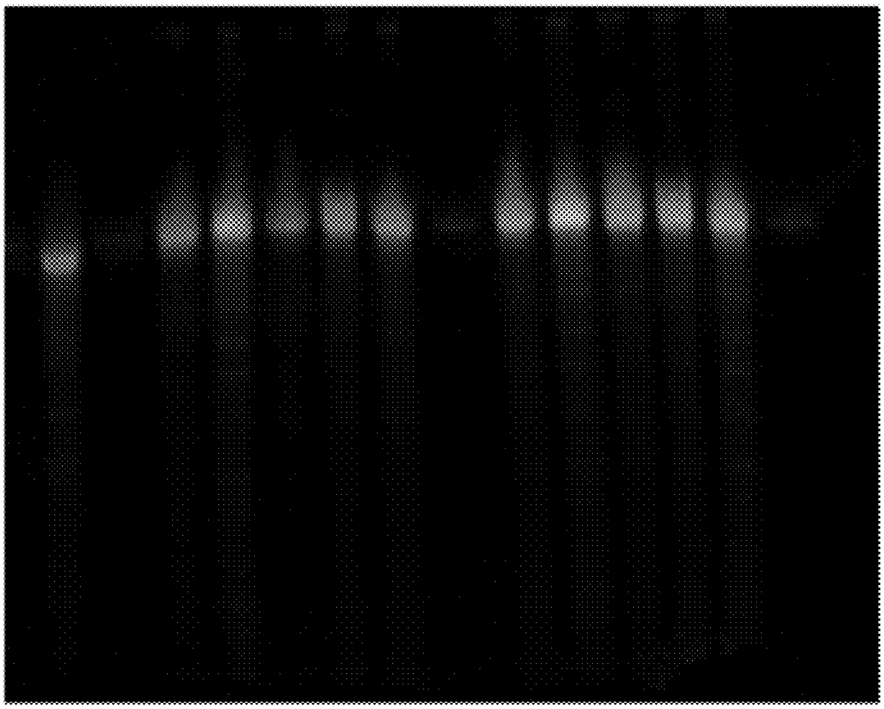

Figure 63
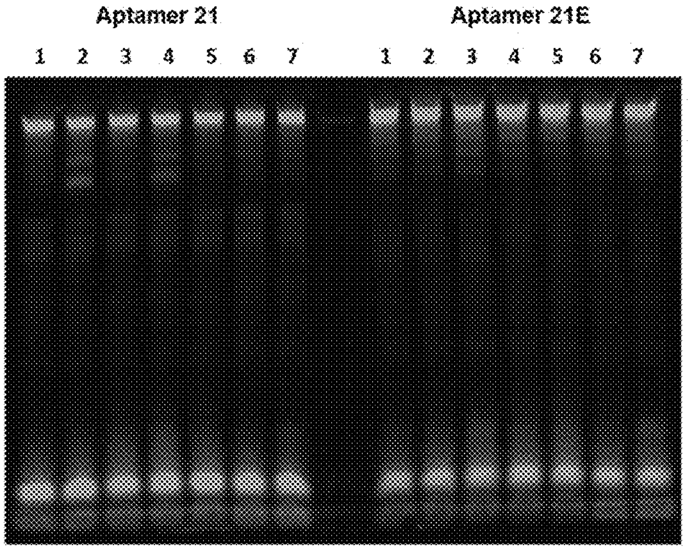
| # | Probe(s) |
| --- | --- |
| 1 | ARK – 139 |
| 2 | ARK – 581 |
| 3 | ARK – 581 + 10x ARK – 139 |
| 4 | ARK – 581 + 10x ARK – 850 |
| 5 | ARK – 581 + 10x ARK – 852 |
| 6 | ARK – 2058 |
| 7 | ARK – 2059 |
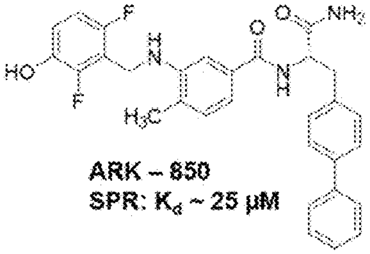
ARK – 850
SPR: $K_d$ ~ 25 μM
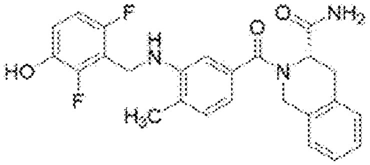
ARK – 852
SPR: $K_d$ ~ 600 nM
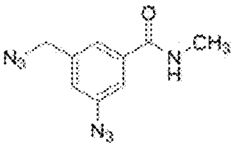
ARK – 2058
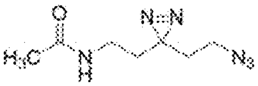
ARK – 2059

Figure 64
RT Pausing
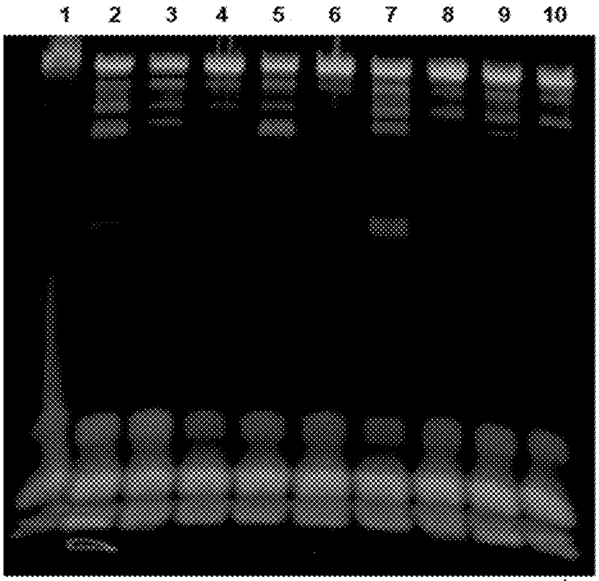
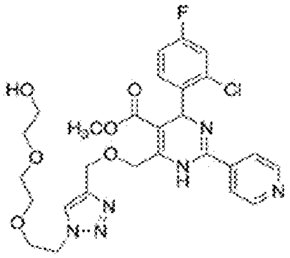
ARK-139 (1)
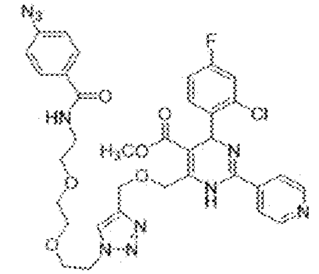
ARK-581 (2)
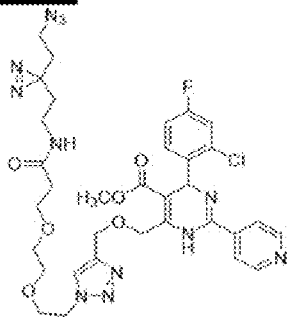
ARK-816 (7)
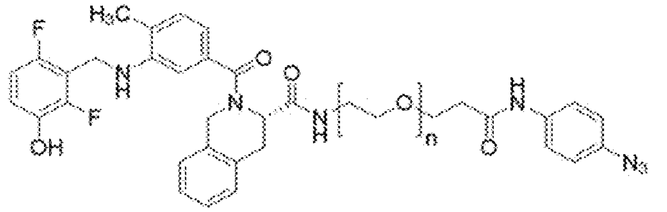
n = 1 (3)
n = 2 (4)
n = 4 (6)
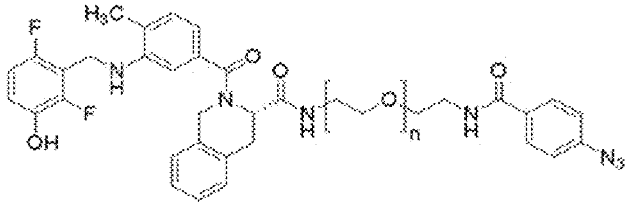
n = 2 (5)
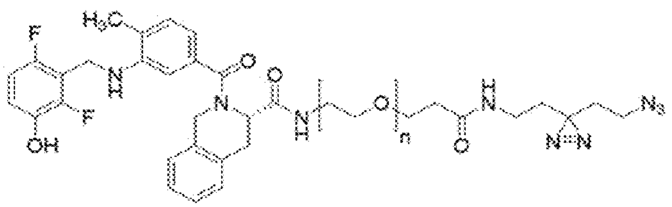
n = 1 (8)
n = 2 (9)
n = 4 (10)

Figure 65
RT Pausing – Competition Assay
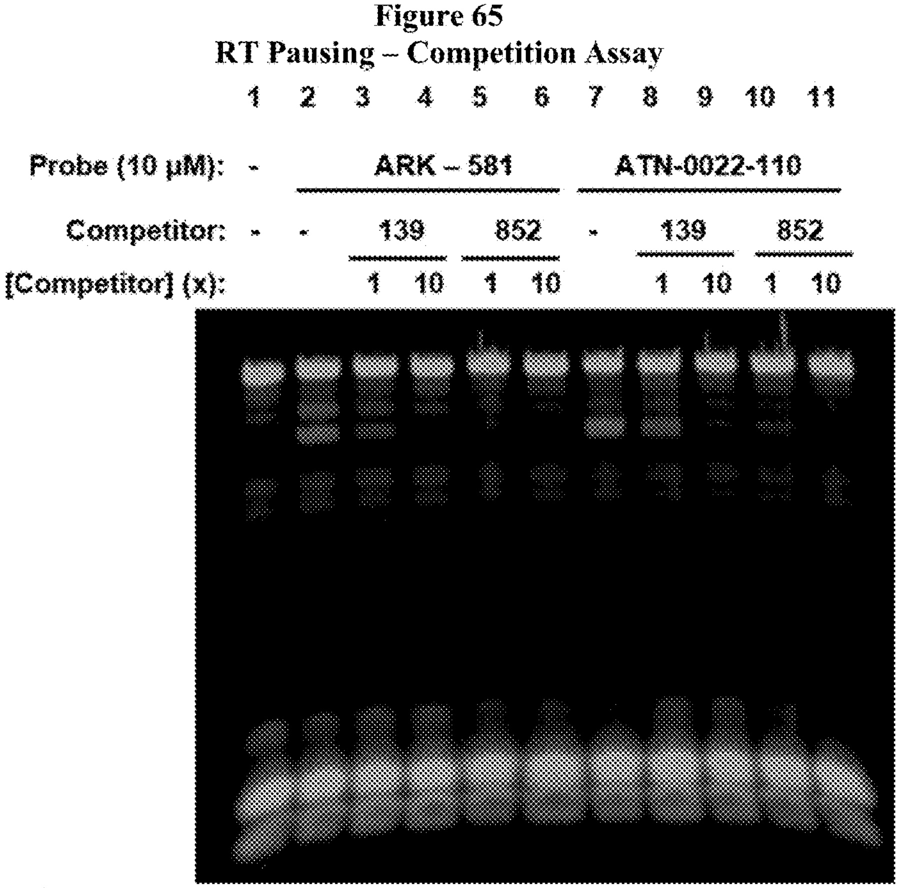
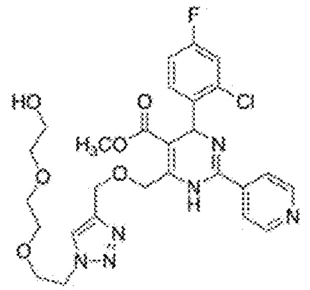
ARK-139
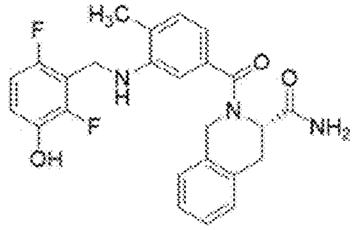
ARK-852
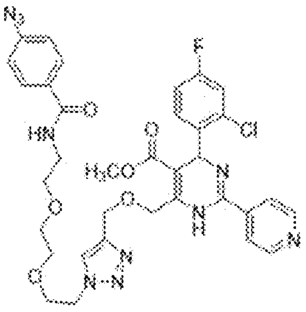
ARK-581
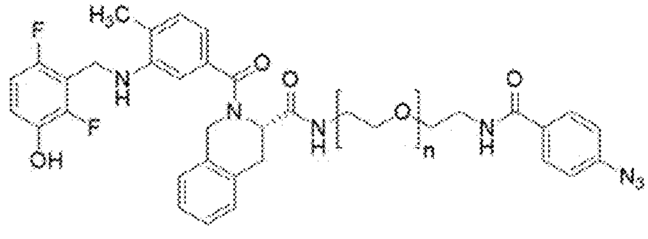
ATN-0022-110 (n = 2)

Figure 66
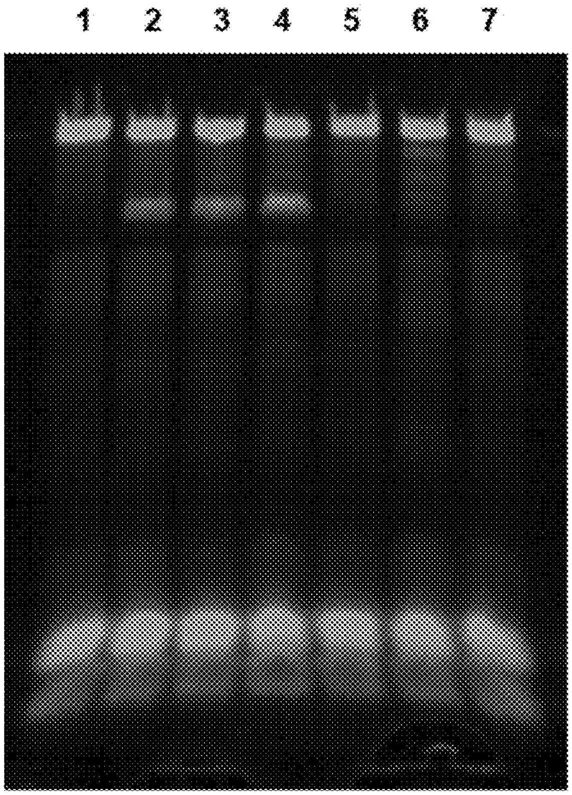
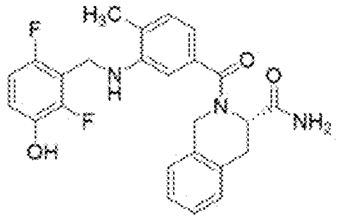
ARK-852 (1)
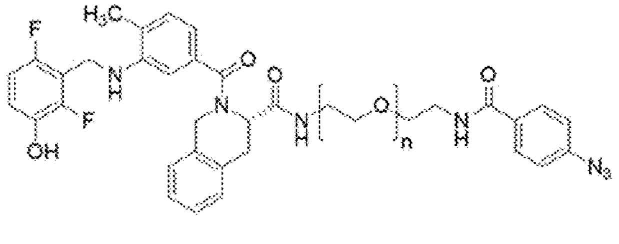
n = 1 (2)
n = 2 (3)
n = 4 (4)
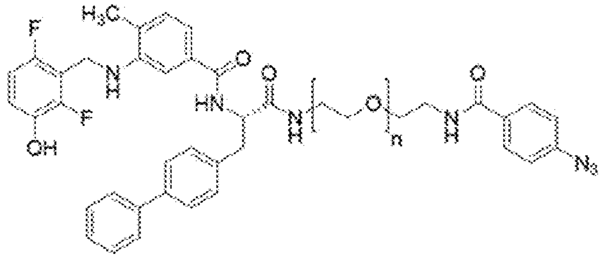
n = 1 (5)
n = 2 (6)
n = 4 (7)

RT Pausing from ARK-670

Enrichment of Aptamer 21 from a Mixture of RNAs

NUCLEIC ACID-BINDING PHOTOPROBES AND USES THEREOF

CROSS-REFERENCE TO RELATED APPLICATIONS

This application is a continuation of U.S. patent application Ser. No. 16/207,062, filed Nov. 30, 2018, which claims the benefit under 35 U.S.C. § 119(e) of the U.S. Provisional Patent Application Ser. No. 62/593,175, filed on Nov. 30, 2017, the entirety of which is hereby incorporated by reference.

TECHNICAL FIELD OF THE INVENTION

The present invention relates to photoactivatable compounds and methods of use thereof for identifying RNA transcripts that bind such compounds and are thus druggable, methods of screening drug candidates, and methods of determining drug binding sites and/or reactive site(s) on a target RNA. The invention also provides methods for modulating the biology of RNA transcripts to treat various diseases and conditions.

SEQUENCE LISTING

The instant application contains a Sequence Listing which has been submitted electronically in XML format and is hereby incorporated by reference in its entirety. Said XML copy, created on Mar. 21, 2023, is named 394457-003USC1 195955 SL.xml and is 89,705 bytes in size.

BACKGROUND OF THE INVENTION

Ribonucleic acids (RNAs) have been conventionally considered mere transient intermediaries between genes and proteins, whereby a protein-coding section of deoxyribonucleic acid (DNA) is transcribed into RNA that is then translated into a protein. RNA was thought to lack defined tertiary structure, and even where tertiary structure was present it was believed to be largely irrelevant to the RNA's function as a transient messenger. This understanding has been challenged by the recognition that RNA, including non-coding RNA (ncRNA), plays a multitude of critical regulatory roles in the cell and that RNA can have complex, defined, and functionally-essential tertiary structure.

All endogenous mammalian diseases are ultimately mediated by the transcriptome. Insofar as messenger mRNA (mRNA) is part of the transcriptome, and all protein expression derives from mRNAs, there is the potential to intervene in protein-mediated diseases by modulating the expression of the relevant protein and by, in turn, modulating the translation of the corresponding upstream mRNA. But mRNA is only a small portion of the transcriptome: other transcribed RNAs also regulate cellular biology either directly by the structure and function of RNA structures (e.g., ribonucleoproteins) as well as via protein expression and action, including (but not limited to) miRNA, lncRNA, lincRNA, snoRNA, snRNA, scaRNA, piRNA, ceRNA, and pseudo-genes. Drugs that intervene at this level have the potential of modulating any and all cellular processes. Existing therapeutic modalities such as antisense RNA or siRNA, in most cases, have yet to overcome significant challenges such as drug delivery, absorption, distribution to target organs, pharmacokinetics, and cell penetration. In contrast, small molecules have a long history of successfully surmounting these barriers and these qualities, which make them suitable as drugs, are readily optimized through a series of analogues to overcome such challenges. In sharp contrast, there are no validated, general methods of screening small molecules for binding to RNA targets in general, much less inside cells. The application of small molecules as ligands for RNA that yield therapeutic benefit has received little to no attention from the drug discovery community.

Targeting the RNA transcriptome with small molecule modulators represents an untapped therapeutic approach to treat a variety of RNA-mediated diseases. Accordingly, there remains a need to develop small-molecule RNA modulators useful as therapeutic agents.

BRIEF DESCRIPTION OF THE FIGURES

FIG. 2 shows structures of tetracycline ligands with points of attachment for the tethering groups.

FIG. 5 shows structures of anthracene-maleimide Diels-Alder adduct ligands with points of attachment for the tethering groups. Note: The corresponding structures having the succinimido group in the opposite stereochemical orientation may also be prepared. Each R is independently selected from halo, —OH, —OMe, —$NH_2$, —NH-(optionally substituted $C_{1-10}$ aliphatic), optionally substituted $C_{1-10}$ aliphatic, or other described tethering groups. The modifier moiety may be attached at any position on R, or at the other functional groups on the above structures.

FIG. 9 shows structures of exemplary click-ready groups.

FIG. 17 shows further examples of tethering groups.

FIG. 22 shows reaction schemes for accessing several tetracycline small molecule ligands that include attachment points for the tethering group.

FIG. 24 shows reaction schemes for accessing several tetracycline small molecule ligands that include attachment points for the tethering group.

FIG. 25 shows reaction schemes for accessing several tetracycline small molecule ligands that include attachment points for the tethering group.

FIG. 27 shows reaction schemes for accessing several triptycene small molecule ligands that include attachment points for the tethering group.

FIG. 29 shows reaction schemes for accessing several triptycene small molecule ligands that include attachment points for the tethering group.

FIG. 30 shows reaction schemes for accessing several triptycene small molecule ligands that include attachment points for the tethering group.

FIG. 31 shows reaction schemes for accessing several triptycene small molecule ligands that include attachment points for the tethering group.

FIG. 32 shows reaction schemes for accessing several triptycene small molecule ligands that include attachment points for the tethering group.

FIG. 33 shows reaction schemes for accessing several triptycene small molecule ligands that include attachment points for the tethering group.

FIG. 46 shows several riboswitch/aptamer-ligand pairs useful as positive control model systems for assay development in accordance with the present invention. The $PreQ_1$ ligand and sequence are disclosed in *Nat Struct Mol Biol* 16, 343-344 (2009), which is hereby incorporated by reference. The TPP ligand and sequence are disclosed in *Nature* 441, 1167-1171 (2006) and Structure 14, 1459-1468 (2006), each of which is hereby incorporated by reference.

Higher peak values signify increased solvent exposure and reactivity of individual nucleotides of the aptamer, with and without the presence of the ligand I-1 (ARK-139).

Figure 1:
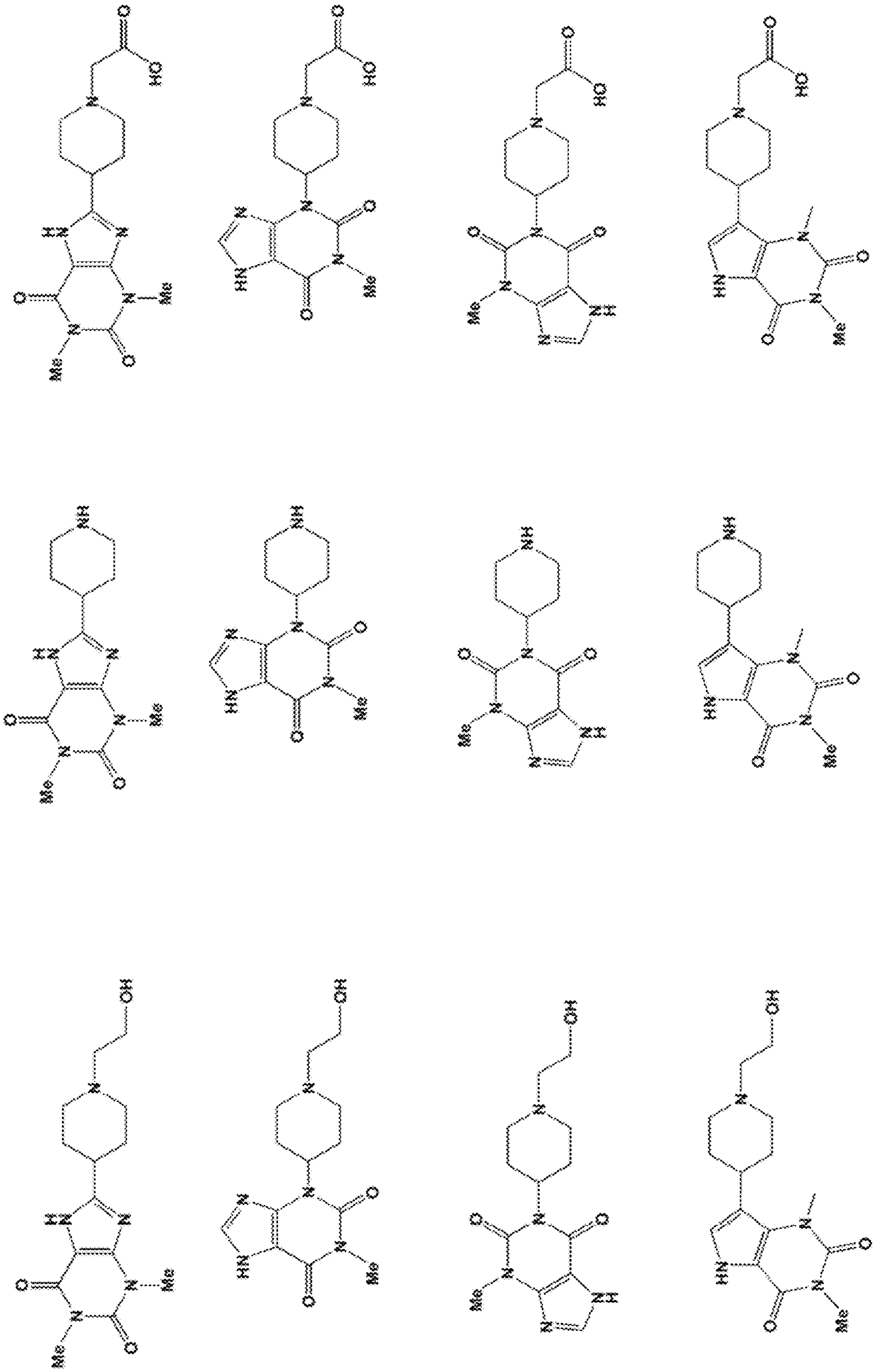
FIG. 1 shows structures of theophylline ligands with points of attachment for the tethering groups.
Figure 3:
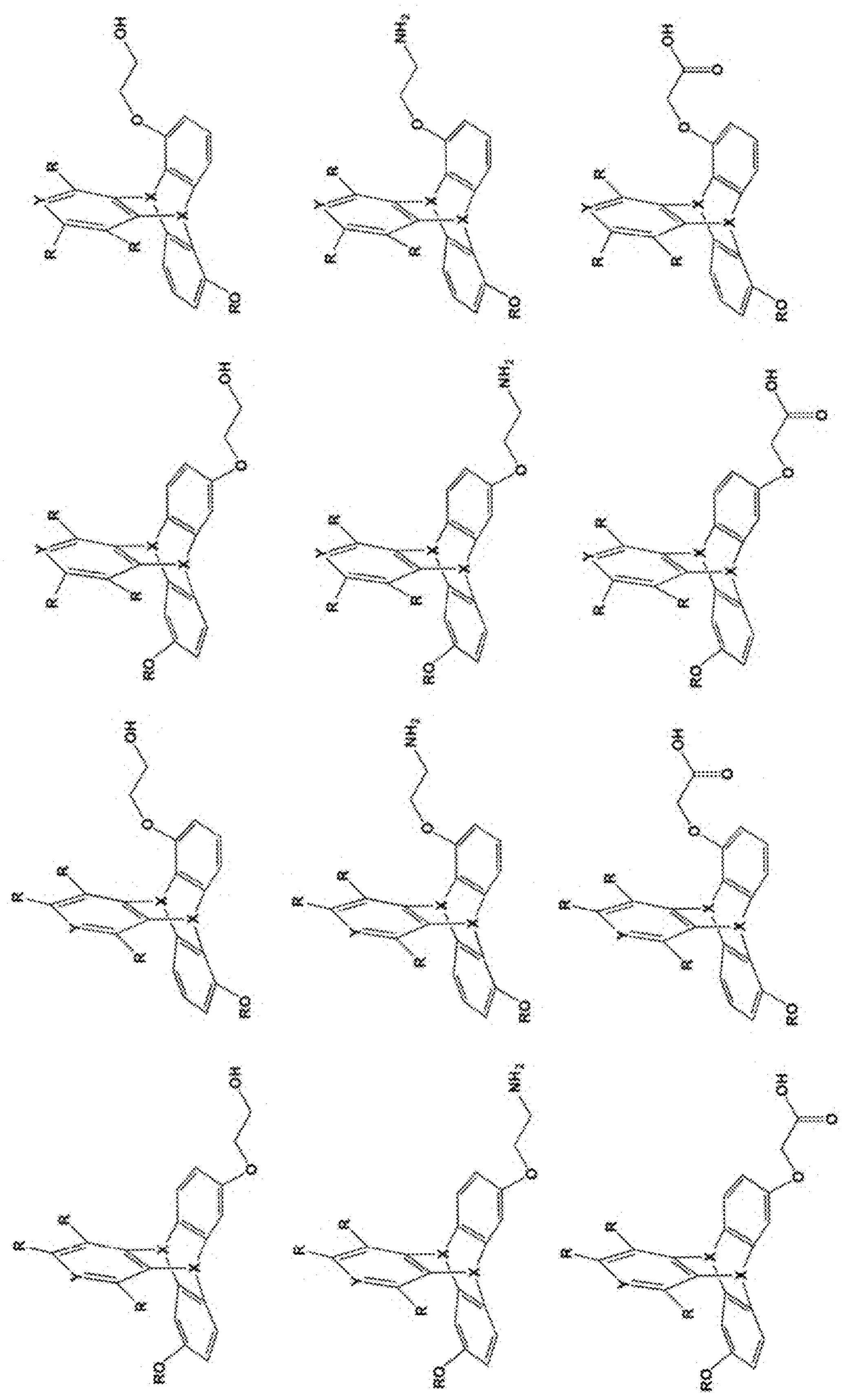
FIG. 3 shows structures of triptycene ligands with points of attachment for the tethering groups.
Figure 4:
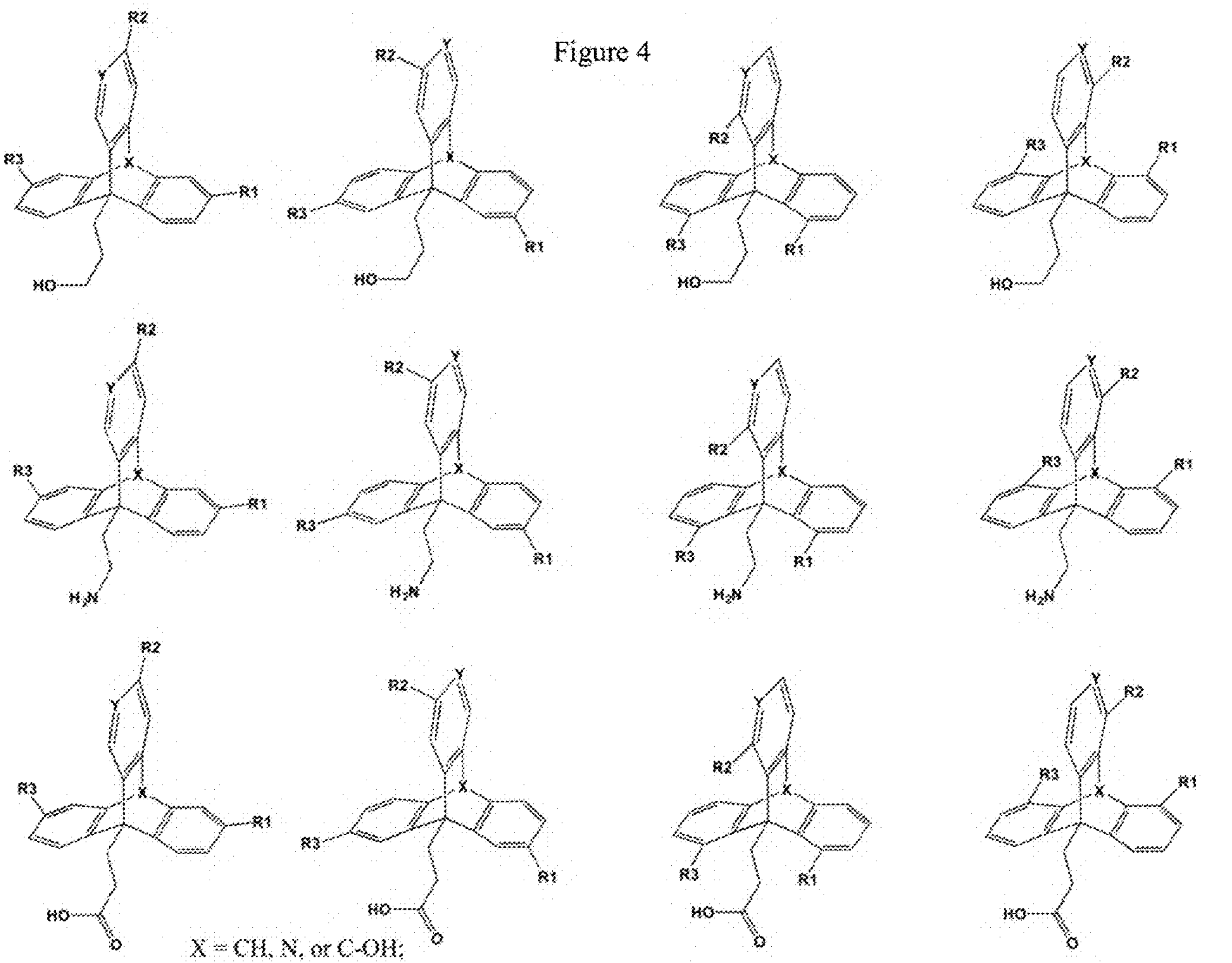
FIG. 4 shows structures of triptycene ligands with points of attachment for the tethering groups. X═CH, N, or C—OH; Y═CH or N; R1, R2, R3=each independently selected from halo, —OH, —OMe, —$NH_2$, —NH-(optionally substituted $C_{1-10}$ aliphatic), optionally substituted $C_{1-10}$ aliphatic, or other described tethering groups. The modifier moiety may be attached at any position on R1, R2, or R3, or at the other functional groups on the above structures.
Figure 6:
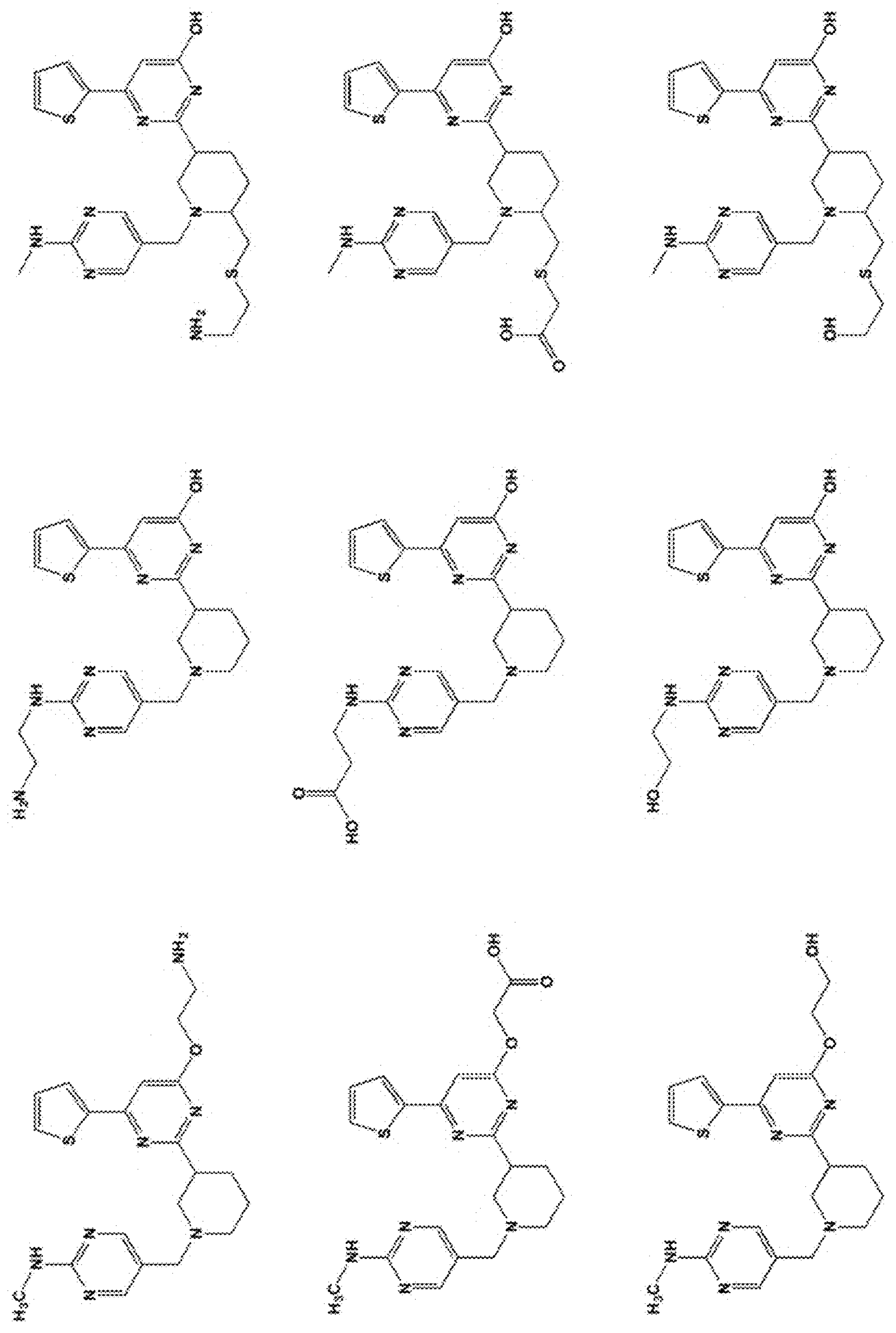
FIG. 6 shows structures of ribocil ligands with points of attachment for the tethering groups.
Figure 7:
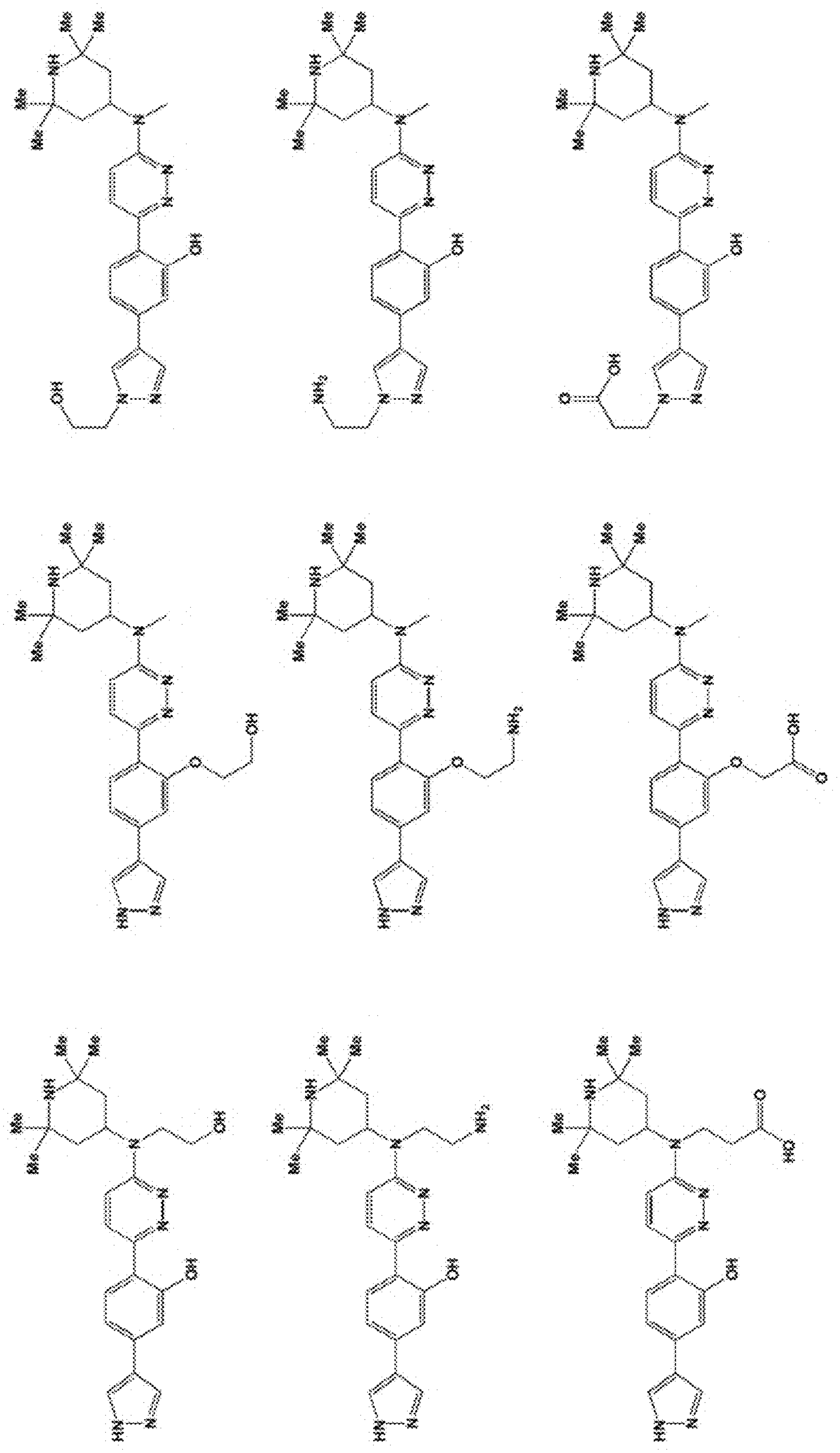
FIG. 7 shows structures of SMN2 ligands with points of attachment for the tethering groups.
Figure 8:
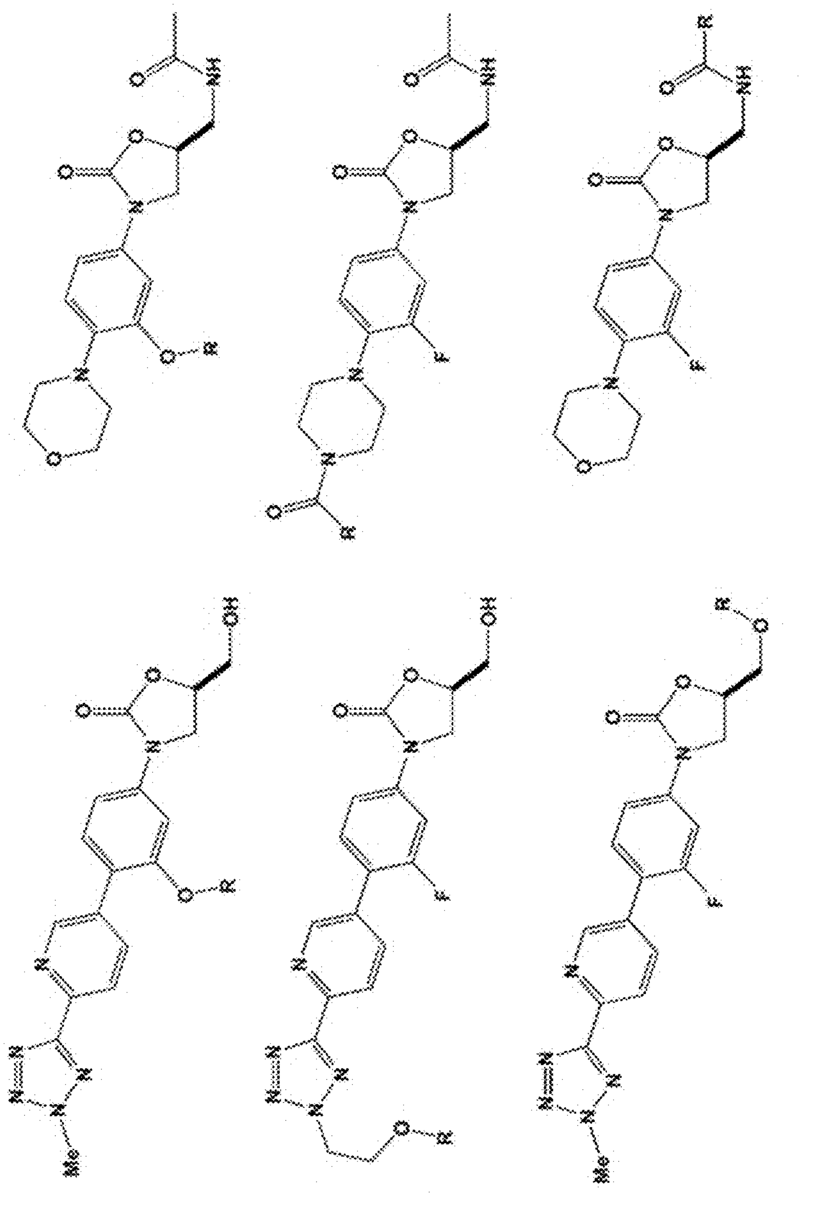
FIG. 8 shows structures of linezolid and tedizolid ligands with points of attachment for the tethering groups.
Figure 10:
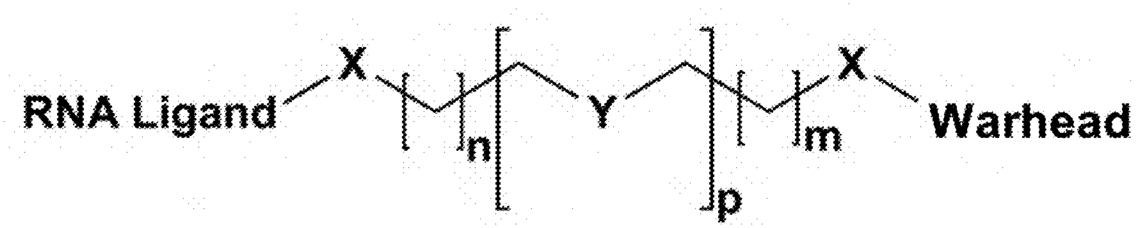
FIG. 10 shows exemplary tethering groups for linking RNA ligands and modifying moieties.
Figure 11:
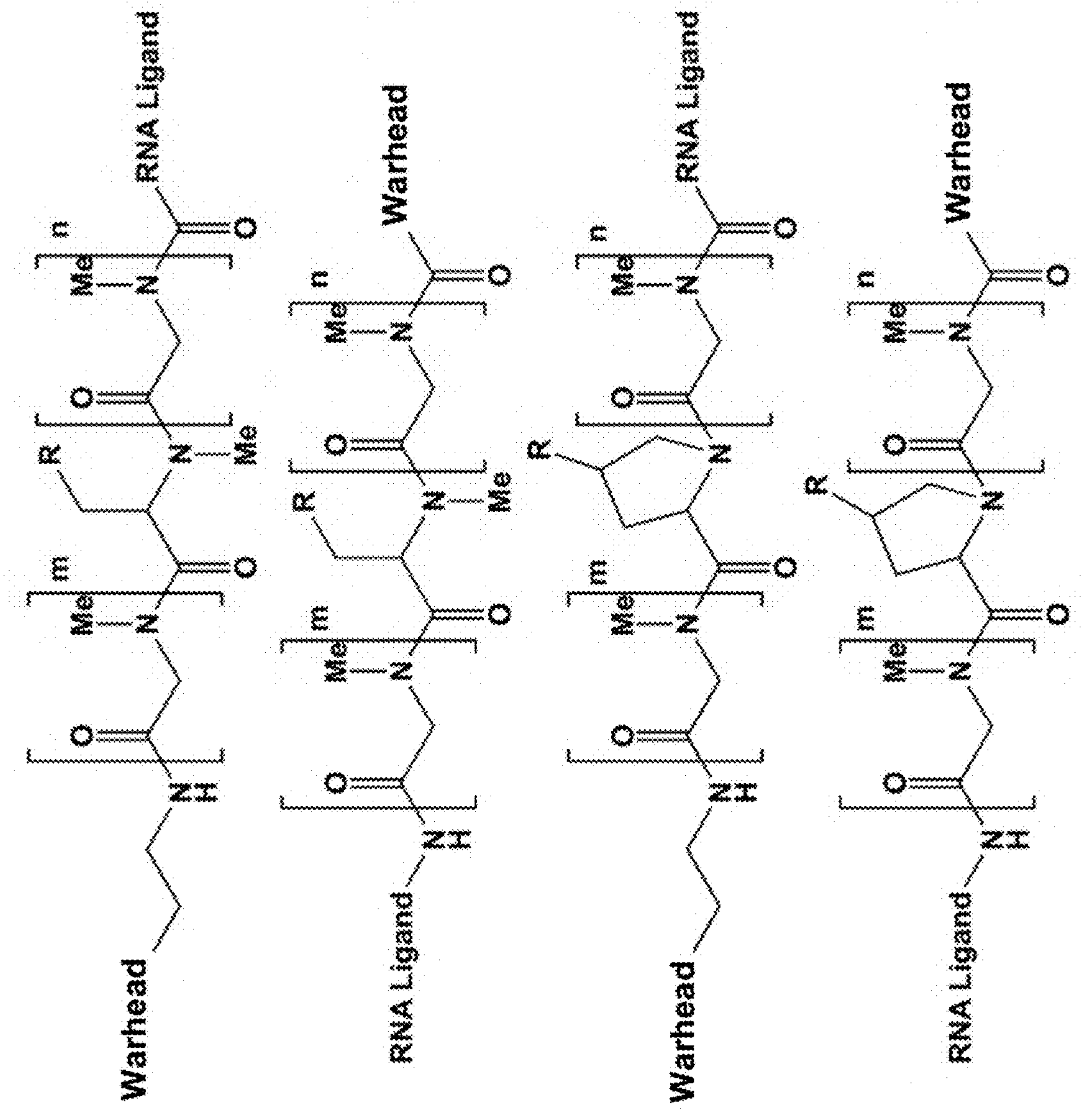
FIG. 11 shows further examples of tethering groups.
Figure 12:
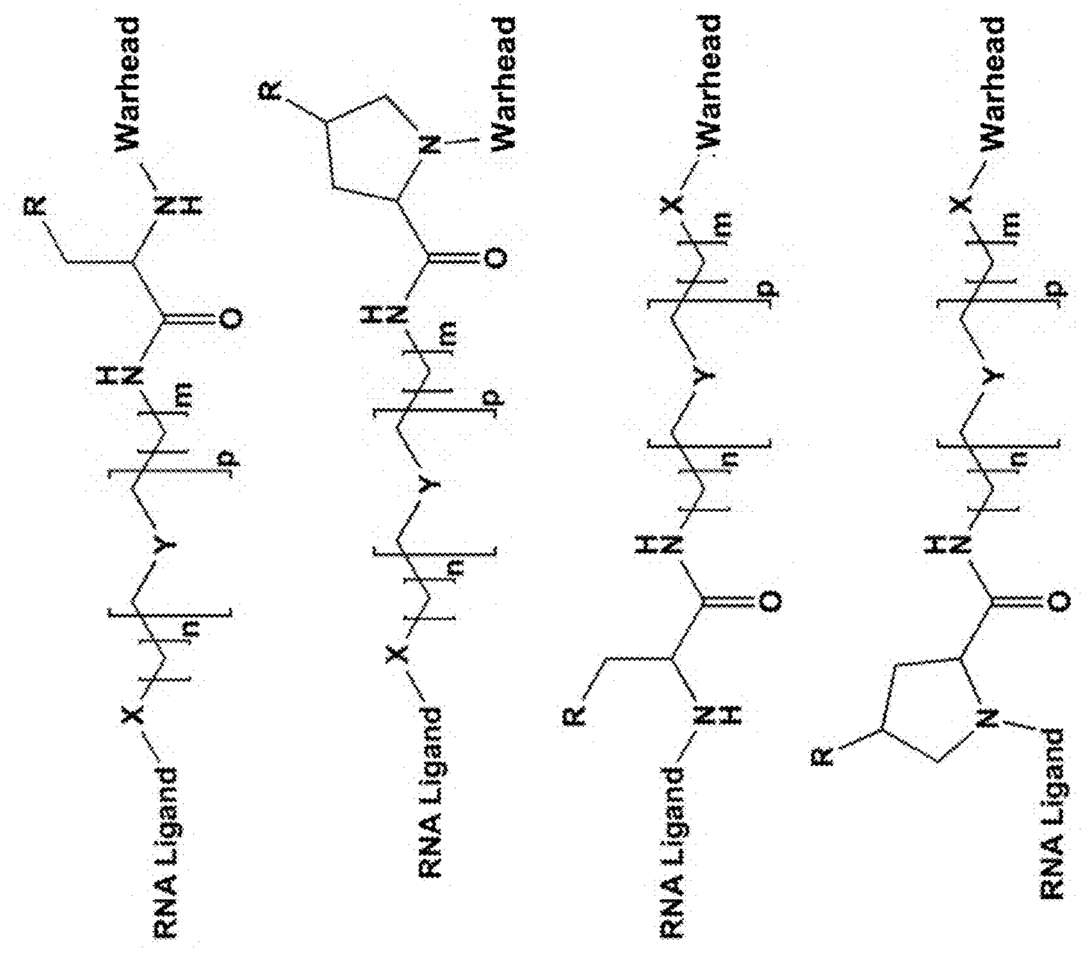
FIG. 12 shows further examples of tethering groups.
Figure 13:
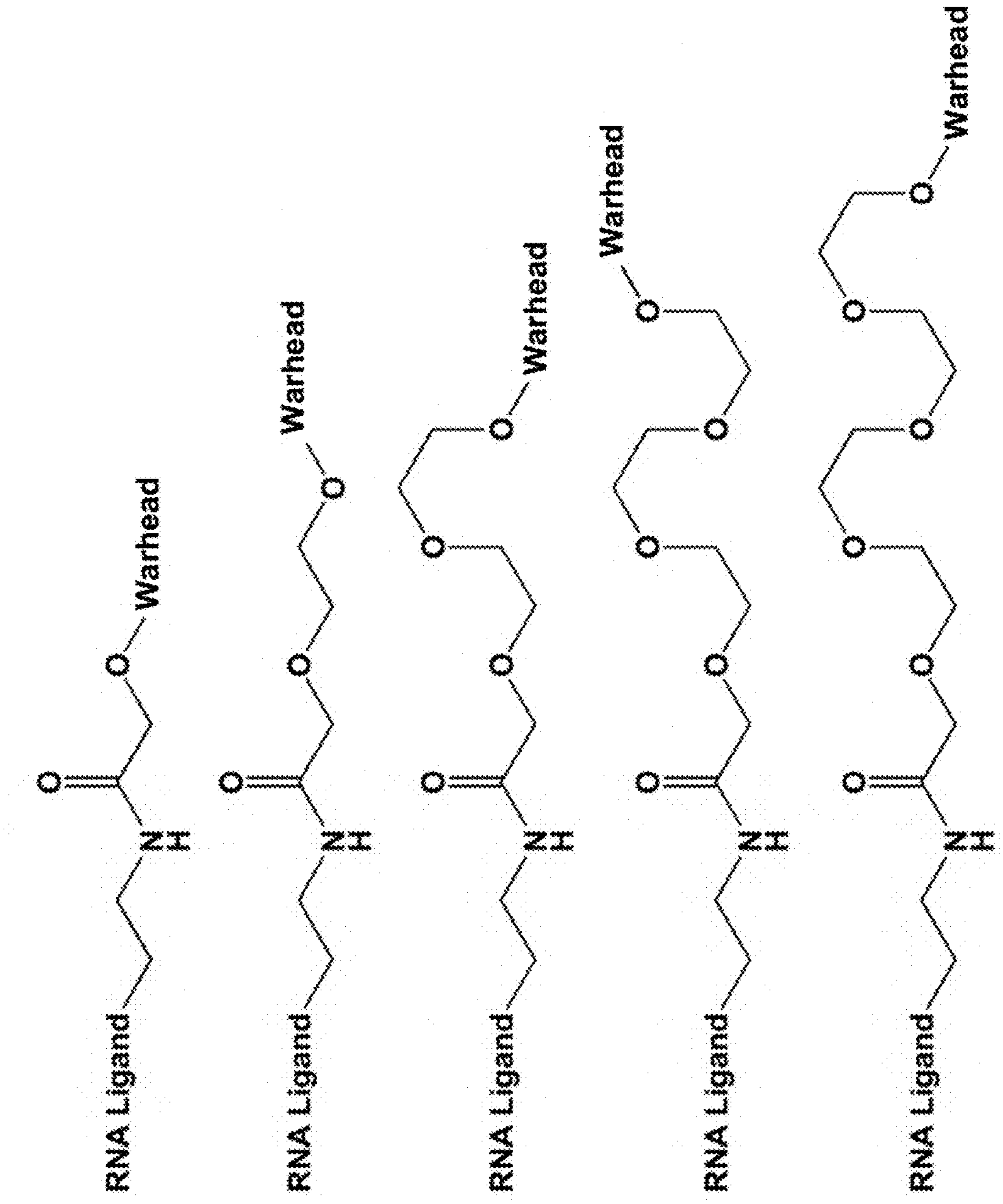
FIG. 13 shows further examples of tethering groups.
Figure 14:
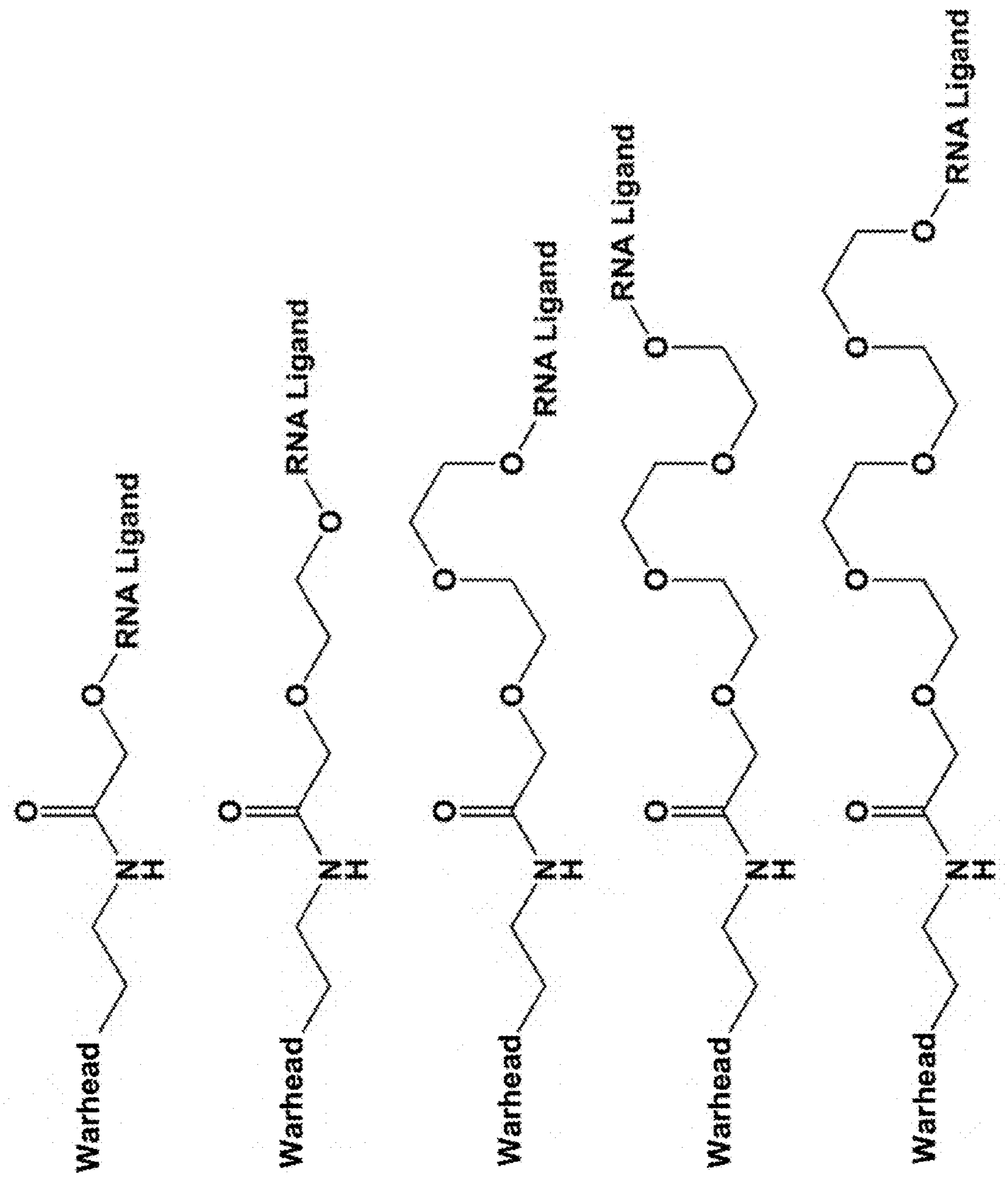
FIG. 14 shows further examples of tethering groups.
Figure 15:
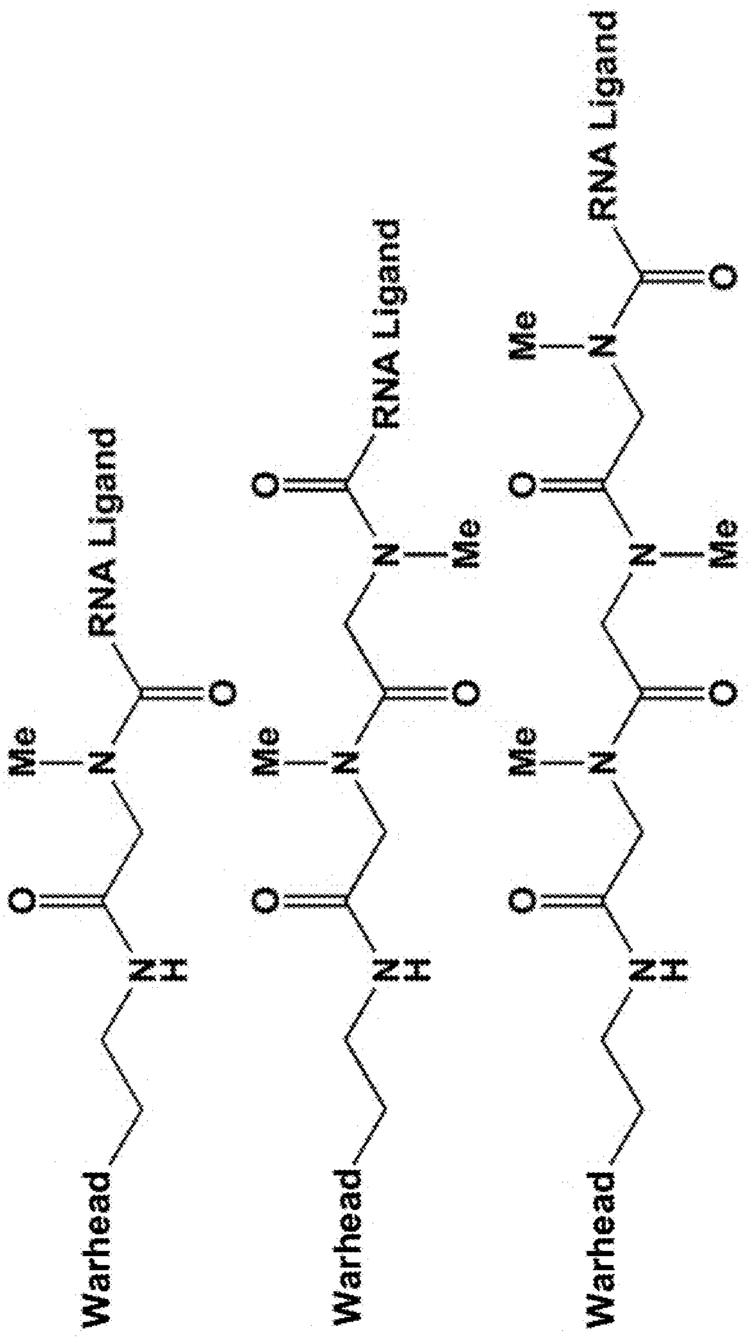
FIG. 15 shows further examples of tethering groups.
Figure 16:
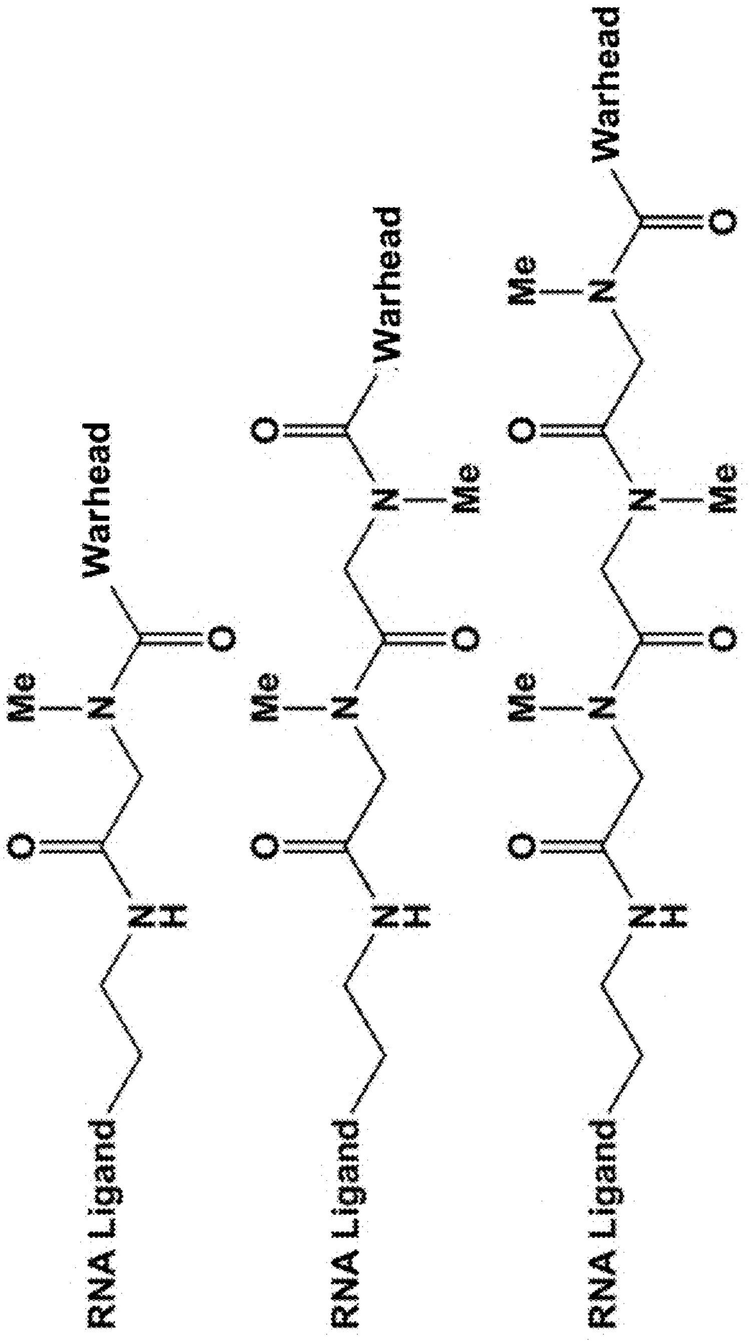
FIG. 16 shows further examples of tethering groups.
Figure 18:
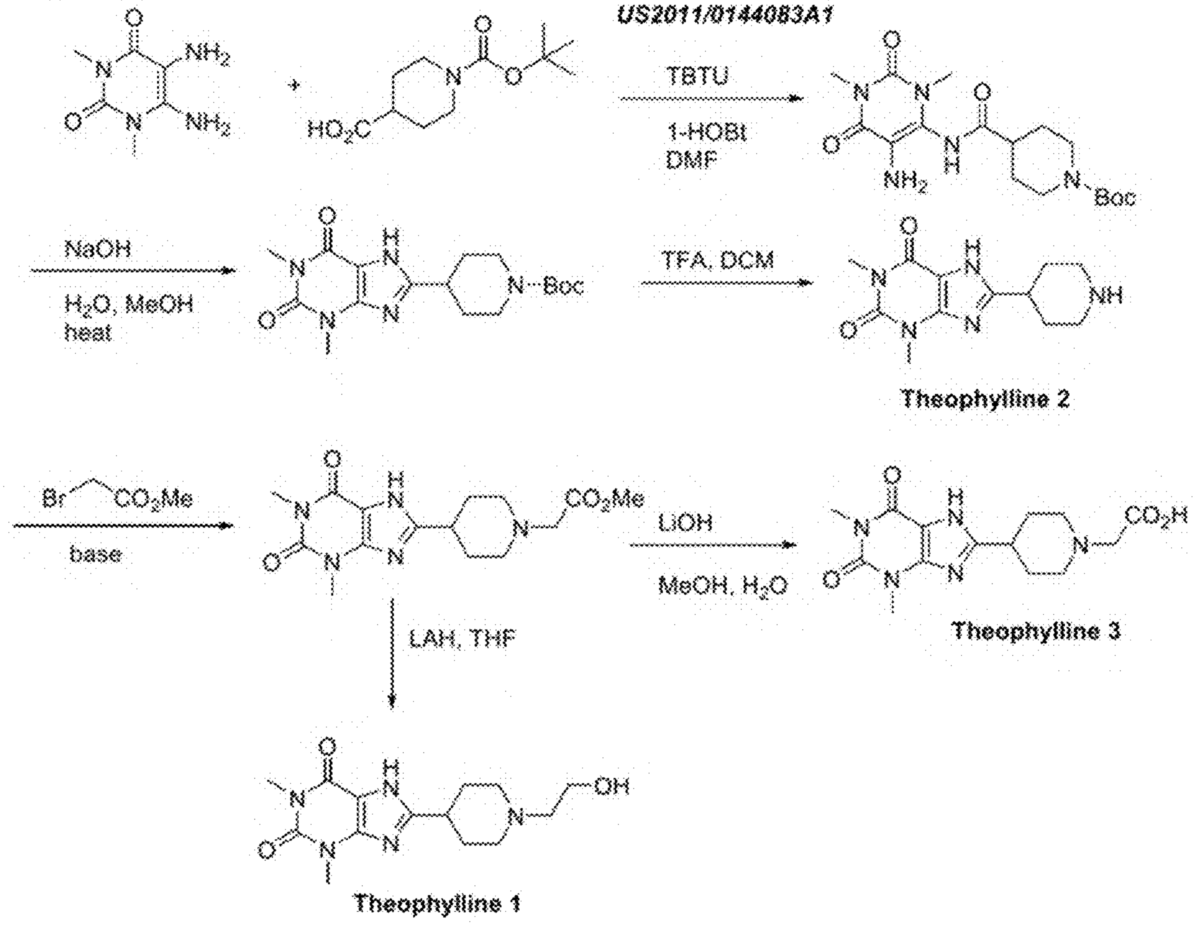
FIG. 18 shows reaction schemes for accessing several theophylline small molecule ligands that include attachment points for the tethering group.
Figure 19:
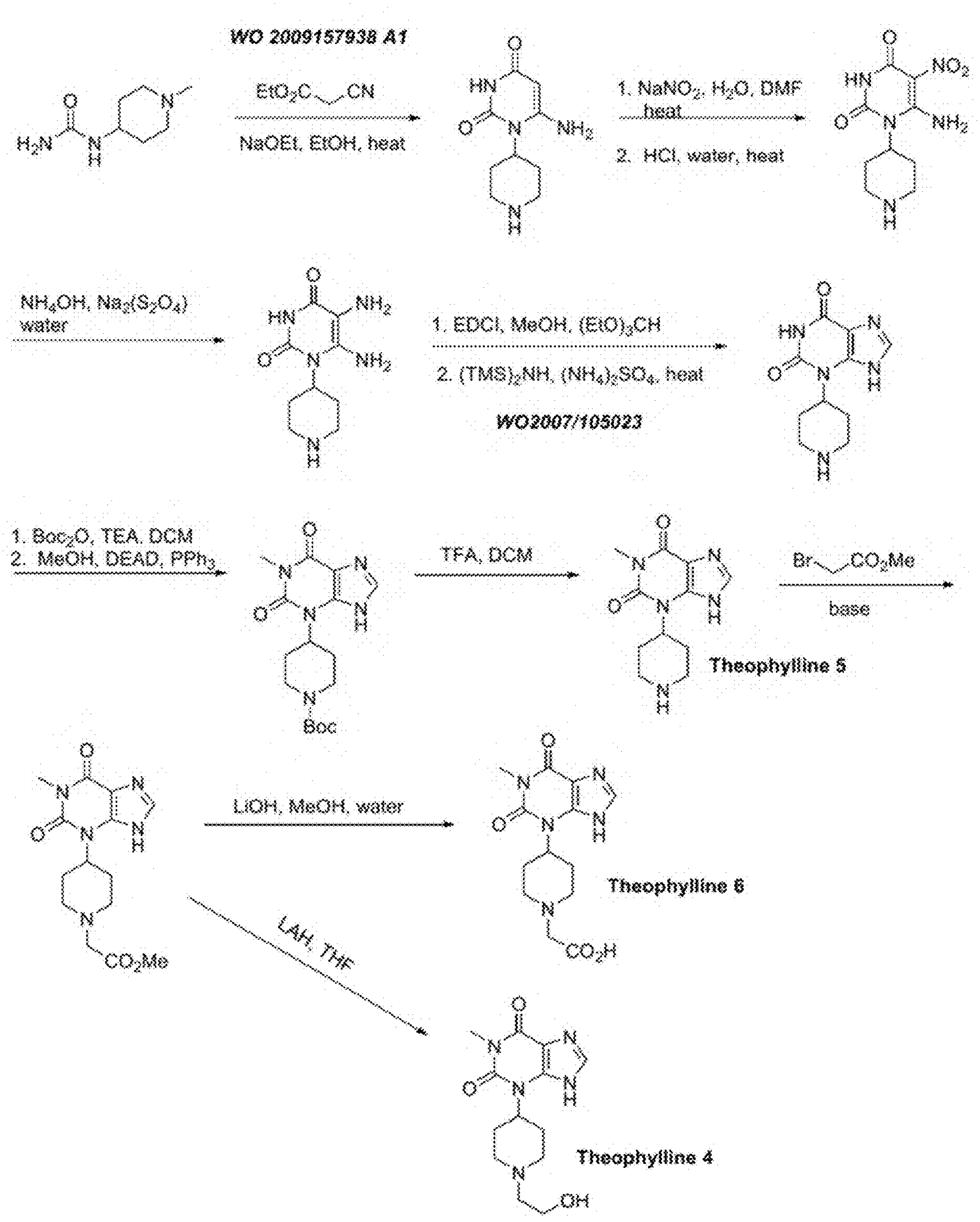
FIG. 19 shows reaction schemes for accessing several theophylline small molecule ligands that include attachment points for the tethering group.
Figure 20:
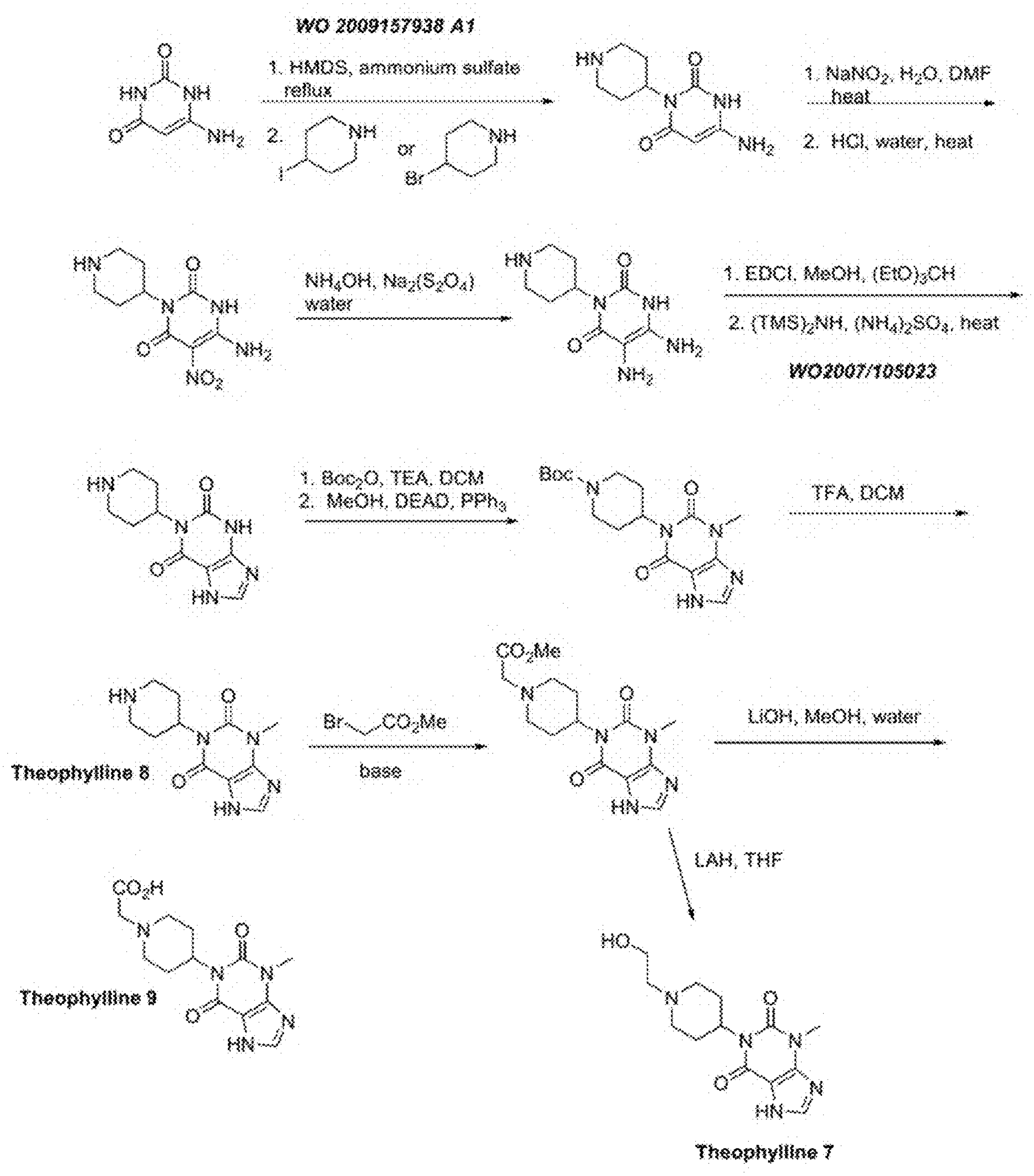
FIG. 20 shows reaction schemes for accessing several theophylline small molecule ligands that include attachment points for the tethering group.
Figure 21:
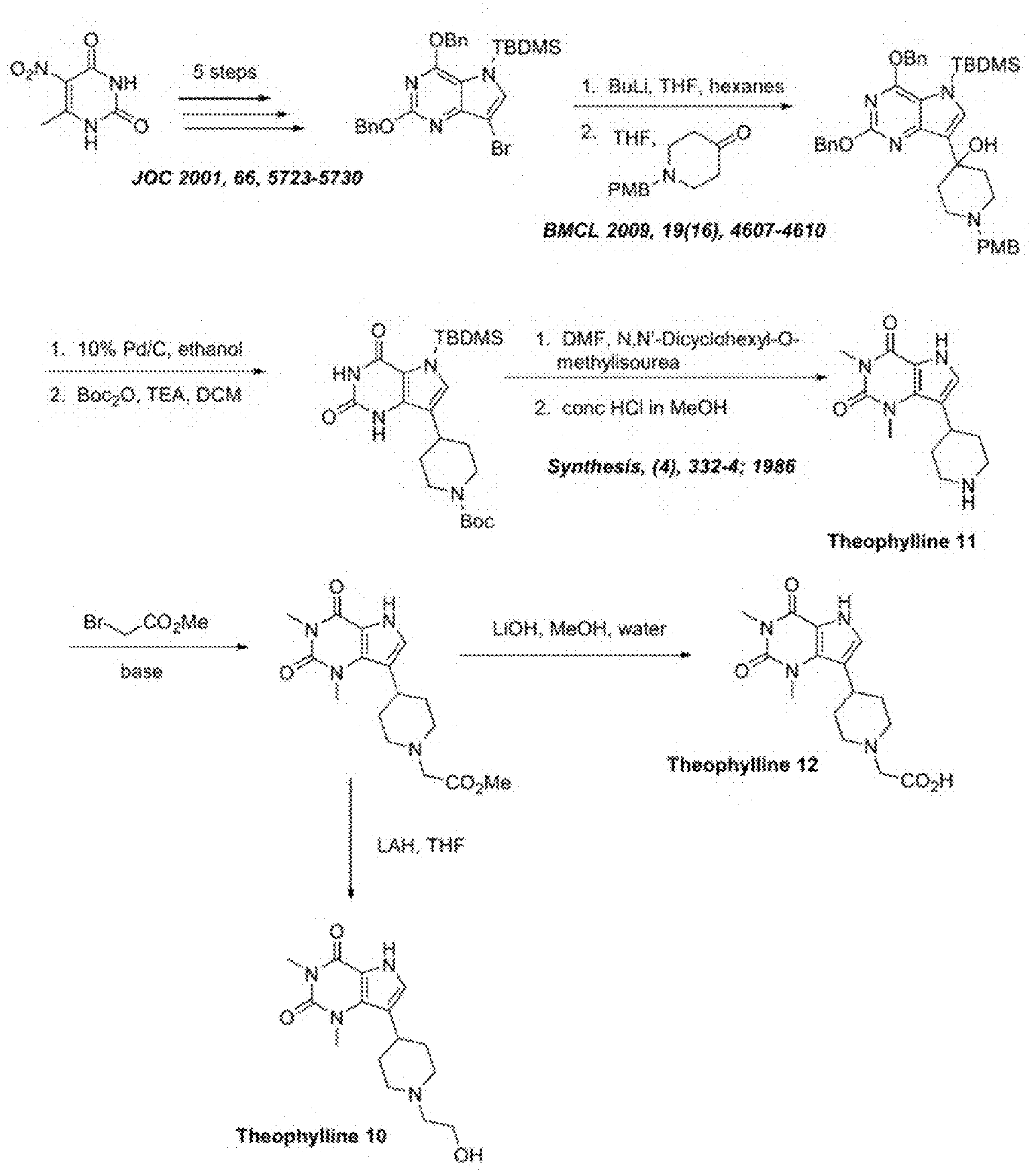
FIG. 21 shows reaction schemes for accessing several theophylline small molecule ligands that include attachment points for the tethering group.
Figure 23:
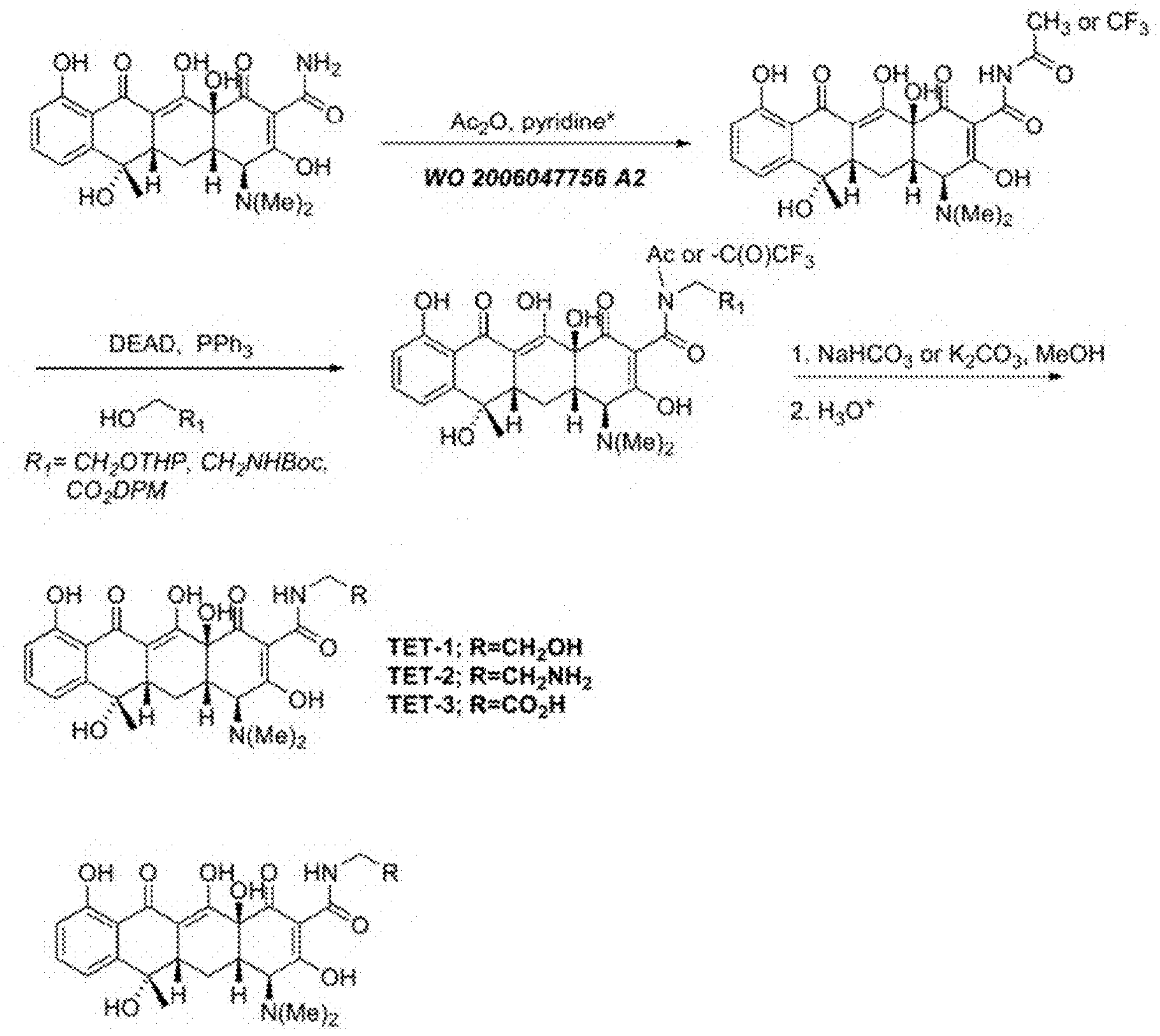
FIG. 23 shows reaction schemes for accessing several tetracycline small molecule ligands that include attachment points for the tethering group.
Figure 26:
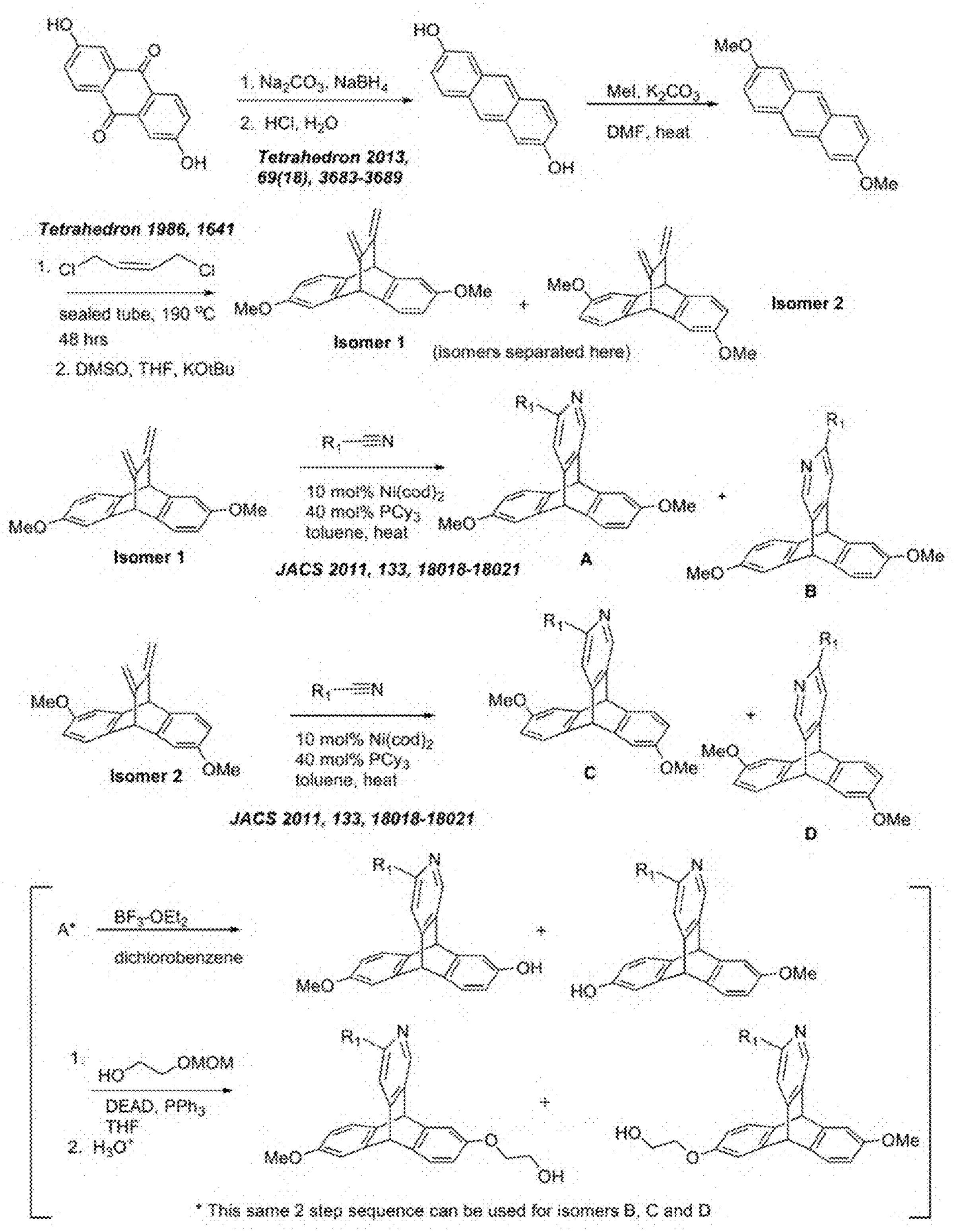
FIG. 26 shows reaction schemes for accessing several triptycene small molecule ligands that include attachment points for the tethering group.
Figure 28:
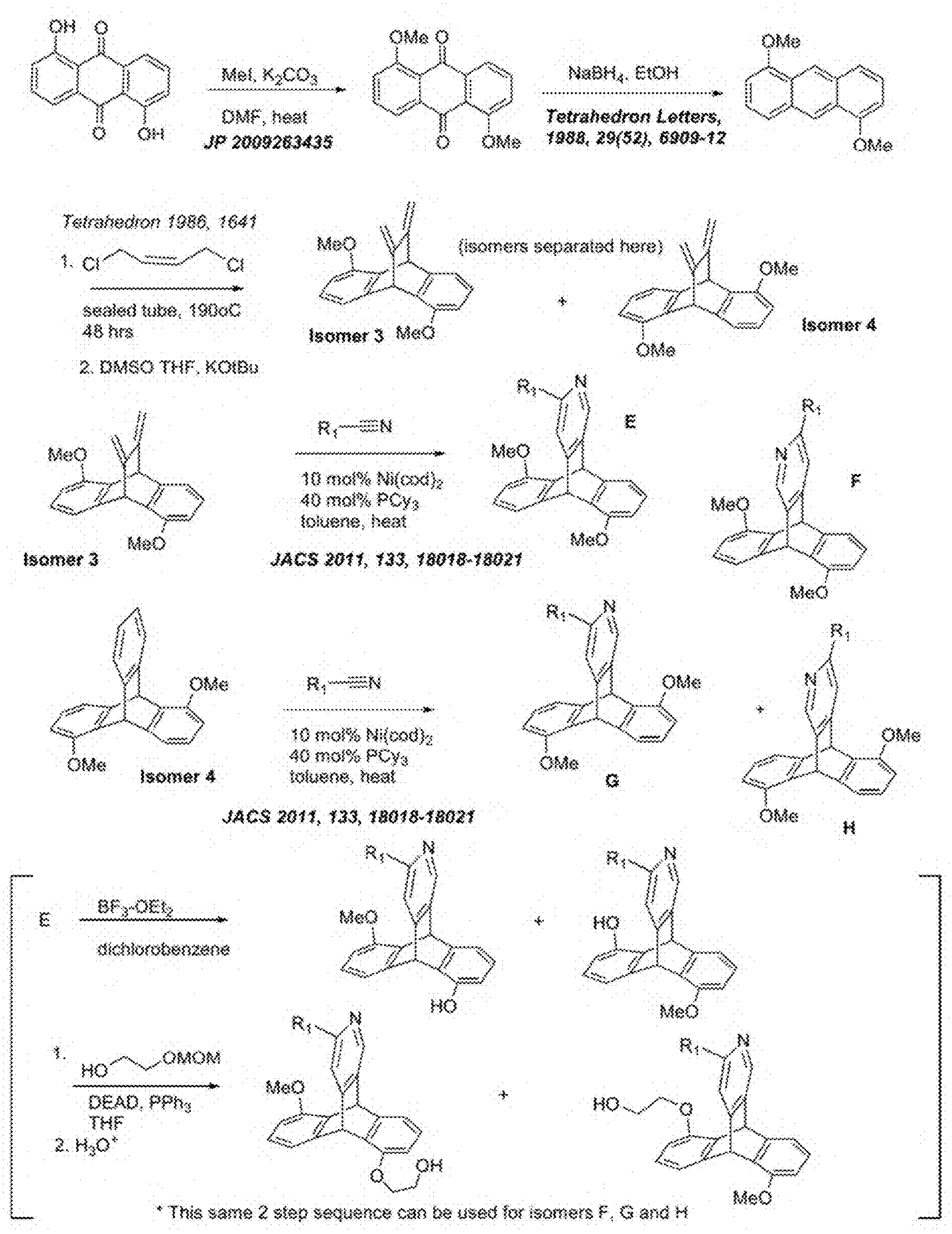
FIG. 28 shows reaction schemes for accessing several triptycene small molecule ligands that include attachment points for the tethering group.
Figure 34:
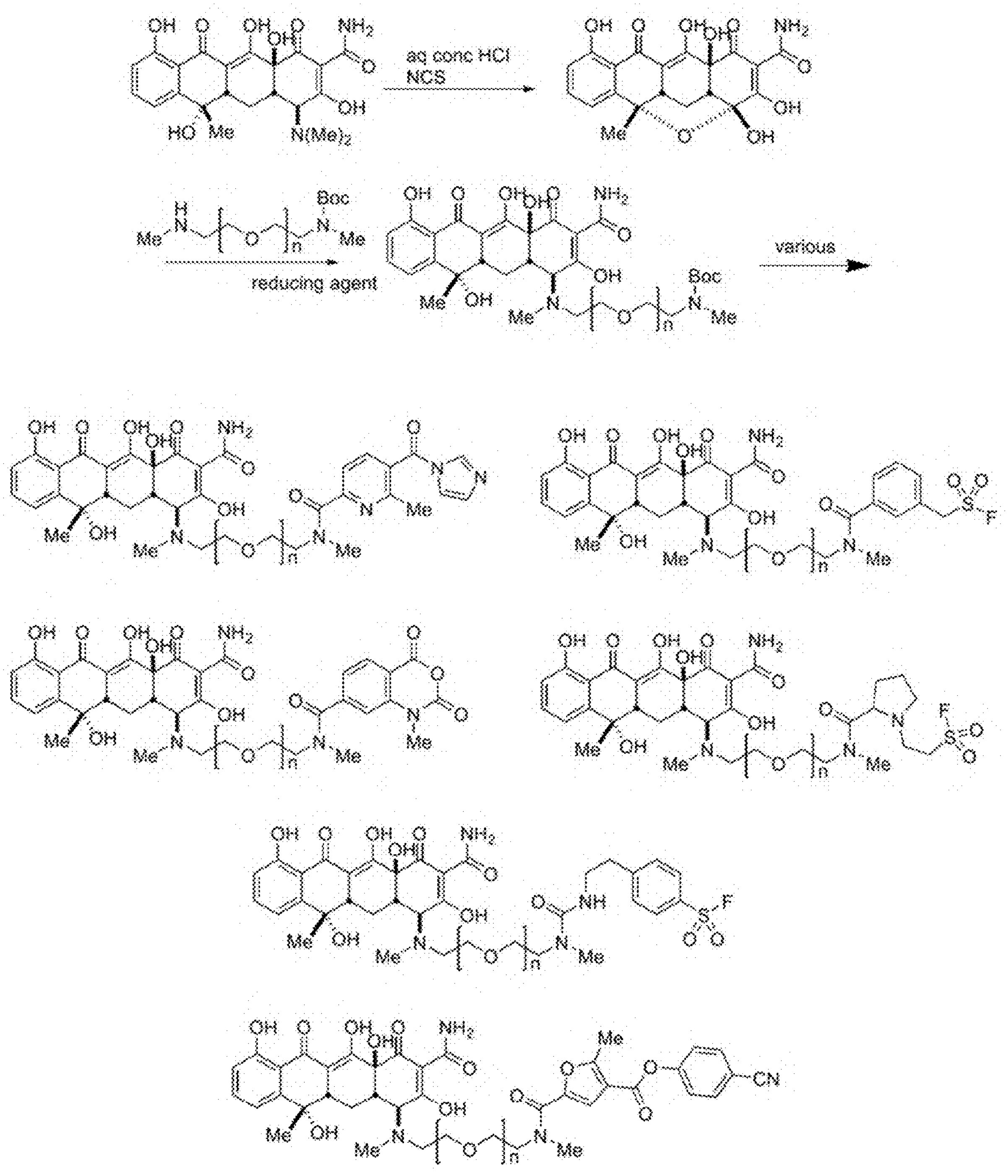
FIG. 34 shows reaction schemes for accessing several tetracycline small molecule ligands that include a tethering group and modifying moiety.
Figure 35:
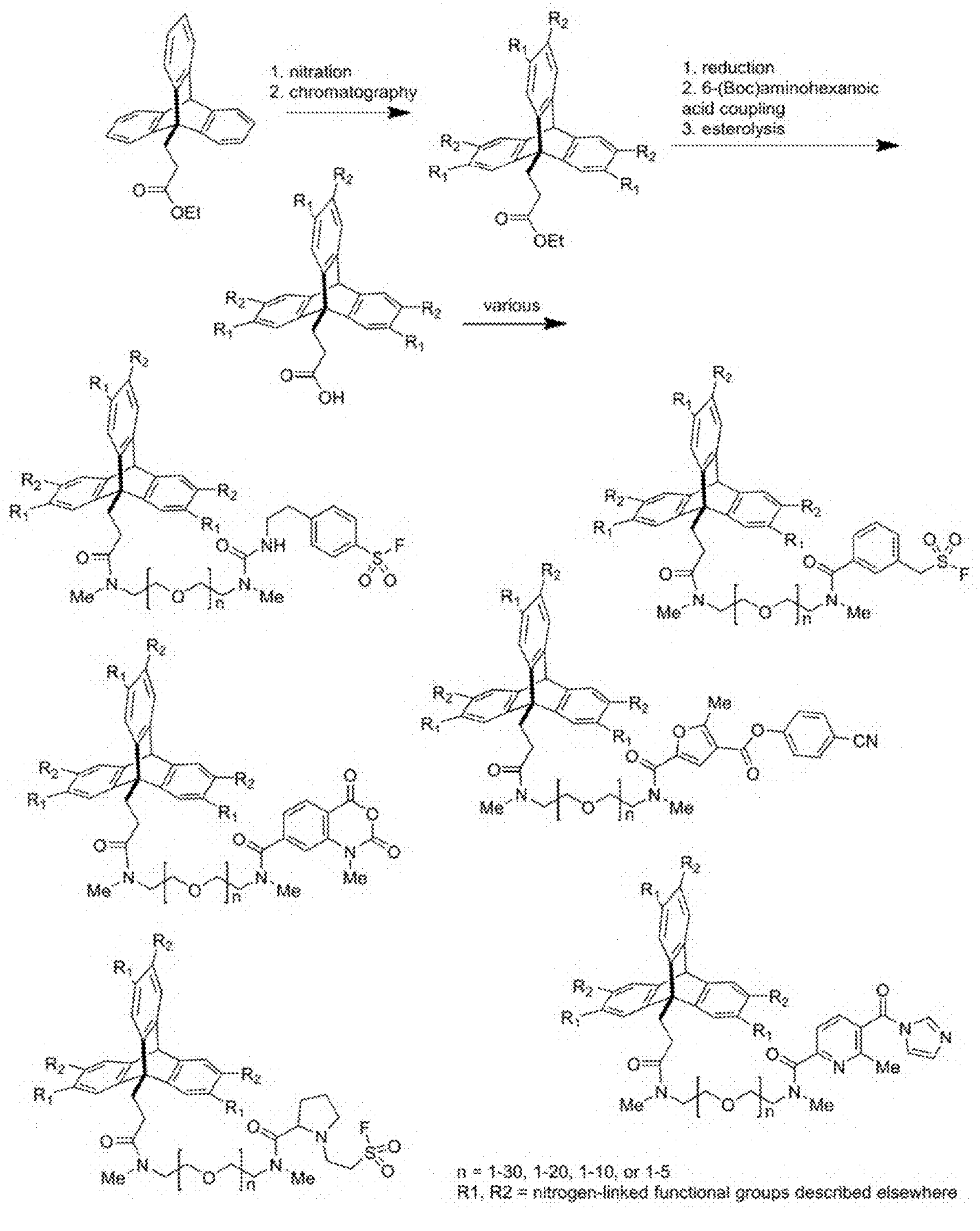
FIG. 35 shows reaction schemes for accessing several triptycene small molecule ligands that include a tethering group and modifying moiety.
Figure 36:
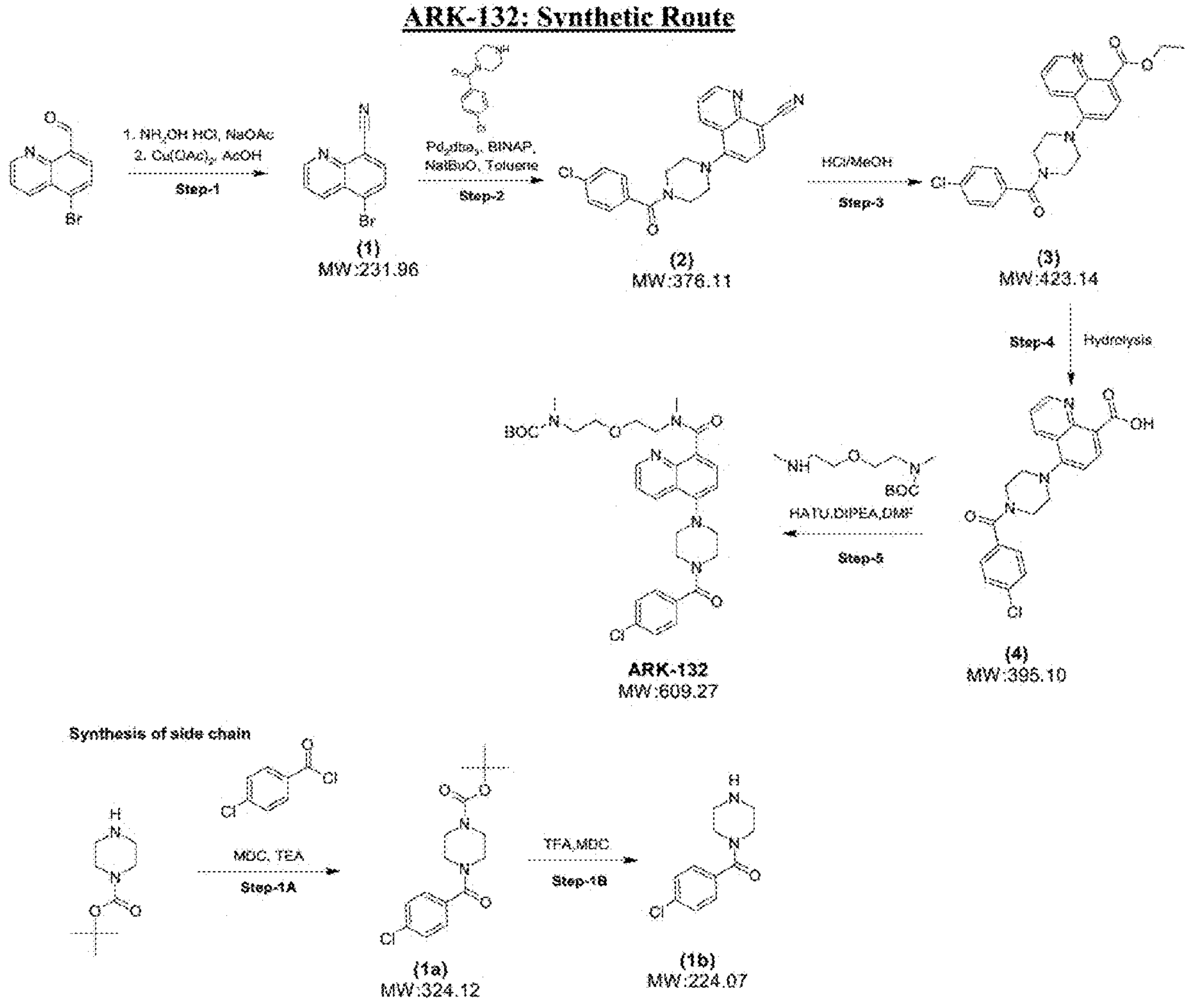
FIG. 36 shows a synthetic route for compound ARK-132.
Figure 37:
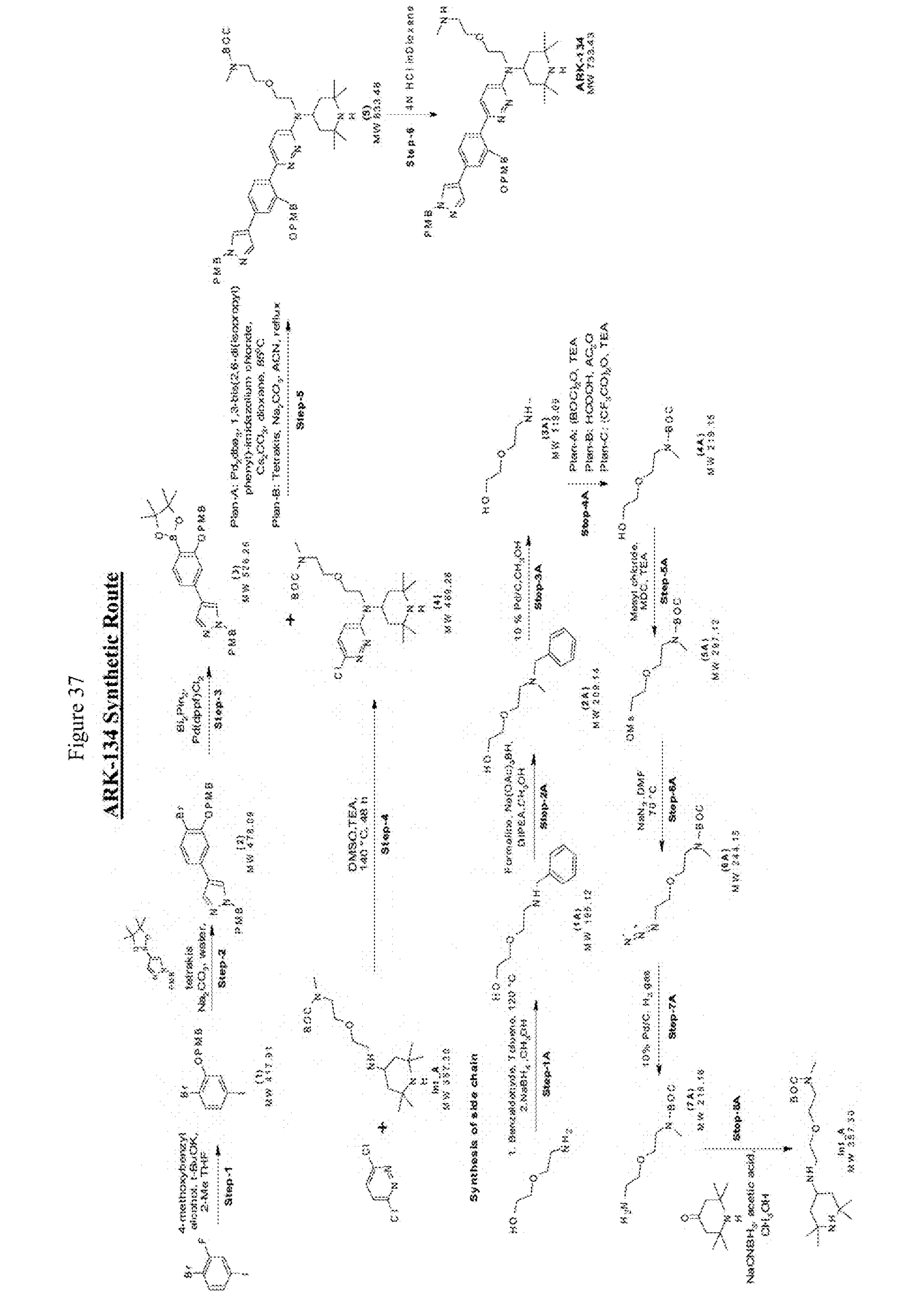
FIG. 37 shows a synthetic route for compound ARK-134.
Figure 38:
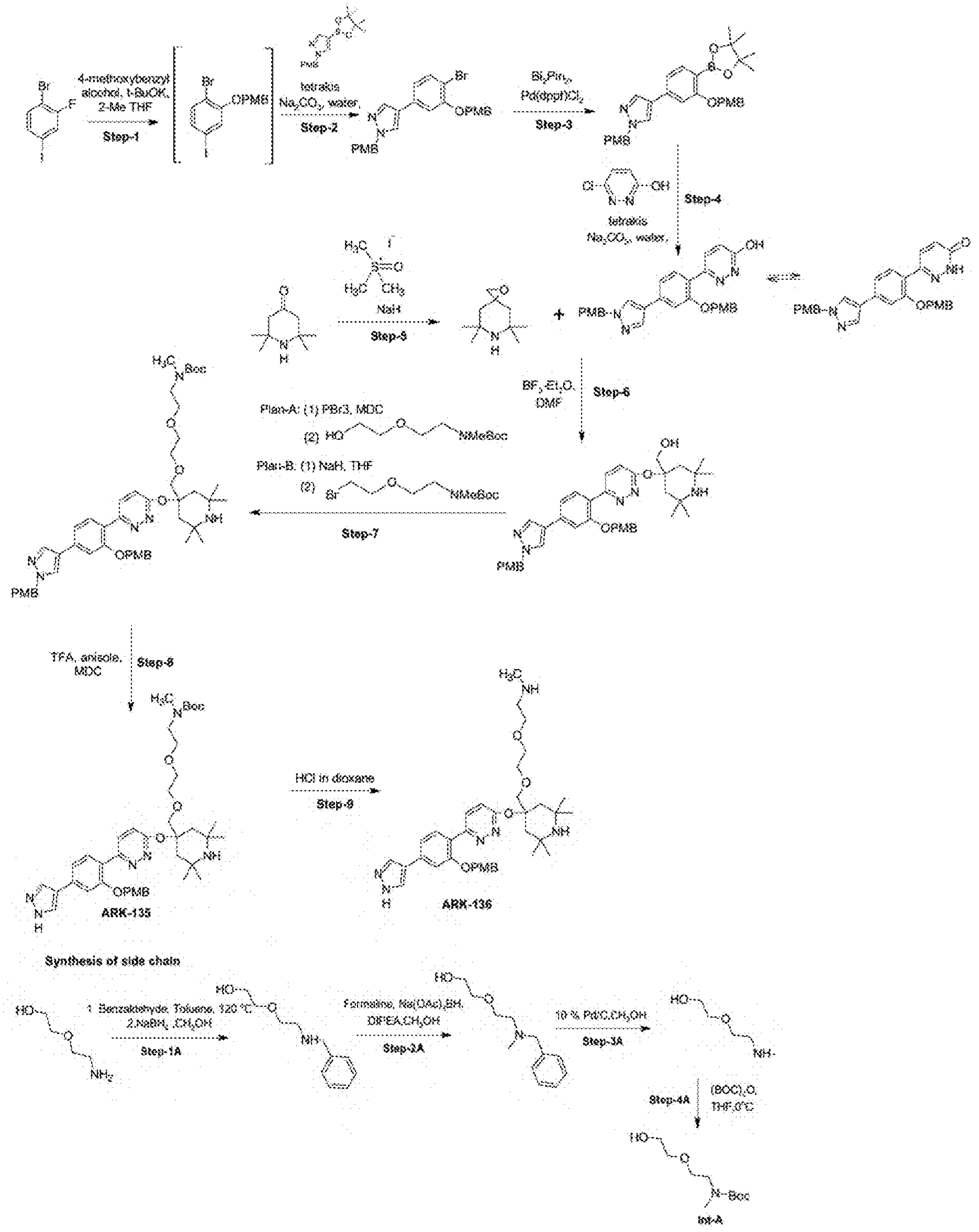
FIG. 38 shows a synthetic route for compounds ARK-135 and ARK-136.
Figure 39:
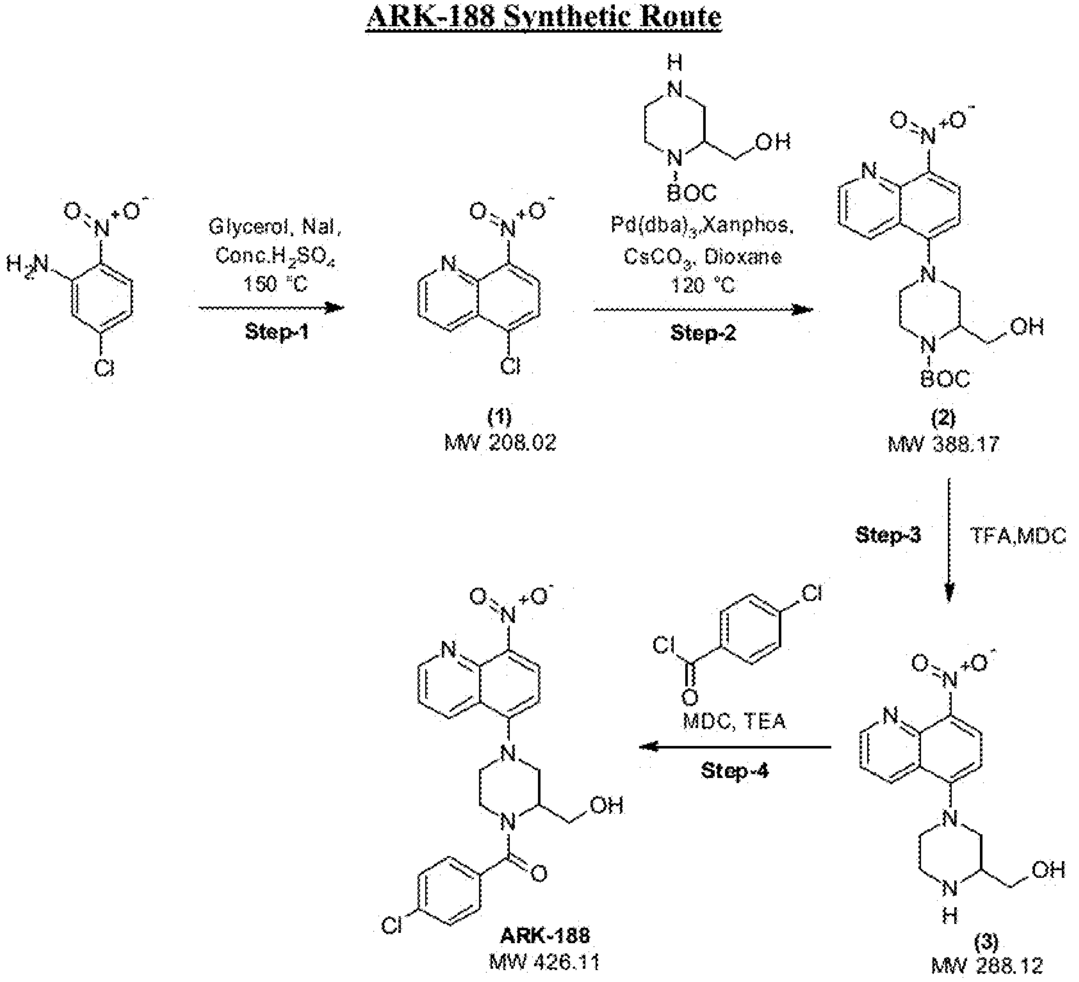
FIG. 39 shows a synthetic route for compound ARK-188.
Figure 40:
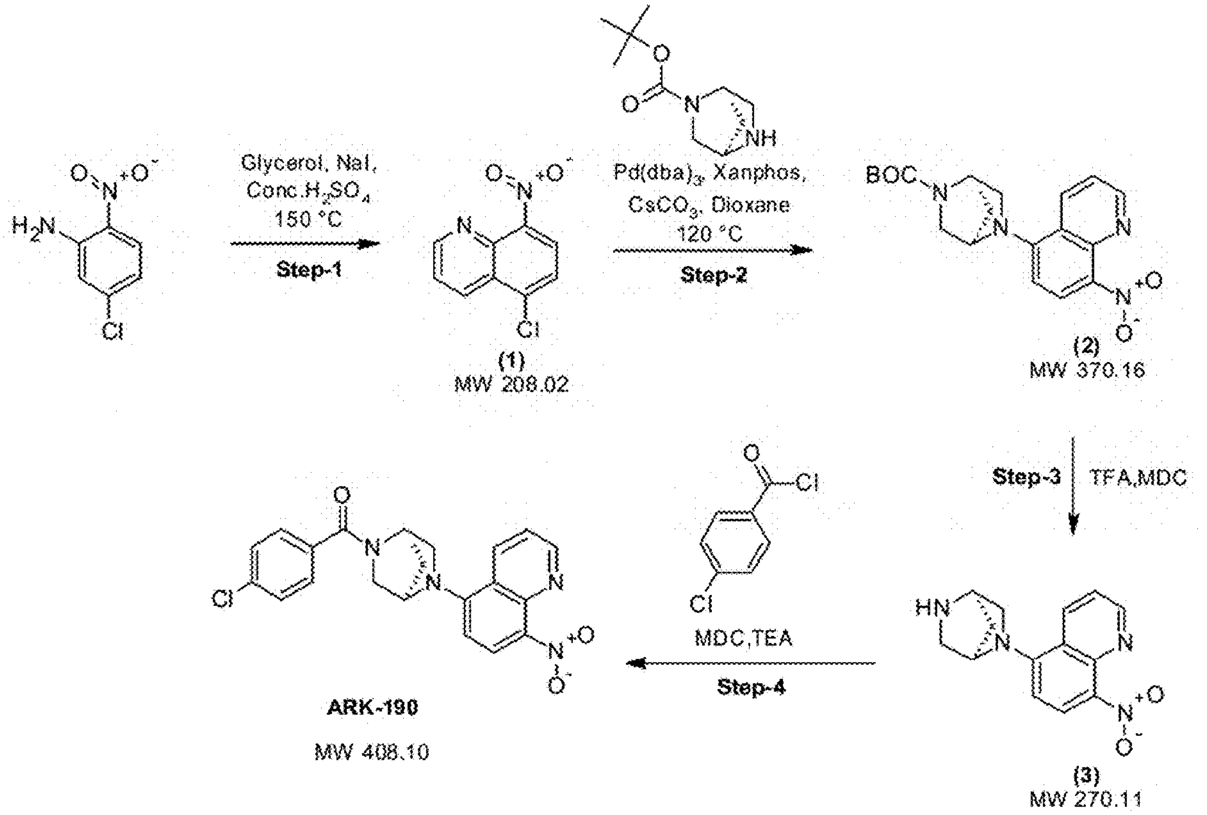
FIG. 40 shows a synthetic route for compound ARK-190.
Figure 41:
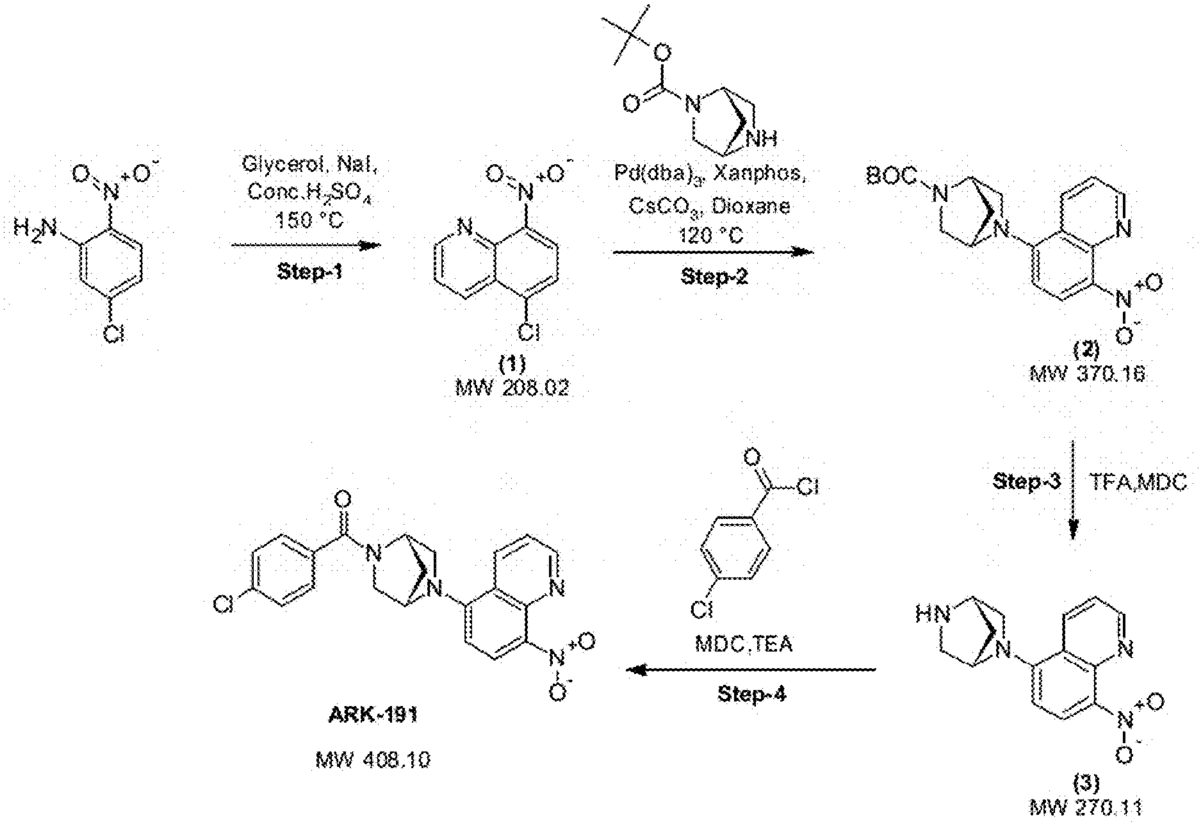
FIG. 41 shows a synthetic route for compound ARK-191.
Figure 42:
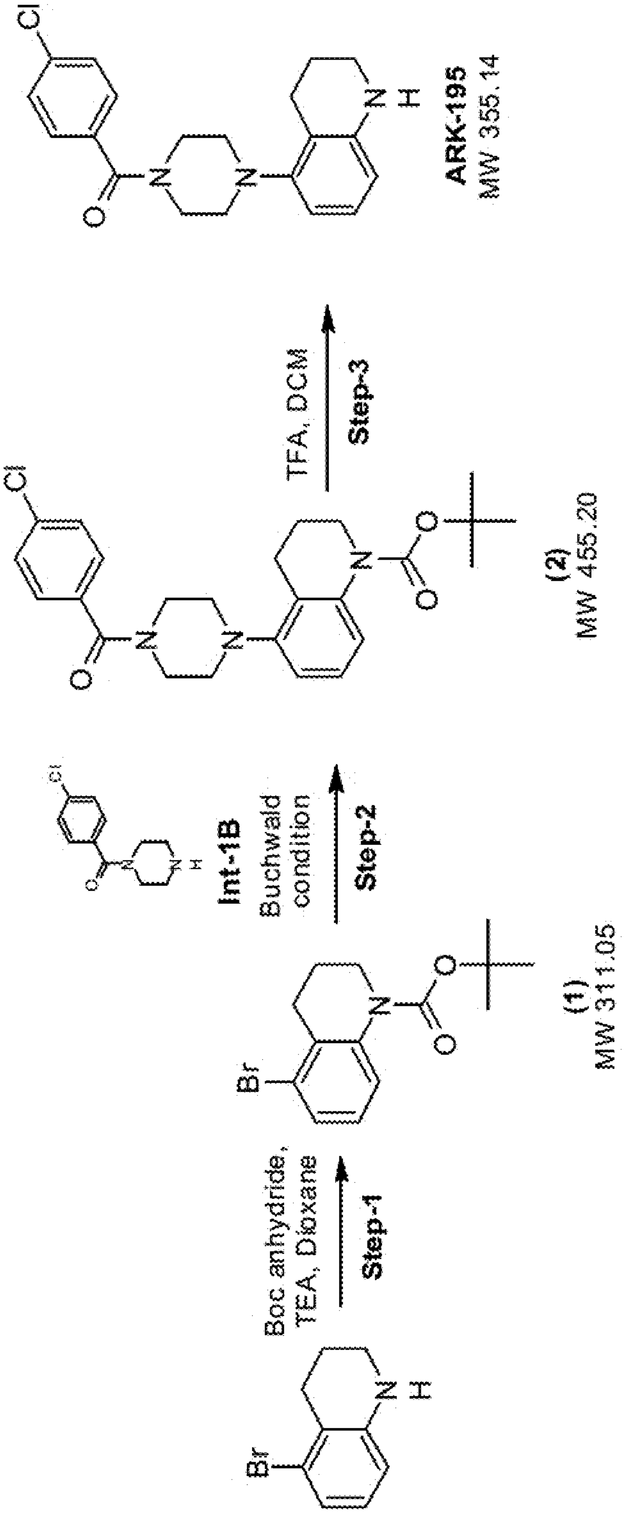
FIG. 42 shows a synthetic route for compound ARK-195.
Figure 43:
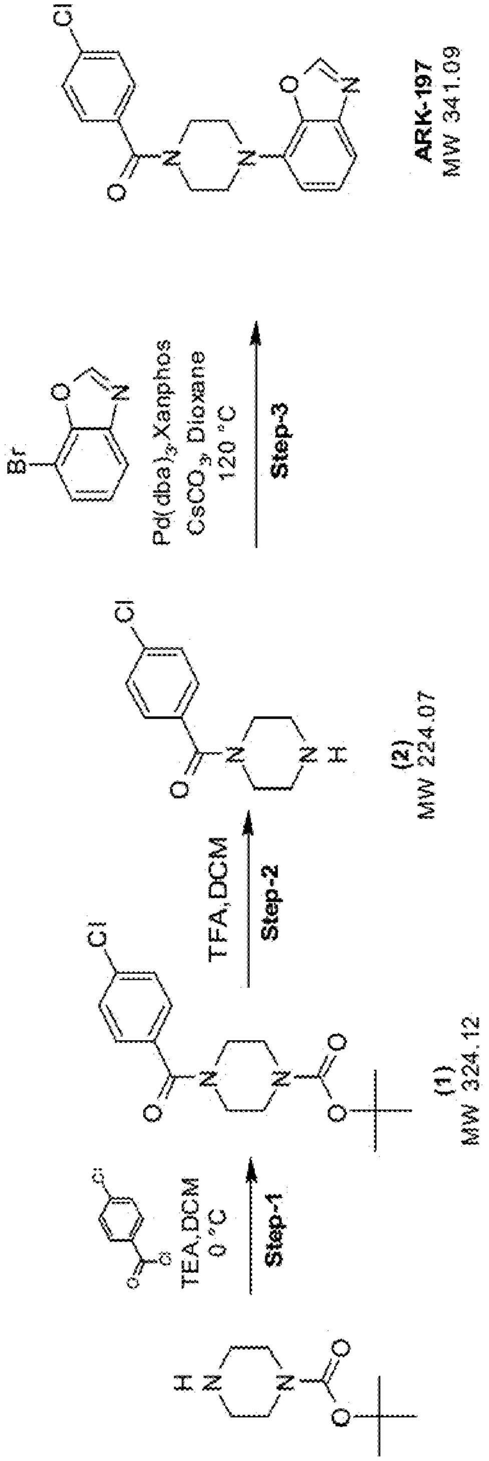
FIG. 43 shows a synthetic route for compound ARK-197.
Figure 44:
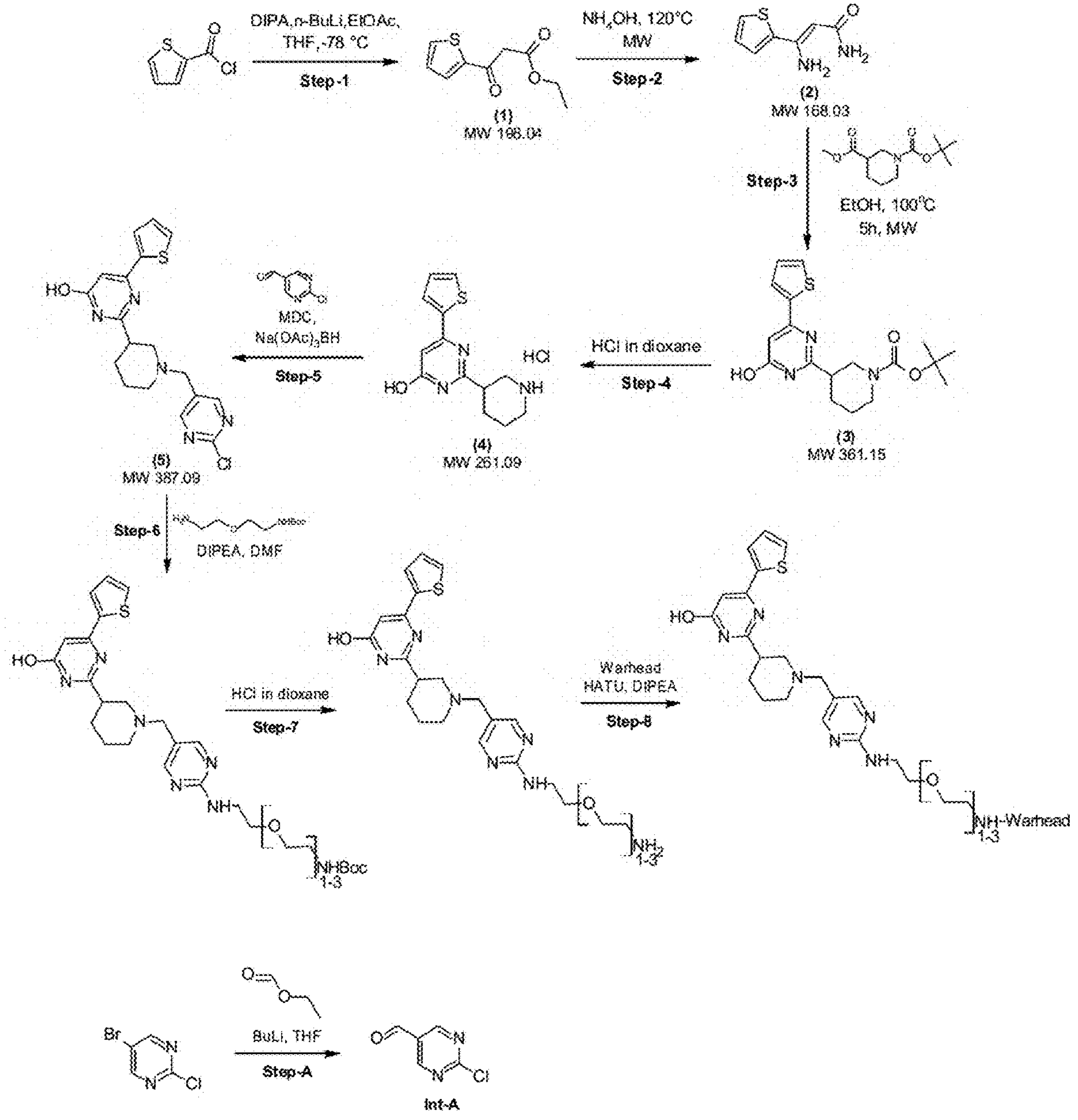
FIG. 44 shows a synthetic route for compounds based on the ribocil scaffold.
Figure 45:
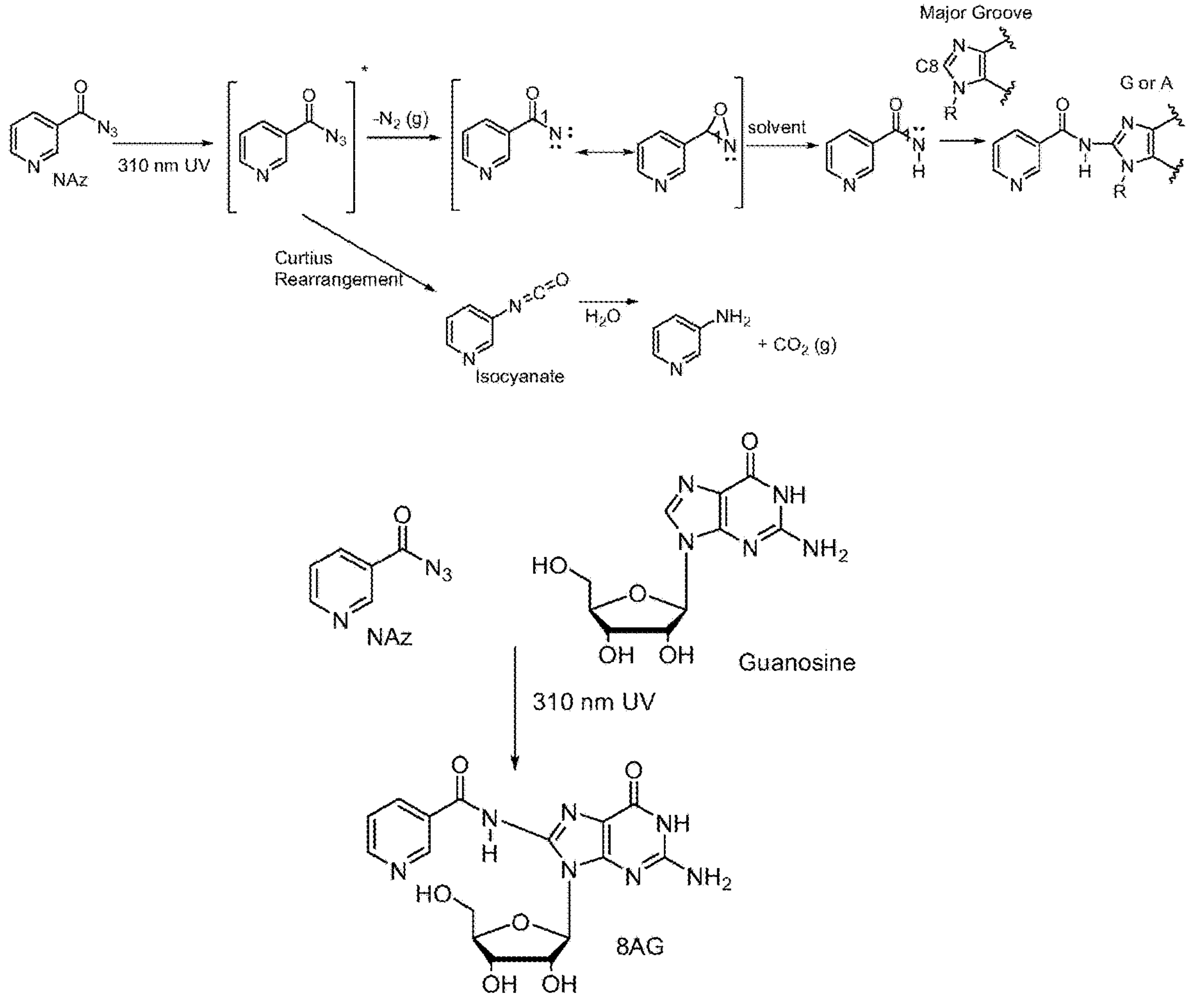
FIG. 45 shows photochemical reactions of NAz photoprobes which contain a (hetero)aroyl azide, as well as C8 modification reactions of the nitrene intermediate with guanosines.
Figure 47:
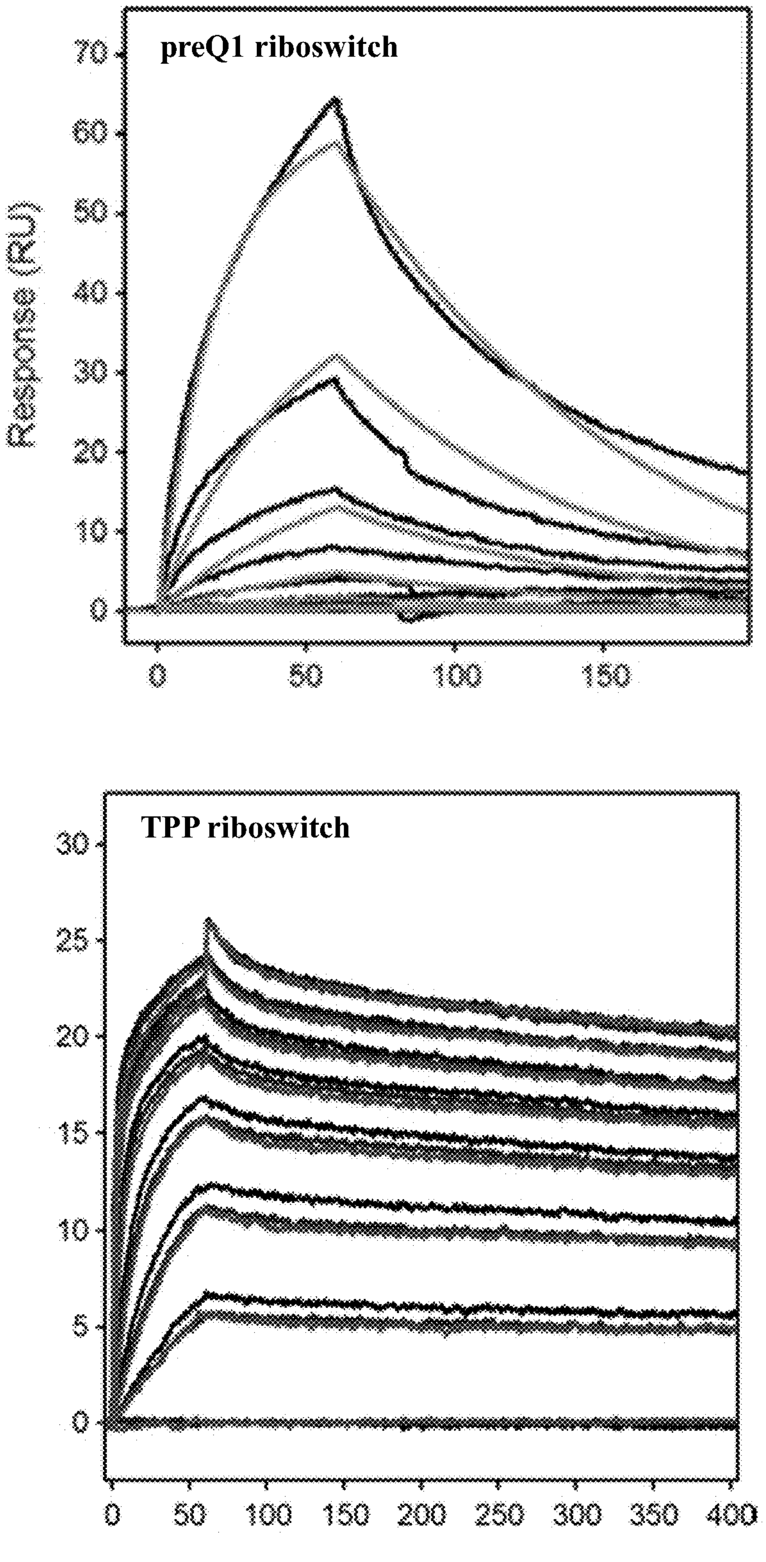
FIG. 47 shows surface plasmon resonance (SPR) results with the riboswitch/aptamer ligand pairs. While compound 1b (compound I-1, ARK-139) binds Aptamer 21, it is known not to bind a mutant sequence, Aptamer 21-E (data not shown).
Figure 48:
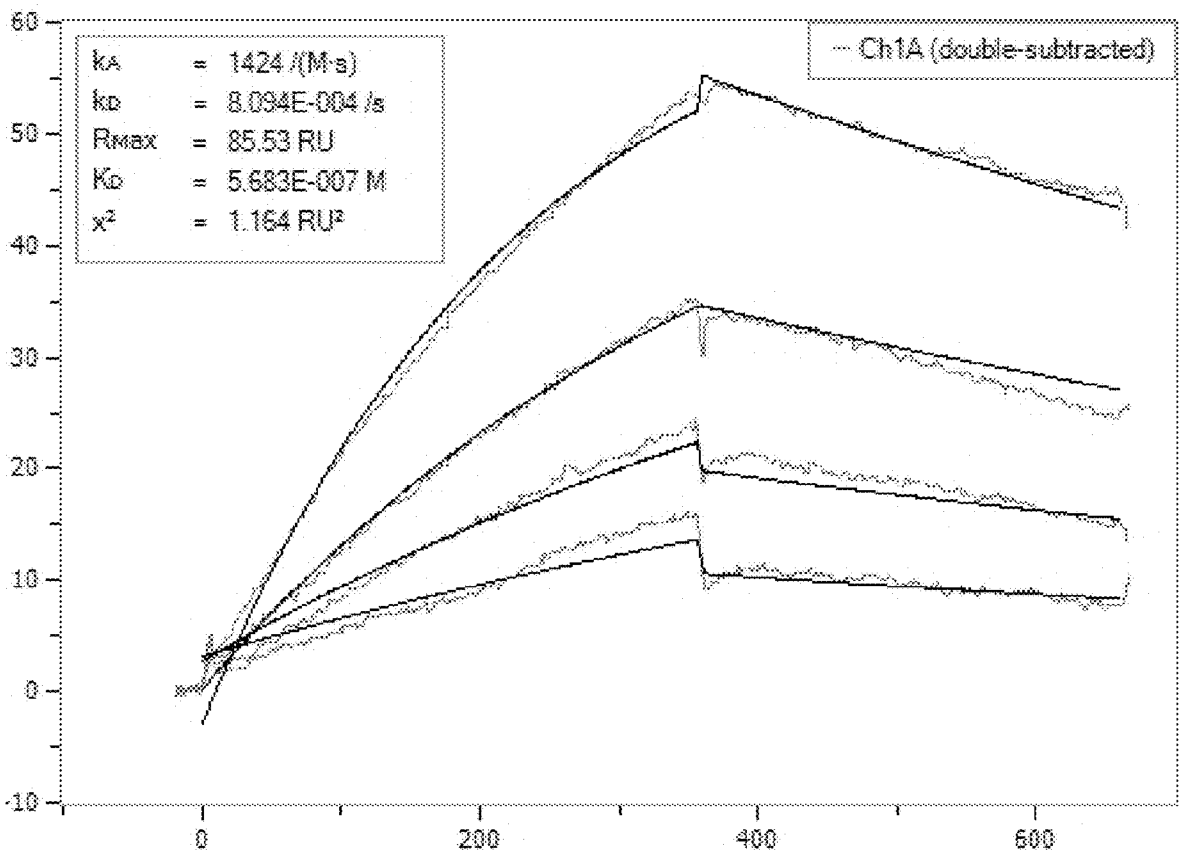
FIG. 48 shows ARK-139 binding to Aptamer 21 by SPR; calculated $K_D$=568 nM by SPR. Binding was also confirmed by SEC-MS (data not shown).
Figure 49:
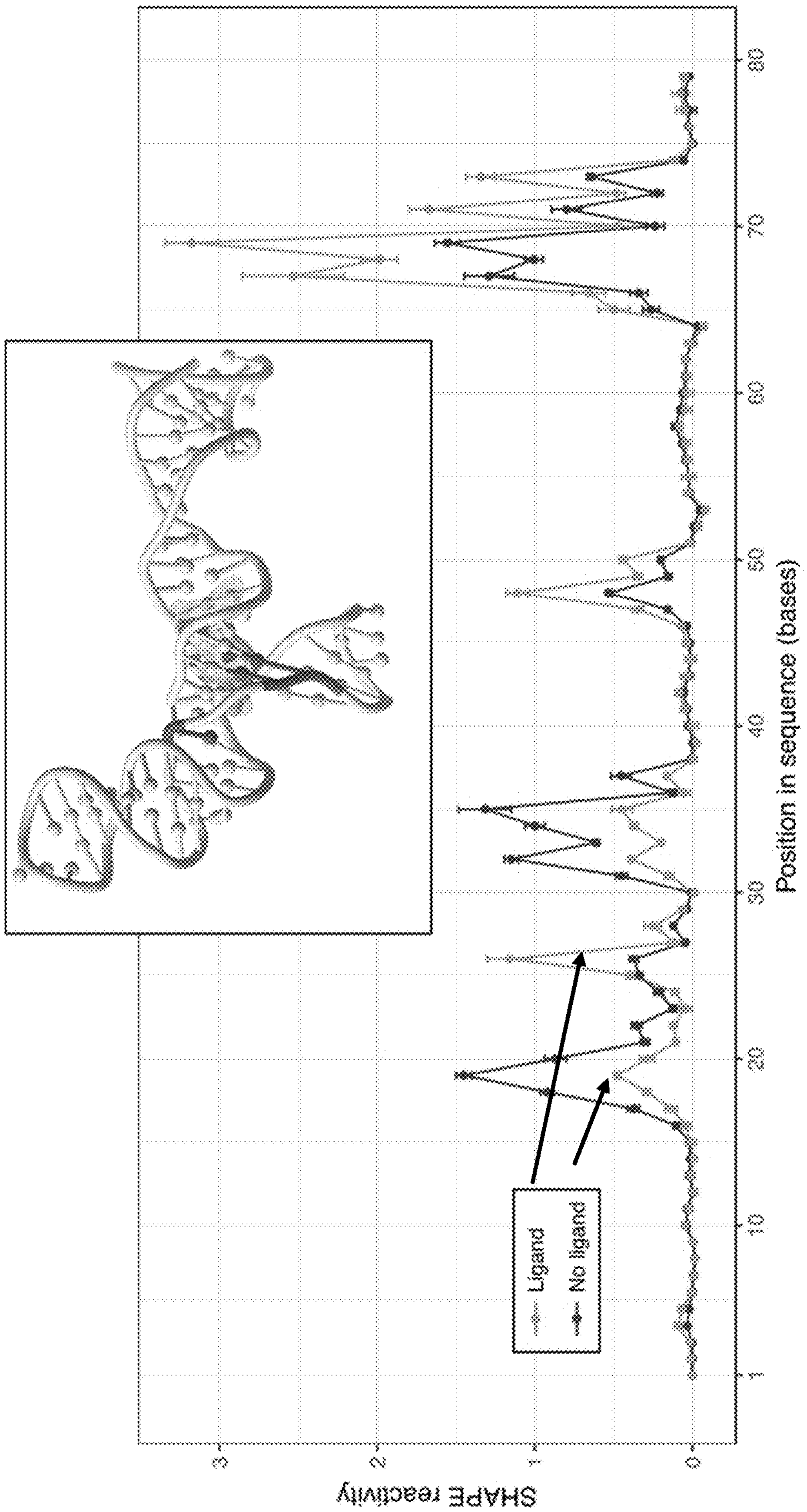
FIG. 49 shows SHAPE reactivity results from the use of SHAPE-MaP on Aptamer 21.
Figure 50:
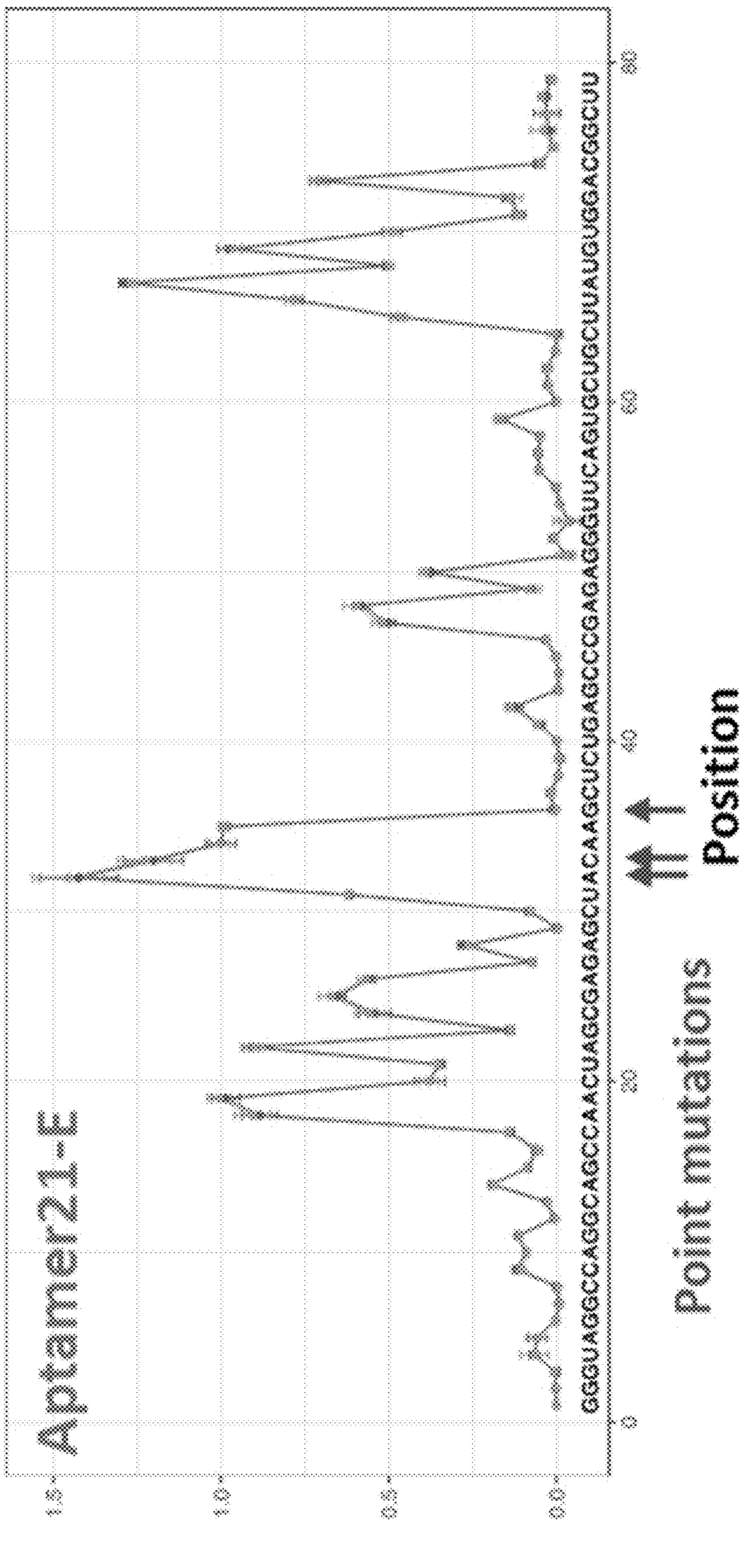

FIG. 50 shows results from the use of SHAPE-MaP on Aptamer 21-E (bottom). Higher peak values signify increased solvent exposure and reactivity of individual nucleotides of the aptamer, with and without the presence of the ligand I-1 (ARK-139). As can be seen, the presence of I-1 caused almost no alteration in the SHAPE reactivity, suggesting weak binding of I-1 to Aptamer 21-E.

FIG. 51 shows the predicted binding mode of photoprobe ARK-547 to Aptamer 21. As the model shows, the predicted binding mode accommodates the linker and photoactivatable group.

FIG. 52 shows gel results of a PEARL-seq reverse transcriptase pausing assay. The transcriptase pauses at covalently modified nucleotides, leading to accumulation of shortened sequences. ARK-547 treatment leads to production of such shortened sequences of particular lengths, indicating that certain nucleotides are more likely to be covalently modified than others. NAI leads to modification at more accessible/reactive nucleotides, leading to less selectivity and producing numerous shortened sequences.

FIG. 53 shows reverse transcriptase (RT) pausing results with Aptamer 21 and PreQ1 RNA. The Aptamer 21 diazirine probe ARK-547 shows specific and UV-dependent cross-linking with Apt21 RNA; PreQ1 probe does not show cross-linking to Apt21 or PreQ1 RNA. Conditions: 1 uM RNA, 10 uM probe, 9 uM PreQ1 probe, 20 mM TrisHCl pH 8, 100 mM KCl, 3 mM $MgCl_2$, 37° C. for 30 min, shielded from light, UV irradiation (~360 nm) for 3 indicated time at room temperature.

Figure 54:
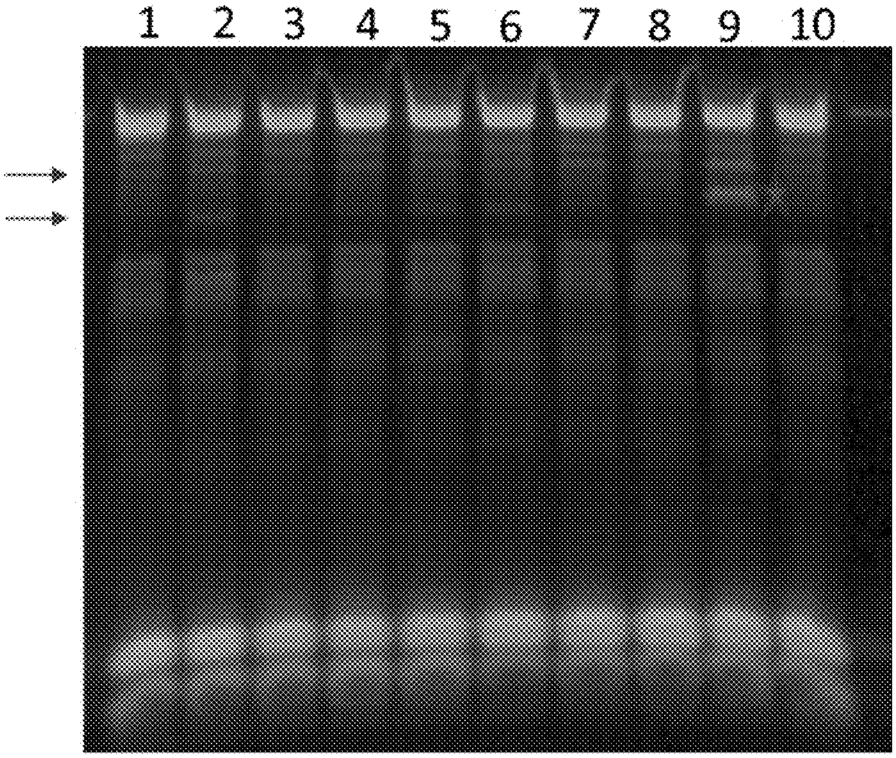

FIG. 54 shows screening results for additional compounds for cross-linking of Aptamer 21. Conditions: 1 μM refolded RNA, 10 μM compound, 20 mM TrisHCl pH 8, 100 mM KCl, 3 mM $MgCl_2$, 2.5% DMSO. Reactions were incubated for 30 min at 37° C. shielded from light, followed by 5 min irradiation with 360 nm light at room temperature in Fisher photo-crosslinker.

Figure 55:
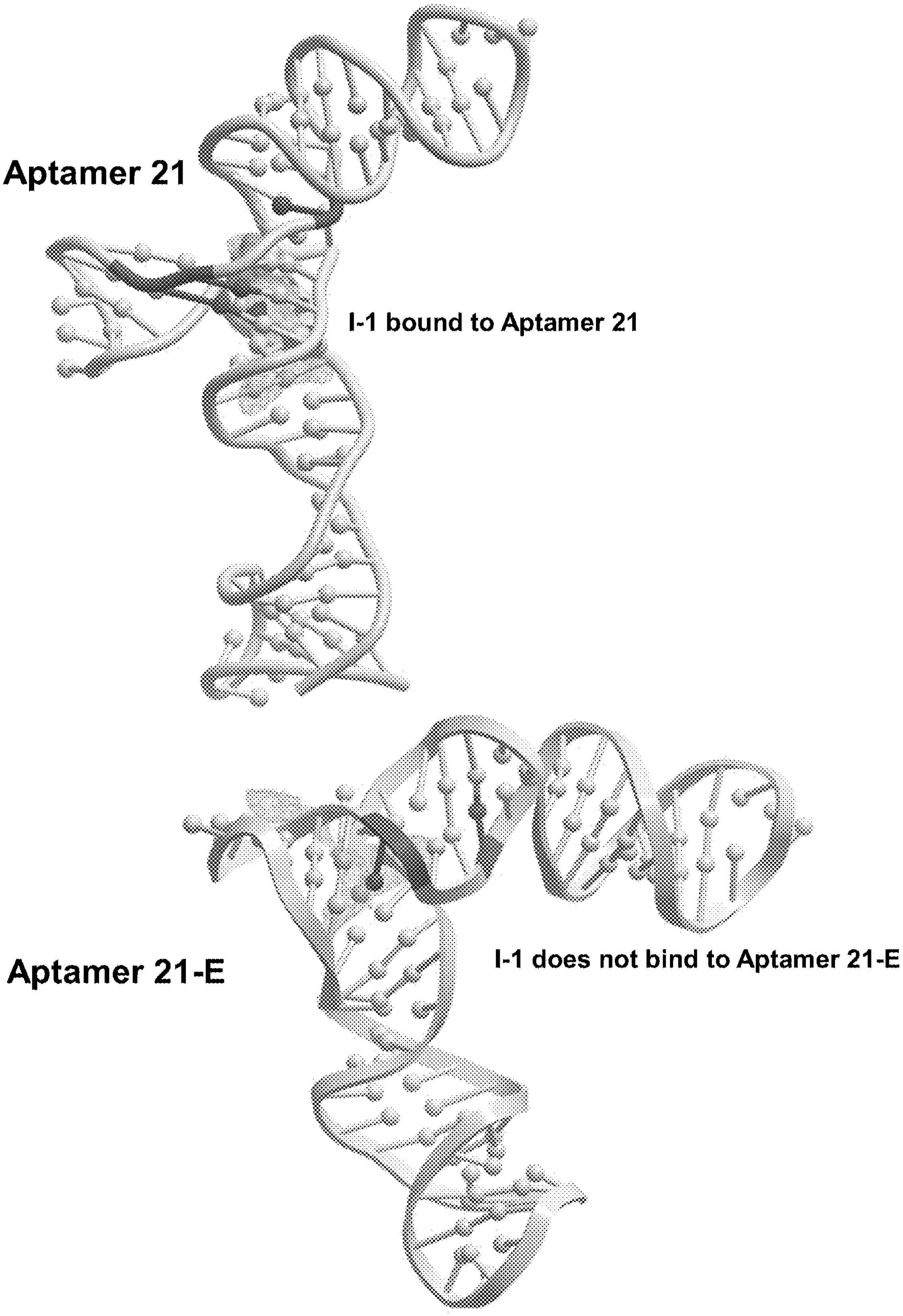

FIG. 55 shows models of Aptamer 21 vs. Aptamer 21-E binding to I-1.

Figure 56:
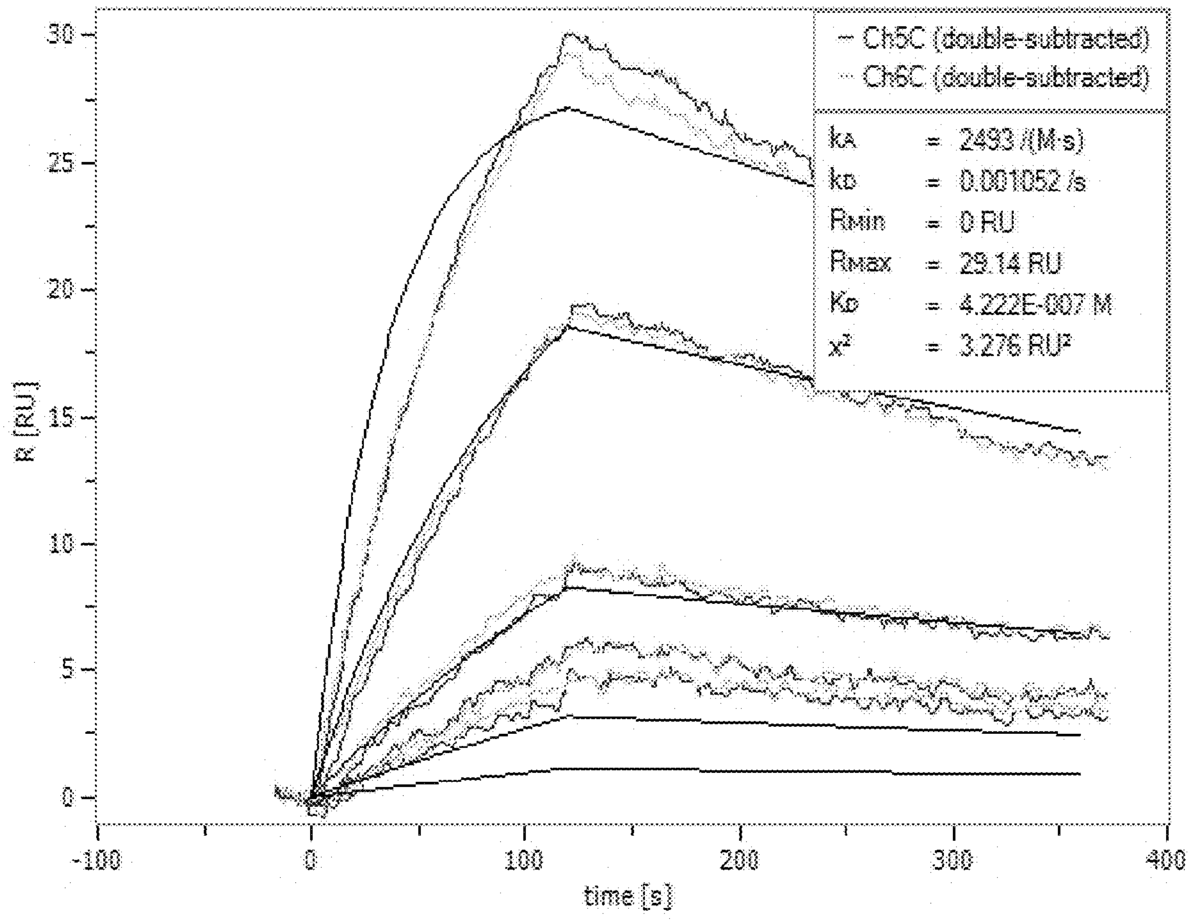

FIG. 56 shows SPR data for I-1 (ARK-139) binding to Aptamer 21. ARK-139 did not bind to Aptamer 21-E (data not shown). The calculated $K_d$ was 420 nM.

Figure 57:
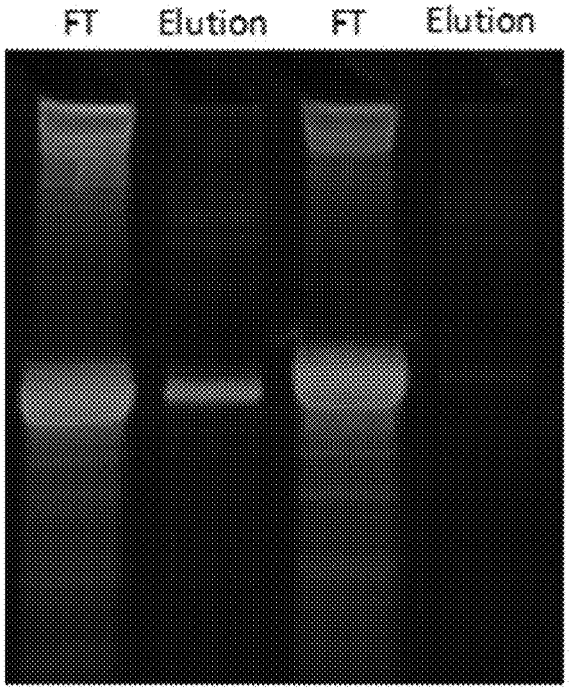

FIG. 57 shows a gel assay in which Aptamer 21 and Aptamer 21-E were incubated with a biotin-photoaffinity bifunctional probe ARK-670, cross-linked, and then captured on streptavidin beads. Only the Aptamer 21 RNA showed significant pull-down.

shows results of sequencing of cross-linked Aptamer 21 after treatment with ARK-547 measuring MaP signal at positions 43 and 60, and selective drop-off at position 60. Combining with streptavidin capture will identify binding sites from a mixture of RNA.

Figure 58A:
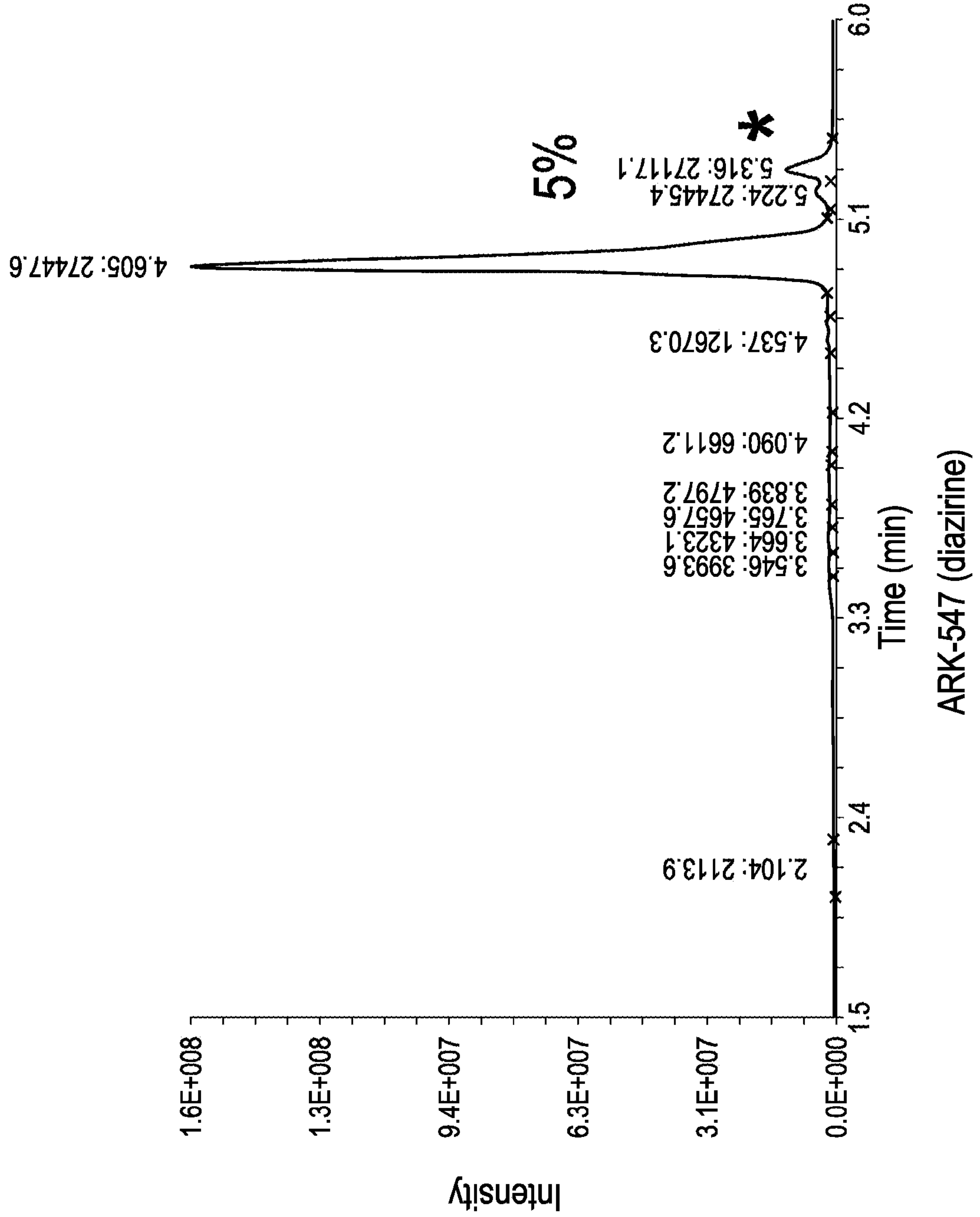
Figure 58B:
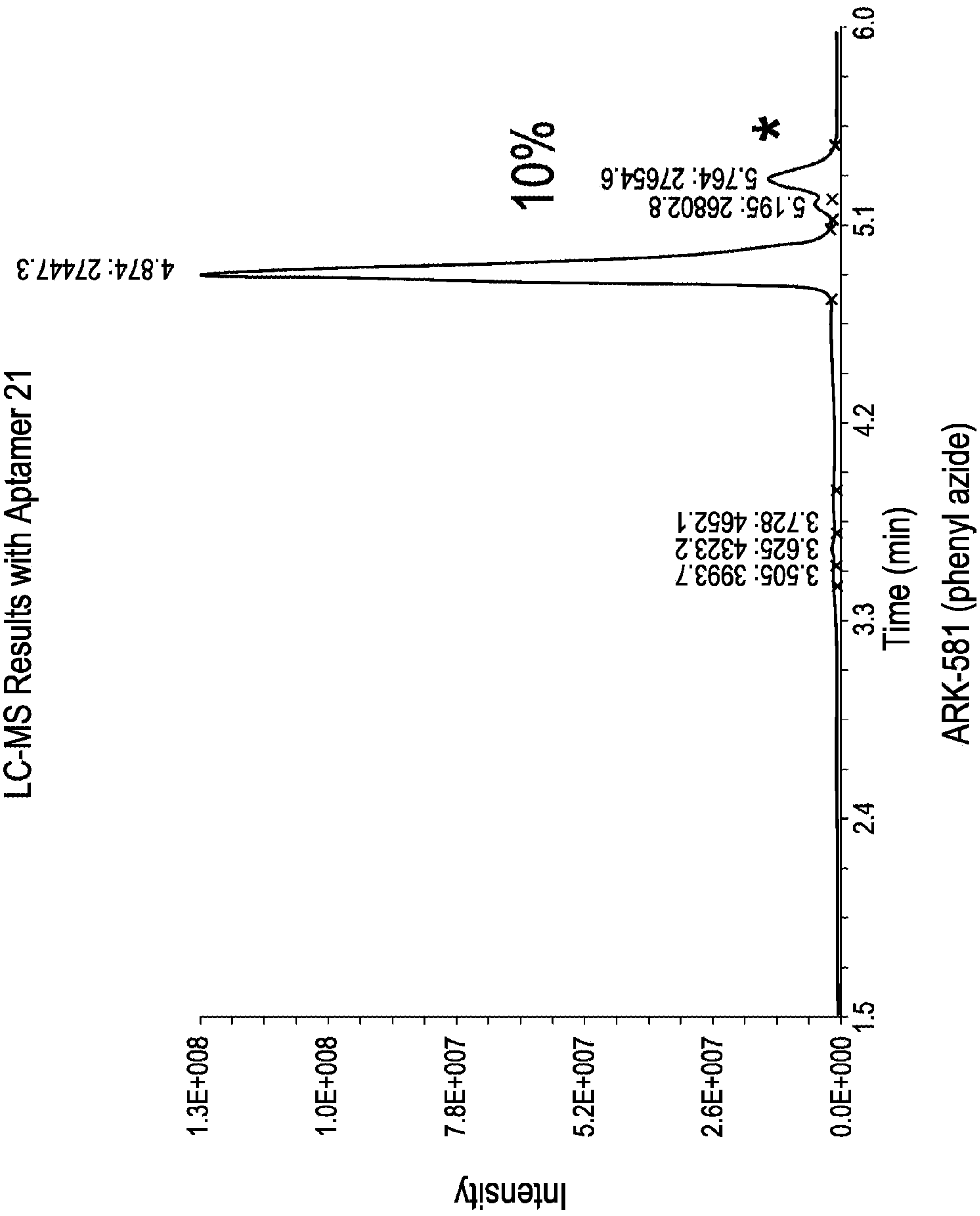

FIGS. 58A and 58B show LC-MS results with Aptamer 21. ARK-547 and ARK-581 showed 5% and 10% covalent modification of the RNA, respectively.

Figure 59:
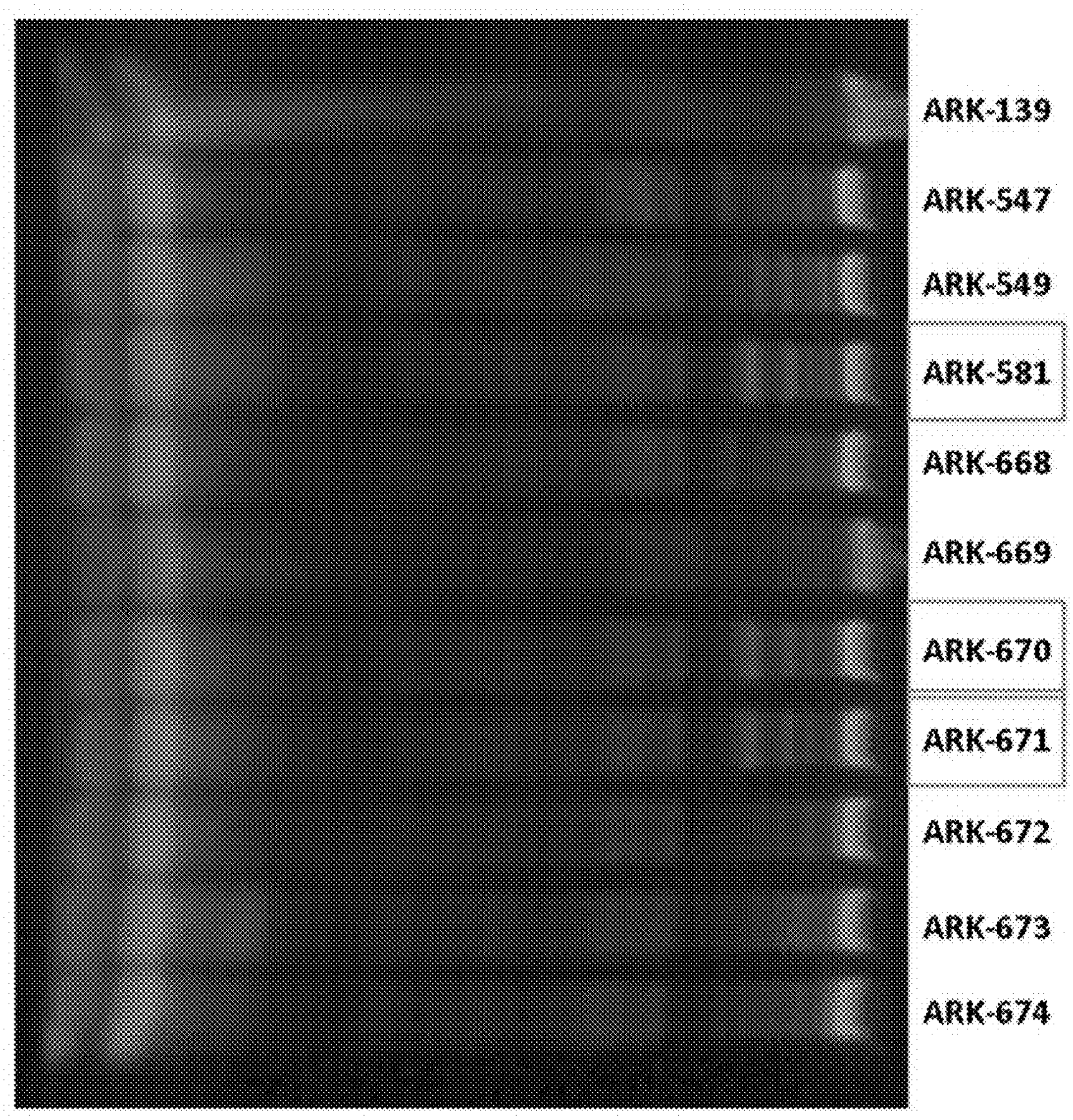

FIG. 59 shows reverse transcriptase (RT) pausing assay results using bifunctional photoactivatable compounds.

Figure 60:
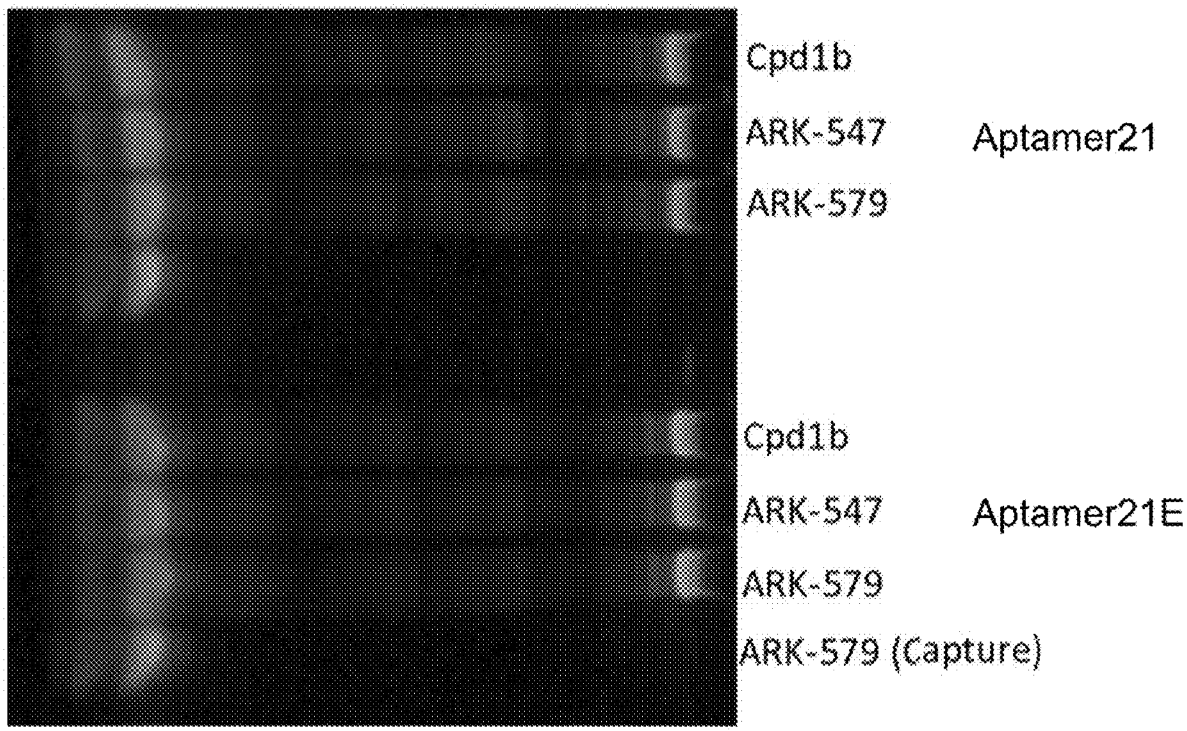

FIG. 60 shows biotin pull-down experiment results. Steps: Cross-linked biotin-diazirine probe (ARK-579) to RNA; Captured on streptavidin magnetic beads; Performed RT on beads; Base-hydrolyzed RNA to elute cDNA; Ran on gel.

Figure 61A:
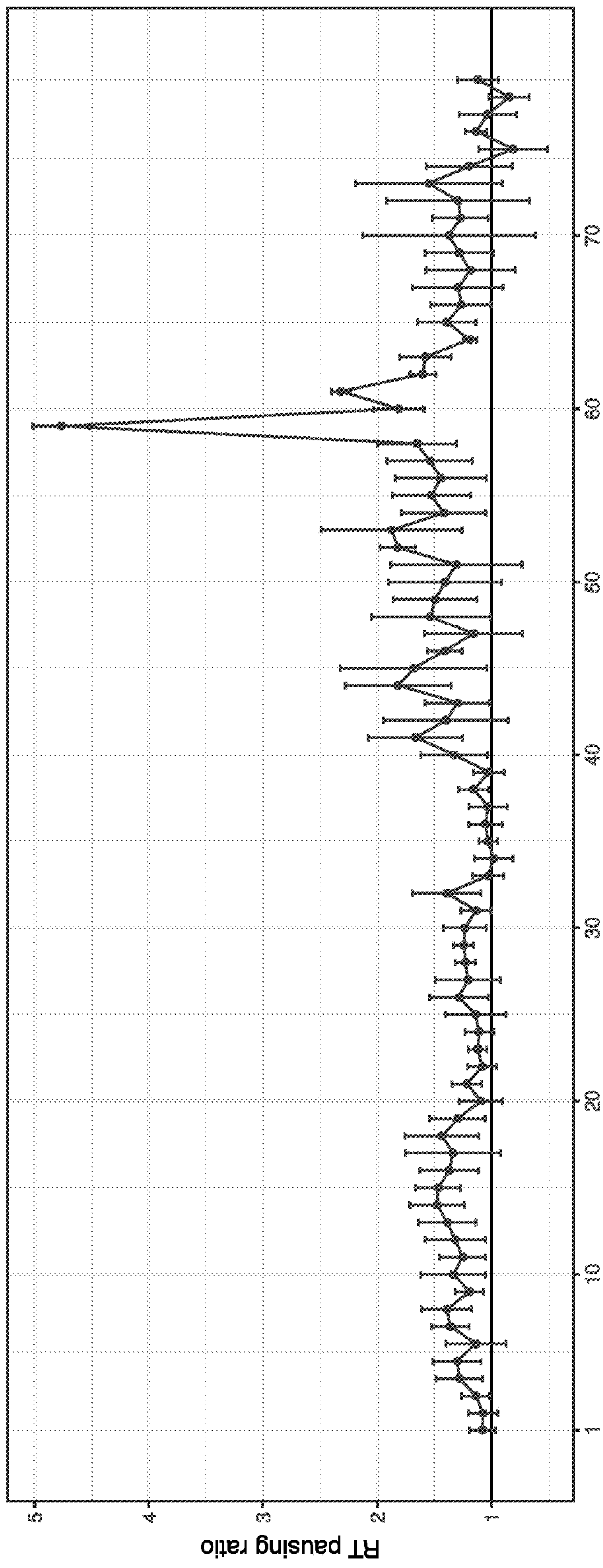
Figure 61B:
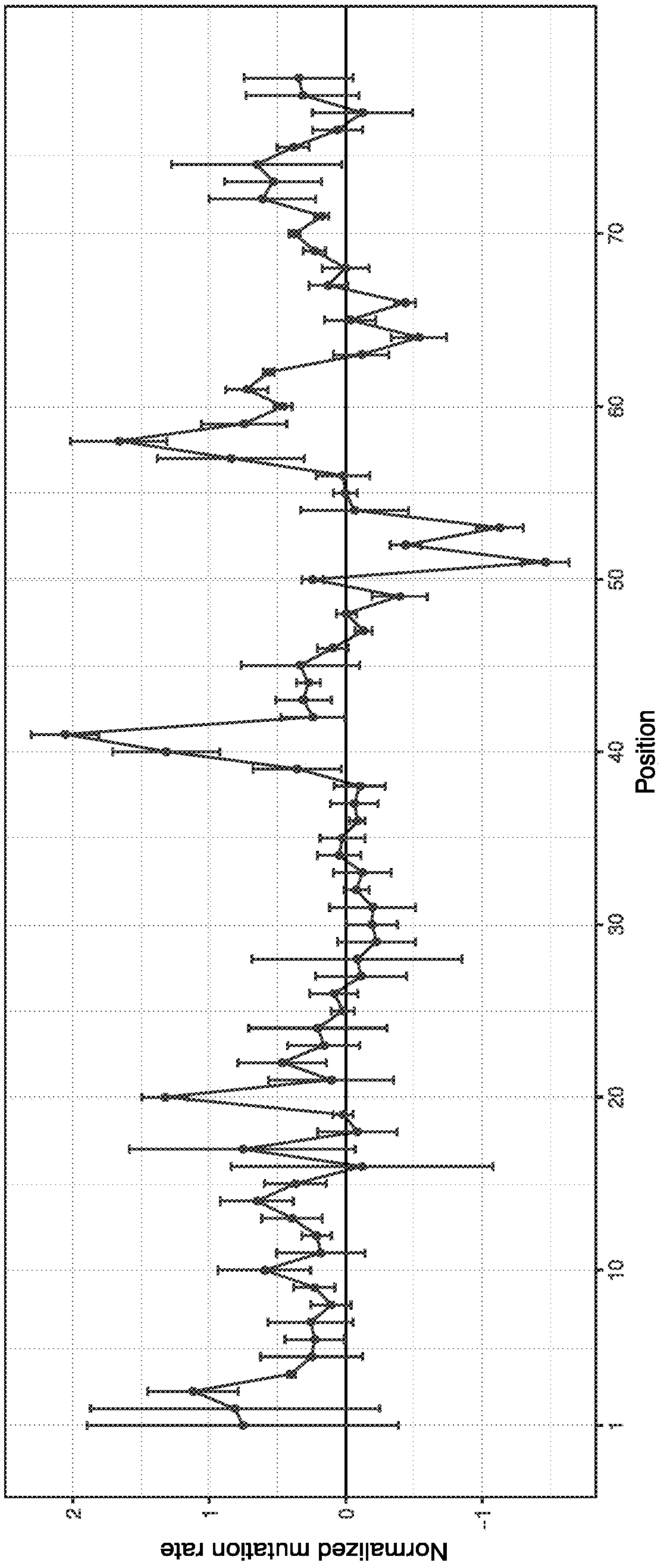

FIGS. 61A and 61B show RT pausing and mutation rate results. Photo-crosslinking of Aptamer 21 and photoprobe ARK-547 revealed that ARK-547 does not bind to negative control Aptamer 21-E and yields no photoadduct. Reverse transcriptase (RT) pausing was maximal at nt 59, consistent with predicted binding mode. Sites of normalized mutational rate were also consistent with the ARK-547 binding mode.

FIG. 62 shows the structures of I-14 (ARK-729) and I-15 (ARK-816) and labeling of RNA-photoprobe adducts via a Cu-free click reaction using these compounds. Lanes 1-5 were run with different combinations of denaturant and Cu-free click reaction conditions. Lane 1: no denaturant/10 mM Tris, 1 mM EDTA, pH 8.0, 37° C. click conditions; Lane 2: no denaturant/10 mM Tris, 10 mM EDTA, pH 8.0, 65° C. click conditions; Lane 3: 6 M Urea denaturant/10 mM Tris, 10 mM EDTA, pH 8.0, 65° C. click conditions; Lane 4: 90% formamide denaturant/10 mM Tris, 10 mM EDTA, pH 8.0, 65° C. click conditions; Lane 5: 1×TBE-Urea buffer, 65° C. Aptamer 21 was treated with ARK-729 or ARK-816, then was subjected to UV photocrosslinking. The resulting photoadducts were then treated with a Cy7-DBCO conjugate under the indicated conditions. Performing the Cu-free click reaction at 65° C. without any additives enabled detection of the Aptamer 21-probe photoadducts by Cy7 fluorescence.

FIG. 63 shows results for competition experiments between Aptamer 21 photoprobes and RNA-binding ligands. Aptamer 21 was either incubated with probe alone (ARK-581) or probe plus a 10-fold excess of RNA-binding ligand. Only SPR-active compounds ARK-139 and ARK-852 efficiently inhibited photocrosslinking of ARK-581 to Aptamer 21.

FIG. 64 shows RT pausing results for photocrosslinking of structurally distinct Aptamer 21 ligands to Aptamer 21.

FIG. 65 shows RT pausing results for a competition assay. Both ARK-852 and ARK-139 inhibit the photocrosslinking of probes to Aptamer 21.

FIG. 66 shows RT pausing results relating to photocrosslinking of chemical probes to Aptamer 21.

Figure 67A:
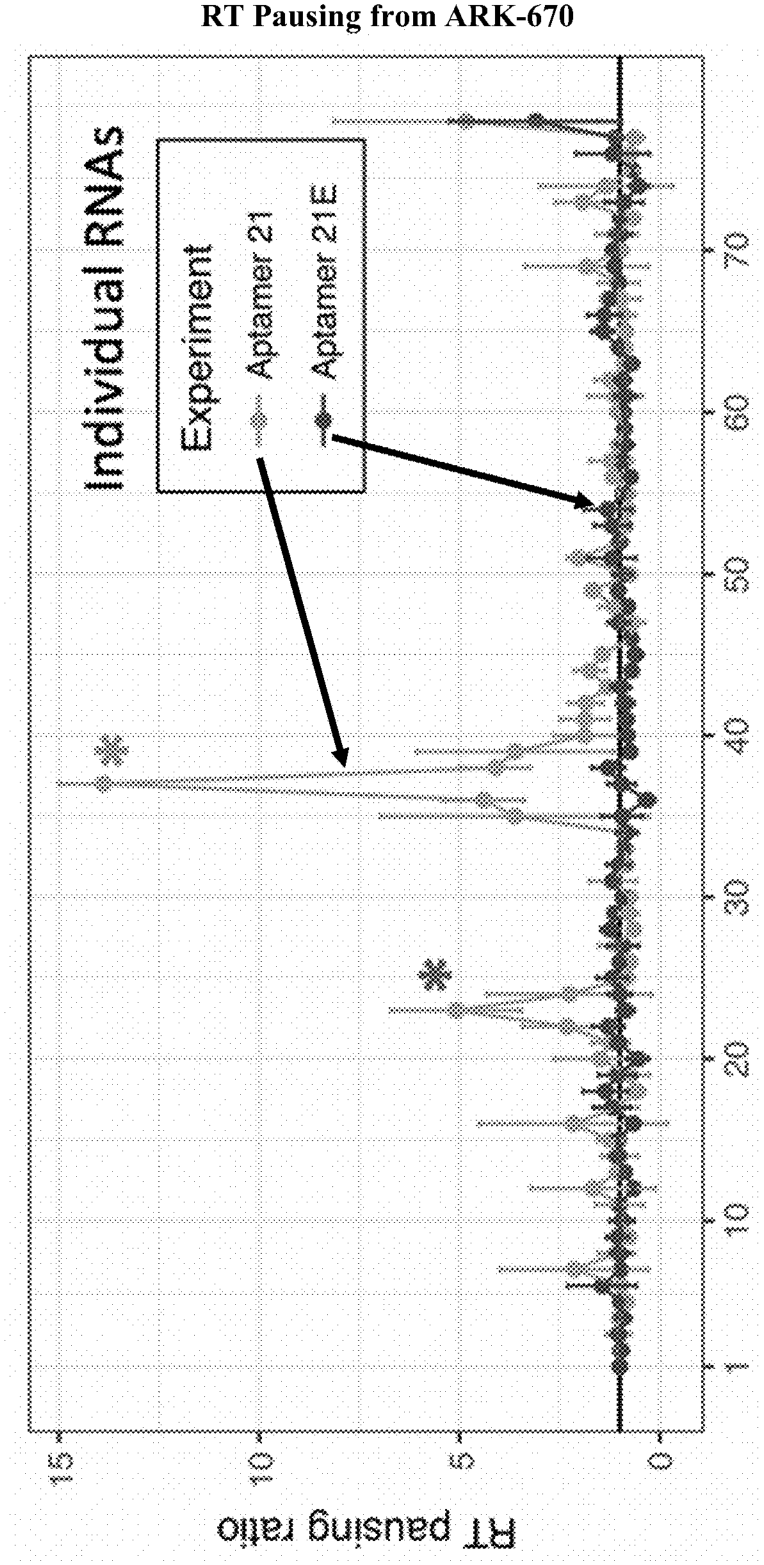
Figure 67B:
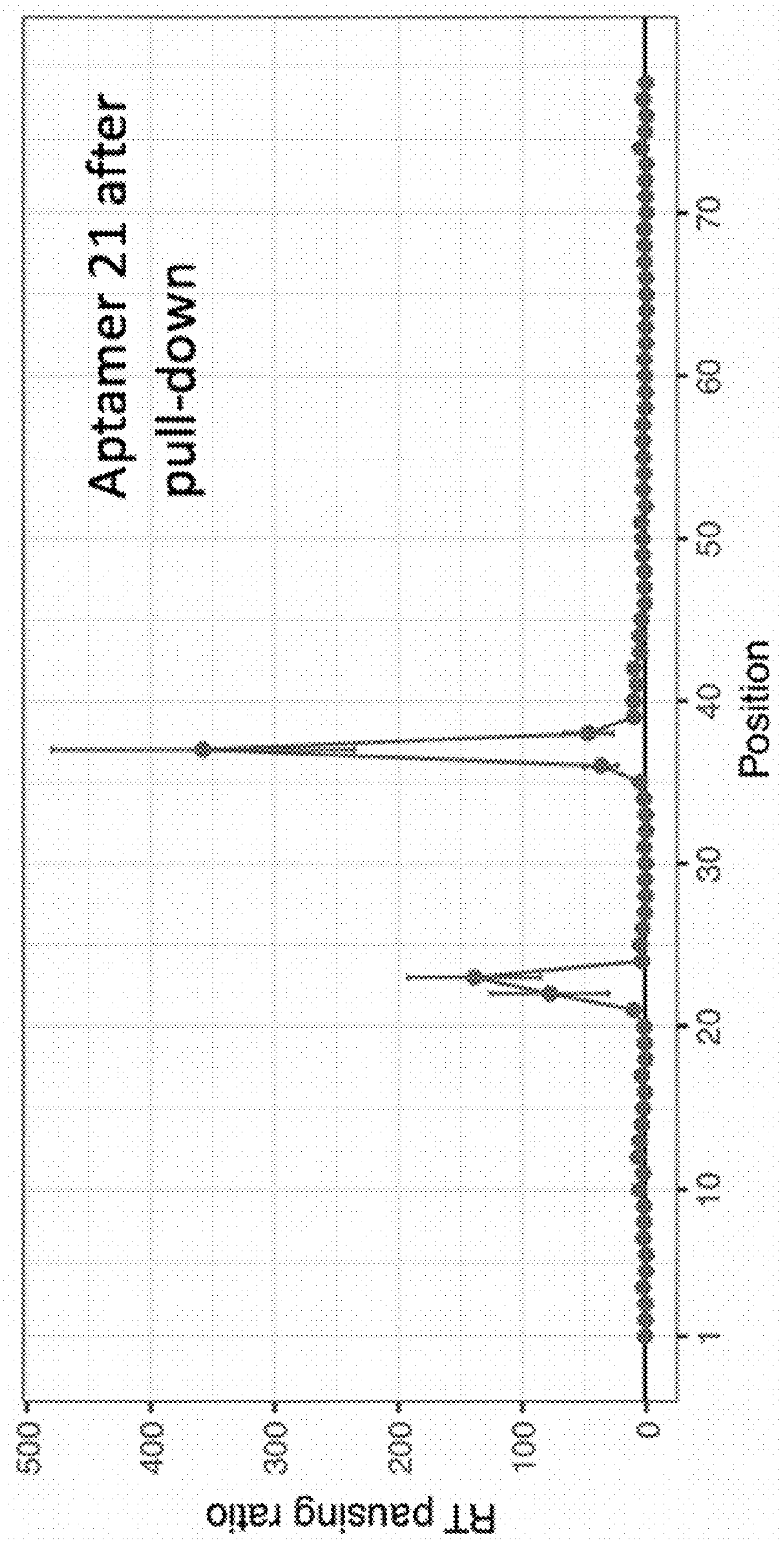

FIG. 67A and FIG. 67B shows photocrosslinking of ARK-670 to Aptamer 21, Aptamer 21-E, or a mixture of Aptamer 21 and four other RNAs. The RT pausing signal from probe adducts was specific for Aptamer 21 and increased in strength after bead enrichment of crosslinked RNA.

Figure 68:
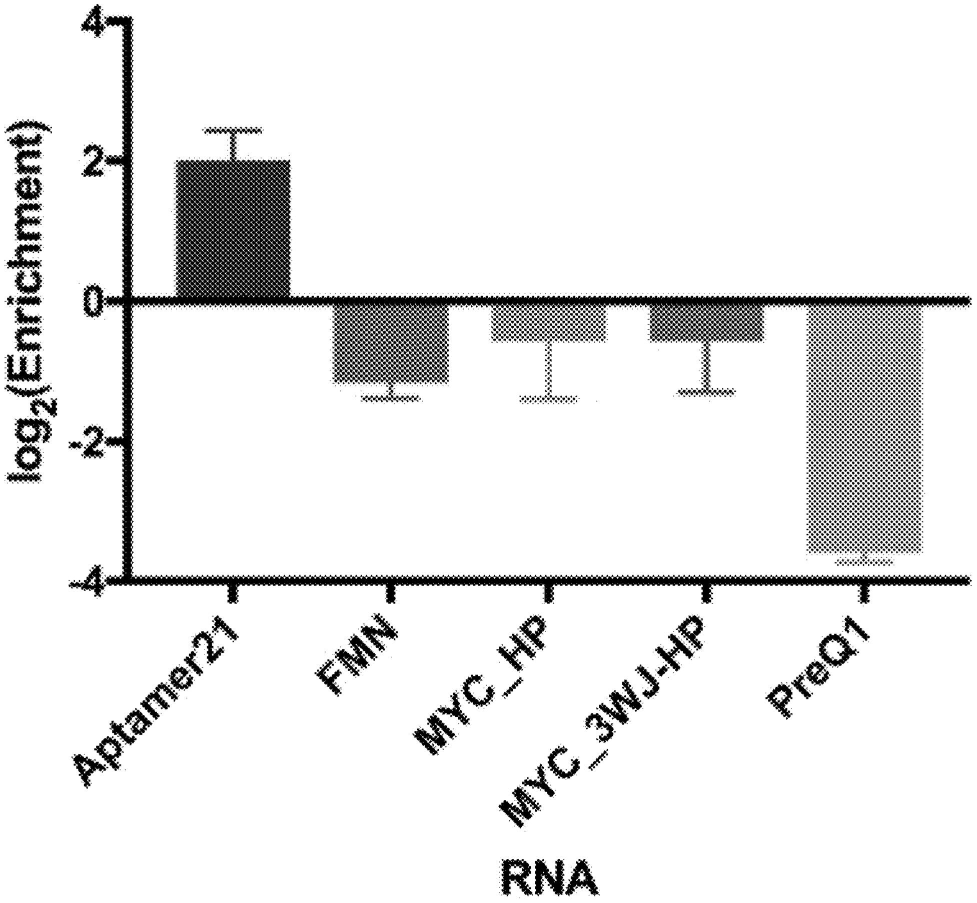

FIG. 68 shows selective enrichment of Aptamer 21 by ARK-670 in the presence of other RNA sequences. Cross-linking of ARK-670 to a mixture of Aptamer 21 and four other RNAs was followed by avidin bead enrichment of cross-linked RNA and sequencing. Sequencing analysis showed that only Aptamer 21 was enriched by ARK-670, which suggests that ARK-670 binds to Aptamer 21 and cross-links selectively in a proximity-driven manner.

Figure 69:
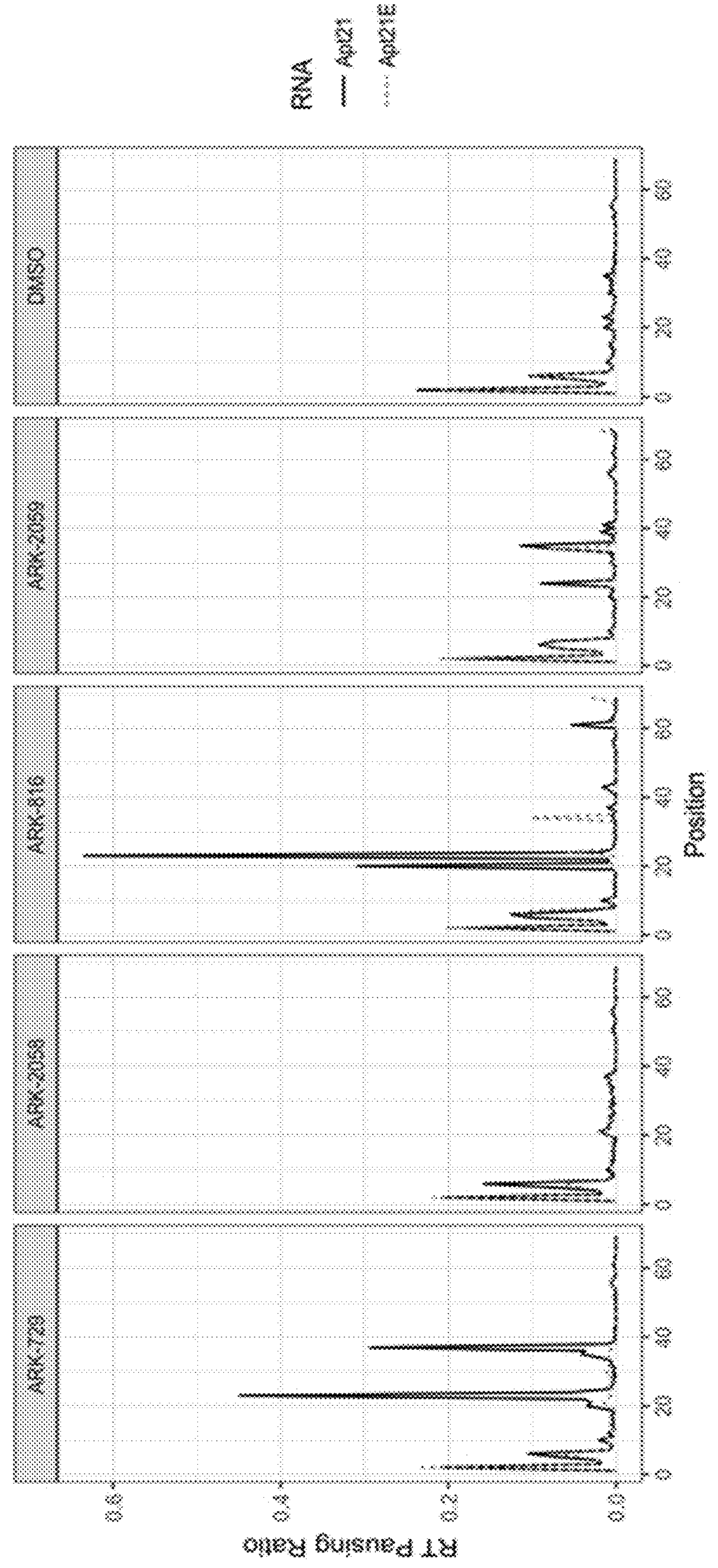

FIG. 69 shows RT pausing data from click-biotinylated probes after enrichment. Crosslinking of Aptamer 21 or Aptamer 21-E to ARK-729 (phenylazide probe), ARK-2058 (phenylazide warhead-only control), ARK-816 (diazirine probe), ARK-2059 (diazirine warhead-only control) or DMSO was followed by enrichment on avidin beads and sequencing. The probes ARK-729 and ARK-816 showed RT pausing peaks specific to Aptamer 21.

Figure 70:
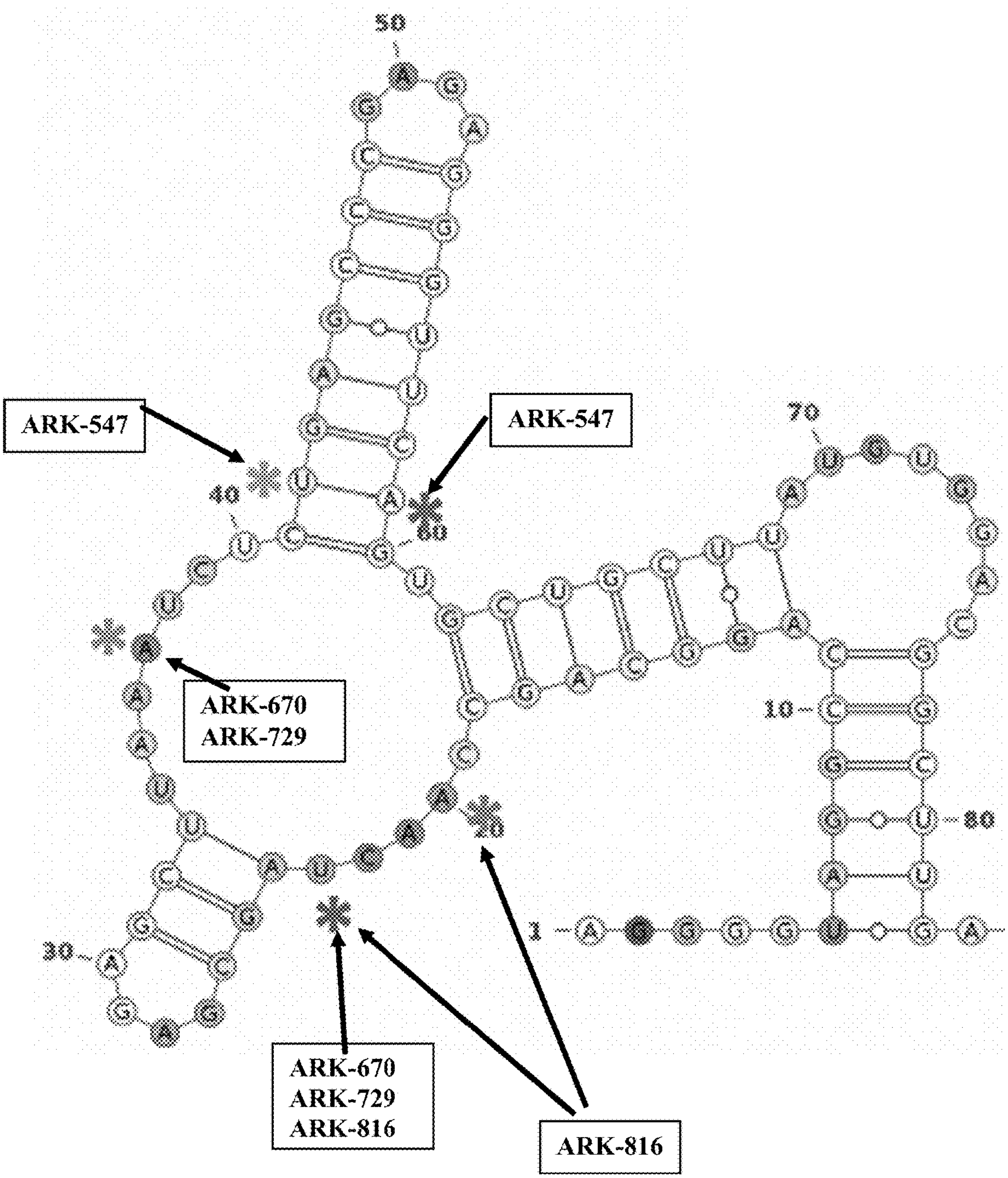

FIG. 70 shows a cartoon mapping the locations of RT pausing peaks on Aptamer 21's sequence.

Figure 71:
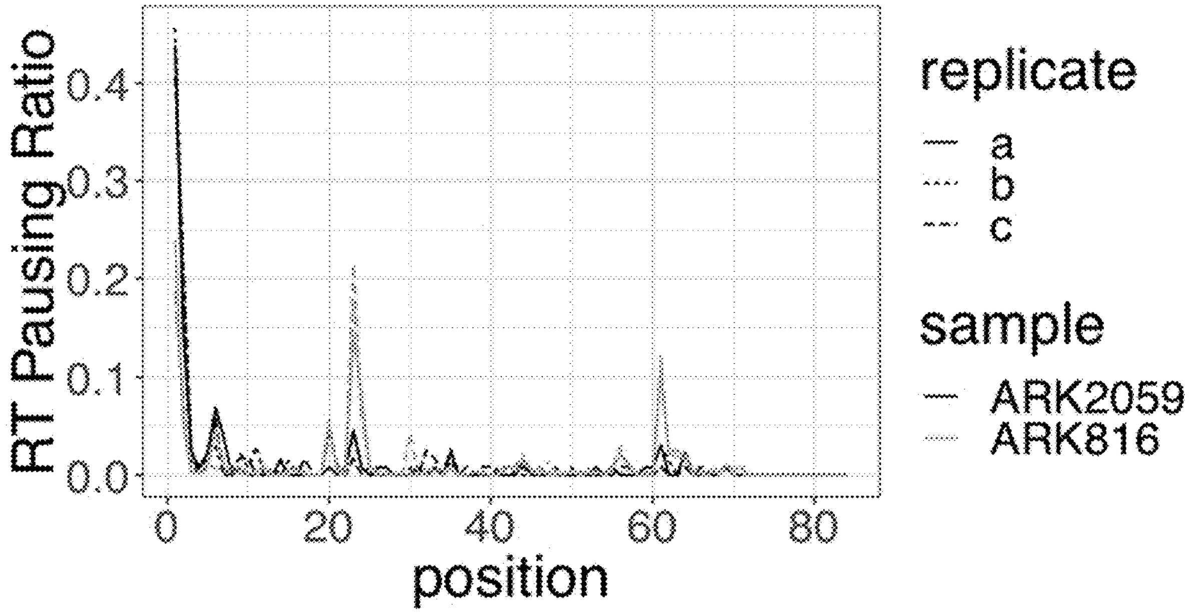

FIG. 71 shows RT pausing on Aptamer 21 spiked into PolyA+ RNA extract. Crosslinking of ARK-816 (diazirine probe) or ARK-2059 (diazirine warhead-only control) to Aptamer 21 spiked into a polyA+ RNA extract and the RT pausing ratio was measured by sequencing. Peaks specific to the ARK-816 probe were observed at the same positions as for isolated Aptamer 21.

Figure 72:
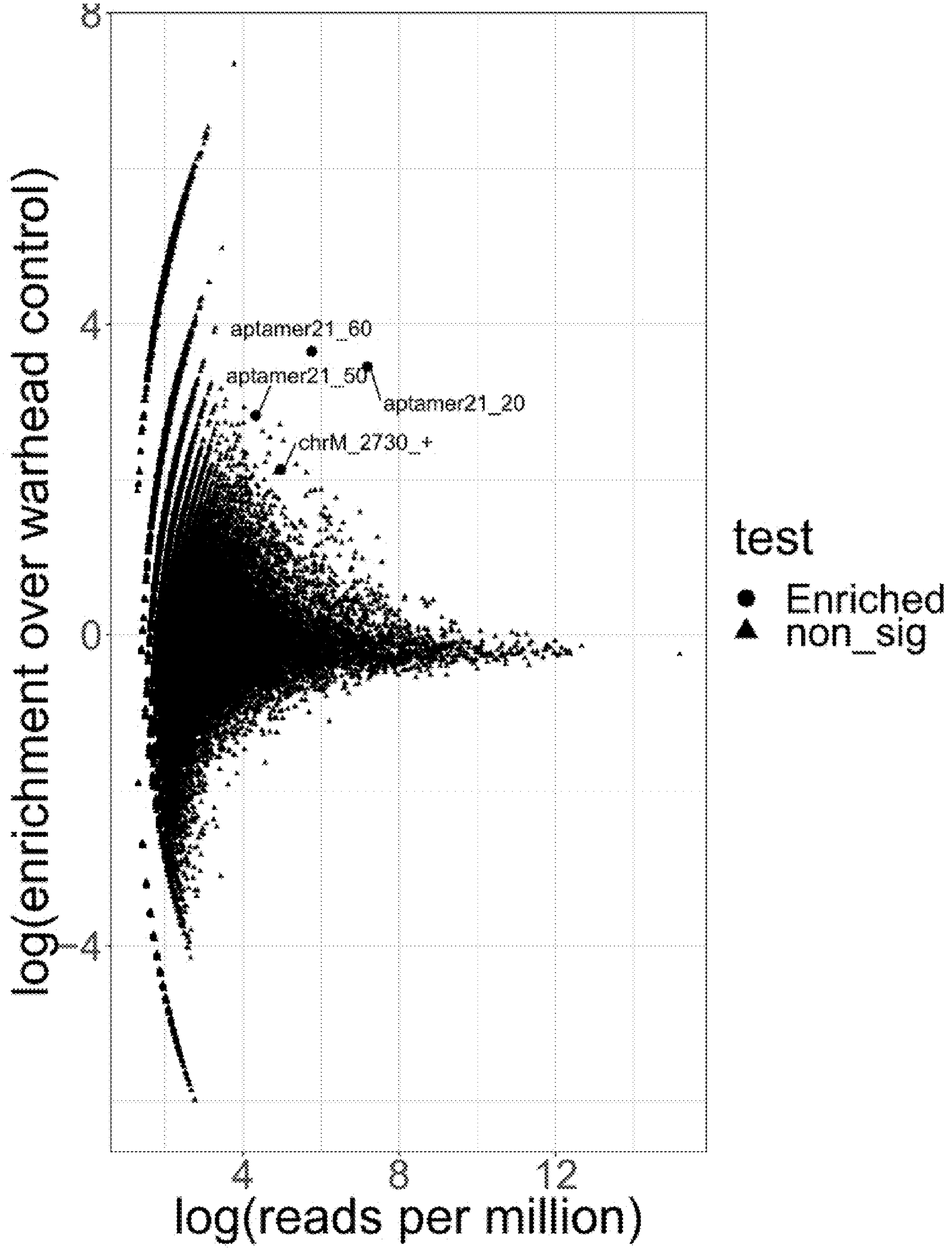

FIG. 72 shows enrichment analysis of Aptamer 21 from a PolyA+ RNA extract. Aptamer 21 was spiked into polyA+ RNA extract and then the mixture was crosslinked to ARK-816 (diazirine probe) and ARK-2059 (warhead-only control) and crosslinked RNA was enriched by avidin capture. Specific enrichment of sequences by the probe as compared to the warhead-only control determined by next-generation sequencing. Enrichment of the sites of probe-specific RT pausing on Aptamer 21 was observed.

DETAILED DESCRIPTION OF CERTAIN EMBODIMENTS

1. General Description of Certain Embodiments of the Invention; Definitions

RNA Targets and Association with Diseases and Disorders

The vast majority of molecular targets that have been addressed therapeutically are proteins. However, it is now understood that a variety of RNA molecules play important regulatory roles in both healthy and diseased cells. While only 1-2% of the human genome codes for proteins, it is now known that the majority of the genome is transcribed (Carninci et al., *Science* 309:1559-1563; 2005). Thus, the noncoding transcripts (the noncoding transcriptome) represent a large group of new therapeutic targets. Noncoding RNAs such as microRNA (miRNA) and long noncoding RNA (lncRNA) regulate transcription, splicing, mRNA stability/decay, and translation. In addition, the noncoding regions of mRNA such as the 5' untranslated regions (5' UTR), the 3' UTR, and introns can play regulatory roles in affecting mRNA expression levels, alternative splicing, translational efficiency, and mRNA and protein subcellular localization. RNA secondary and tertiary structures are critical for these regulatory activities.

Remarkably, GWAS studies have shown that there are far more single nucleotide polymorphisms (SNPs) associated with human disease in the noncoding transcriptome relative to the coding transcripts (Maurano et al., *Science* 337:1190-1195; 2012). Therefore, the therapeutic targeting of noncoding RNAs and noncoding regions of mRNA can yield novel agents to treat to previously intractable human diseases.

Current therapeutic approaches to interdict mRNA require methods such as gene therapy (Naldini, *Nature* 2015, 526, 351-360), genome editing (Cox et al., Nature Medicine 2015, 21, 121-131), or a wide range of oligonucleotide technologies (antisense, RNAi, etc.) (Bennett & Swayze, *Annu. Rev. Pharmacol. Toxicol.* 2010, 50, 259-293). Oligonucleotides modulate the action of RNA via canonical base/base hybridization. The appeal of this approach is that the basic pharmacophore of an oligonucleotide can be defined in a straightforward fashion from the sequence subject to interdiction. Each of these therapeutic modalities suffers from substantial technical, clinical, and regulatory challenges. Some limitations of oligonucleotides as therapeutics (e.g. anti sense, RNAi) include unfavorable pharmacokinetics, lack of oral bioavailability, and lack of blood-brain-barrier penetration, with the latter precluding delivery to the brain or spinal cord after parenteral drug administration for the treatment of neurological diseases. In addition, oligonucleotides are not taken up effectively into solid tumors without a complex delivery system such as lipid nanoparticles. Lastly, a vast majority of the oligonucleotides that are taken up into cells and tissues remain in a non-functional compartment such as endosomes, and only a small fraction of the material escapes to gain access to the cytosol and/or nucleus where the target is located.

"Traditional" small molecules can be optimized to exhibit excellent absorption from the gut, excellent distribution to target organs, and excellent cell penetration. The use of "traditional" (i.e., "Lipinski-compliant" (Lipinski et al., *Adv. Drug Deliv. Rev.* 2001, 46, 3-26) small molecules with favorable drug properties that bind and modulate the activity of a target RNA would solve many of the problems noted above.

In one aspect, the present invention provides a method of identifying the identity or structure of a binding or active site to which a small molecule binds in a target RNA, comprising the steps of i) contacting the target RNA with a disclosed compound and ii) analyzing the results by an assay disclosed herein, optionally in combination with a computational method. In some embodiments, the target RNA is selected from a mRNA or a noncoding RNA. In some embodiments, the target RNA is an aptamer or riboswitch. In some embodiments, the RNA is the FMN riboswitch, $PreQ_1$, or Aptamer 21. In some embodiments, the assay identifies the location in the primary sequence of the binding site(s) on the target RNA.

Targeting mRNA

Within mRNAs, noncoding regions can affect the level of mRNA and protein expression. Briefly, these include IRES and upstream open reading frames (uORF) that affect translation efficiency, intronic sequences that affect splicing efficiency and alternative splicing patterns, 3' UTR sequences that affect mRNA and protein localization, and elements that control mRNA decay and half-life. Therapeutic modulation of these RNA elements can have beneficial effects. Also, mRNAs may contain expansions of simple repeat sequences such as trinucleotide repeats. These repeat expansion containing RNAs can be toxic and have been observed to drive disease pathology, particularly in certain neurological and musculoskeletal diseases (see Gatchel & Zoghbi, *Nature Rev. Gen.* 2005, 6, 743-755), In addition, splicing can be modulated to skip exons having mutations that introduce stop codons in order to relieve premature termination during translation.

Small molecules can be used to modulate splicing of pre-mRNA for therapeutic benefit in a variety of settings. One example is spinal muscular atrophy (SMA). SMA is a consequence of insufficient amounts of the survival of motor neuron (SMN) protein. Humans have two versions of the SMN gene, SMN1 and SMN2. SMA patients have a mutated SMN1 gene and thus rely solely on SMN2 for their SMN protein. The SMN2 gene has a silent mutation in exon 7 that causes inefficient splicing such that exon 7 is skipped in the majority of SMN2 transcripts, leading to the generation of a defective protein that is rapidly degraded in cells, thus limiting the amount of SMN protein produced from this locus. A small molecule that promotes the efficient inclusion of exon 7 during the splicing of SMN2 transcripts would be an effective treatment for SMA (Palacino et al., *Nature Chem. Biol.,* 2015, 11, 511-517). Accordingly, in one aspect, the present invention provides a method of identifying a small molecule that modulates the splicing of a target pre-mRNA to treat a disease or disorder, comprising the steps of: screening one or more disclosed compounds for binding to the target pre-mRNA; and analyzing the results by an RNA binding assay disclosed herein. In some embodiments, the pre-mRNA is an SMN2 transcript. In some embodiments, the disease or disorder is spinal muscular atrophy (SMA).

Even in cases in which defective splicing does not cause the disease, alteration of splicing patterns can be used to correct the disease. Nonsense mutations leading to premature translational termination can be eliminated by exon skipping if the exon sequences are in-frame. This can create a protein that is at least partially functional. One example of the use of exon skipping is the dystrophin gene in Duchenne muscular dystrophy (DMD). A variety of different mutations leading to premature termination codons in DMD patients can be eliminated by exon skipping promoted by oligonucleotides (reviewed in Fairclough et al., *Nature Rev. Gen.,* 2013, 14, 373-378). Small molecules that bind RNA structures and affect splicing are expected to have a similar effect. Accordingly, in one aspect, the present invention provides a method of identifying a small molecule that modulates the splicing pattern of a target pre-mRNA to treat a disease or disorder, comprising the steps of: screening one or more disclosed compounds for binding to the target pre-mRNA; and analyzing the results by an RNA binding assay disclosed herein. In some embodiments, the pre-mRNA is a dystrophin gene transcript. In some embodiments, the small molecule promotes exon skipping to eliminate premature translational termination. In some embodiments, the disease or disorder is Duchenne muscular dystrophy (DMD).

Lastly, the expression of an mRNA and its translation products could be affected by targeting noncoding sequences and structures in the 5' and 3' UTRs. For instance, RNA structures in the 5' UTR can affect translational efficiency. RNA structures such as hairpins in the 5' UTR have been shown to affect translation. In general, RNA structures are believed to play a critical role in translation of mRNA. Two examples of these are internal ribosome entry sites (IRES) and upstream open reading frames (uORF) that can affect the level of translation of the main open reading frame (Komar and Hatzoglou, *Frontiers Oncol.* 5:233, 2015; Weingarten-Gabbay et al., *Science* 351:pii:aad4939, 2016; Calvo et al., *Proc. Natl. Acad. Sci. USA* 106:7507-7512; Le Quesne et al., *J. Pathol.* 220:140-151, 2010; Barbosa et al., PLOS Genetics 9:e10035529, 2013). For example, nearly half of all human mRNAs have uORFs, and many of these reduce the translation of the main ORF. Small molecules targeting these RNAs could be used to modulate specific protein levels for therapeutic benefit. Accordingly, in one aspect, the present invention provides a method of producing a small molecule that modulates the expression or translation efficiency of a target pre-mRNA or mRNA to treat a disease or disorder, comprising the steps of: screening one or more disclosed compounds for binding to the target pre-mRNA or mRNA; and analyzing the results by an RNA binding assay disclosed herein. In some embodiments, the small molecule binding site is a 5' UTR, internal ribosome entry site, or upstream open reading frame.

Targeting Regulatory RNA

The largest set of RNA targets is RNA that is transcribed but not translated into protein, termed "non-coding RNA". Non-coding RNA is highly conserved and the many varieties of non-coding RNA play a wide range of regulatory functions. The term "non-coding RNA," as used herein, includes but is not limited to micro-RNA (miRNA), long non-coding RNA (lncRNA), long intergenic non-coding RNA (lincRNA), Piwi-interacting RNA (piRNA), competing endogenous RNA (ceRNA), and pseudo-genes. Each of these sub-categories of non-coding RNA offers a large number of RNA targets with significant therapeutic potential. Accordingly, in some embodiments, the present invention provides methods of treating a disease mediated by non-coding RNA. In some embodiments, the disease is caused by a miRNA, lncRNA, lincRNA, piRNA, ceRNA, or pseudo-gene. In another aspect, the present invention provides a method of producing a small molecule that modulates the activity of a target non-coding RNA to treat a disease or disorder, comprising the steps of: screening one or more disclosed compounds for binding to the target non-coding RNA; and analyzing the results by an RNA binding assay disclosed herein. In some embodiments, the target non-coding RNA is a miRNA, lncRNA, lincRNA, piRNA, ceRNA, or pseudo-gene.

miRNA are short double-strand RNAs that regulate gene expression (see Elliott & Ladomery, Molecular Biology of RNA, $2^{nd}$ Ed.). Each miRNA can affect the expression of many human genes. There are nearly 2,000 miRNAs in humans. These RNAs regulate many biological processes, including cell differentiation, cell fate, motility, survival, and function. miRNA expression levels vary between different tissues, cell types, and disease settings. They are frequently aberrantly expressed in tumors versus normal tissue, and their activity may play significant roles in cancer (for reviews, see Croce, *Nature Rev. Genet.* 10:704-714, 2009; Dykxhoorn *Cancer Res.* 70:6401-6406, 2010). miRNAs have been shown to regulate oncogenes and tumor suppressors and themselves can act as oncogenes or tumor suppressors. Some have been shown to promote epithelial-mesenchymal transition (EMT) and cancer cell invasiveness and metastasis. In the case of oncogenic miRNAs, their inhibition could be an effective anti-cancer treatment. Accordingly, in one aspect, the present invention provides a method of producing a small molecule that modulates the activity of a target miRNA to treat a disease or disorder, comprising the steps of: screening one or more disclosed compounds for binding to the target miRNA; and analyzing the results by an RNA binding assay disclosed herein. In some embodiments, the miRNA regulates an oncogene or tumor suppressor, or acts as an oncogene or tumor suppressor. In some embodiments, the disease is cancer. In some embodiments, the cancer is a solid tumor.

There are multiple oncogenic miRNA that could be therapeutically targeted including miR-155, miR-17~92, miR-19, miR-21, and miR-10b (see Stahlhut & Slack, *Genome Med.* 2013, 5, 111). miR-155 plays pathological roles in inflammation, hypertension, heart failure, and cancer. In cancer, miR-155 triggers oncogenic cascades and apoptosis resistance, as well as increasing cancer cell invasiveness. Altered expression of miR-155 has been described in multiple cancers, reflecting staging, progress and treatment outcomes. Cancers in which miR-155 over-expression has been reported are breast cancer, thyroid carcinoma, colon cancer, cervical cancer, and lung cancer. It is reported to play a role in drug resistance in breast cancer. miR-17~92 (also called Oncomir-1) is a polycistronic 1 kb primary transcript comprising miR-17, 20a, 18a, 19a, 92-1 and 19b-1. It is activated by MYC. miR-19 alters the gene expression and signal transduction pathways in multiple hematopoietic cells, and it triggers leukemogenesis and lymphomagenesis. It is implicated in a wide variety of human solid tumors and hematological cancers. miR-21 is an oncogenic miRNA that reduces the expression of multiple tumor suppressors. It stimulates cancer cell invasion and is associated with a wide variety of human cancers including breast, ovarian, cervix, colon, lung, liver, brain, esophagus, prostate, pancreas, and thyroid cancers. Accordingly, in some embodiments of the methods described above, the target miRNA is selected from miR-155, miR-17~92, miR-19, miR-21, or miR-10b. In some embodiments, the disease or disorder is a cancer selected from breast cancer, ovarian cancer, cervical cancer, thyroid carcinoma, colon cancer, liver cancer, brain cancer, esophageal cancer, prostate cancer, lung cancer, leukemia, or lymph node cancer. In some embodiments, the cancer is a solid tumor.

Beyond oncology, miRNAs play roles in many other diseases including cardiovascular and metabolic diseases (Quiant and Olson, *J. Clin. Invest.* 123:11-18, 2013; Olson, Science Trans. Med. 6: 239ps3, 2014; Baffy, *J. Clin. Med.* 4:1977-1988, 2015).

Many mature miRNAs are relatively short in length and thus may lack sufficient folded, three-dimensional structure to be targeted by small molecules. However, it is believed that the levels of such miRNA could be reduced by small molecules that bind the primary transcript or the pre-miRNA to block the biogenesis of the mature miRNA. Accordingly, in some embodiments of the methods described above, the target miRNA is a primary transcript or pre-miRNA.

lncRNA are RNAs of over 200 nucleotides (nt) that do not encode proteins (see Rinn & Chang, *Ann. Rev. Biochem.* 2012, 81, 145-166; (for reviews, see Morris and Mattick, *Nature Reviews Genetics* 15:423-437, 2014; Mattick and Rinn, *Nature Structural & Mol. Biol.* 22:5-7, 2015; Iyer et al., *Nature Genetics* 47(:199-208, 2015)). They can affect the expression of the protein-encoding mRNAs at the level of transcription, splicing and mRNA decay. Considerable research has shown that lncRNA can regulate transcription by recruiting epigenetic regulators that increase or decrease transcription by altering chromatin structure (e.g., Holoch and Moazed, *Nature Reviews Genetics* 16:71-84, 2015). lncRNAs are associated with human diseases including cancer, inflammatory diseases, neurological diseases and cardiovascular disease (for instance, Presner and Chinnaiyan, *Cancer Discovery* 1:391-407, 2011; Johnson, *Neurobiology of Disease* 46:245-254, 2012; Gutscher and Diederichs, *RNA Biology* 9:703-719, 2012; Kumar et al., *PLOS Genetics* 9:e1003201, 2013; van de Vondervoort et al., *Frontiers in Molecular Neuroscience,* 2013; Li et al., *Int. J Mol. Sci.* 14:18790-18808, 2013). The targeting of lncRNA could be done to up-regulate or down-regulate the expression of specific genes and proteins for therapeutic benefit (e.g., Wahlestedt, *Nature Reviews Drug Discovery* 12:433-446, 2013; Guil and Esteller, *Nature Structural & Mol. Biol.* 19:1068-1075, 2012). In general, lncRNA are expressed at a lower level relative to mRNAs. Many lncRNAs are physically associated with chromatin (Werner et al., *Cell Reports* 12, 1-10, 2015) and are transcribed in close proximity to protein-encoding genes. They often remain physically associated at their site of transcription and act locally, in cis, to regulate the expression of a neighboring mRNA. The mutation and dysregulation of lncRNA is associated with human diseases; therefore, there are a multitude of lncRNAs that could be therapeutic targets. Accordingly, in some embodiments of the methods described above, the target non-coding RNA is a lncRNA. In some embodiments, the lncRNA is associated with a cancer, inflammatory disease, neurological disease, or cardiovascular disease.

lncRNAs regulate the expression of protein-encoding genes, acting at multiple different levels to affect transcription, alternative splicing and mRNA decay. For example, lncRNA has been shown to bind to the epigenetic regulator PRC2 to promote its recruitment to genes whose transcription is then repressed via chromatin modification. lncRNA may form complex structures that mediate their association with various regulatory proteins. A small molecule that binds to these lncRNA structures could be used to modulate the expression of genes that are normally regulated by an individual lncRNA.

One exemplary target lncRNA is HOTAIR, an lncRNA expressed from the HoxC locus on human chromosome 12. Is expression level is low (~100 RNA copies per cell). Unlike many lncRNAs, HOTAIR can act in trans to affect the expression of distant genes. It binds the epigenetic repressor PRC2 as well as the LSD1/CoREST/REST complex, another repressive epigenetic regulator (Tsai et al., *Science* 329, 689-693, 2010). HOTAIR is a highly structured RNA with over 50% of its nucleotides being involved in base pairing. It is frequently dysregulated (often up-regulated) in various types of cancer (Yao et al., *Int. J. Mol. Sci.* 15:18985-18999, 2014; Deng et al., *PLOS One* 9:e110059, 2014). Cancer patients with high expression levels of HOTAIR have a significantly poorer prognosis, compared with those with low expression levels. HOTAIR has been reported to be involved in the control of apoptosis, proliferation, metastasis, angiogenesis, DNA repair, chemoresistance and tumor cell metabolism. It is highly expressed in metastatic breast cancers. High levels of expression in primary breast tumors are a significant predictor of subsequent metastasis and death. HOTAIR also has been reported to be associated with esophageal squamous cell carcinoma, and it is a prognostic factor in colorectal cancer, cervical cancer, gastric cancer and endometrial carcinoma. Therefore, HOTAIR-binding small molecules are novel anticancer drug candidates. Accordingly, in some embodiments of the methods described above, the target non-coding RNA is HOTAIR. In some embodiments, the disease or disorder is breast cancer, esophageal squamous cell carcinoma, colorectal cancer, cervical cancer, gastric cancer, or endometrial carcinoma.

Another potential cancer target among lncRNA is MALAT-1 (metastasis-associated lung adenocarcinoma transcript 1), also known as NEAT2 (nuclear-enriched abundant transcript 2) (Gutschner et al., *Cancer Res.* 73:1180-1189, 2013; Brown et al., *Nat. Structural & Mol. Biol.* 21:633-640, 2014). It is a highly conserved 7 kb nuclear lncRNA that is localized in nuclear speckles. It is ubiquitously expressed in normal tissues, but is up-regulated in many cancers. MALAT-1 is a predictive marker for metastasis development in multiple cancers including lung cancer. It appears to function as a regulator of gene expression, potentially affecting transcription and/or splicing. MALAT-1 knockout mice have no phenotype, indicating that it has limited normal function. However, MALAT-1-deficient cancer cells are impaired in migration and form fewer tumors in a mouse xenograft tumor models. Antisense oligonucleotides (ASO) blocking MALAT-1 prevent metastasis formation after tumor implantation in mice. Some mouse xenograft tumor model data indicates that MALAT-1 knockdown by ASOs may inhibit both primary tumor growth and metastasis. Thus, a small molecule targeting MALAT-1 is expected to be effective in inhibiting tumor growth and metastasis. Accordingly, in some embodiments of the methods described above, the target non-coding RNA is MALAT-1. In some embodiments, the disease or disorder is a cancer in which MALAT-1 is upregulated, such as lung cancer.

In some embodiments, the present invention provides a method of treating a disease or disorder mediated by non-coding RNA (such as HOTAIR or MALAT-1), comprising the step of administering to a patient in need thereof a compound of the present invention. Such compounds are described in detail herein.

Targeting Toxic RNA (Repeat RNA)

Simple repeats in mRNA often are associated with human disease. These are often, but not exclusively, repeats of three nucleotides such as CAG ("triplet repeats") (for reviews, see Gatchel and Zoghbi, *Nature Reviews Genetics* 6:743-755, 2005; Krzyzosiak et al., *Nucleic Acids Res.* 40:11-26, 2012; Budworth and McMurray, *Methods Mol. Biol.* 1010:3-17, 2013). Triplet repeats are abundant in the human genome, and they tend to undergo expansion over generations. Approximately 40 human diseases are associated with the expansion of repeat sequences. Diseases caused by triplet expansions are known as Triplet Repeat Expansion Diseases (TRED). Healthy individuals have a variable number of triplet repeats, but there is a threshold beyond which a higher repeat number causes disease. The threshold varies in different disorders. The triplet repeat can be unstable. As the gene is inherited, the number of repeats may increase, and the condition may be more severe or have an earlier onset from generation to generation. When an individual has a number of repeats in the normal range, it is not expected to expand when passed to the next generation. When the repeat number is in the permutation range (a normal, but unstable repeat number), then the repeats may or may not expand upon transmission to the next generation. Normal individuals who carry a permutation do not have the condition, but are at risk of having a child who has inherited a triplet repeat in the full mutation range and who will be affected. TREDs can be autosomal dominant, autosomal recessive or X-linked. The more common triplet repeat disorders are autosomal dominant.

The repeats can be in the coding or noncoding portions of the mRNA. In the case of repeats within noncoding regions, the repeats may lie in the 5' UTR, introns, or 3' UTR sequences. Some examples of diseases caused by repeat sequences within coding regions are shown in Table 1.

TABLE 1

Repeat Expansion Diseases in Which the Repeat Resides in the Coding Regions of mRNA

| Disease | Gene | Repeat | Normal repeat number | Disease repeat number |
|---|---|---|---|---|
| HD | HTT | CAG | 6-35 (SEQ ID NO: 1) | 36-250 (SEQ ID NO: 8) |
| DRPLA | ATN1 | CAG | 6-35 (SEQ ID NO: 1) | 49-88 (SEQ ID NO: 9) |
| SBMA | AR | CAG | 9-36 (SEQ ID NO: 2) | 38-62 (SEQ ID NO: 10) |
| SCA1 | ATXN1 | CAG | 6-35 (SEQ ID NO: 1) | 49-88 (SEQ ID NO: 9) |
| SCA2 | ATXN2 | CAG | 14-32 (SEQ ID NO: 3) | 33-77 (SEQ ID NO: 11) |
| SCA3 | ATXN3 | CAG | 12-40 (SEQ ID NO: 4) | 55-86 (SEQ ID NO: 12) |
| SCA6 | CACNA1A | CAG | 4-18 (SEQ ID NO: 5) | 21-30 (SEQ ID NO: 13) |
| SCA7 | ATXN7 | CAG | 7-17 (SEQ ID NO: 6) | 38-120 (SEQ ID NO: 14) |
| SCA17 | TBP | CAG | 25-42 (SEQ ID NO: 7) | 47-63 (SEQ ID NO: 15) |

Some examples of diseases caused by repeat sequences within noncoding regions of mRNA are shown in Table 2.

TABLE 2

Repeat Expansion Diseases in Which the Repeat Resides in the Noncoding Regions of mRNA

| Disease | Gene | Repeat | Repeat location | Normal repeat number | Disease repeat number |
|---|---|---|---|---|---|
| Fragile X | FMR1 | CGG | 5' UTR | 6-53 (SEQ ID NO: 16) | ≥230 |
| DM1 | DMPK | CTG | 3' UTR | 5-37 (SEQ ID NO: 17) | ≥50 |
| FRDA | FXN | GAA | Intron | 7-34 (SEQ ID NO: 18) | ≥100 |
| SCA8 | ATXN8 | CTG | Noncoding antisense | 16-37 (SEQ ID NO: 19) | 110-250 (SEQ ID NO: 22) |
| SCA10 | ATXN10 | ATTCT | Intron | 9-32 (SEQ ID NO: 20) | 800-4500 (SEQ ID NO: 23) |
| SCA12 | PPP2R2B | CAG | 5' UTR | 7-28 (SEQ ID NO: 21) | 66-78 (SEQ ID NO: 24) |
| C9FTD/ALS | C9orf72 | GGGGCC | Intron | ~30 | 100s |

The toxicity that results from the repeat sequence can be direct consequence of the action of the toxic RNA itself, or, in cases in which the repeat expansion is in the coding sequence, due to the toxicity of the RNA and/or the aberrant protein. The repeat expansion RNA can act by sequestering critical RNA-binding proteins (RBP) into foci. One example of a sequestered RBP is the Muscleblind family protein MBNL1. Sequestration of RBPs leads to defects in splicing as well as defects in nuclear-cytoplasmic transport of RNA and proteins. Sequestration of RBPs also can affect miRNA biogenesis. These perturbations in RNA biology can profoundly affect neuronal function and survival, leading to a variety of neurological diseases.

Repeat sequences in RNA form secondary and tertiary structures that bind RBPs and affect normal RNA biology. One specific example disease is myotonic dystrophy (DM1; dystrophia myotonica), a common inherited form of muscle disease characterized by muscle weakness and slow relaxation of the muscles after contraction (Machuca-Tzili et al., *Muscle Nerve* 32:1-18, 2005). It is caused by a CUG expansion in the 3' UTR of the dystrophia myotonica protein kinase (DMPK) gene. This repeat-containing RNA causes the misregulation of alternative splicing of several developmentally regulated transcripts through effects on the splicing regulators MBNL1 and the CUG repeat binding protein (CELF1) (Wheeler et al., *Science* 325:336-339, 2009). Small molecules that bind the CUG repeat within the DMPK transcript would alter the RNA structure and prevent focus formation and alleviate the effects on these spicing regulators. Fragile X Syndrome (FXS), the most common inherited form of mental retardation, is the consequence of a CGG repeat expansion within the 5' UTR of the FMR1 gene (Lozano et al., *Intractable Rare Dis. Res.* 3:134-146, 2014). FMRP is critical for the regulation of translation of many mRNAs and for protein trafficking, and it is an essential protein for synaptic development and neural plasticity. Thus, its deficiency leads to neuropathology. A small molecule targeting this CGG repeat RNA may alleviate the suppression of FMR1 mRNA and FMRP protein expression. Another TRED having a very high unmet medical need is Huntington's disease (HD). HD is a progressive neurological disorder with motor, cognitive, and psychiatric changes (Zuccato et al., *Physiol Rev.* 90:905-981, 2010). It is characterized as a poly-glutamine or polyQ disorder since the CAG repeat within the coding sequence of the HTT gene leads to a protein having a poly-glutamine repeat that appears to have detrimental effects on transcription, vesicle trafficking, mitochondrial function, and proteasome activity. However, the HTT CAG repeat RNA itself also demonstrates toxicity, including the sequestration of MBNL1 protein into nuclear inclusions. One other specific example is the GGGGCC repeat expansion in the C9orf72 (chromosome 9 open reading frame 72) gene that is prevalent in both familial frontotemporal dementia (FTD) and amyotrophic lateral sclerosis (ALS) (Ling et al., *Neuron* 79:416-438, 2013; Haeusler et al., *Nature* 507:195-200, 2014). The repeat RNA structures form nuclear foci that sequester critical RNA binding proteins. The GGGGCC repeat RNA also binds and sequesters RanGAP1 to impair nucleocytoplasmic transport of RNA and proteins (Zhang et al., *Nature* 525:56-61, 2015). Selectively targeting any of these repeat expansion RNAs could add therapeutic benefit in these neurological diseases.

The present invention contemplates a method of treating a disease or disorder wherein aberrant RNAs themselves cause pathogenic effects, rather than acting through the agency of protein expression or regulation of protein expression. In some embodiments, the disease or disorder is mediated by repeat RNA, such as those described above or in Tables 1 and 2. In some embodiments, the disease or disorder is a repeat expansion disease in which the repeat resides in the coding regions of mRNA. In some embodiments, the disease or disorder is a repeat expansion disease in which the repeat resides in the noncoding regions of mRNA. In some embodiments, the disease or disorder is selected from Huntington's disease (HD), dentatorubral-pallidoluysian atrophy (DRPLA), spinal-bulbar muscular atrophy (SBMA), or a spinocerebellar ataxia (SCA) selected from SCA1, SCA2, SCA3, SCA6, SCAT, or SCA17. In some embodiments, the disease or disorder is selected from Fragile X Syndrome, myotonic dystrophy (DM1 or dystrophia myotonica), Friedreich's Ataxia (FRDA), a spinocerebellar ataxia (SCA) selected from SCAB, SCA10, or SCA12, or C9FTD (amyotrophic lateral sclerosis or ALS).

In some embodiments, the disease is amyotrophic lateral sclerosis (ALS), Huntington's disease (HD), frontotemporal dementia (FTD), myotonic dystrophy (DM1 or dystrophia myotonica), or Fragile X Syndrome.

In some embodiments, the present invention provides a method of treating a disease or disorder mediated by repeat RNA, comprising the step of administering to a patient in need thereof a compound of the present invention. Such compounds are described in detail herein.

Also provided is a method of producing a small molecule that modulates the activity of a target repeat expansion RNA to treat a disease or disorder, comprising the steps of: screening one or more disclosed compounds for binding to the target repeat expansion RNA; and analyzing the results by an RNA binding assay disclosed herein. In some embodiments, the repeat expansion RNA causes a disease or disorder selected from HD, DRPLA, SBMA, SCA1, SCA2, SCA3, SCA6, SCAT, or SCA17. In some embodiments, the disease or disorder is selected from Fragile X Syndrome, DM1, FRDA, SCAB, SCA10, SCA12, or C9FTD.

Other Target RNAs and Diseases/Conditions

An association is known to exist between a large number of additional RNAs and diseases or conditions, some of which are shown below in Table 3. Accordingly, in some embodiments of the methods described above, the target RNA is selected from those in Table 3. In some embodiments, the disease or disorder is selected from those in Table 3.

TABLE 3

Target RNAs and Associated Diseases/Conditions

| GENE | CLASS | UP/DOWN REGULATED? | TA | INDICATION(S) |
|---|---|---|---|---|
| MYC | TF | down | Onco | cancer |
| STAT3 | TF | down | Onco | cancer |
| C9orf72 | TRED | down | Neuro | ALS, FTD |
| FOXP3 | TF | down | I&I, I-O | immuno-oncology; I&I |
| MIR155 | miRNA | down | Onco, I&I, Neuro | ALS, fibrosis, cancer |
| APOC3 | apoprotein | down | Cardio | chylomicronemia syndrome |
| JUN | TF | down | I&I | I&I |
| RSV | genomic | down | Viral | RSV |
| KRAS | TF | down | Onco | cancer |
| BCL2L1 | IAP | down | Onco | cancer |
| HIF1A | TF | down | Onco | cancer |
| SMARCA2 | helicase | down | Onco | cancer |
| SNCA | | down | Neuro | PD |
| CCNE1 | cyclin | down | Onco | cancer |
| FOXM1 | TA | down | Onco | cancer |
| MYB | TF | down | Onco | cancer |
| PTPN11 | phosphatase | down | Onco, I&I | cancer, SLE |
| CD40LG | TNF | down | I&I | inflammation |
| NFE2L2 | TF | up | I&I | multiple sclerosis |
| RORC | NHR | down | I&I | I&I |
| ZIKV | genomic | down | Viral | ZIKV |
| DENV | genomic | down | Viral | DENV |
| AR | NHR | down | Onco | prostate cancer |
| ASGR1 | | down | Cardio | CVD |
| BCL2 | IAP | down | Onco | cancer |
| BDNF | NF | up | Neuro | Huntington's Disease |
| BRD4 | epi | down | Onco | cancer |
| CD40 | TNF | down | I&I | immuno-oncology |
| CD47 | Ig | down | I&I, I-O | immuno-oncology |
| CTLA4 | Ig | down | I&I, I-O | immuno-oncology; I&I |
| CTNNB1 | adhesion | down | Onco | cancer |
| DMPK | TRED | down | Neuro | Myotonic dystrophy type 1 (DM1) |
| EIF4E | IF | down | Onco | cancer |
| FOXA1 | TA | down | Onco | cancer |
| GATA3 | TF | down | Onco | cancer |
| IKZF1 | TF | down | Onco | cancer |
| IKZF3 | TF | down | Onco | cancer |
| IL17A | IL | down | I&I | inflammatory & autoimmune diseases |
| IL23A | IL | down | I&I | inflammatory & autoimmune diseases |
| IL6 | IL | down | I&I | rheumatoid arthritis |
| ITGA1 | integrin | down | I&I | RA |
| ITGA5 | integrin | down | Onco | solid tumors |
| ITGAE | integrin | down | I&I | UC, Crohns |
| ITGB2, ITGAL | integrin | down | I&I | psoriasis |
| ITGB7 | integrin | down | I&I | UC, Crohns |
| MAPT | cytoskeleton | down | Neuro | Alzheimer's disease |
| MAX | TF | down | Onco | cancer |
| MDM2 | E3 | down | Onco | cancer |
| MDM4 | E3 | down | Onco | cancer |
| MIR21 | miRNA | down | Onco | cancer |
| NR4A2 | TF | down | Neuro | PD |
| PTEN | phosphatase | up | Onco | cancer |
| PTPN1 | phosphatase | down | Metab | Type 2 diabetes |
| RUNX1 | TF | down | Onco | cancer |
| SIRPA | glycoprotein | down | I&I, I-O | immuno-oncology |
| SMAD7 | TGF | down | I&I | IBD |

TABLE 3-continued

Target RNAs and Associated Diseases/Conditions

| GENE | CLASS | UP/DOWN REGULATED? | TA | INDICATION(S) |
|---|---|---|---|---|
| SOX2 | TF | down | Onco | cancer |
| STAT5A | TF | down | Onco | cancer |
| TERT | telomerase | down | Onco | cancer |
| TGFB1 | TGF | down | Fibrosis | fibrosis |
| TNF | TNF | down | I&I | inflammatory disease |
| TNFRSF11A | TNF | down | | osteoporosis |
| TNFSF11 | TNF | down | | osteoporosis |
| TWIST1 | TF | down | Onco | cancer |
| WNT1 | | | Onco | cancer |
| HepB | | down | Viral | HepB |
| influenza | | down | Viral | influenza |
| DGAT2 | transferase | down | | NASH |
| DNMT3 | DNMT | down | Onco | cancer |
| ERBB3 | pseudokinase | down | Onco | cancer |
| FBXW7 | F-box (E3) | down | Onco | cancer |
| FMR1 | TRED | down | Neuro | Fragile × Syndrome; FTXAS |
| FOS | TF | down | | |
| FXN | TRED | down | Neuro | Friedreich's Ataxia |
| IRAK3 | pseudokinase | down | I&I | I&I |
| MECP2 | TF | up/down | Genetic Dz | Rett Syndrome |
| MIR17HG | miRNA | down | Onco | cancer |
| NF1 | | down | | neurofibromatosis |
| ORAI1 | ion channel | down | I&I | I&I |
| PCSK9 | convertase | down | Cardio | hypercholesterolemia |
| PSMB8 | protease | down | I&I | I&I |
| SKP2 | F-box (E3) | down | Onco | cancer |
| USP1 | protease | down | Onco | cancer |
| USP7 | protease | down | Onco | cancer |
| HIF1A | TF | up | I&I | wound repair & regeneration |
| HOTAIR | IncRNA | down | Onco | cancer |
| IKBKG | | down | I&I | I&I |
| IKK2 | kinase | down | I&I | I&I |
| MALAT1 | IncRNA | down | Onco | cancer |
| PRMT5 | KMT | down | Onco | cancer |
| BCL6 | IAP | down | Onco | cancer |
| GRN | | down | Neuro | neurological diseases |
| ABCA1 | transporter | | Cardio | coronary artery disease |
| ABCB11 | transporter | | | Primary Biliary Sclerosis |
| ABCB4 | transporter | | | Primary Biliary Sclerosis |
| ABCG5 | transporter | | Cardio | coronary artery disease |
| ABCG8 | transporter | | Cardio | coronary artery disease |
| ADIPOQ | hormone | up | Metab | diabetes; obesity; metabolic syndrome |
| APOA1 | | | Cardio | hypercholesterolemia |
| APOA5 | | | Cardio | hypercholesterolemia |
| ATPA2 | Ca ATPase | up | Genetic Dz | congestive heart failure |
| ATXN1 | TRED | | Neuro | spinocerebellar ataxia 1 |
| ATXN10 | TRED | down | Neuro | spinocerebellar ataxia 10 |
| ATXN2 | TRED | | Neuro | spinocerebellar ataxia 2 |
| ATXN3 | TRED | | Neuro | spinocerebellar ataxia 3 |
| ATXN7 | TRED | | Neuro | spinocerebellar ataxia 7 |
| ATXN8 | TRED | | Neuro | spinocerebellar ataxia 8 |
| BACE1 | protease | down | Neuro | Alzheimer's disease |
| BIRC2 | IAP | down | Onco | cancer |
| BIRC3 | IAP | down | Onco | cancer |
| BIRC5 | IAP | down | Onco | cancer |
| BRCA1 | DNA repair | up | Onco | cancer |
| CACNA1A | ion channel | | Neuro | episodic ataxia type 2 |
| CD247 | TCR | | I&I | I&I |
| CD274 | | down | I-O | immuno-oncology |
| CETP | transfer | down | | cardiovascular |
| CFH | complement | | | macular degeneration |
| CFTR | ion channel | up | Genetic Dz | Cystic Fibrosis |
| CNBP | TRED | down | Neuro | Myotonic dystrophy type 2 (DM2) |
| CNTF | NF | | | macular degeneration |
| DIO2 | deiodinase | | Metab | dyslipidemia |
| DMD | cytoskeleton | | Neuro | Duchenne Muscular Dystrophy; Becker's MD |
| F7 | protease | up | Hematology | hemophilia |
| F8 | protease | up | Hematology | hemophilia |
| F9 | protease | up | Hematology | hemophilia |
| FGF3 | | down | Genetic Dz | achondroplasia |
| HAMP | | down | Genetic Dz | thalassemia; hereditary hemochromatosis |

TABLE 3-continued

Target RNAs and Associated Diseases/Conditions

| GENE | CLASS | UP/DOWN REGULATED? | TA | INDICATION(S) |
|---|---|---|---|---|
| HAVCR2 | | down | I&I, I-O | inflammatory diseases; immuno-oncology |
| HBG1, HBG2 | hemoglobin | up | Hematology | sickle cell anemia; beta-thalassemia |
| HIF1AN | | | Onco | cancer |
| IDH1 | dehydrogenase | down | Onco | cancer |
| IL1 | IL | down | I&I | rheumatoid arthritis |
| IRAK4 | kinase | down | I&I | I&I |
| IRF5 | TF | | I-O | immuno-oncology |
| LAMA1 | ECM | | Genetic Dz | Merosin-deficient congenital MD (MDCA1) |
| LARGE1 | | | Genetic Dz | Muscular Dystroglycanopathy Type B, 6 |
| LINGO1 | | down | Neuro | neurodegeneration |
| MBNL1 | splice factor | | Neuro | Myotonic Dystrophy |
| MCL1 | IAP | down | Onco | cancer |
| MERTK | kinase | | I&I | Lupus |
| METAP2 | peptidase | down | Onco, I&I | cancer, obesity, autoimmune |
| MTOR | kinase | | Onco | cancer |
| NANOG | TF | | Neuro | neurological diseases |
| NF2 | | | | neurofibromatosis |
| NSD-3 | KMT | down | Onco | cancer |
| PAH | hydroxylase | | Genetic Dz | phenylketonuria |
| PCSK6 | convertase | up | Cardio | hypertension |
| PDCD1 | | | I-O | immuno-oncology |
| PDK1, PDK2 | kinase | | | polycystic kidney disease |
| PDX1 | TF | | Metab | diabetes |
| PPARGC1A | PPAR | | Neuro | Neurological diseases; obesity |
| PRKAA1 | kinase | | Metab | diabetes |
| PRKAB1 | kinase | | Metab | diabetes |
| PRKAG1 | kinase | | Metab | diabetes |
| RTN4 | | down | Neuro | neurodegeneration |
| RTN4R | | down | Neuro | neurodegeneration |
| SCARB1 | HDL receptor | | Cardio | coronary artery disease |
| SIRT6 | KDAC | down | Onco | cancer |
| SMN2 | | up | Neuro | Spinal Muscular Atrophy |
| SMURF2 | | down | | |
| SORT1 | glycoprotein | | Cardio | coronary artery disease |
| SSPN | cytoskeleton | | Genetic Dz | Duchenne's MD |
| TBX21 | | | I-O | immuno-oncology |
| THRB | NHR | | | dyslipidemia; NASH; NAFLD |
| TNFAIP3 | | | I&I | inflammatory dz; liver failure; liver transplant |
| TRIB1 | pseudokinase | | Cardio | coronary artery disease |
| TTR | | down | Genetic Dz | amyloidosis |
| UTRN | cytoskeleton | | Genetic Dz | Duchenne Muscular Dystrophy |
| XIAP | IAP | down | Onco | cancer |
| RAGE | | | | |
| ANGPTL3 | | | | |

TABLE 4

Additional Target RNAs

| GENE | COMMON NAME | CLASS | UP/DOWN REGULATED? | TA | INDICATION(S) |
|---|---|---|---|---|---|
| CTSL | cathepsin L | protease | up | neuro | PD |
| AR | AR-V7 | NHR | down | cancer | CRPC |
| JMJD6 | JMJD6 | HDM | down | cancer | GBM |
| DNMT1 | DNMT1 | Me-transferase | down | cancer | GBM |
| ASGR1 | ASGR1 | ASG receptor | down | CVD | CVD |
| NAMPT | NAMPT | transferase | down | cancer | various |
| | IRE | | | | |

TABLE 4-continued

| Additional Target RNAs | | | | | |
|---|---|---|---|---|---|
| GENE | COMMON NAME | CLASS | UP/DOWN REGULATED? | TA | INDICATION(S) |
| ARID1B | ARID1B | | | | |
| SOX10 | SOX10 | | | | |
| HNF1B | TCF2 | | | | |
| PTPN2 | PTPN2 | | | | |
| NLGN3 | NLGN3 | | | | |
| | ETS | | | | |

2. Compounds and Uses Thereof

It has now been found that compounds of this invention, and pharmaceutically acceptable compositions thereof, are effective as agents for use in drug discovery and for preparing nucleic acid conjugates that are useful in drug discovery. For example, compounds of the present invention, and pharmaceutical compositions thereof, are useful in determining the location and/or structure of an active site or allosteric sites and/or the tertiary structure of a target RNA.

In one aspect, disclosed compounds are useful as diagnostic or assay reagents. In some embodiments, the present invention provides a method of determining the three-dimensional structure, binding site of a ligand of interest, or accessibility of a nucleotide in a target nucleic acid, comprising: contacting the target nucleic acid with a disclosed compound; irradiating the compound; determining whether covalent modification of a nucleotide of the nucleic acid has occurred; and optionally deriving the pattern of nucleotide modification, the three-dimensional structure, ligand binding site, or other structural information about the nucleic acid.

In another aspect, the present invention provides a method of preparing a nucleic acid conjugate, comprising: contacting a target nucleic acid with a disclosed compound; irradiating the compound; and optionally isolating the resulting nucleic acid conjugate by an affinity assay, pull-down method, or other means known in the art. Such nucleic acid conjugates are useful for determining structural information about the target nucleic acid comprised in the conjugate that allows one of ordinary skill to design small molecule drugs that bind to the target nucleic acid in vivo to treat a disease, disorder, or condition, such as those disclosed herein. In some embodiments, the nucleic acid is a RNA, such as a disease-causing RNA as described herein.

In another aspect, the present invention provides a method of assessing selectivity across a transcriptome for a drug candidate, comprising contacting a biological sample comprising two or more RNA transcripts with a drug candidate comprising a disclosed photoactivatable group tethered to the drug candidate; irradiating the drug candidate; and determining covalent modification of an RNA transcript.

In another aspect, the present invention provides a method of determining target occupancy in cells of a drug candidate, comprising contacting a biological sample comprising a target RNA with a disclosed compound or drug candidate comprising a disclosed photoactivatable group tethered to the drug candidate; irradiating the compound or drug candidate; and determining covalent modification of the target RNA. In some embodiments, the method confirms target engagement and correlates binding with cellular biology.

In some embodiments, the method enables assembling a binding site map by identifying subsite binding to explicate the biochemical mode of action.

In some embodiments, the method further enables relating target engagement to target mutations and cell function. This is useful for understanding the molecular mechanism of drug candidates in cells.

In another aspect, the present invention provides a method of determining the presence of a RNA binding protein (RBP) that is associated with a target RNA comprising: contacting the target RNA with a disclosed compound; irradiating the compound; and determining whether covalent modification of an amino acid of the RBP has occurred.

In some embodiments, the present invention provides a compound comprising:

(a) a small molecule ligand that binds selectively to one or more binding sites on a target RNA;
(b) a photoactivatable group (or "warhead") that is covalently conjugated to the small molecule ligand and that forms a covalent bond to the target RNA upon irradiation with visible light or ultraviolet light;
(c) optionally, a click-ready group;
(d) optionally, a pull-down group; and
(e) optionally, one or two tethering groups that covalently link the small molecule ligand and the photoactivatable group and, optionally, the click-ready group.

Without wishing to be bound by any particular theory, it is believed that compounds of the present invention bind selectively to one or more active or allosteric sites on a target RNA, or other sites determined by binding interactions between the small molecule ligand and the structure of the target RNA; upon irradiation, covalently modify one or more positions of the target RNA, such as a C8 carbon of an adenosine or guanosine nucleotide or a 2'-OH group of the target RNA; and may subsequently be used to identify the active site or other binding sites by sequencing or other analysis of the distribution of modified nucleotides because the pattern of modification will be constrained by the length and conformation of the tether that connects the ligand with the RNA warhead. The target RNA may be inside a cell, in a cell lysate, or in isolated form prior to contacting the compound. Screening of libraries of disclosed compounds will identify highly potent small-molecule modulators of the activity of the target RNA. It is understood that such small molecules identified by such screening may be used as modulators of a target RNA to treat, prevent, or ameliorate a disease or condition in a patient in need thereof.

In one aspect, the present invention provides a compound of the general Formula I:

I

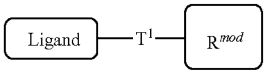

or a pharmaceutically acceptable salt thereof; wherein:

Ligand is a small molecule RNA binder;

$T^1$ is a bivalent tethering group; and $R^{mod}$ is a photoactivatable group; wherein each variable is as defined below.

In another aspect, the present invention provides a compound of the general Formula II:

II

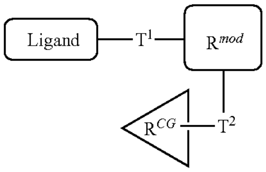

or a pharmaceutically acceptable salt thereof; wherein:

Ligand is a small molecule RNA binder;

$T^1$ is a bivalent tethering group;

$T^2$ is a covalent bond or a bivalent tethering group;

$R^{mod}$ is a photoactivatable group; and

G is a click-ready group or a pull-down group.

In another aspect, the present invention provides a compound of the general Formula III:

III

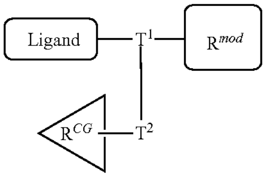

or a pharmaceutically acceptable salt thereof; wherein:

Ligand is a small molecule RNA binder;

$T^1$ is a trivalent tethering group;

$T^2$ is a bivalent tethering group;

$R^{mod}$ is a photoactivatable group; and $R^{CG}$ is a click-ready group or a pull-down group; wherein each variable is as defined below.

In another aspect, the present invention provides a compound of the general formula II-a:

II-a

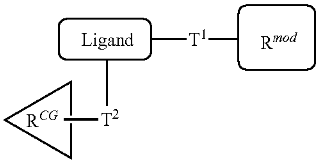

or a pharmaceutically acceptable salt thereof; wherein:

Ligand is a small molecule RNA binder;

$T^1$ is a covalent bond or a bivalent tethering group;

$T^2$ is a covalent bond or a bivalent tethering group;

$R^{mod}$ is a photoactivatable group; and $R^{CG}$ is a click-ready group or a pull-down group; wherein each variable is as defined below.

In another aspect, the present invention provides a compound of the general formulae II-b or II-c:

II-b

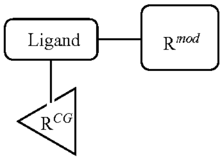

II-c

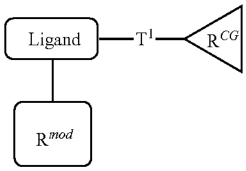

or a pharmaceutically acceptable salt thereof; wherein:

Ligand is a small molecule RNA binder;

$T^1$ is a bivalent tethering group;

$R^{mod}$ is a photoactivatable group; and $R^{CG}$ is a click-ready group or a pull-down group; wherein each variable is as defined below.

In another aspect, the present invention provides a RNA conjugate comprising a target RNA and a compound of any of Formulae I, II, II-a, or III, wherein R'd forms a covalent bond to the target RNA after irradiation with visible light or ultraviolet light.

In some embodiments, the present invention provides a RNA conjugate of Formula IV:

IV

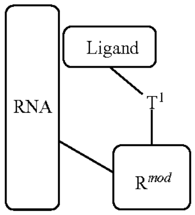

wherein Ligand is a small molecule that binds to a target RNA;

RNA represents the target RNA;

$T^1$ is a bivalent tethering group; and $R^{mod}$ is a photoactivatable group;

wherein each variable is as defined below.

In some embodiments, the present invention provides a RNA conjugate of Formula V:

V

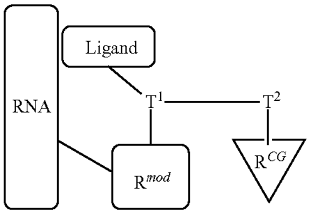

wherein Ligand is a small molecule that binds to a target RNA;

RNA represents the target RNA;

$T^1$ is a trivalent tethering group;

$T^2$ is a bivalent tethering group;

$R^{mod}$ is a photoactivatable group; and $R^{CG}$ is a click-ready group or a pull-down group;

wherein each variable is as defined below.

In some embodiments, the present invention provides a RNA conjugate of Formula VI:

VI

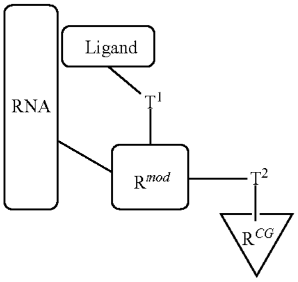

wherein Ligand is a small molecule that binds to a target RNA;

RNA represents the target RNA;

$T^1$ is a bivalent tethering group;

$T^2$ is a covalent bond or a bivalent tethering group;

$R^{mod}$ is a photoactivatable group; and $R^{CG}$ is a click-ready group or a pull-down group;

wherein each variable is as defined below.

In some embodiments, the present invention provides a RNA conjugate of Formula VI-a:

VI-a

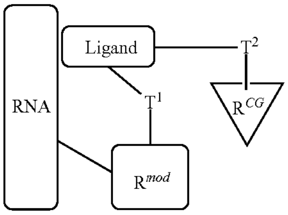

wherein Ligand is a small molecule that binds to a target RNA;

RNA represents the target RNA;

$T^1$ is a bivalent tethering group;

$T^2$ is a covalent bond or a bivalent tethering group;

$R^{mod}$ is a photoactivatable group; and $R^{CG}$ is a click-ready group or a pull-down group;

wherein each variable is as defined below.

In another aspect, the present invention provides a conjugate comprising a target RNA, a compound of Formulae II or III, and a pull-down group, wherein $R^{mod}$ forms a covalent bond to the target RNA.

In some embodiments, the present invention provides a RNA conjugate of Formula VII:

VII

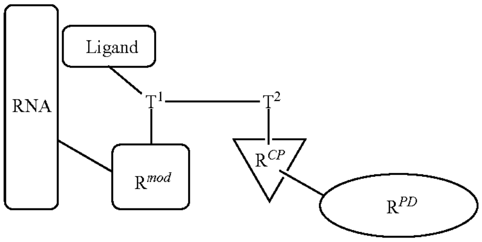

wherein Ligand is a small molecule that binds to a target RNA;

RNA represents the target RNA;

$T^1$ is a trivalent tethering group;

$T^2$ is a bivalent tethering group;

$R^{mod}$ is a photoactivatable group;

$R^{CP}$ is a reaction product resulting from a click reaction between a click-ready group and an appropriate functional group on $R^{PD}$; and $R^{PD}$ is a pull-down group;

wherein each variable is as defined below. In some embodiments, $R^{CP}$ is

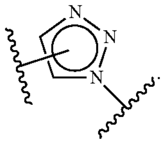

In some embodiments, the present invention provides a RNA conjugate of Formula VIII:

VIII

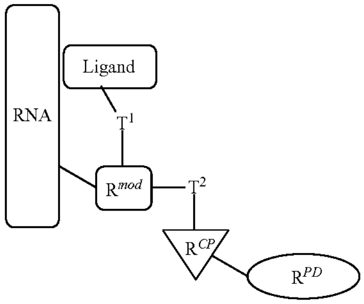

wherein Ligand is a small molecule that binds to a target RNA;

RNA represents the target RNA;

$T^1$ is a bivalent tethering group;

$T^2$ is a covalent bond or a bivalent tethering group;

$R^{mod}$ is a photoactivatable group;

$R^{CP}$ is a reaction product resulting from a click reaction between a click-ready group and an appropriate functional group on $R^{PD}$; and $R^{PD}$ is a pull-down group;

wherein each variable is as defined below. In some embodiments, $R^{CP}$ is

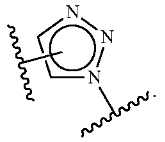

In some embodiments, the present invention provides a RNA conjugate of Formula VIII-a:

VIII-a

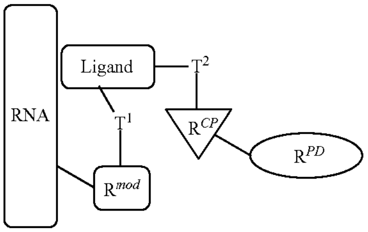

wherein Ligand is a small molecule that binds to a target RNA;

RNA represents the target RNA;

$T^1$ is a bivalent tethering group;

$T^2$ is a covalent bond or a bivalent tethering group;

$R^{mod}$ is a photoactivatable group;

$R^{CP}$ is a reaction product resulting from a click reaction between a click-ready group and an appropriate functional group on $R^{PD}$; and $R^{PD}$ is a pull-down group;

wherein each variable is as defined below. In some embodiments, $R^{CP}$ is

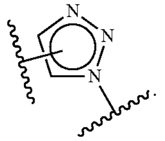

In one aspect, the present invention provides a compound of Formula X-a:

X-a

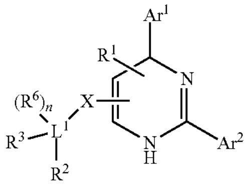

or a tautomer or pharmaceutically acceptable salt thereof, wherein:

$Ar^1$ is an optionally substituted phenyl or optionally substituted 5-6 membered monocyclic heteroaromatic ring having 1-4 heteroatoms independently selected from nitrogen, oxygen, or sulfur;

$Ar^2$ is an optionally substituted 5-6 membered monocyclic heteroaromatic ring having 1-4 heteroatoms independently selected from nitrogen, oxygen, or sulfur, or an optionally substituted 8-10 membered bicyclic heteroaromatic ring having 1-5 heteroatoms independently selected from nitrogen, oxygen, or sulfur;

X is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;

$R^1$ is selected from —C(O)$R^6$, —$CO_2$R, —C(O)$NR_2$, —$C_{1-6}$ aliphatic, —CN, —$(CH_2)_{1-3}$OR, —$(CH_2)_{1-3}$NHR, —N(R)C(O)O$R^6$, —N($R^6$)C(O)R, —OC(O)R, —OR, —NH$R^6$, or —N(R)C(O)NHR;

$R^2$ is a photoactivatable group that optionally comprises a click-ready group if $R^3$ is absent;

$R^3$ is absent or is a click-ready group or a pull-down group;

each $R^6$ is independently hydrogen or $C_{1-6}$ alkyl optionally substituted with 1, 2, 3, 4, 5, or 6 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^1$ is a $C_{1-20}$ bivalent, trivalent, or tetravalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur; and n is 0 or 1.

In another aspect, the present invention provides a compound of Formula X-b:

X-b

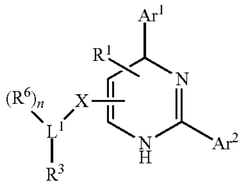

or a tautomer or pharmaceutically acceptable salt thereof, wherein:

$Ar^1$ is an optionally substituted phenyl or optionally substituted 5-6 membered monocyclic heteroaromatic ring having 1-4 heteroatoms independently selected from nitrogen, oxygen, or sulfur;

$Ar^2$ is an optionally substituted 5-6 membered monocyclic heteroaromatic ring having 1-4 heteroatoms independently selected from nitrogen, oxygen, or sulfur, or an optionally substituted 8-10 membered bicyclic heteroaromatic ring having 1-5 heteroatoms independently selected from nitrogen, oxygen, or sulfur;

wherein one of $Ar^1$ or $Ar^2$ is substituted with one $R^2$;

X is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;

$R^1$ is selected from —C(O)$R^6$, —$CO_2$R, —C(O)$NR_2$, —$C_{1-6}$ aliphatic, —CN, —$(CH_2)_{1-3}$ OR, —$(CH_2)_{1-3}$ NHR, —N(R)C(O)$OR^6$, —N($R^6$)C(O)R, —OC(O)R, —OR, —$NHR^6$, or —N(R)C(O)NHR;

$R^2$ is a photoactivatable group that optionally comprises a click-ready group if $R^3$ is absent;

$R^3$ is absent or is a click-ready group or a pull-down group;

each $R^6$ is independently hydrogen or $C_{1-6}$ alkyl optionally substituted with 1, 2, 3, 4, 5, or 6 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^1$ is a $C_{1-20}$ bivalent or trivalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)$NSO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur; and n is 0 or 1.

As defined generally above, $Ar^1$ is an optionally substituted phenyl or optionally substituted 5-6 membered monocyclic heteroaromatic ring having 1-4 heteroatoms independently selected from nitrogen, oxygen, or sulfur.

In some embodiments, $Ar^1$ is an optionally substituted phenyl. In some embodiments, $Ar^1$ is an optionally substituted 5-6 membered monocyclic heteroaromatic ring having 1-4 heteroatoms independently selected from nitrogen, oxygen, or sulfur.

In some embodiments, $Ar^1$ is phenyl optionally substituted with 1, 2, 3, or 4 substituents selected from halogen, —$C_{1-6}$ aliphatic, —CN, —OR, —$NR_2$, —$CO_2$R, —C(O)R, —SR, or —C(O)$NR_2$. In some embodiments, the optional substituents are selected from halogen, —CN, —$C_{1-6}$ alkyl, or —OMe. In some embodiments, the optional substituents are halogen. In some embodiments, 1 or 2 substituents are present. In some embodiments, $Ar^1$ is selected from those depicted in Table 5, below.

As defined generally above, $Ar^2$ is an optionally substituted 5-6 membered monocyclic heteroaromatic ring having 1-4 heteroatoms independently selected from nitrogen, oxygen, or sulfur, or an optionally substituted 8-10 membered bicyclic heteroaromatic ring having 1-5 heteroatoms independently selected from nitrogen, oxygen, or sulfur.

In some embodiments, $Ar^2$ is an optionally substituted 5-6 membered monocyclic heteroaromatic ring having 1-4 heteroatoms independently selected from nitrogen, oxygen, or sulfur. In some embodiments, $Ar^2$ is an optionally substituted 8-10 membered bicyclic heteroaromatic ring having 1-5 heteroatoms independently selected from nitrogen, oxygen, or sulfur.

In some embodiments, $Ar^2$ is an optionally substituted pyridinyl, pyrimidinyl, imidazolyl, or pyrrolyl. In some embodiments, $Ar^2$ is an optionally substituted pyridinyl. In some embodiments, $Ar^2$ is pyridinyl. In some embodiments, $Ar^2$ is 3- or 4-pyridinyl. In some embodiments, $Ar^2$ is selected from those depicted in Table 5, below.

As defined generally above, X is a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—.

In some embodiments, X is —$CH_2$—, —O—, —$NR^6$—, —S—, —C(O)—, —$CO_2$— —CS—, —C($NR^6$)—, —S(O)—, or —$S(O)_2$—. In some embodiments, X is a $C_2$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—. In some embodiments, X is a $C_3$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—.

In some embodiments, X is selected from —$CH_2O$—, $CH_2C(O)$—, —$C(O)CH_2$—, —$CH_2C(O)O$—, —C(O)$CH_2O$—, —C(O)O—, —C(O)N($R^6$)—, —$CH_2N(R^6)$—, or —N($R^6$)C(O)—. In some embodiments, X is —$OCH_2$— or —$CH_2O$—. In some embodiments, X is selected from those depicted in Table 5, below.

As defined generally above, $R^1$ is selected from —C(O)$R^6$, —$CO_2R$, —C(O)$NR_2$, —$C_{1-6}$ aliphatic, —CN, —$(CH_2)_{1-3}OR$, —$(CH_2)_{1-3}NHR$, —N(R)C(O)$OR^6$, —N($R^6$)C(O)R, —OC(O)R, —OR, —$NHR^6$, or —N(R)C(O)NHR.

In some embodiments, $R^1$ is —C(O)$R^6$. In some embodiments, $R^1$ is —$CO_2R$. In some embodiments, $R^1$ is —C(O)$NR_2$. In some embodiments, $R^1$ is —$C_{1-6}$ aliphatic. In some embodiments, le is —CN. In some embodiments, $R^1$ is —$(CH_2)_{1-3}OR$. In some embodiments, $R^1$ is —$(CH_2)_{1-3}NHR$. In some embodiments, $R^1$ is —N(R)C(O)$OR^6$. In some embodiments, $R^1$ is —N($R^6$)C(O)R. In some embodiments, $R^1$ is —OC(O)R. In some embodiments, $R^1$ is —OR. In some embodiments, $R^1$ is —$NHR^6$. In some embodiments, $R^1$ is —N(R)C(O)NUR. In some embodiments, $R^1$ is selected from those depicted in Table 5, below.

As defined generally above, $R^2$ is a photoactivatable group that optionally comprises a click-ready group if $R^3$ is absent. In some embodiments, $R^2$ is a photoactivatable group. In some embodiments, $R^2$ is a photoactivatable group further substituted with a click-ready group.

In some embodiments, $R^2$ is a functional group that generates a radical, an aryl or heteroaryl carbocation, a nitrene, or a carbene intermediate upon irradiation with ultraviolet (UV) radiation, and that is optionally substituted with a click-ready group or pull-down group if $R^3$ is absent. In some embodiments, $R^2$ is an optionally substituted phenyl or 8-10 membered bicyclic aromatic carbocyclic azide or 5-8 membered heteroaryl or 8-10 membered bicyclic heteroaryl azide, optionally substituted benzoyl azide or 5-8 membered heteroaroyl azide or 8-10 membered heteroaroyl azide wherein 1-3 atoms of the ring atoms are selected from nitrogen, sulfur, or oxygen, optionally substituted phenyl or 8-10 membered bicyclic aromatic carbocyclic diazonium salt, optionally substituted 5-8 membered heteroaryl or 8-10 membered bicyclic heteroaryl diazonium salt wherein 1-3 atoms of the ring atoms are selected from nitrogen, sulfur, or oxygen, optionally substituted $C_{2-6}$ aliphatic diazo functional group, optionally substituted $C_{2-6}$ aliphatic diazirine, or optionally substituted diphenyl or 8-10-membered diheteroaryl ketone wherein 1-3 atoms of the ring atoms are selected from nitrogen, sulfur, or oxygen, optionally substituted dihydropyrene, optionally substituted spirooxazine, optionally substituted anthracene, optionally substituted fulgide, optionally substituted spiropyran, optionally substituted α-pyrone or optionally substituted pyrimidone; and which is optionally substituted with a click-ready group or pull-down group. In some embodiments, the click-ready group is a $C_{1-6}$ alkyl azide or alkyne. In some embodiments, $R^2$ is selected from

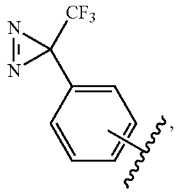,
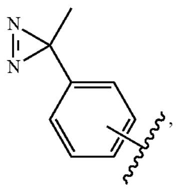,
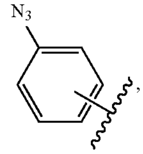,
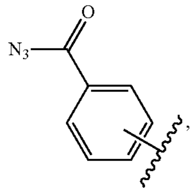,
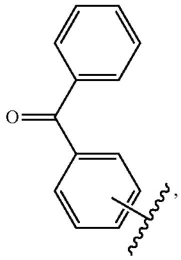,
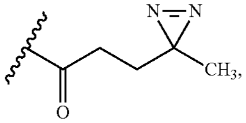,
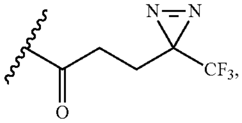,
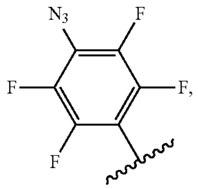
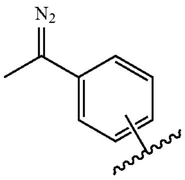,
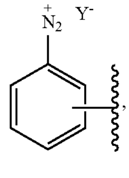,
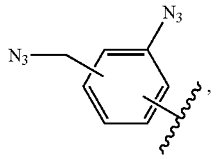,
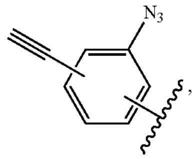,
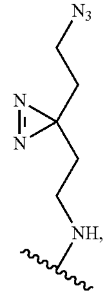
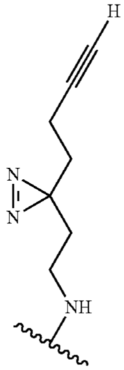,
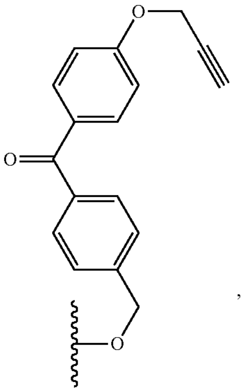, or
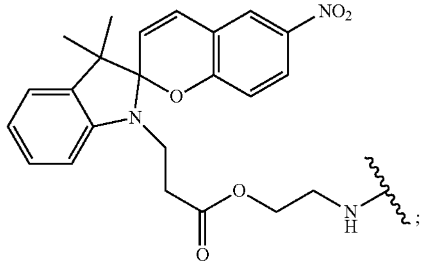;

wherein $Y^+$ is a pharmaceutically acceptable anion.

In some embodiments, $R^2$ is selected from those depicted in Table 5, below.

As defined generally above, $R^3$ is absent or is a click-ready group or a pull-down group. In some embodiments, $R^3$ is absent. In some embodiments, $R^3$ is a click-ready group. In some embodiments, $R^3$ is a pull-down group. In some embodiments, $R^3$ is a $C_{1-6}$ alkyl azide, $C_{1-6}$ alkyne, or biotin.

In some embodiments, $R^3$ is selected from those depicted in Table 5, below.

As defined generally above, each $R^6$ is independently hydrogen or $C_{1-6}$ alkyl optionally substituted with 1, 2, 3, 4, 5, or 6 deuterium or halogen atoms.

In some embodiments, $R^6$ is hydrogen. In some embodiments, $R^6$ is $C_{1-6}$ alkyl optionally substituted with 1, 2, 3, 4, 5, or 6 deuterium or halogen atoms.

In some embodiments, $R^6$ is $C_{1-3}$ alkyl optionally substituted with 1, 2, or 3 halogen atoms.

In some embodiments, $R^6$ is selected from those depicted in Table 5, below.

As defined generally above, $L^1$ is a $C_{1-20}$ bivalent or trivalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—.

In some embodiments, $L^1$ is a $C_{1-10}$ bivalent or trivalent straight or branched hydrocarbon chain wherein 1, 2, 3, 4, or 5 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-5 of the methylene units of the chain are independently and optionally replaced with —$OCH_2CH_2$—. In some embodiments, $L^1$ comprises 1-3 natural amino acids. In some embodiments, the amino acids are selected from proline, lysine, glycine, or alanine. In some embodiments, $L^1$ comprises 1-2 -Cy- groups selected from 1,2,3-triazolylene or 1,2,4-triazolylene. In some embodiments, $L^1$ comprises 1-10, 1-8, 1-6, 1-4, 1-3, 1-2, 1, 2, or 3 —$OCH_2CH_2$— units.

In some embodiments, $L^1$ is selected from those depicted in Table 5, below.

As defined generally above, each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur.

In some embodiments, -Cy- is a bivalent optionally substituted 3-8 membered saturated or partially unsaturated monocyclic carbocyclic ring. In some embodiments, -Cy- is an optionally substituted phenylene. In some embodiments, -Cy- is an optionally substituted 4-8 membered saturated or partially unsaturated monocyclic heterocyclic ring having 1-3 heteroatoms independently selected from nitrogen, oxygen, or sulfur. In some embodiments, -Cy- is an optionally substituted 5-6 membered monocyclic heteroaromatic ring having 1-4 heteroatoms independently selected from nitrogen, oxygen, or sulfur. In some embodiments, -Cy- is an optionally substituted 8-10 membered bicyclic or bridged bicyclic saturated or partially unsaturated heterocyclic ring having 1-5 heteroatoms independently selected from nitrogen, oxygen, or sulfur. In some embodiments, -Cy- is an optionally substituted 8-10 membered bicyclic or bridged bicyclic heteroaromatic ring having 1-5 heteroatoms independently selected from nitrogen, oxygen, or sulfur.

In some embodiments, -Cy- is phenylene, pyridiylene, pyrimidinylene, 1,2,3-triazolylene, or 1,2,4-triazolylene.

In some embodiments, -Cy- is selected from those depicted in Table 5, below.

As defined generally above, n is 0 or 1.

In some embodiments, n is 0. In some embodiments, n is 1.

In another aspect, the present invention provides a compound of Formula XXV:

XXV

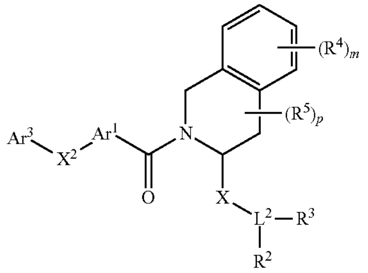

or a pharmaceutically acceptable salt thereof, wherein:

- $Ar^1$ is an optionally substituted phenyl or optionally substituted 5-6 membered monocyclic heteroaromatic ring having 1-4 heteroatoms independently selected from nitrogen, oxygen, or sulfur;
- $Ar^3$ is an optionally substituted phenyl, an optionally substituted 5-6 membered monocyclic heteroaromatic ring having 1-4 heteroatoms independently selected from nitrogen, oxygen, or sulfur, an optionally substituted 8-12 membered bicyclic aromatic ring, or an optionally substituted 8-10 membered bicyclic heteroaromatic ring having 1-5 heteroatoms independently selected from nitrogen, oxygen, or sulfur;
- X is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;
- $X^2$ is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;
- $R^2$ is a photoactivatable group that optionally comprises a click-ready group if $R^3$ is absent;
- $R^3$ is absent or is a click-ready group or a pull-down group;

each $R^4$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, or —N(R)$S(O)_2NR_2$; or two instances of $R^4$ may be taken together with the atoms to which they are attached to form a $C_{4-8}$ partially unsaturated carbocyclic ring;

each $R^5$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, or —N(R)$S(O)_2NR_2$; or two instances of $R_5$ may be taken together to form =O or =S;

each $R^6$ is independently hydrogen or $C_{1-6}$ alkyl optionally substituted with 1, 2, 3, 4, 5, or 6 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^2$ is a $C_{1-20}$ bivalent or trivalent, straight or branched, optionally substituted hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)$NSO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur;

m is 0, 1, 2, 3, or 4; and p is 0, 1, 2, 3, or 4.

In another aspect, the present invention provides a compound of Formula XXVI:

XXVI

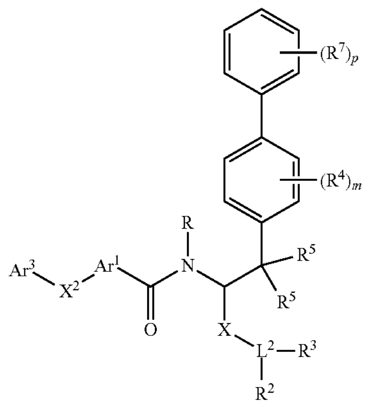

or a pharmaceutically acceptable salt thereof, wherein:

$Ar^1$ is an optionally substituted phenyl or optionally substituted 5-6 membered monocyclic heteroaromatic ring having 1-4 heteroatoms independently selected from nitrogen, oxygen, or sulfur;

$Ar^3$ is an optionally substituted phenyl, an optionally substituted 5-6 membered monocyclic heteroaromatic ring having 1-4 heteroatoms independently selected from nitrogen, oxygen, or sulfur, an optionally substituted 8-12 membered bicyclic aromatic ring, or an optionally substituted 8-10 membered bicyclic heteroaromatic ring having 1-5 heteroatoms independently selected from nitrogen, oxygen, or sulfur;

X is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;

$X^2$ is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—;

$R^2$ is a photoactivatable group that optionally comprises a click-ready group if $R^3$ is absent;

$R^3$ is absent or is a click-ready group or a pull-down group;

each $R^4$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, or —N(R)$S(O)_2NR_2$; or two instances of $R^4$ may be taken together with the atoms to which they are attached to form a $C_{4-8}$ partially unsaturated carbocyclic ring;

each $R^5$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, or —N(R)$S(O)_2NR_2$; or two instances of $R^5$ may be taken together to form =O or =S;

each $R^6$ is independently hydrogen or $C_{1-6}$ alkyl optionally substituted with 1, 2, 3, 4, 5, or 6 deuterium or halogen atoms;

each $R^7$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)

OR, —OC(O)R, —OC(O)$NR_2$, —N(R)C(O)OR, —N(R)C(O)R, —N(R)C(O)$NR_2$, —N(R)S$(O)_2$R, or —N(R)S$(O)_2NR_2$; or two instances of $R^4$ may be taken together with the atoms to which they are attached to form a $C_{4-8}$ partially unsaturated carbocyclic ring;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^2$ is a $C_{1-20}$ bivalent or trivalent, straight or branched, optionally substituted hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)$NSO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur;

m is 0, 1, 2, 3, or 4; and p is 0, 1, 2, 3, or 4.

As defined generally above, $Ar^1$ is an optionally substituted phenyl or optionally substituted 5-6 membered monocyclic heteroaromatic ring having 1-4 heteroatoms independently selected from nitrogen, oxygen, or sulfur.

In some embodiments, $Ar^1$ is an optionally substituted phenyl. In some embodiments, $Ar^1$ is an optionally substituted 5-6 membered monocyclic heteroaromatic ring having 1-4 heteroatoms independently selected from nitrogen, oxygen, or sulfur.

In some embodiments, $Ar^1$ is phenyl optionally substituted with 1, 2, 3, or 4 substituents selected from halogen, —$C_{1-6}$ aliphatic, —CN, —OR, —$NR_2$, —$CO_2$R, —C(O)R, —SR, or —C(O)$NR_2$. In some embodiments, the optional substituents are selected from halogen, —CN, —$C_{1-6}$ alkyl, or —OMe. In some embodiments, at least one of the optional substituents is $C_{1-6}$ alkyl. In some embodiments, 1, 2, or 3 substituents are present. In some embodiments, $Ar^1$ is selected from those depicted in Table 5, below.

As defined generally above, $Ar^3$ is an optionally substituted phenyl, an optionally substituted 5-6 membered monocyclic heteroaromatic ring having 1-4 heteroatoms independently selected from nitrogen, oxygen, or sulfur, an optionally substituted 8-12 membered bicyclic aromatic ring, or an optionally substituted 8-10 membered bicyclic heteroaromatic ring having 1-5 heteroatoms independently selected from nitrogen, oxygen, or sulfur.

In some embodiments, $Ar^3$ is an optionally substituted phenyl. In some embodiments, $Ar^3$ is an optionally substituted 5-6 membered monocyclic heteroaromatic ring having 1-4 heteroatoms independently selected from nitrogen, oxygen, or sulfur. In some embodiments, $Ar^3$ is an optionally substituted 8-12 membered bicyclic aromatic ring. In some embodiments, $Ar^3$ is an optionally substituted 8-10 membered bicyclic heteroaromatic ring having 1-5 heteroatoms independently selected from nitrogen, oxygen, or sulfur.

In some embodiments, $Ar^3$ is an optionally substituted pyridinyl, pyrimidinyl, imidazolyl, or pyrrolyl. In some embodiments, $Ar^3$ is an optionally substituted pyridinyl. In some embodiments, $Ar^3$ is pyridinyl. In some embodiments, the optional substituents are selected from halogen, —$C_{1-6}$ aliphatic, —CN, —OR, —$NR_2$, —$CO_2$R, —C(O)R, —SR, or —C(O)$NR_2$.

In some embodiments, $Ar^3$ is phenyl optionally substituted with 1, 2, 3, or 4 substituents selected from halogen, —$C_{1-6}$ aliphatic, —CN, —OR, —$NR_2$, —$CO_2$R, —C(O)R, —SR, or —C(O)$NR_2$. In some embodiments, the optional substituents are selected from halogen, —CN, —$C_{1-6}$ alkyl, or —OMe. In some embodiments, at least one of the optional substituents is halogen. In some embodiments, 1, 2, or 3 substituents are present. In some embodiments, $Ar^3$ is phenyl substituted with 3 substituents selected from halogen, —$C_{1-6}$ aliphatic, and —OR. In some embodiments, $Ar^3$ is selected from those depicted in Table 5, below.

As defined generally above, X is selected from a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—.

In some embodiments, X is a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —$S(O)_2$—. In some embodiments, X is —O—, —$NR^6$—, —S—, —C(O)—, —$CO_2$— —CS—, —C($NR^6$)—, —S(O)—, or —$S(O)_2$— (i.e., a $C_1$ alkylene wherein the methylene unit is replaced with —O—, —$NR^6$—, etc.). In some embodiments, X is a bivalent $C_{1-2}$ alkylene chain wherein one methylene unit of the chain is optionally replaced with —O—, —S—, —C(O)—, —$CO_2$— —CS—, —C($NR^6$)—, —S(O)—, or —$S(O)_2$—. In some embodiments, X is —O—, —C(O)—, —C(O)—O—, —O—C(O)—, —NH—C(O)—, or —C(O)—NH—. In some embodiments, X is selected from those depicted in Table 5, below.

As defined generally above, $X^2$ is selected from a bivalent $C_{1-3}$ alkylene chain wherein 1-2 methylene units of the chain are independently and optionally replaced with —O—, —S—, —C(O)—, —$CO_2$— —CS—, —C($NR^6$)—, —S(O)—, or —$S(O)_2$—.

In some embodiments, $X^2$ is a bivalent $C_{1-3}$ alkylene chain wherein 1-2 methylene units of the chain are independently and optionally replaced with —O—, —$NR^6$—, —S—, —C(O)—, —$CO_2$— —CS—, —C($NR^6$)—, —S(O)—, or —S(O)$_2$—. In some embodiments, $X^2$ is —O—, —NR$^6$—, —S—, —C(O)—, —CO$_2$— —CS—, —C(NR$^6$)—, —S(O)—, or —S(O)$_2$— (i.e., a $C_1$ alkylene wherein the methylene unit is replaced with —O—, —NR$^6$—, etc.). In some embodiments, $X^2$ is a bivalent $C_{1-2}$ alkylene chain wherein one methylene unit of the chain is optionally replaced with —O—, —NR$^6$—, —S—, —C(O)—, —CO$_2$— —CS—, —C(NR$^6$)—, —S(O)—, or —S(O)$_2$—. In some embodiments, $X^2$ is —CH$_2$—NH—, —OCH$_2$—, —CH$_2$O—, —O—, —C(O)—, —C(O)—O—, —O—C(O)—, —NH—C(O)—, or —C(O)—NH—. In some embodiments, $X^2$ is selected from those depicted in Table 5, below.

As defined generally above, $R^2$ is a photoactivatable group that optionally comprises a click-ready group if $R^3$ is absent. In some embodiments, $R^2$ is a photoactivatable group. In some embodiments, $R^2$ is a photoactivatable group further substituted with a click-ready group.

In some embodiments, $R^2$ is a functional group that generates a radical, an aryl or heteroaryl carbocation, a nitrene, or a carbene intermediate upon irradiation with ultraviolet (UV) radiation, and that is optionally substituted with a click-ready group or pull-down group if $R^3$ is absent. In some embodiments, $R^2$ is an optionally substituted phenyl or 8-10 membered bicyclic aromatic carbocyclic azide or 5-8 membered heteroaryl or 8-10 membered bicyclic heteroaryl azide, optionally substituted benzoyl azide or 5-8 membered heteroaroyl azide or 8-10 membered heteroaroyl azide wherein 1-3 atoms of the ring atoms are selected from nitrogen, sulfur, or oxygen, optionally substituted phenyl or 8-10 membered bicyclic aromatic carbocyclic diazonium salt, optionally substituted 5-8 membered heteroaryl or 8-10 membered bicyclic heteroaryl diazonium salt wherein 1-3 atoms of the ring atoms are selected from nitrogen, sulfur, or oxygen, optionally substituted $C_{2-6}$ aliphatic diazo functional group, optionally substituted $C_{2-6}$ aliphatic diazirine, or optionally substituted diphenyl or 8-10-membered diheteroaryl ketone wherein 1-3 atoms of the ring atoms are selected from nitrogen, sulfur, or oxygen, optionally substituted dihydropyrene, optionally substituted spirooxazine, optionally substituted anthracene, optionally substituted fulgide, optionally substituted spiropyran, optionally substituted α-pyrone or optionally substituted pyrimidone; and which is optionally substituted with a click-ready group or pull-down group. In some embodiments, the click-ready group is a $C_{1-6}$ alkyl azide or alkyne. In some embodiments, $R^2$ is selected from

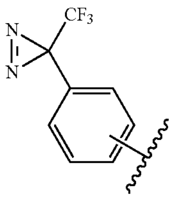,
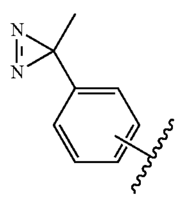,
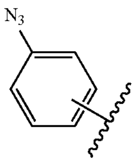,
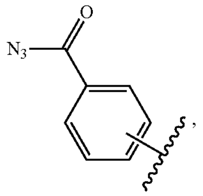,
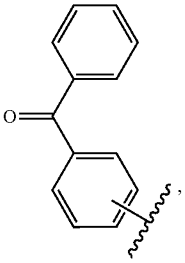,
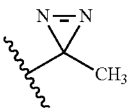,

-continued

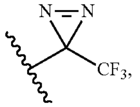
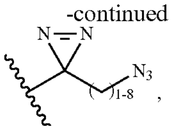,
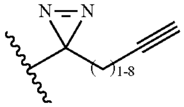,
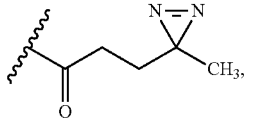
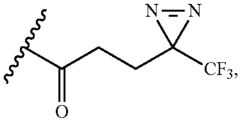
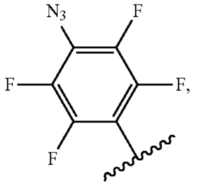
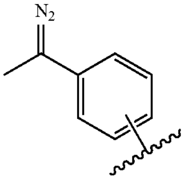,
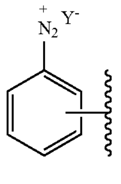,
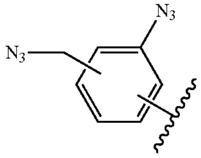,
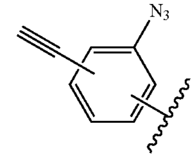,
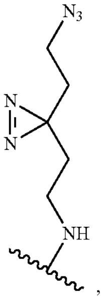,
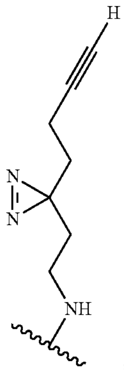,
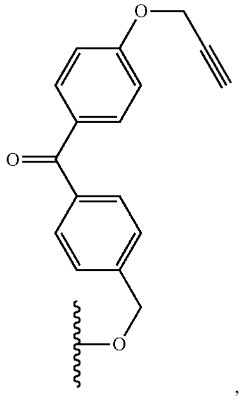, or
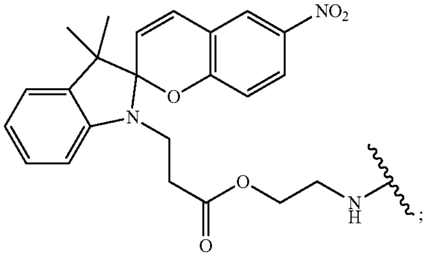;

wherein $Y^+$ is a pharmaceutically acceptable anion.

In some embodiments, $R^2$ is selected from those depicted in Table 5, below.

As defined generally above, $R^3$ is absent or is a click-ready group or a pull-down group. In some embodiments, $R^3$ is absent. In some embodiments, $R^3$ is a click-ready group. In some embodiments, $R^3$ is a pull-down group. In some embodiments, $R^3$ is a $C_{1-6}$ alkyl azide, $C_{1-6}$ alkyne, or a hapten such as biotin.

In some embodiments, $R^3$ is selected from those depicted in Table 5, below.

As defined generally above, each $R^4$ is independently R, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R) OR, —OC(O)R, —OC(O)NR$_2$, —N(R)C(O) OR, —N(R) C(O)R, —N(R)C(O)NR$_2$, —N(R)S(O)$_2$R, or —N(R)S(O)$_2$NR$_2$; or two instances of $R^4$ may be taken together with the atoms to which they are attached to form a $C_{4-8}$ partially unsaturated carbocyclic ring.

In some embodiments, $R^4$ is R. In some embodiments, $R^4$ is halogen. In some embodiments, $R^4$ is —CN. In some embodiments, $R^4$ is —$NO_2$. In some embodiments, $R^4$ is —OR.

In some embodiments, $R^4$ is —SR. In some embodiments, $R^4$ is —$NR_2$. In some embodiments, $R^4$ is —$S(O)_2R$. In some embodiments, $R^4$ is —$S(O)_2NR_2$. In some embodiments, $R^4$ is —S(O)R. In some embodiments, $R^4$ is —C(O)R. In some embodiments, $R^4$ is —C(O)OR. In some embodiments, $R^4$ is —C(O)$NR_2$.

In some embodiments, $R^4$ is —C(O)N(R)OR. In some embodiments, $R^4$ is —OC(O)R. In some embodiments, $R^4$ is —OC(O)$NR_2$. In some embodiments, $R^4$ is —N(R)C(O)OR. In some embodiments, $R^4$ is —N(R)C(O)R. In some embodiments, $R^4$ is —N(R)C(O)$NR_2$. In some embodiments, $R^4$ is —N(R)$S(O)_2R$. In some embodiments, $R^4$ is —N(R)$S(O)_2NR_2$. In some embodiments, two instances of $R^4$ are taken together with the atoms to which they are attached to form a $C_{4-8}$ partially unsaturated carbocyclic ring.

In some embodiments, $R^4$ is hydrogen, $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; an 8-10 membered bicyclic heteroaromatic ring having 1-5 heteroatoms independently selected from nitrogen, oxygen, or sulfur; halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —OC(O)R, or —N(R)C(O)R.

In some embodiments, $R^4$ is hydrogen, $C_{1-6}$ alkyl optionally substituted with 1, 2, 3, 4, 5, or 6 deuterium or halogen atoms; a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; halogen, —CN, —OR, —$NR_2$, —$S(O)_2NR_2$, —C(O)R, —C(O)OR, —C(O)$NR_2$, —OC(O)R, or —N(R)C(O)R. In some embodiments, $R^4$ is hydrogen, $C_{1-6}$ alkyl, phenyl, halogen, —CN, —OR, or —$NR_2$. In some embodiments, $R^4$ is selected from those depicted in Table 5, below.

As defined generally above, each $R^5$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R) OR, —OC(O)R, —OC(O)$NR_2$, —N(R)C(O)OR, —N(R) C(O)R, —N(R)C(O)$NR_2$, —N(R)$S(O)_2R$, or —N(R)$S(O)_2NR_2$; or two instances of $R^5$ may be taken together to form =O or =S.

In some embodiments, $R^5$ is R. In some embodiments, $R^5$ is halogen. In some embodiments, $R^5$ is —CN. In some embodiments, $R^5$ is —$NO_2$. In some embodiments, $R^5$ is —OR. In some embodiments, $R^5$ is —SR. In some embodiments, $R^5$ is —$NR_2$. In some embodiments, $R^5$ is —$S(O)_2R$. In some embodiments, $R^5$ is —$S(O)_2NR_2$. In some embodiments, $R^5$ is —S(O)R. In some embodiments, $R^5$ is —C(O)R. In some embodiments, $R^5$ is —C(O)OR. In some embodiments, $R^5$ is —C(O)$NR_2$.

In some embodiments, $R^5$ is —C(O)N(R)OR. In some embodiments, $R^5$ is —OC(O)R. In some embodiments, $R^5$ is —OC(O)$NR_2$. In some embodiments, $R^5$ is —N(R)C(O)OR. In some embodiments, $R^5$ is —N(R)C(O)R. In some embodiments, $R^5$ is —N(R)C(O)$NR_2$. In some embodiments, $R^5$ is —N(R)$S(O)_2R$. In some embodiments, $R^5$ is —N(R)$S(O)_2NR_2$. In some embodiments, two instances of $R^5$ are taken together to form =O or =S.

In some embodiments, $R^5$ is hydrogen, $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; an 8-10 membered bicyclic heteroaromatic ring having 1-5 heteroatoms independently selected from nitrogen, oxygen, or sulfur; halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —OC(O)R, or —N(R)C(O)R.

In some embodiments, $R^5$ is hydrogen, $C_{1-6}$ alkyl optionally substituted with 1, 2, 3, 4, 5, or 6 deuterium or halogen atoms; a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; halogen, —CN, —OR, —$NR_2$, —$S(O)_2NR_2$, —C(O)R, —C(O)OR, —C(O)$NR_2$, —OC(O)R, or —N(R)C(O)R. In some embodiments, $R^5$ is hydrogen, $C_{1-6}$ alkyl, phenyl, halogen, —CN, —OR, or —$NR_2$.

As defined generally above, each $R^6$ is independently hydrogen or $C_{1-6}$ alkyl optionally substituted with 1, 2, 3, 4, 5, or 6 deuterium or halogen atoms.

In some embodiments, $R^6$ is hydrogen. In some embodiments, $R^6$ is $C_{1-6}$ alkyl optionally substituted with 1, 2, 3, 4, 5, or 6 deuterium or halogen atoms.

In some embodiments, $R^6$ is $C_{1-3}$ alkyl optionally substituted with 1, 2, or 3 halogen atoms.

In some embodiments, $R^6$ is selected from those depicted in Table 5, below.

As defined generally above, each $R^7$ is independently R, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R) OR, —OC(O)R, —OC(O)$NR_2$, —N(R)C(O)OR, —N(R) C(O)R, —N(R)C(O)$NR_2$, —N(R)$S(O)_2R$, or —N(R)$S(O)_2NR_2$; or two instances of $R^7$ may be taken together with the atoms to which they are attached to form a $C_{4-8}$ partially unsaturated carbocyclic ring.

In some embodiments, $R^7$ is R. In some embodiments, $R^7$ is halogen. In some embodiments, $R^7$ is —CN. In some embodiments, $R^7$ is —$NO_2$. In some embodiments, $R^7$ is —OR. In some embodiments, $R^7$ is —SR. In some embodiments, $R^7$ is —$NR_2$. In some embodiments, $R^7$ is —$S(O)_2R$. In some embodiments, $R^7$ is —$S(O)_2NR_2$. In some embodiments, $R^7$ is —S(O)R. In some embodiments, $R^7$ is —C(O)R. In some embodiments, $R^7$ is —C(O)OR. In some embodiments, $R^7$ is —C(O)$NR_2$.

In some embodiments, $R^7$ is —C(O)N(R)OR. In some embodiments, $R^7$ is —OC(O)R. In some embodiments, $R^7$ is —OC(O)$NR_2$. In some embodiments, $R^7$ is —N(R)C(O)OR. In some embodiments, $R^7$ is —N(R)C(O)R. In some embodiments, $R^7$ is —N(R)C(O)$NR_2$. In some embodiments, $R^7$ is —N(R)$S(O)_2R$. In some embodiments, $R^7$ is —N(R)$S(O)_2NR_2$. In some embodiments, two instances of $R^7$ are taken together with the atoms to which they are attached to form a $C_{4-8}$ partially unsaturated carbocyclic ring.

In some embodiments, $R^7$ is hydrogen, $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; an 8-10 membered bicyclic heteroaromatic ring having 1-5 heteroatoms independently selected from nitrogen, oxygen, or sulfur; halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —OC(O)R, or —N(R)C(O)R.

In some embodiments, $R^7$ is hydrogen, $C_{1-6}$ alkyl optionally substituted with 1, 2, 3, 4, 5, or 6 deuterium or halogen atoms; a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur; a 5-6 membered monocyclic heteroaromatic ring having 1-4 heteroatoms independently selected from nitrogen, oxygen, or sulfur; halogen, —CN, —OR, —$NR_2$, —$S(O)_2NR_2$, —C(O)R, —C(O)OR, —C(O)$NR_2$, —OC(O)R, or —N(R)C(O)R. In some embodiments, $R^7$ is hydrogen, $C_{1-6}$ alkyl, phenyl, halogen, —CN, —OR, or —$NR_2$. In some embodiments, $R^7$ is selected from those depicted in Table 5, below.

As defined generally above, $L^2$ is a $C_{1-20}$ bivalent or trivalent, straight or branched, optionally substituted hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—.

In some embodiments, $L^2$ is a $C_{1-10}$ bivalent or trivalent, straight or branched, optionally substituted hydrocarbon chain wherein 1, 2, 3, 4, or 5 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-5 of the methylene units of the chain are independently and optionally replaced with —$OCH_2CH_2$—. In some embodiments, $L^2$ comprises 1-3 natural amino acids. In some embodiments, the amino acids are selected from proline, lysine, glycine, or alanine. In some embodiments, $L^2$ comprises 1-2 -Cy- groups selected from 1,2,3-triazolylene or 1,2,4-triazolylene. In some embodiments, $L^2$ comprises 1-10, 1-8, 1-6, 1-4, 1-3, 1-2, 1, 2, or 3 —$OCH_2CH_2$— units.

In some embodiments, $L^2$ is a $C_{1-20}$ bivalent or trivalent, straight or branched, optionally substituted hydrocarbon chain wherein 1, 2, 3, 4, or 5 methylene units of the chain are independently and optionally replaced with —O—, —C(O)—, —C(O)O—, —OC(O)—, —N(R)—, —C(O)N(R)—, —(R)NC(O)—, —S—, —SO—, —$SO_2$—, —C(S)—, or -Cy-; and 1-20 of the methylene units of the chain are independently and optionally replaced with —$OCH_2CH_2$—.

In some embodiments, $L^2$ is a $C_{1-20}$ bivalent or trivalent, straight, optionally substituted hydrocarbon chain wherein 1, 2, 3, 4, or 5 methylene units of the chain are independently and optionally replaced with —O—, —C(O)—, —N(R)—, or -Cy-; and 1-20 of the methylene units of the chain are independently and optionally replaced with —$OCH_2CH_2$—.

In some embodiments, 1, 2, 3, 4, 5, 6, 7, 8, 9, 10, 11, 12, 13, 14, or 15 methylene units of the chain are replaced with —$OCH_2CH_2$—. In some embodiments, 1, 2, 3, 4, 5, 6, 7, or 8; or 1, 2, 3, 4, or 5 methylene units of the chain are replaced with —$OCH_2CH_2$—.

In some embodiments, $L^2$ is selected from those depicted in Table 5, below.

As defined generally above, each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur.

In some embodiments, -Cy- is a bivalent optionally substituted 3-8 membered saturated or partially unsaturated monocyclic carbocyclic ring. In some embodiments, -Cy- is an optionally substituted phenylene. In some embodiments, -Cy- is an optionally substituted 4-8 membered saturated or partially unsaturated monocyclic heterocyclic ring having 1-3 heteroatoms independently selected from nitrogen, oxygen, or sulfur. In some embodiments, -Cy- is an optionally substituted 5-6 membered monocyclic heteroaromatic ring having 1-4 heteroatoms independently selected from nitrogen, oxygen, or sulfur. In some embodiments, -Cy- is an optionally substituted 8-10 membered bicyclic or bridged bicyclic saturated or partially unsaturated heterocyclic ring having 1-5 heteroatoms independently selected from nitrogen, oxygen, or sulfur. In some embodiments, -Cy- is an optionally substituted 8-10 membered bicyclic or bridged bicyclic heteroaromatic ring having 1-5 heteroatoms independently selected from nitrogen, oxygen, or sulfur.

In some embodiments, -Cy- is phenylene, pyridiylene, pyrimidinylene, 1,2,3-triazolylene, or 1,2,4-triazolylene.

In some embodiments, -Cy- is selected from those depicted in Table 5, below.

As defined generally above, m is 0, 1, 2, 3, or 4. In some embodiments, m is 0. In some embodiments, m is 1. In some embodiments, m is 2. In some embodiments, m is 3. In some embodiments, m is 4. In some embodiments, m is 0, 1, 2, or 3. In some embodiments, m is 0, 1, or 2. In some embodiments, m is 1 or 2.

As defined generally above, p is 0, 1, 2, 3, or 4. In some embodiments, p is 0. In some embodiments, p is 1. In some embodiments, p is 2. In some embodiments, p is 3. In some embodiments, p is 4. In some embodiments, p is 0, 1, 2, or 3. In some embodiments, p is 0, 1, or 2. In some embodiments, p is 1 or 2.

In some embodiments, the present invention provides a compound of Formulae X-c, X-d, X-e, or X-f:

X-c

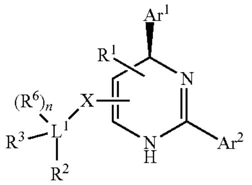

X-d

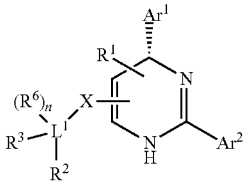

X-e

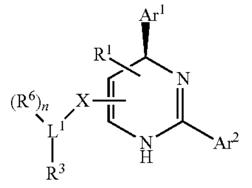

X-f

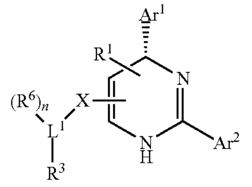

or a tautomer or pharmaceutically acceptable salt thereof, wherein each of $Ar^1$, $Ar^2$, X, $L^1$, $R^1$, $R^2$, $R^3$, $R^6$, R, -Cy-, and n is as defined above and described in embodiments herein, both singly and in combination.

In some embodiments, the present invention provides a compound of Formulae XI or XII:

XI

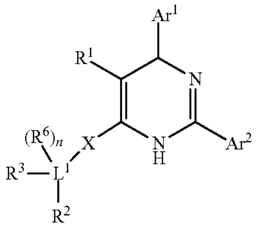

XII

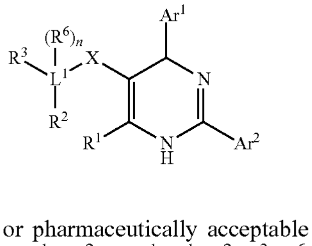

or a tautomer or pharmaceutically acceptable salt thereof, wherein each of $Ar^1$, $Ar^2$, X, $L^1$, $R^1$, $R^2$, $R^3$, $R^6$, R, -Cy-, and n is as defined above and described in embodiments herein, both singly and in combination.

In some embodiments, the present invention provides a compound of Formula XIII.

XIII

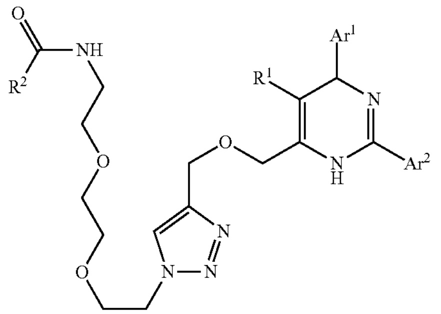

or a tautomer or pharmaceutically acceptable salt thereof, wherein each of $Ar^1$, $Ar^2$, $R^1$, $R^2$, $R^6$, R, and -Cy- is as defined above and described in embodiments herein, both singly and in combination.

In some embodiments, the present invention provides a compound of Formula XIV:

XIV

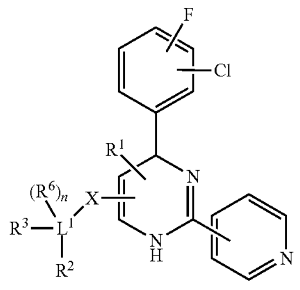

or a tautomer or pharmaceutically acceptable salt thereof, wherein each of X, $L^1$, $R^1$, $R^2$, $R^3$, $R^6$, R, -Cy-, and n is as defined above and described in embodiments herein, both singly and in combination.

In some embodiments, the present invention provides a compound of Formula XV:

XV

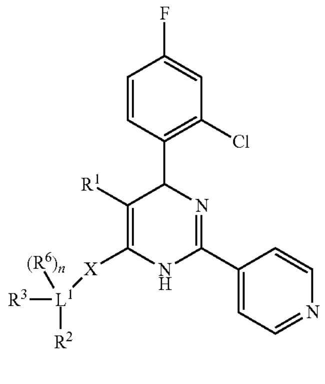

or a tautomer or pharmaceutically acceptable salt thereof, wherein each of X, $L^1$, $R^1$, $R^2$, $R^3$, $R^6$, R, -Cy-, and n is as defined above and described in embodiments herein, both singly and in combination.

In some embodiments, the present invention provides a compound of Formulae XVI, XVII, XVIII, or XIX:

XVI

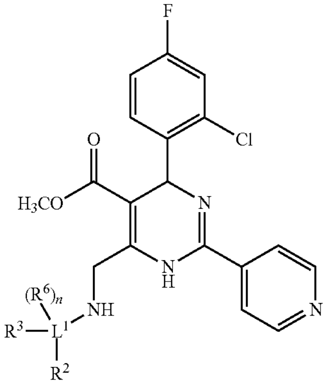

XVII

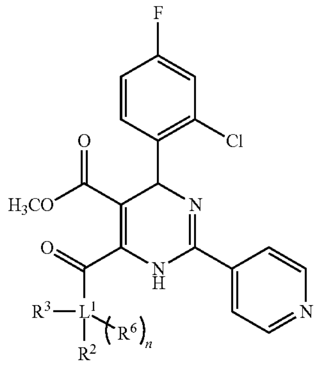

XVIII

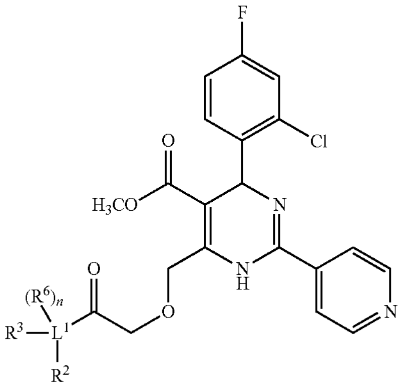

XIX

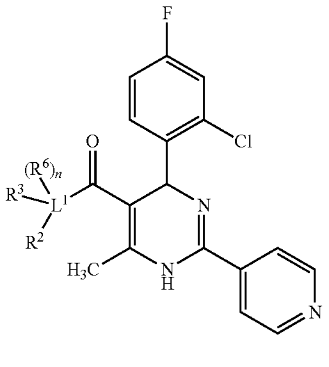

or a tautomer or pharmaceutically acceptable salt thereof, wherein each of $L^1$, $R^1$, $R^2$, $R^3$, $R^6$, R, -Cy-, and n is as defined above and described in embodiments herein, both singly and in combination.

In some embodiments, the present invention provides a compound of Formulae XX, XXI, XXII, XXIII, or XXIV:

XX

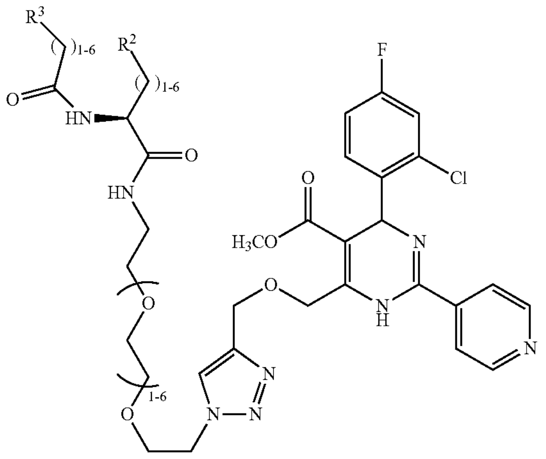

XXI

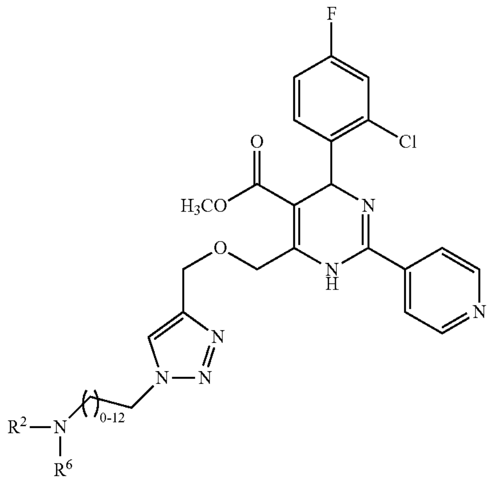

XXII

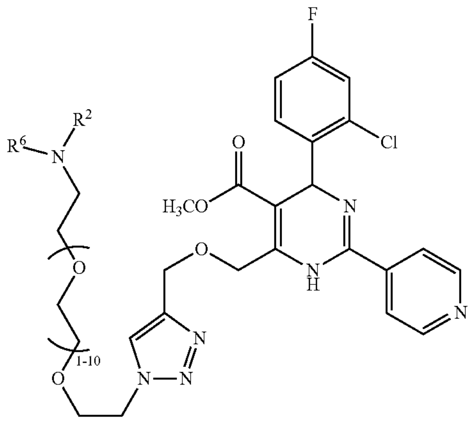

-continued

XXIII

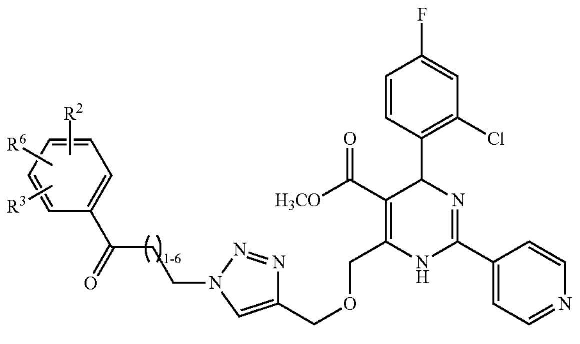

XXIV

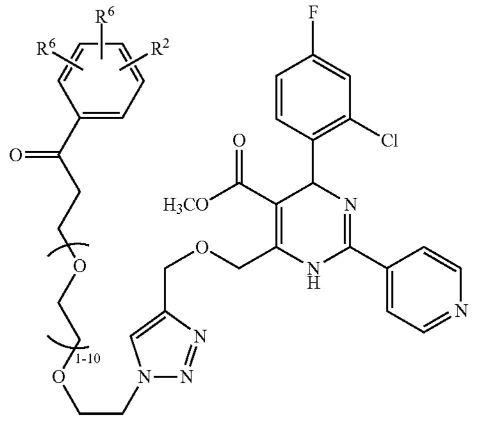

or a tautomer or pharmaceutically acceptable salt thereof, wherein each of $R^2$, $R^3$, $R^6$, R, -Cy-, and n is as defined above and described in embodiments herein, both singly and in combination.

In some embodiments, the present invention provides a compound of Formulae XXVII or XXVIII:

XXVII

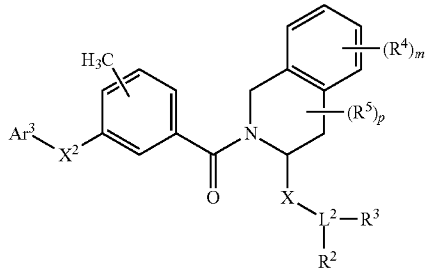

XXVIII

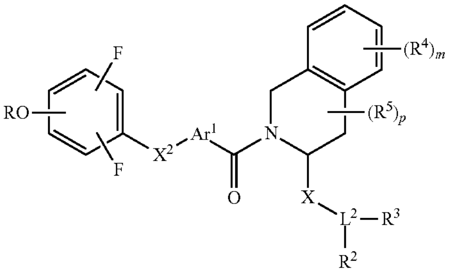

or a pharmaceutically acceptable salt thereof, wherein each of $Ar^1$, $Ar^3$, X, $X^2$, $L^2$, $R^2$, $R^3$, $R^4$, $R^5$, $R^6$, R, -Cy-, m, and p is as defined above and described in embodiments herein, both singly and in combination.

In some embodiments, the present invention provides a compound of Formulae XXIX, XXX, XXXI, XXXII, or XXXIII:

XXIX

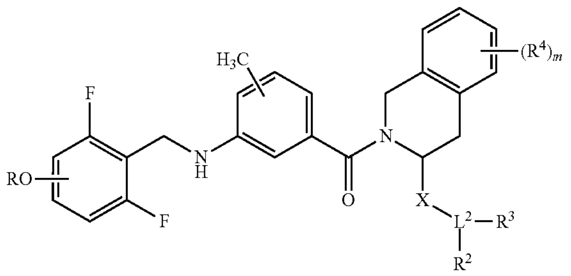

XXX

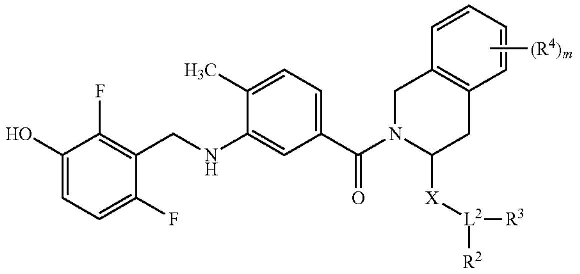

XXXI

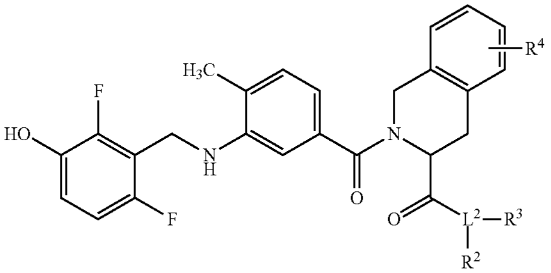

XXXII

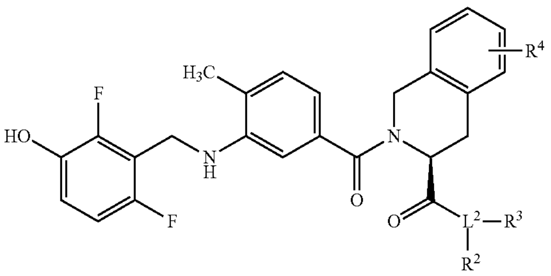

-continued

XXXIII

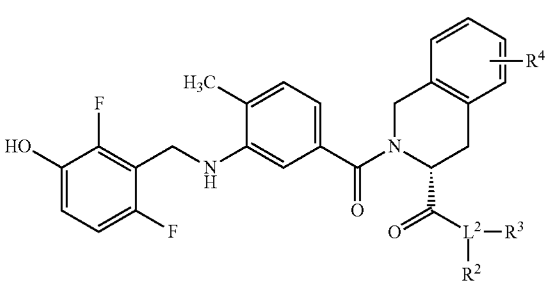

or a pharmaceutically acceptable salt thereof, wherein each of X, $X^2$, $L^2$, $R^2$, $R^3$, $R^4$, $R^6$, R, and m is as defined above and described in embodiments herein, both singly and in combination.

In some embodiments, the present invention provides a compound of Formulae XXXIV, XXXV, XXXVI, or XXXVII:

XXXIV

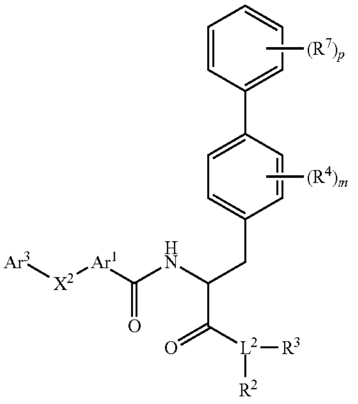

XXXV

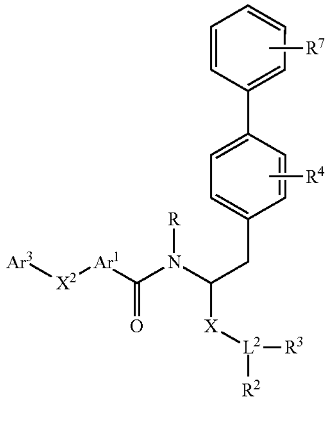

-continued

XXXVI

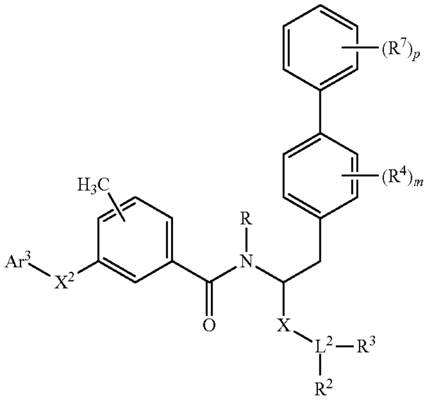

XXXVII

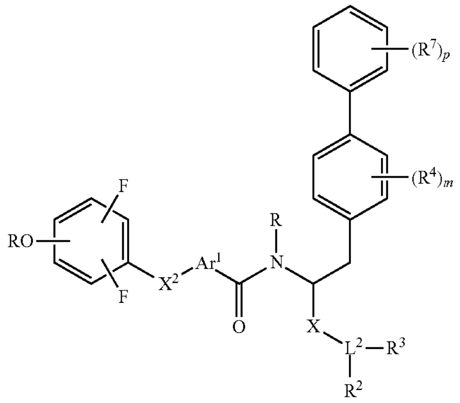

or a pharmaceutically acceptable salt thereof, wherein each of $Ar^1$, $Ar^3$, $X^2$, $L^2$, $R^2$, $R^3$, $R^4$, $R^6$, $R^7$, R, -Cy-, m, and p is as defined above and described in embodiments herein, both singly and in combination.

In some embodiments, the present invention provides a compound of Formulae XXXVIII, XXXIX, XL, XLI, or XLII:

XXXVIII

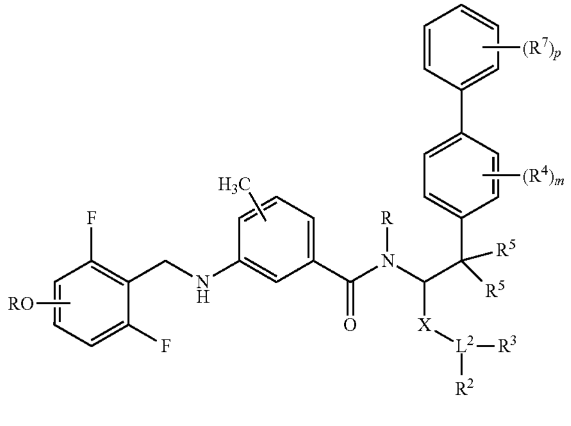

-continued
XXXIX
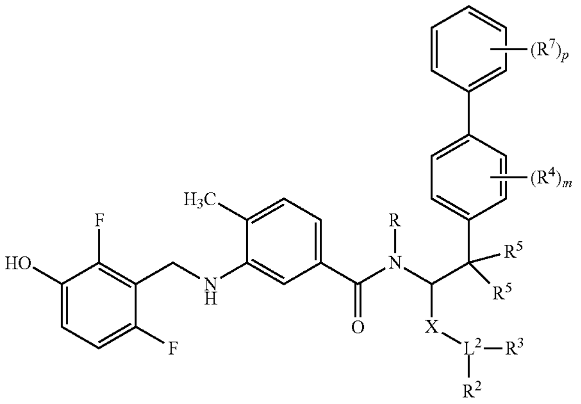
XL
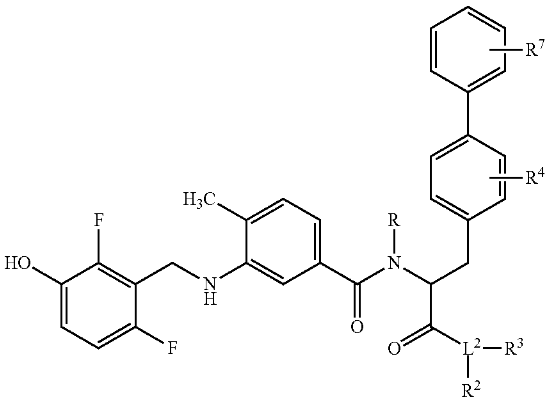
-continued
XLI
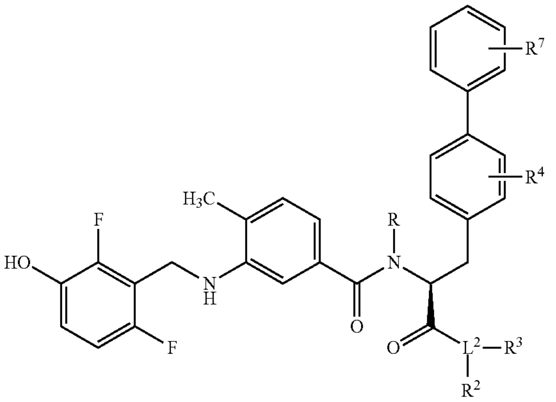
XLII
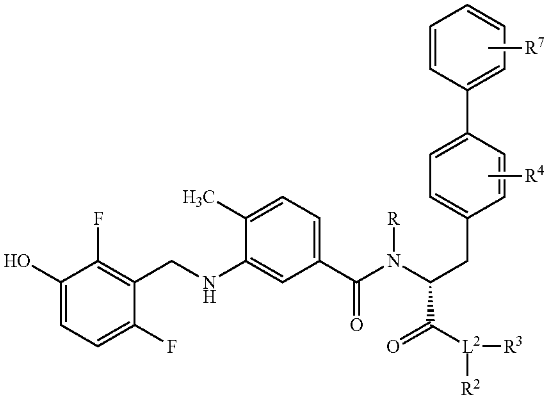
or a pharmaceutically acceptable salt thereof, wherein each of X, $L^2$, $R^2$, $R^3$, $R^4$, $R^6$, $R^7$, R, -Cy-, m, and p is as defined above and described in embodiments herein, both singly and in combination.
Exemplary compounds of the invention are set forth in Table 5, below.

TABLE 5
| Exemplary Compounds |
| --- |
| I-1<br>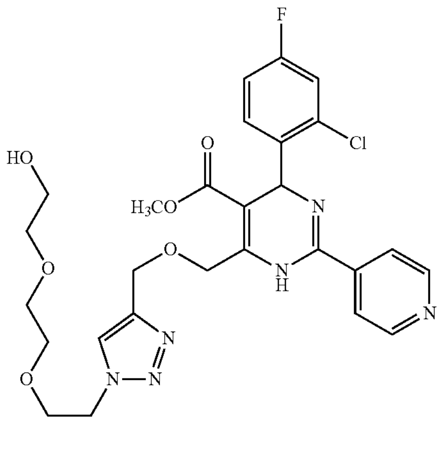 [SMILES: COC(=O)C1=C(COCc2cn(CCOCCOCCO)nn2)NC(c2ccncc2)=NC1c1ccc(F)cc1Cl]<br>(ARK-139) |
| I-2<br>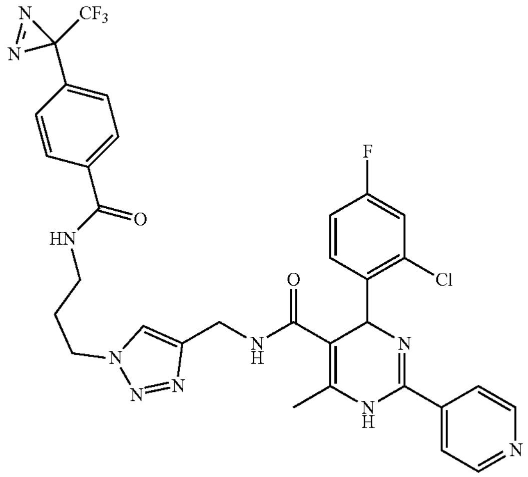 [SMILES: CC1=C(C(=O)NCc2cn(CCCNC(=O)c3ccc(C4(C(F)(F)F)N=N4)cc3)nn2)C(c2ccc(F)cc2Cl)N=C(c2ccncc2)N1]<br>(ARK-673) |
| I-3<br>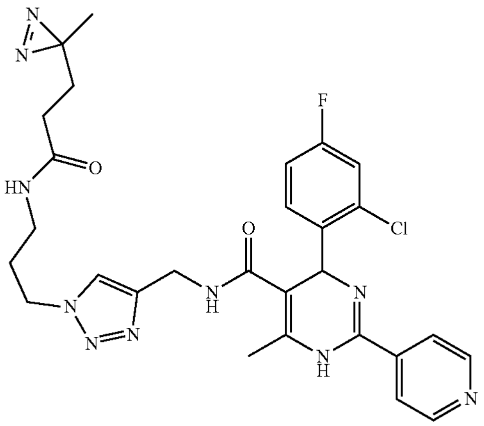 [SMILES: CC1=C(C(=O)NCc2cn(CCCNC(=O)CCC3(C)N=N3)nn2)C(c2ccc(F)cc2Cl)N=C(c2ccncc2)N1]<br>(ARK-674) |

TABLE 5-continued
Exemplary Compounds
I-4
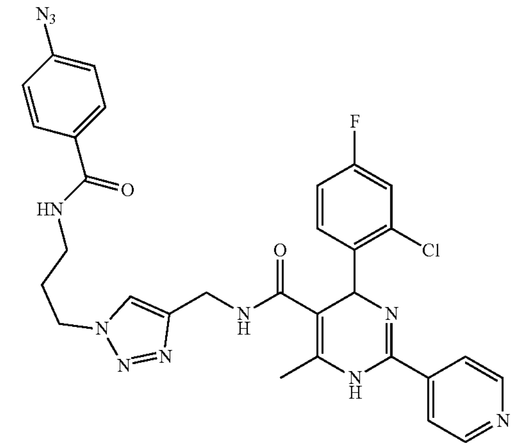 [SMILES: CC1=C(C(=O)NCc2cn(CCCNC(=O)c3ccc(N=[N+]=[N-])cc3)nn2)C(c2ccc(F)cc2Cl)N=C(c2ccncc2)N1]
(ARK-672)
I-5
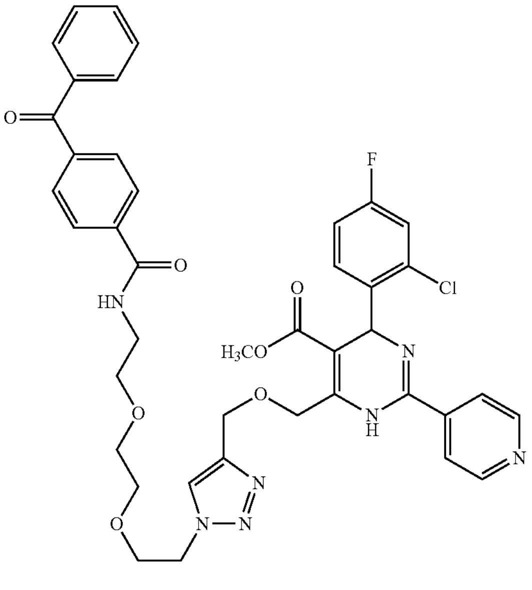 [SMILES: COC(=O)C1=C(COCc2cn(CCOCCOCCNC(=O)c3ccc(C(=O)c4ccccc4)cc3)nn2)NC(c2ccncc2)=NC1c1ccc(F)cc1Cl]
(ARK-544)

TABLE 5-continued
| Exemplary Compounds |
| --- |
| 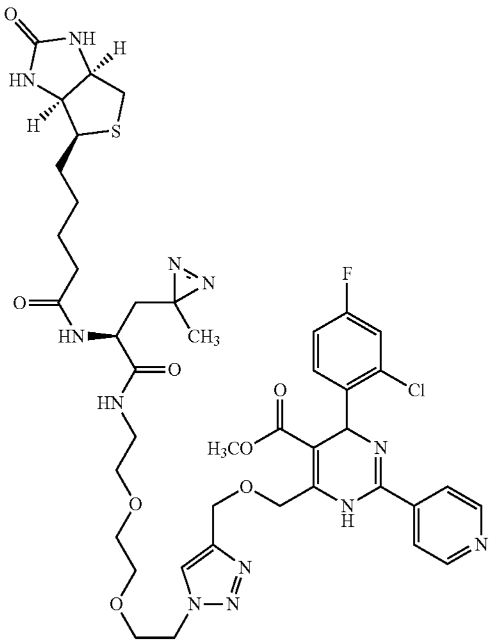 [SMILES: COC(=O)C1=C(COCc2cn(CCOCCOCCNC(=O)[C@H](CC3(C)N=N3)NC(=O)CCCC[C@@H]3SC[C@@H]4NC(=O)N[C@@H]43)nn2)NC(c2ccncc2)=NC1c1ccc(F)cc1Cl] I-6 |
| (ARK-546) |
| I-7 |
| 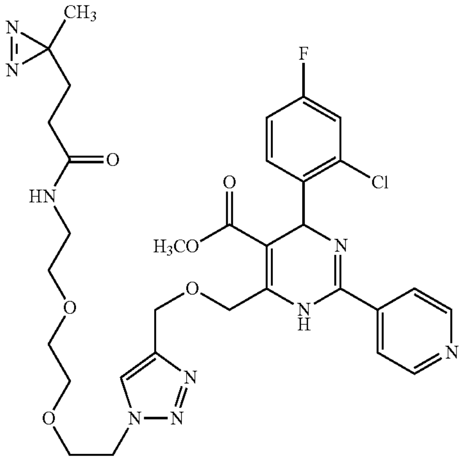 [SMILES: COC(=O)C1=C(COCc2cn(CCOCCOCCNC(=O)CCC3(C)N=N3)nn2)NC(c2ccncc2)=NC1c1ccc(F)cc1Cl] |
| (ARK-547) |

TABLE 5-continued
| Exemplary Compounds |
| --- |
I-8
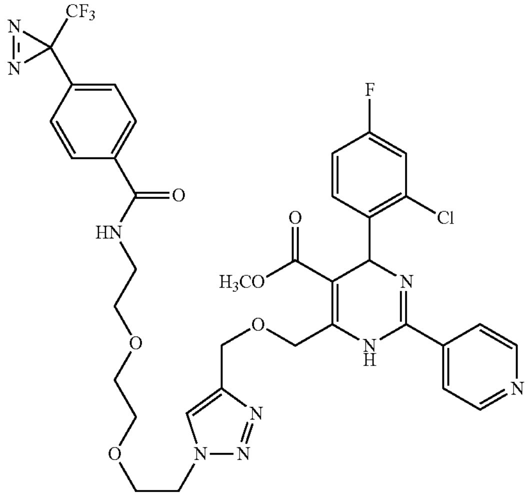 [SMILES: COC(=O)C1=C(COCc2cn(CCOCCOCCNC(=O)c3ccc(C4(C(F)(F)F)N=N4)cc3)nn2)NC(c2ccncc2)=NC1c1ccc(F)cc1Cl]
(ARK-549)
I-9
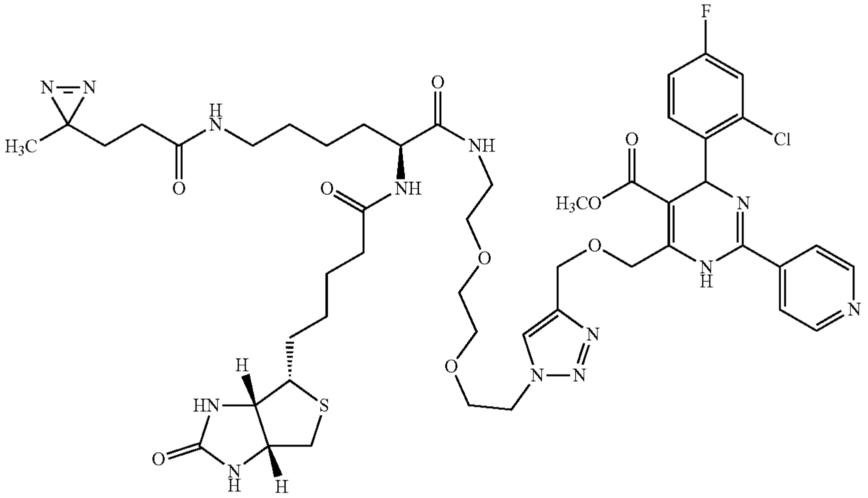 [SMILES: COC(=O)C1=C(COCc2cn(CCOCCOCCNC(=O)[C@H](CCCCNC(=O)CCC3(C)N=N3)NC(=O)CCCC[C@@H]3SC[C@@H]4NC(=O)N[C@@H]43)nn2)NC(c2ccncc2)=NC1c1ccc(F)cc1Cl]
(ARK-579)
I-10
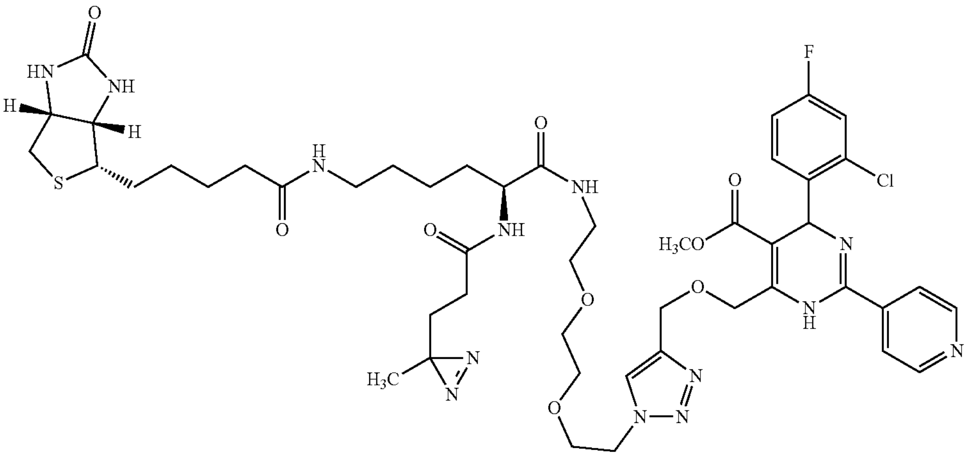 [SMILES: COC(=O)C1=C(COCc2cn(CCOCCOCCNC(=O)[C@H](CCCCNC(=O)CCCC[C@@H]3SC[C@@H]4NC(=O)N[C@@H]43)NC(=O)CCC3(C)N=N3)nn2)NC(c2ccncc2)=NC1c1ccc(F)cc1Cl]
(ARK-580)

TABLE 5-continued
| Exemplary Compounds |
| --- |
I-11
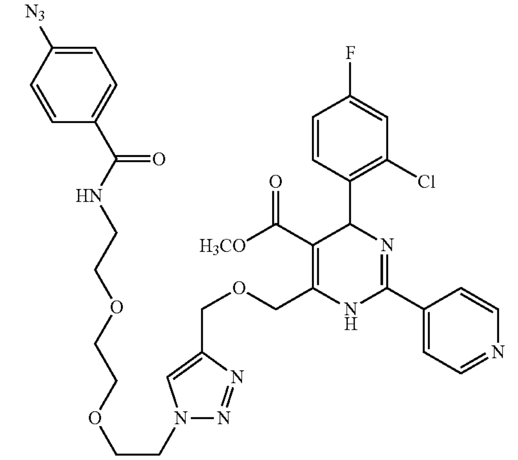 [SMILES: COC(=O)C1=C(COCc2cn(CCOCCOCCNC(=O)c3ccc(N=[N+]=[N-])cc3)nn2)NC(c2ccncc2)=NC1c1ccc(F)cc1Cl]
(ARK-581)
I-12
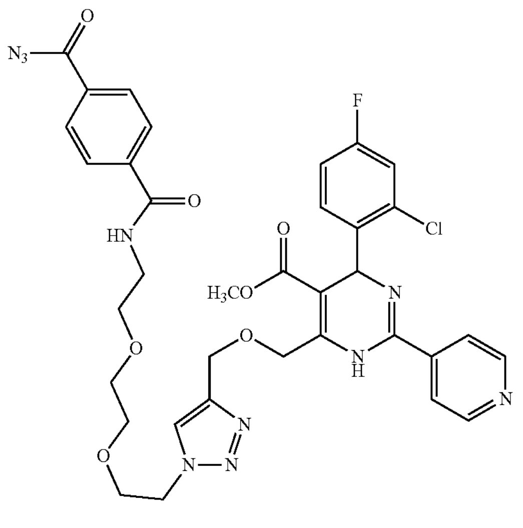 [SMILES: COC(=O)C1=C(COCc2cn(CCOCCOCCNC(=O)c3ccc(C(=O)N=[N+]=[N-])cc3)nn2)NC(c2ccncc2)=NC1c1ccc(F)cc1Cl]

TABLE 5-continued
| Exemplary Compounds |
| --- |
I-13
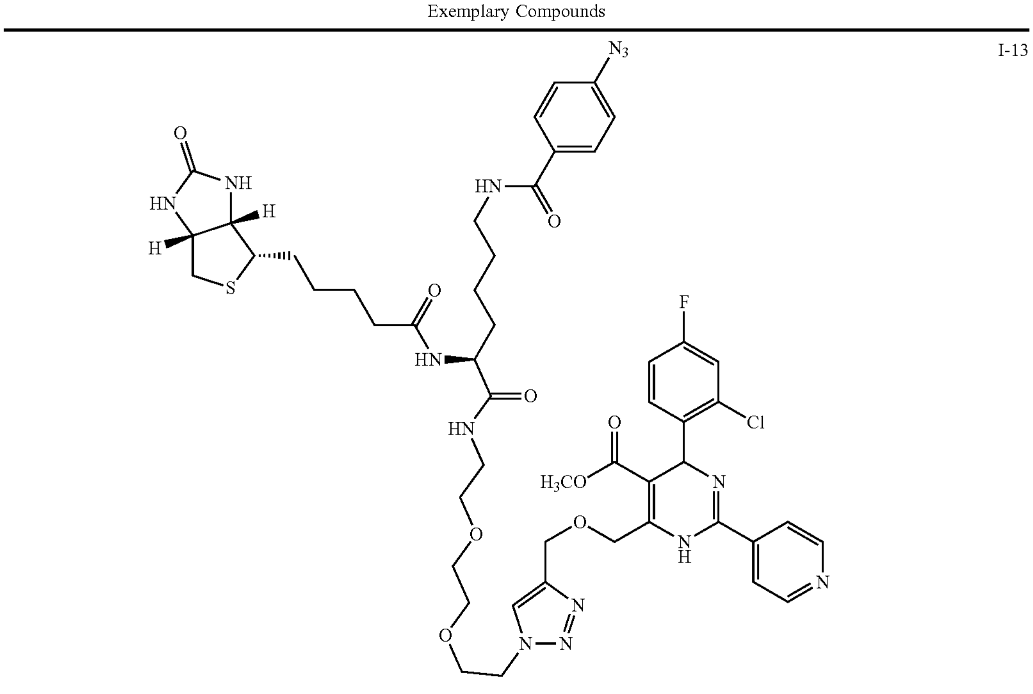
(ARK-670)
I-14
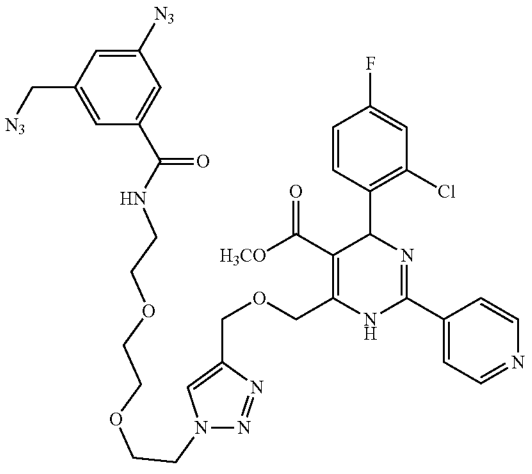 [SMILES: COC(=O)C1=C(COCc2cn(CCOCCOCCNC(=O)c3cc(CN=[N+]=[N-])cc(N=[N+]=[N-])c3)nn2)NC(c2ccncc2)=NC1c1ccc(F)cc1Cl]
(ARK-729)

TABLE 5-continued
| Exemplary Compounds |
| --- |
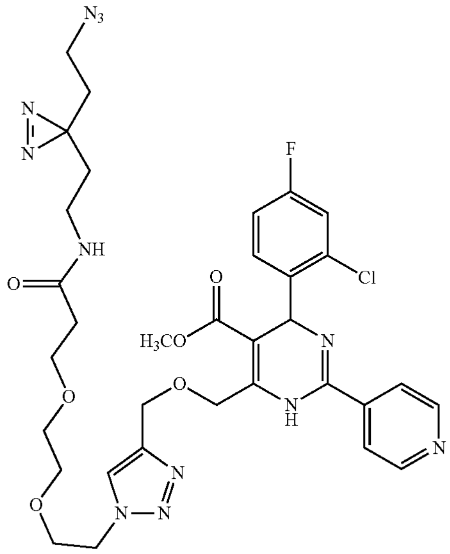 [SMILES: COC(=O)C1=C(COCc2cn(CCOCCOCCC(=O)NCCC3(CCN=[N+]=[N-])N=N3)nn2)NC(c2ccncc2)=NC1c1ccc(F)cc1Cl]
I-15
(ARK-816)
I-16
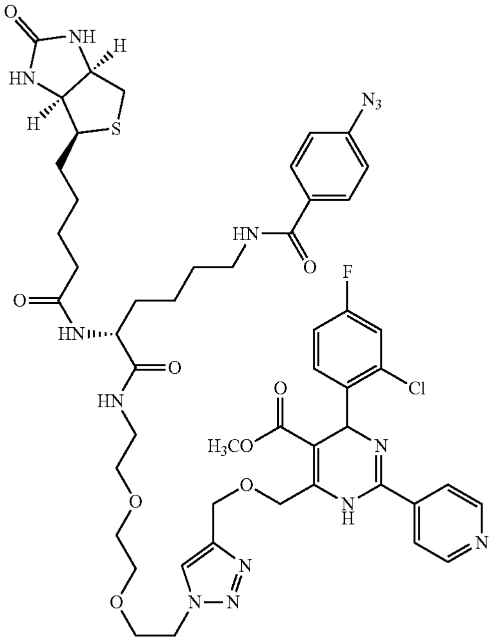 [SMILES: COC(=O)C1=C(COCc2cn(CCOCCOCCNC(=O)[C@@H](CCCCNC(=O)c3ccc(N=[N+]=[N-])cc3)NC(=O)CCCC[C@@H]3SC[C@@H]4NC(=O)N[C@@H]43)nn2)NC(c2ccncc2)=NC1c1ccc(F)cc1Cl]
(ARK-671)

TABLE 5-continued
| Exemplary Compounds |
| --- |
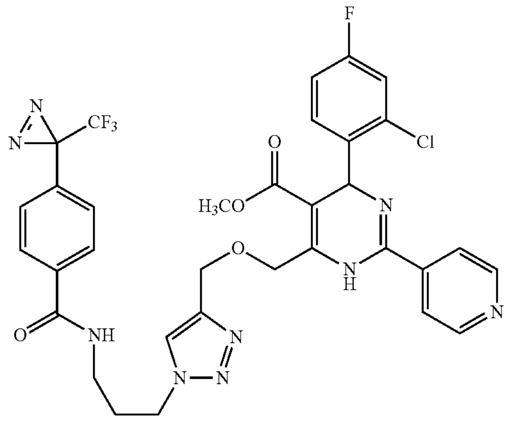 [SMILES: COC(=O)C1=C(COCc2cn(CCCNC(=O)c3ccc(C4(C(F)(F)F)N=N4)cc3)nn2)NC(c2ccncc2)=NC1c1ccc(F)cc1Cl]
I-17
(ARK-669)
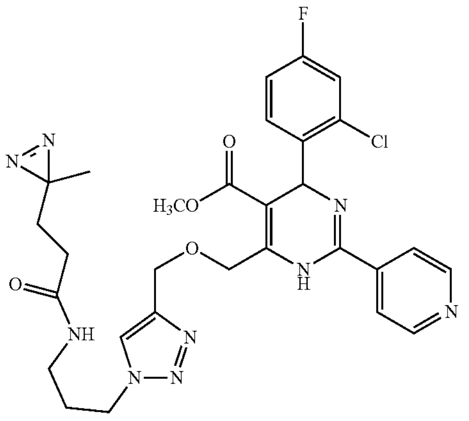 [SMILES: COC(=O)C1=C(COCc2cn(CCCNC(=O)CCC3(C)N=N3)nn2)NC(c2ccncc2)=NC1c1ccc(F)cc1Cl]
I-18
(ARK-668)
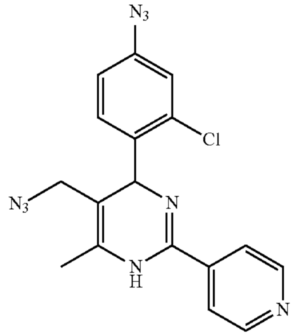 [SMILES: CC1=C(CN=[N+]=[N-])C(c2ccc(N=[N+]=[N-])cc2Cl)N=C(c2ccncc2)N1]
I-19
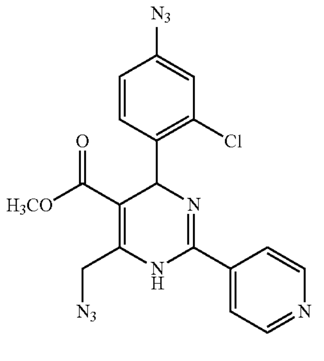 [SMILES: COC(=O)C1=C(CN=[N+]=[N-])NC(c2ccncc2)=NC1c1ccc(N=[N+]=[N-])cc1Cl]
I-20

TABLE 5-continued
| Exemplary Compounds |
| --- |
| I-21 |
| 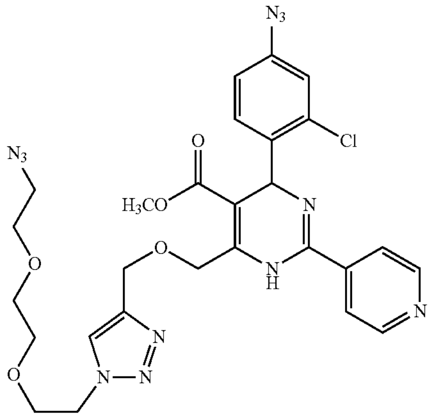 [SMILES: COC(=O)C1=C(COCc2cn(CCOCCOCCN=[N+]=[N-])nn2)NC(c2ccncc2)=NC1c1ccc(N=[N+]=[N-])cc1Cl] |
| I-22 |
| 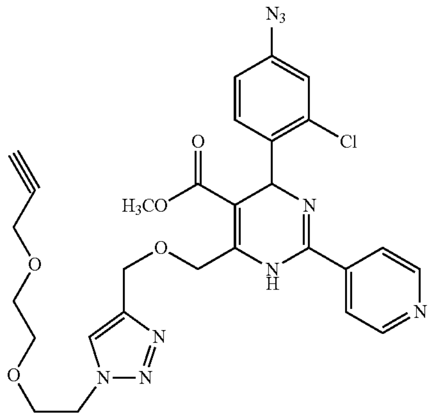 [SMILES: C#CCOCCOCCn1cc(COCC2=C(C(=O)OC)C(c3ccc(N=[N+]=[N-])cc3Cl)N=C(c3ccncc3)N2)nn1] |
| I-23 |
| 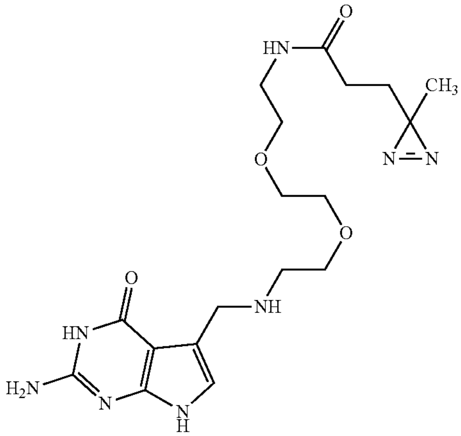 [SMILES: CC1(CCC(=O)NCCOCCOCCNCc2c[nH]c3nc(N)[nH]c(=O)c23)N=N1] |
| I-24 |
| 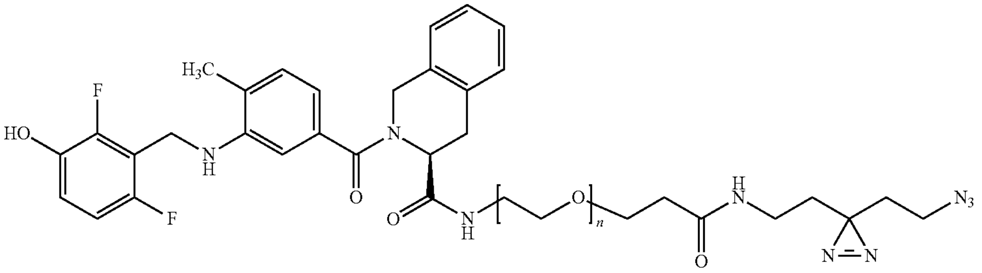 |
| n = 1 |

TABLE 5-continued
| Exemplary Compounds |
| --- |
| I-25 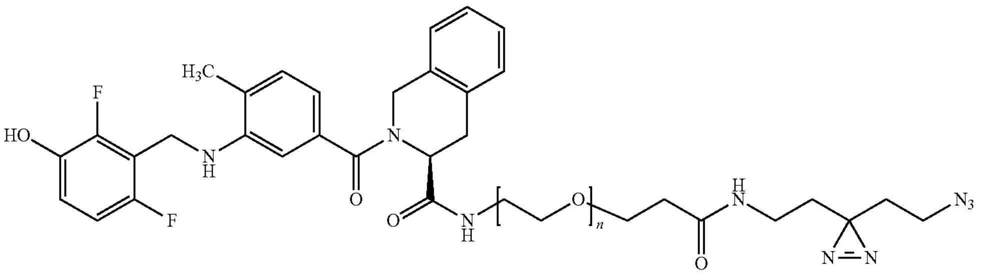 n = 2 |
| I-26 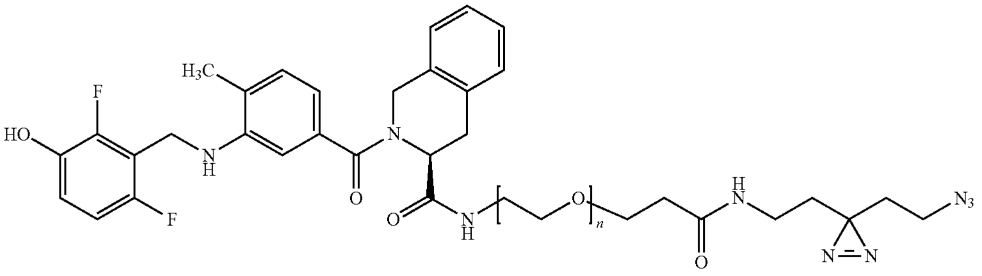 n = 4 |
| I-27 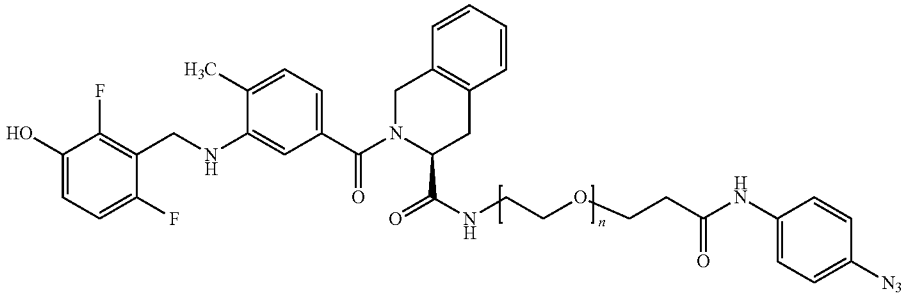 n = 1 |
| I-28 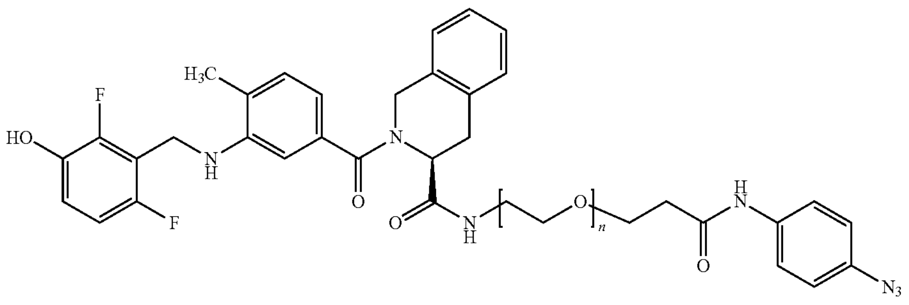 n = 2 |

TABLE 5-continued
| Exemplary Compounds |
| --- |
I-29
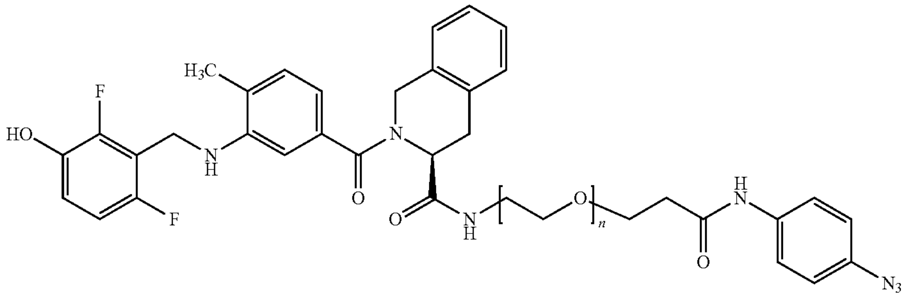
n = 4
I-30
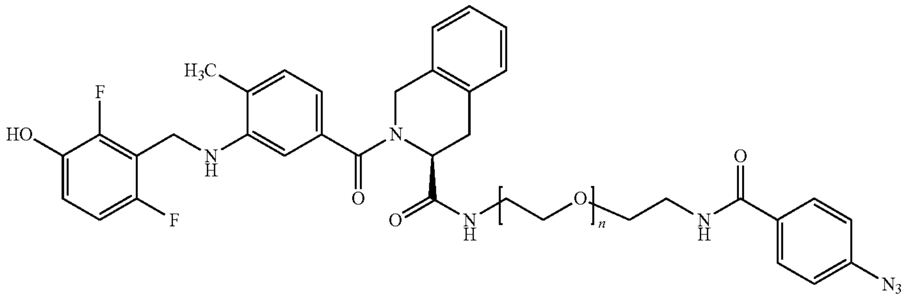
n = 1
I-31
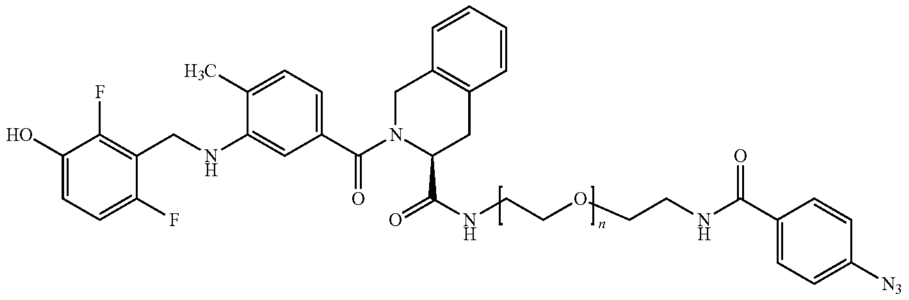
n = 2
I-32
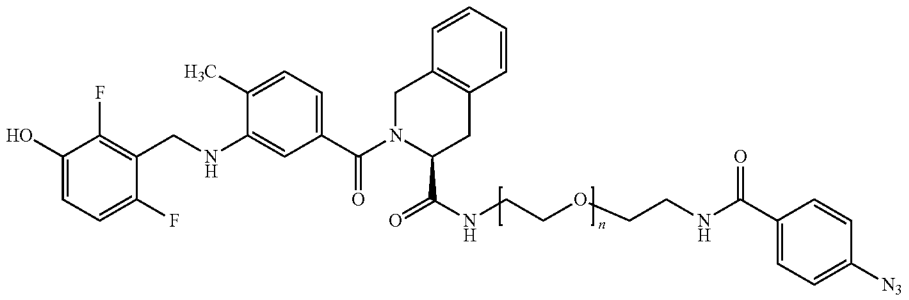
n = 4

TABLE 5-continued
| Exemplary Compounds |
| --- |
| I-33 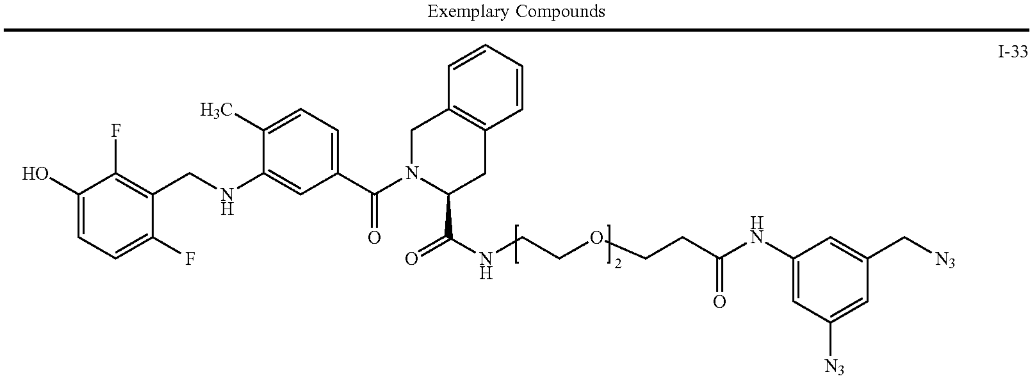 |
| I-34 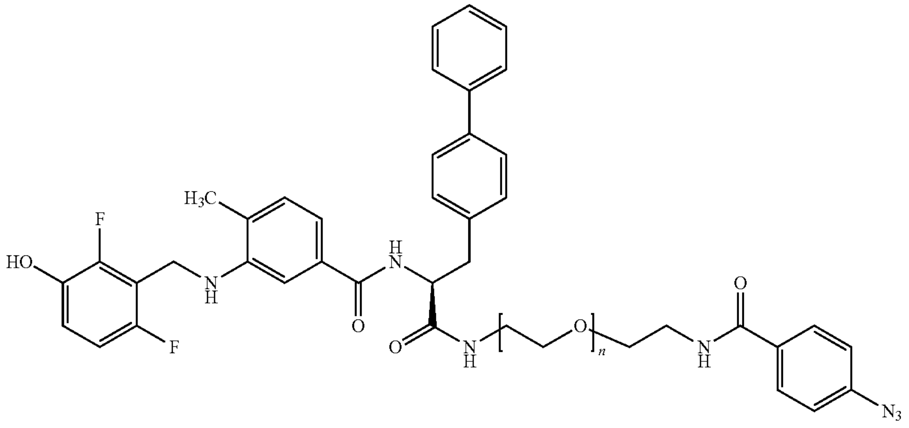 n = 1 |
| I-35 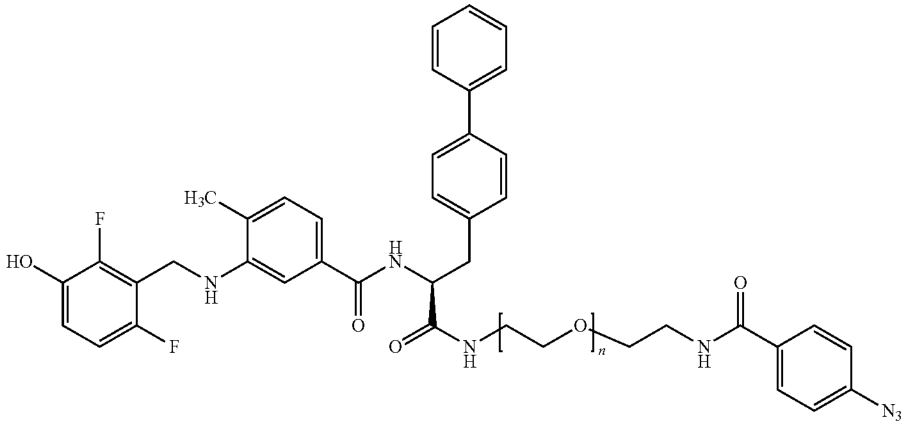 n = 2 |

TABLE 5-continued

| Exemplary Compounds |
| --- |
| I-36 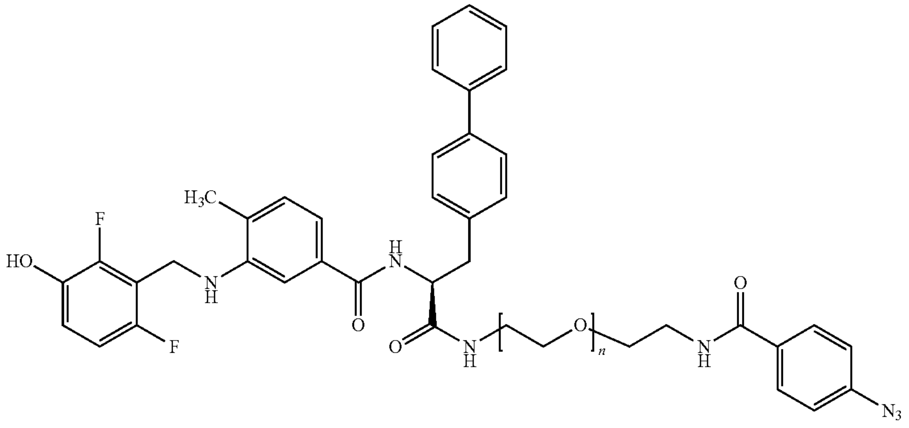 n = 4 |

In some embodiments, the present invention provides a compound set forth in Table 1, above, or a pharmaceutically acceptable salt thereof.

In some embodiments, the compound or conjugate is selected from those formulae shown in FIGS. 1-44, or a pharmaceutically acceptable salt, stereoisomer, or tautomer thereof.

Small Molecule RNA Ligands

The design and synthesis of novel, small molecule ligands capable of binding RNA represents largely untapped therapeutic potential. In some embodiments, the small molecule ligand is selected from a compound known to bind to RNA, such as a heteroaryldihydropyrimidine (HAP), a macrolide (e.g., erythromycin, azithromycin), alkaloid (e.g., berberine, palmatine), aminoglycoside (e.g., paromomycin, neomycin B, kanamycin A), tetracycline (e.g., doxycycline, oxytetracycline), a theophylline, ribocil, clindamycin, chloramphenicol, LMI070, a triptycene-based scaffold, an oxazolidinone (e.g., linezolid, tedizolid), or CPNQ.

In some embodiments, the small molecule ligand is ribocil, which has the following structure:

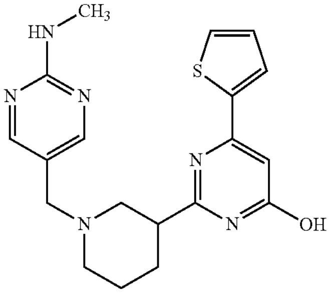 [SMILES: CNc1ncc(CN2CCCC(c3nc(O)cc(-c4cccs4)n3)C2)cn1]

or a pharmaceutically acceptable salt thereof. Ribocil is a drug-like ligand that binds to the FMN riboswitch (PDB 5KX9) and inhibits riboswitch function (*Nature* 2015, 526, 672-677).

In some embodiments, the small molecule ligand is an oxazolidinone such as linezolid, tedizolid, eperezolid, or PNU 176798. Exemplary oxazolidinone-based photoprobes are described in, e.g., Matassova, N. B. et al., *RNA* (1999), 5:939-946; Leach, K. L. et al., *Molecular Cell* 2007, 26, 393-402; Colca, J. R. et al., *J. Biol. Chem.* 2003, 278 (24), 21972-21979; and each of which is hereby incorporated by reference. Such oxazolidinones include the following:

1

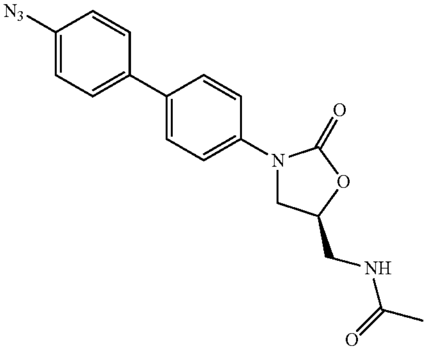

2

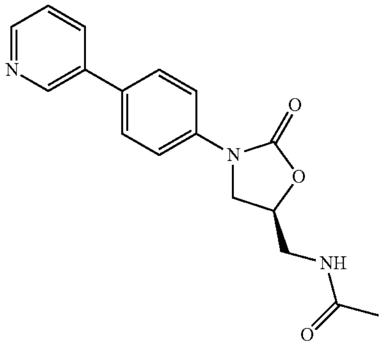

-continued

3

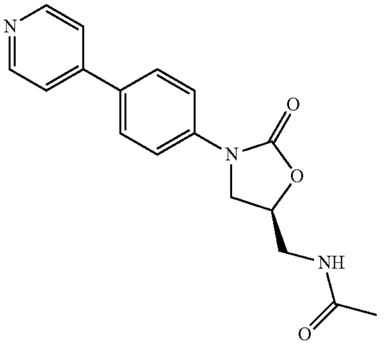

XL1

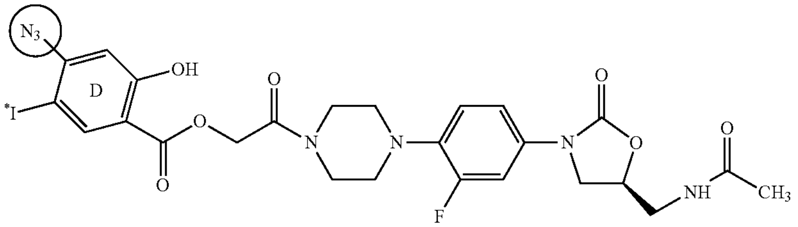

XL2

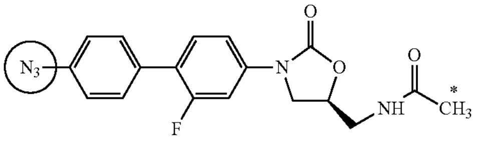

XL3

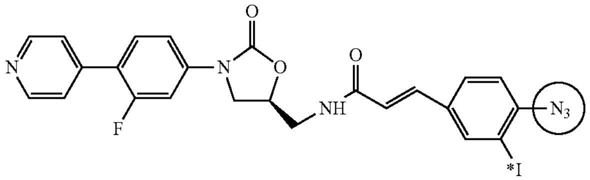

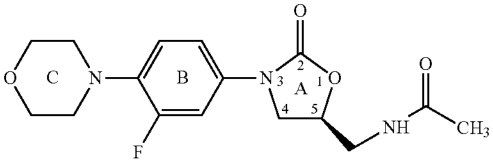

Linezolid

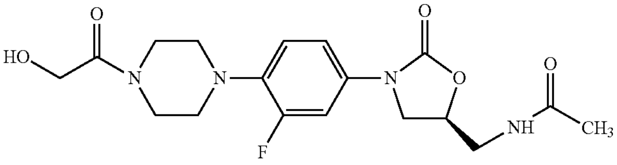

Eperezolid

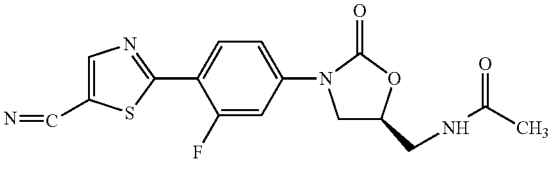

PNU 176798

The foregoing oxazolidinones may be substituted with a photoactivatable group as described herein at any available position, optionally with a tether linking the photoactivatable group with the oxazolidinone. Azide photoactivatable groups are optionally replaced with other photoactivatable groups described herein. The asterisks (*) indicate the position of a $^{125}I$ or $^{14}C$ radioligand used in the original reference, and which is optional for use as a pull-down group in the present invention.

Aryldiazonium salts, for example the p-diazonium anilide of L-5-carboxyspermine and L-2-carboxyputrescine, have also been shown to be useful as photoactivatable probes for RNA mapping and footprinting of RNA/protein interaction. See, e.g., Garcia, A. et al., *Nucleic Acids Res.* 1990, 18 (1), 89-95.

Furthermore, certain compounds comprising a quinoline core, of which CPNQ is one, are capable of binding RNA. CPNQ has the following structure:

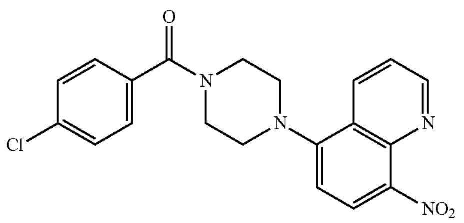 [SMILES: O=C(c1ccc(Cl)cc1)N1CCN(c2ccc([N+](=O)[O-])c3ncccc23)CC1]

Accordingly, in some embodiments, the small molecule ligand is selected from CPNQ or a pharmaceutically acceptable salt thereof. In other embodiments, the ligand is selected from a quinoline compound related to CPNQ, such as those provided in any one of FIG. 36 or 39-43; or a pharmaceutically acceptable salt thereof.

In some embodiments, CPNQ or a quinoline related to CPNQ is modified at one or more available positions to replace a hydrogen with a tether ($-T^1-$ and/or $-T^2-$), click-ready group ($—R^{CG}$), or warhead ($R^{mod}$), according to embodiments of each as described herein. For example, CPNQ or a quinoline related to CPNQ may have one of the following formulae:

IX-a

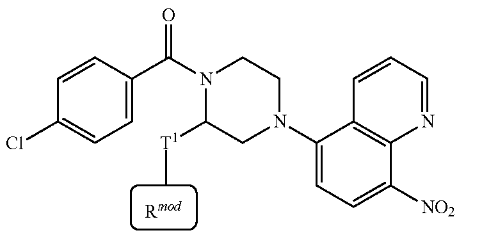

IX-b

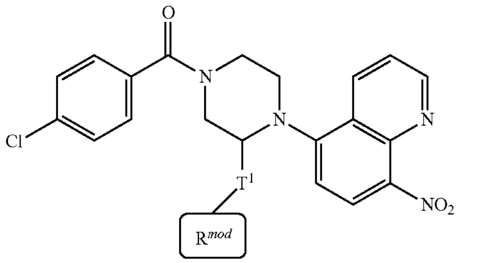

or a pharmaceutically acceptable salt thereof; wherein $R^{mod}$ is optionally substituted with $—R^{CG}$ or $-T^2-R^{CG}$, and further optionally substituted with a pull-down group. The compound of formulae IX-a or IX-b may further be optionally substituted with one or more optional substituents, as defined below, such as 1 or 2 optional substituents.

Organic dyes, amino acids, biological cofactors, metal complexes as well as peptides also show RNA binding ability. It is possible to modulate RNAs such as riboswitches, RNA molecules with expanded nucleotide repeats, and viral RNA elements.

The term "small molecule that binds a target RNA," "small molecule RNA binder," "affinity moiety," "ligand," or "ligand moiety," as used herein, includes all compounds generally classified as small molecules that are capable of binding to a target RNA with sufficient affinity and specificity for use in a disclosed method, or to treat, prevent, or ameliorate a disease associated with the target RNA. Small molecules that bind RNA for use in the present invention may bind to one or more secondary or tertiary structure elements of a target RNA. These sites include RNA triplexes, hairpins, bulge loops, pseudoknots, internal loops, junctions, and other higher-order RNA structural motifs described or referred to herein.

Accordingly, in some embodiments, the small molecule that binds to a target RNA (e.g., Ligand in Formulae I-VIII above) is selected from a heteroaryldihydropyrimidine (HAP), a macrolide, alkaloid, aminoglycoside, a member of the tetracycline family, an oxazolidinone, a SMN2 pre-mRNA ligand such as LMI070 (NVS-SM1), ribocil or an analogue thereof, clindamycin, chloramphenicol, an anthracene, a triptycene, theophylline or an analogue thereof, or CPNQ or an analogue thereof. In some embodiments, the small molecule that binds to a target RNA is selected from paromomycin, a neomycin (such as neomycin B), a kanamycin (such as kanamycin A), linezolid, tedizolid, pleuromutilin, ribocil, anthracene, triptycene, or CPNQ or an analogue thereof wherein each small molecule may be optionally substituted with one or more "optional substituents" as defined below, such as 1, 2, 3, or 4, for example 1 or 2, optional substituents. In some embodiments, the small molecule is selected from those shown in FIG. 1-8 or 18-44, or a pharmaceutically acceptable salt, stereoisomer, or tautomer thereof.

In some embodiments, the Ligand is selected from

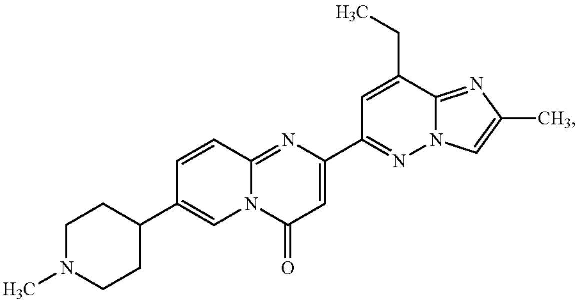

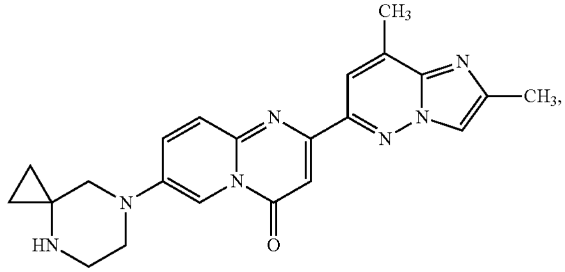

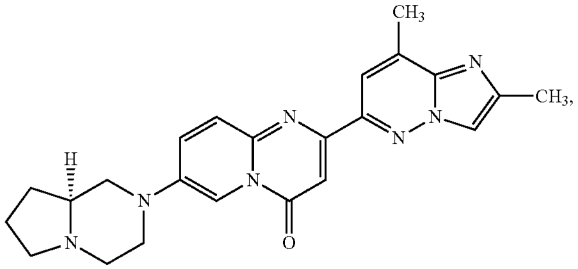

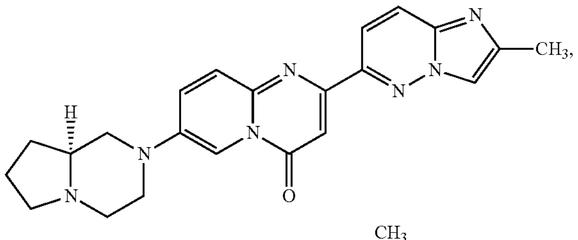

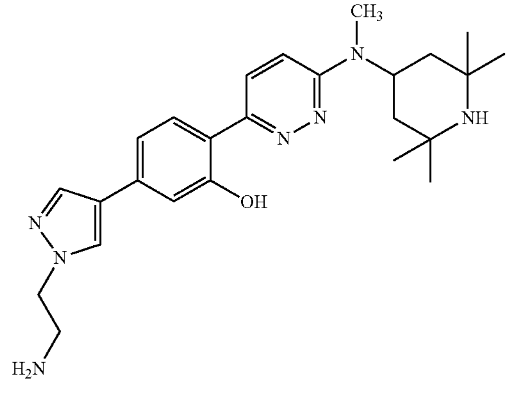 ,

-continued

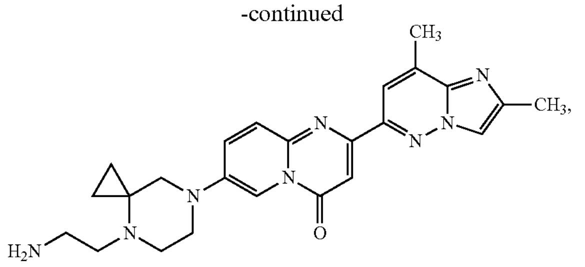

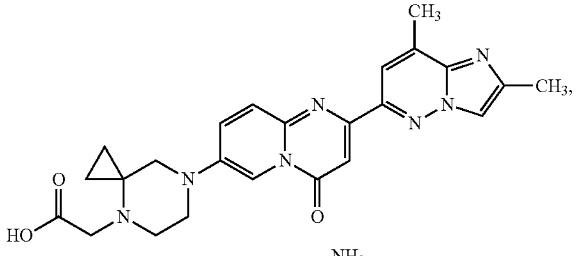

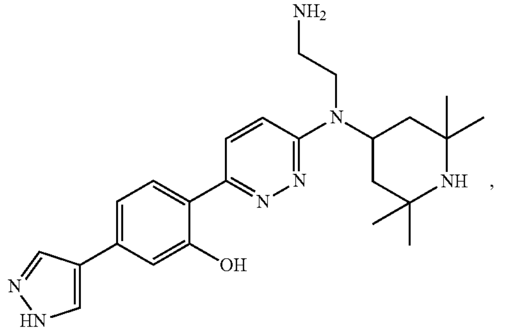

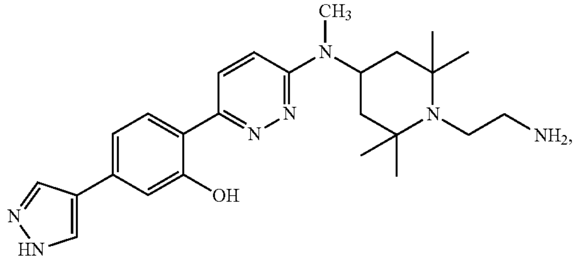

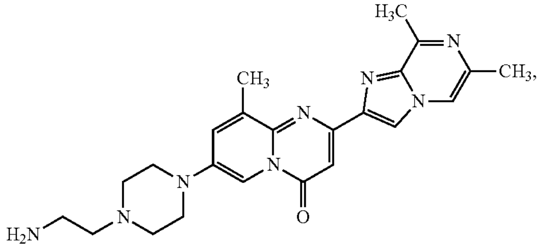

or

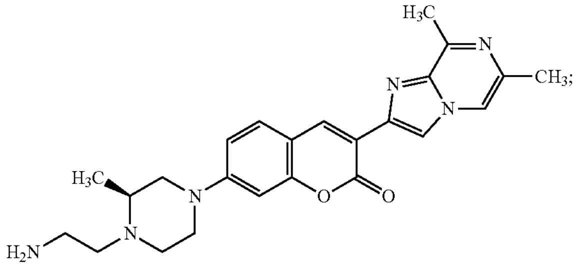

or a pharmaceutically acceptable salt thereof.

In some embodiments, the Ligand binds to a junction, stem-loop, or bulge in a target RNA. In some embodiments, Ligand binds to a nucleic acid three-way junction (3WJ). In some embodiments, the 3WJ is a trans 3WJ between two RNA molecules. In some embodiments, the 3WJ is a trans 3WJ between a miRNA and mRNA. In some embodiments, the Ligand binds to DNA, such as a DNA loop or junction.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

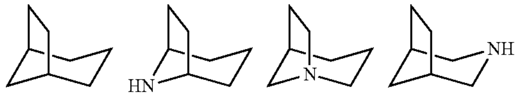

-continued

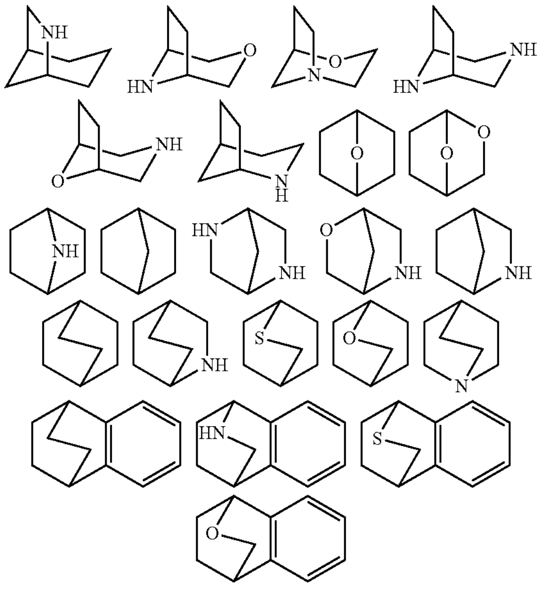

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted with a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, di azepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted with a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent ("optional substituent") at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$, $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene$)O-N(R^{\circ})_2$; or $-(C_{1-4}$ straight or branched$)$alkylene$)C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2-$(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{1-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene$)C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-NR^{\dagger}$, $-NR^{\dagger}_2$, $-C(O)R^{\dagger}$, $-C(O)OR^{\dagger}$, $-C(O)C(O)R^{\dagger}$, $C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "inhibitor" is defined as a compound that binds to and/or modulates or inhibits a target RNA with measurable affinity. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, mean a measurable change in a downstream biological effect between a sample comprising a compound of the present invention, or composition thereof, and a target RNA, and an equivalent sample comprising the target RNA, in the absence of said compound, or composition thereof.

The term "RNA" (ribonucleic acid) as used herein, means naturally-occurring or synthetic oligoribonucleotides independent of source (e.g., the RNA may be produced by a human, animal, plant, virus, or bacterium, or may be synthetic in origin), biological context (e.g., the RNA may be in the nucleus, circulating in the blood, in vitro, cell lysate, or isolated or pure form), or physical form (e.g., the RNA may be in single-, double-, or triple-stranded form (including RNA-DNA hybrids), may include epigenetic modifications, native post-transcriptional modifications, artificial modifications (e.g., obtained by chemical or in vitro modification), or other modifications, may be bound to, e.g., metal ions, small molecules, protein chaperones, or cofactors, or may be in a denatured, partially denatured, or folded state including any native or unnatural secondary or tertiary structure such as junctions (e.g., cis or trans three-way junctions (3WJ)), quadruplexes, hairpins, triplexes, hairpins, bulge loops, pseudoknots, and internal loops, etc., and any transient forms or structures adopted by the RNA). In some embodiments, the RNA is 100 or more nucleotides in length. In some embodiments, the RNA is 250 or more nucleotides in length. In some embodiments, the RNA is 350, 450, 500, 600, 750, or 1,000, 2,000, 3,000, 4,000, 5,000, 7,500, 10,000, 15,000, 25,000, 50,000, or more nucleotides in length. In some embodiments, the RNA is between 250 and 1,000 nucleotides in length. In some embodiments, the RNA is a pre-RNA, pre-miRNA, or pretranscript. In some embodiments, the RNA is a non-coding RNA (ncRNA), messenger RNA (mRNA), micro-RNA (miRNA), a ribozyme, riboswitch, lncRNA, lincRNA, snoRNA, snRNA, scaRNA, piRNA, ceRNA, pseudo-gene, viral RNA, or bacterial RNA. The term "target RNA," as used herein, means any type of RNA having a secondary or tertiary structure capable of binding a small molecule ligand described herein. The target RNA may be inside a cell, in a cell lysate, or in isolated form prior to contacting the compound.

Photoactivatable Groups

Suitable covalent modifier moieties (e.g. $R^{mod}$ shown in Formulae I-VIII above) for use in the present invention generally include photoactivatable groups that generate a reactive intermediate upon irradiation with visible or ultraviolet light. In some embodiments, the photoactivatable group is a functional group that generates a carbon- or oxygen-centered radical, an aryl or heteroaryl carbocation, a nitrene, or a carbene intermediate upon irradiation with ultraviolet (UV) radiation; and wherein R'd is capable of reacting with a target RNA to which Ligand binds to produce a covalent bond with the target RNA. Exemplary photoactivatable chromophores and the reactive species generated after irradiation are shown below.

Scheme 1: Reactions of Benzophenones and Aryl Azides
Benzophenone
Aryl azide
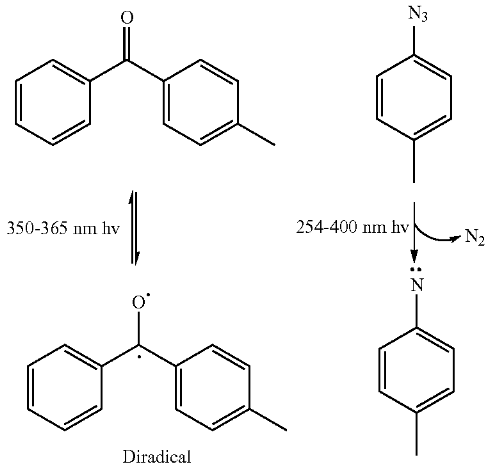
Diradical
Nitrene
Scheme 2: Reactions of Diazirines
Trifluoromethy phenyl diazirine
Alkyl diazirine
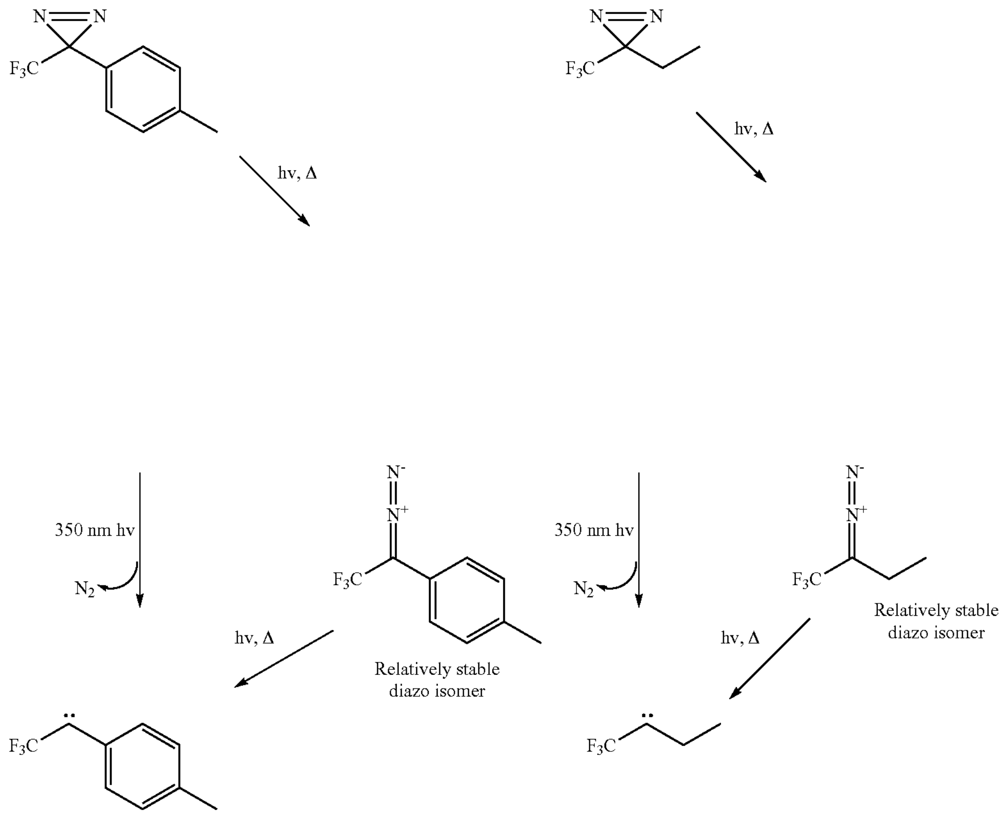
Carbene
Carbene Scheme 3: Exemplary Reactions of Nucleic Acid Purines with Photoactivatable Groups
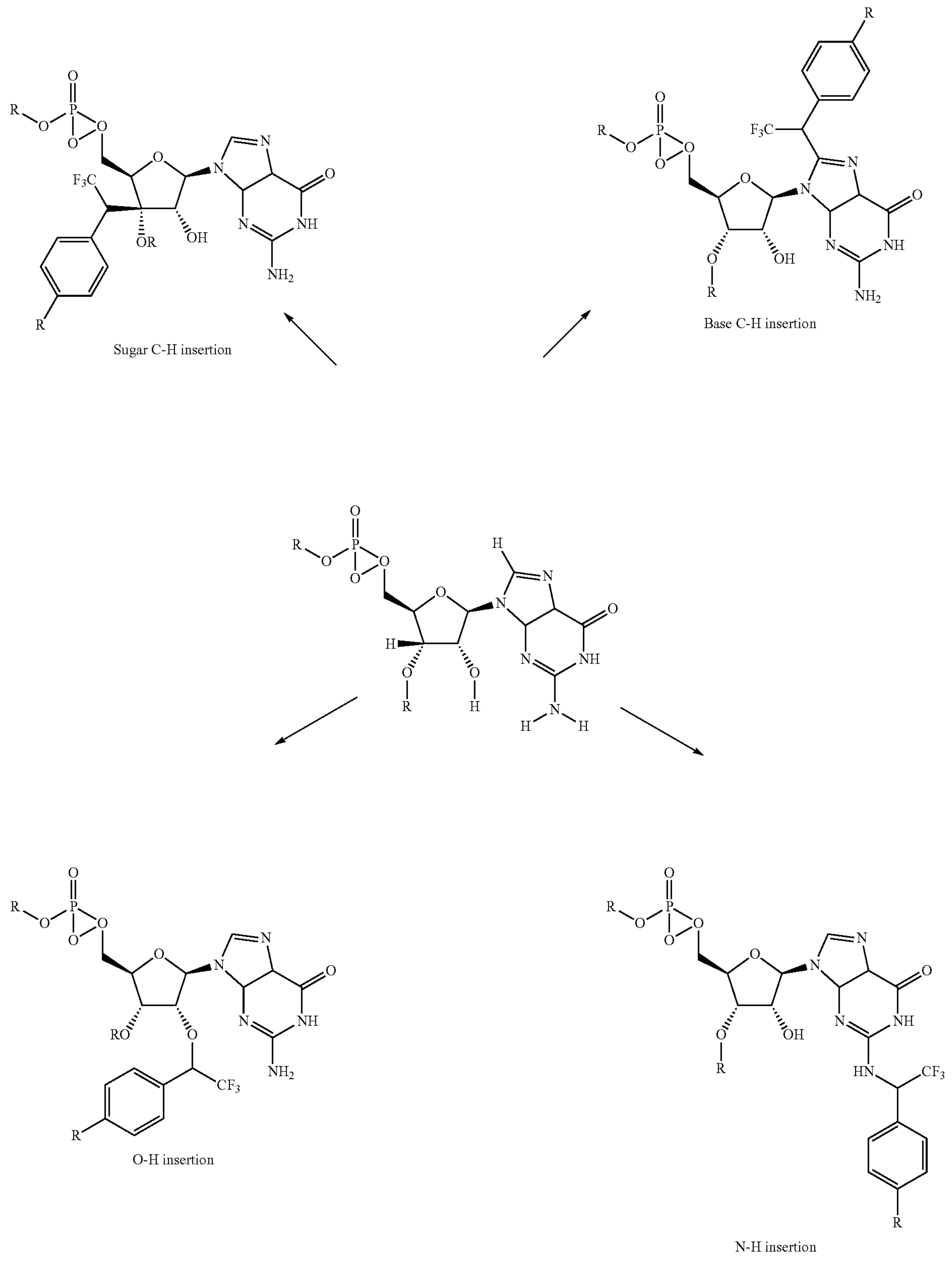

Since the warhead is unreactive prior to activation, a non-covalent RNA-ligand interaction is required for successful photoactivated modification. The reactive carbene/nitrene intermediates are rapidly quenched by water if a suitably positioned macromolecule is not present.

α-pyrones and pyrimidones are also photoactivatable groups that may be used in the present invention. For example, Battenberg, 0. A. et al. (*J. Org. Chem.* 2011, 76, 6075-6087) disclose photoprobes such as the following:

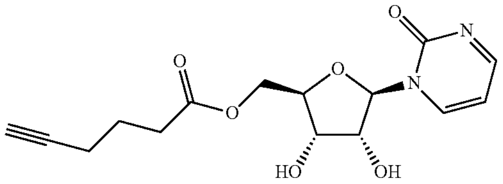

-continued

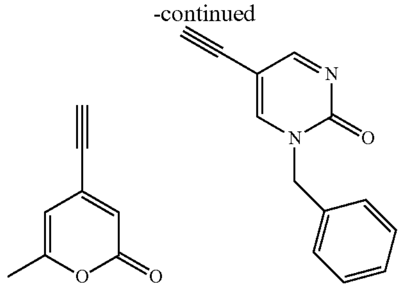

In some embodiments, the photoactivatable group is selected from a pyrone or pyrimidone such as those above.

In other embodiments, the photoactivable group, after irradiation and formation of a covalent bond with the target RNA, undergoes an equilibrium process that optionally includes reversion to its original state. Synthetic molecules that are isomerizable in a reversible fashion under light irradiation of different wavelengths and which may be used as photoactivatable groups include diazobenzenes, dihydropyrenes, spirooxazines, anthracenes, fulgides, and spiropyrans. An exemplary spiropyran and its irradiation-induced equilibrium process are shown in the scheme below.

Scheme 4: Exemplary Spiropyran Photoprobe

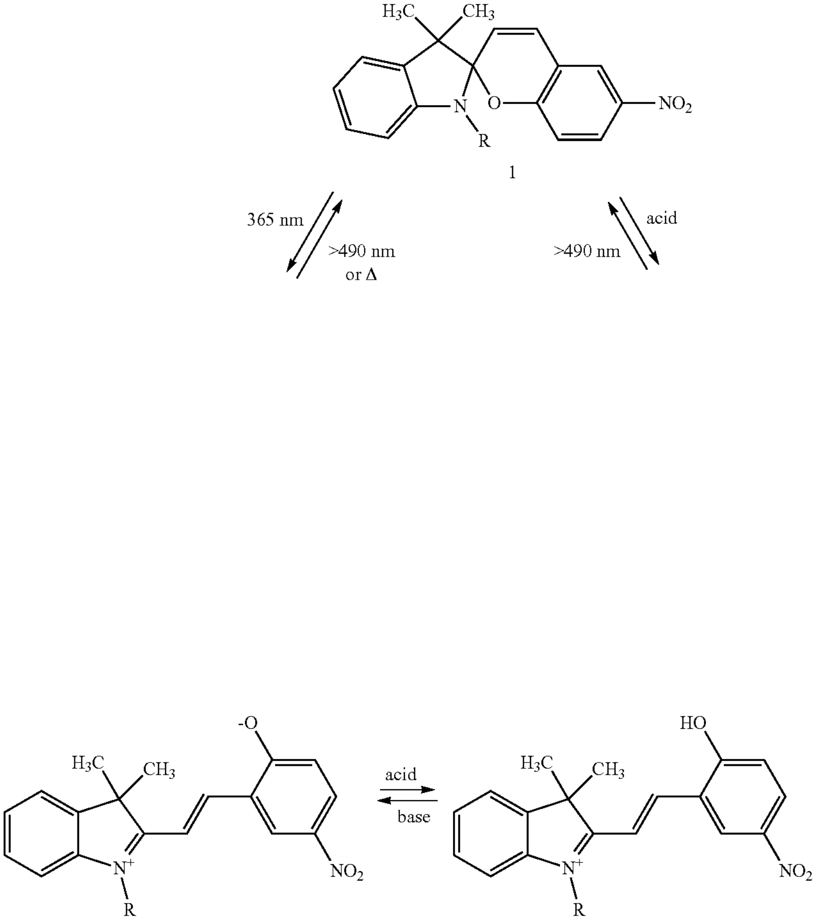

1

2a

2b wherein R=—$(CH_2)_2O_2C(CH_2)_2NH_2$ and 1 above may be optionally substituted; the spiropyran may be linked to a small molecule ligand and optional pull-down group by a covalent bond or tether as described herein. One characteristic of spiropyran 1 in comparison with other reversible systems lies in its photochemical switching being virtually complete (>95% of 2a after UV irradiation at 365 nm) because of the distinctively different absorption maxima of 1 (350 nm) and 2a (563 nm), unlike diazobenzenes, which reach a photostationary state of 70-90% cis when exposed to UV light of 365 nm. The equilibrium of 2a and 2b can also be influenced by pH. See, e.g., Young, D. D. et al., *ChemBioChem* 2008, 9, 1225-1228.

In some embodiments, the photoactivatable group is selected from an optionally substituted phenyl or 8-10 membered bicyclic aromatic carbocyclic azide or 5-8 membered heteroaryl or 8-10 membered bicyclic heteroaryl azide, optionally substituted benzoyl azide or 5-8 membered heteroaroyl azide or 8-10 membered heteroaroyl azide wherein 1-3 atoms of the ring atoms are selected from nitrogen, sulfur, or oxygen, optionally substituted phenyl or 8-10 membered bicyclic aromatic carbocyclic diazonium salt, optionally substituted 5-8 membered heteroaryl or 8-10 membered bicyclic heteroaryl diazonium salt wherein 1-3 atoms of the ring atoms are selected from nitrogen, sulfur, or oxygen, optionally substituted $C_{2-6}$ aliphatic diazo functional group, optionally substituted $C_{2-6}$ aliphatic diazirine, or optionally substituted diphenyl or 8-10-membered diheteroaryl ketone wherein 1-3 atoms of the ring atoms are selected from nitrogen, sulfur, or oxygen, optionally substituted dihydropyrene, optionally substituted spirooxazine, optionally substituted anthracene, optionally substituted fulgide, optionally substituted spiropyran, optionally substituted α-pyrone or optionally substituted pyrimidone.

In some embodiments, the photoactivatable group is selected from, e.g.

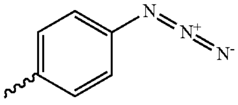

Phenyl Azide

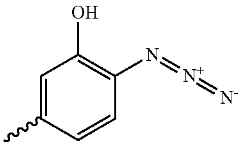

ortho-Hydroxyphenyl Azide

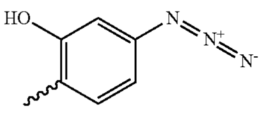

meta-Hydroxyphenyl Azide

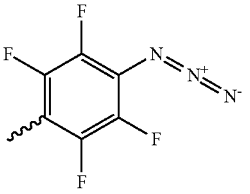

Tetrafluorophenyl Azide

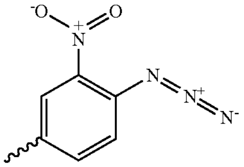

ortho-Nitrophenyl Azide

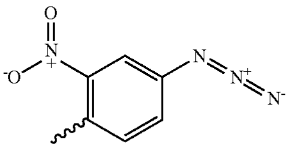

meta-Nitrophenyl Azide

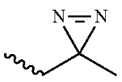

Diazirine

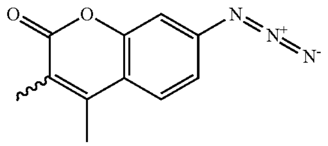

Azido-methylcoumarin

-continued

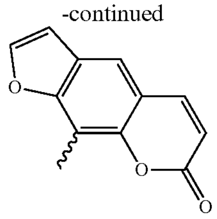

Psoralen

Photoactivatable groups can be conjugated to small molecule ligands or tethers by conventional coupling reactions known to those of ordinary skill in the art and as described herein. For example, photoactivatable amino acids such as D- or L-photoleucine, photomethionine, photolysine, para-benzoylphenylalanine, and others can serve as convenient means of introducing a photoactivatable group into a compound in accordance with the present invention.

In some embodiments, the photoactivatable group is an aroyl or heteroaroyl azide, such as nicotinoyl azide (NAz). Such compounds form nitrene intermediates upon irradiation, and have been used to study solvent accessibility of nucleic acids such as the SAM-1 riboswitch and rRNA in cells. NAz probes react, for example, with the C8 position of accessible purines.

The term "covalent modifier moiety" or "warhead" as used herein, means any photoactivatable group capable of forming a covalent bond with an available nucleotide of a RNA to produce a modified RNA (such as a C8-modified purine or 2'-O-modified RNA) after irradiation with visible or UV light.

The wavelength of visible or UV light for activating the photoactivatable group is generally selected to generate the reactive intermediate such as a nitrene without substantially degrading the biological system under investigation or causing off-target reactivity. The wavelength is generally a wavelength known to function to generate the reactive intermediate for each specific photoactivatable group. In some embodiments, the wavelenegth is about 252 nm, 302 nm, or 365 nm; or 254 nm, 265-275 nm, 365 nm, 300-460 nm, or about 250 nm to about 350 nm.

When an aryl azide is exposed to UV light (250 to 350 nm), it forms a nitrene group that can initiate addition reactions with double bonds, insertion into C—H and N—H sites, or subsequent ring expansion to react with a nucleophile (e.g., primary amines). The latter reaction path dominates when primary amines are present in the sample.

Thiol-containing reducing agents (e.g., DTT or 2-mercaptoethanol) must be avoided in the sample solution during all steps before and during photo-activation, because they reduce the azide functional group to an amine, preventing photo-activation. Reactions can be performed in a variety of amine-free buffer conditions. If working with heterobifunctional photoreactive crosslinkers, use buffers compatible with both reactive chemistries involved. In general, experiments are performed in subdued light and/or with reaction vessels covered in foil until photoreaction is intended. Typically, photo-activation is accomplished with a hand-held UV lamp positioned close to the reaction solution and shining directly on it (i.e., not through glass or polypropylene) for several minutes.

Examples of aryl azides include simple phenyl azides, hydroxyphenyl azides, and nitrophenyl azides. Generally, short-wavelength UV light (e.g., 254 nm; 265 to 275 nm) is needed to efficiently activate simple phenyl azides, while long-UV light (e.g, 365 nm; 300 to 460 nm) is sufficient for nitrophenyl azides.

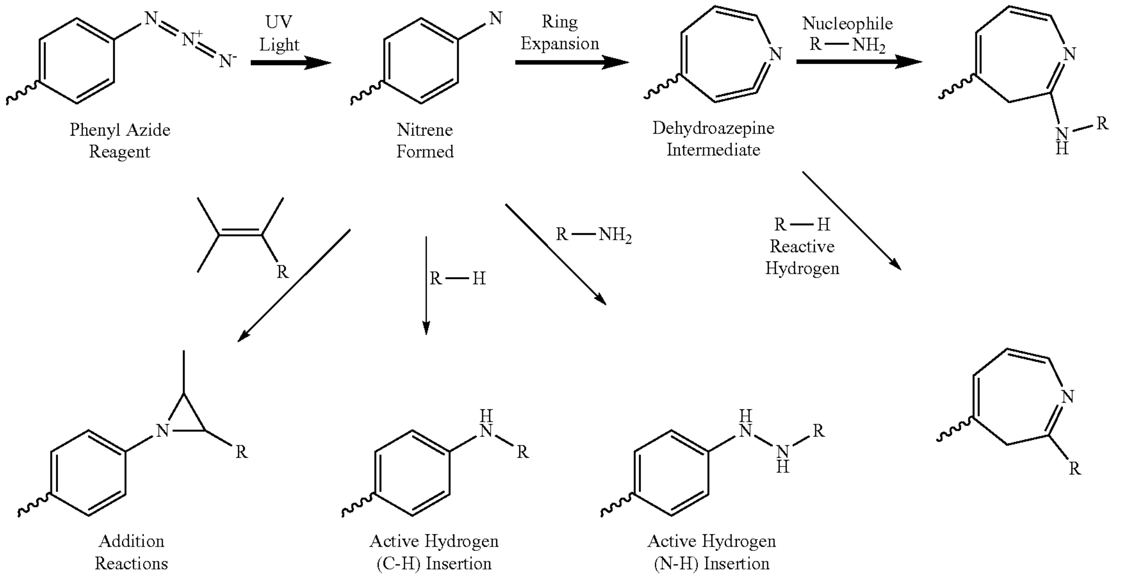

Covalent Modification of RBP Proteins and Other Proximate Biomolecules

In some embodiments, the photoactivatable group reacts with a protein in proximity to the small molecule ligand binding site on a target RNA. RNA binding proteins (RBPs) are frequently associated with target RNAs of interest. In some cases, a RBP is associated with or otherwise in proximity to the targeted RNA sub-structure to which a disclosed photoactivatable compound binds. Accordingly, an advantage of the photoaffinity warheads is that they are agnostic about covalent modification of RNAs or proteins such as RBPs proximal to the photoactivatable group that is attached to the small molecule ligand. Thus, in some embodiments, a disclosed compound covalently modifies either a target RNA or a RBP associated with the target RNA. This in turn yields insight into which RBPs are bound to a target RNA and in which cells or tissues of an organism, as well as the effect of the small molecule binding on RBP binding.

Thus, in one aspect, the present invention provides a method of determining the presence of or association/binding of a RNA binding protein (RBP) with a target RNA, comprising the step of contacting the target RNA with a disclosed compound and irradiating the compound with visible or UV light, and optionally performing one or more assays to determine whether a RBP has been covalently modified by the photoactivatable group of the compound.

The highly reactive and thus relatively indiscriminate carbenes, nitrenes, diradicals, and other intermediates produced by activation of the photoaffinity warheads thus have the advantage of covalently modifying a target RNA or any biomolecule in proximity, unlike previously known methods.

Tethering Groups (Linkers)

The present invention contemplates the use of a wide variety of tethering groups (tethers; e.g., variables $T^1$ and $T^2$ as shown in Formulae I-VIII above) to provide optimal binding and reactivity toward nucleotides or RBPs proximal to the binding site of a target RNA. In some embodiments, $T^1$ and $T^2$ are selected from those shown in FIGS. 10-17. For example, in some embodiments, $T^1$ and/or $T^2$ is a polyethylene glycol (PEG) group of, e.g., 1-10 ethylene glycol subunits. In some embodiments, $T^1$ and/or $T^2$ is an optionally substituted $C_{1-12}$ aliphatic group or a peptide comprising 1-8 amino acids.

In some embodiments, $T^1$ and $T^2$ are each independently selected from $L^1$ or $L^2$, as $L^1$ and $L^2$ are defined in embodiments herein.

In some embodiments, the physical properties such as the length, rigidity, hydrophobicity, and/or other properties of the tether are selected to optimize the pattern of proximity-induced covalent bond formation between the target RNA or an associated RBP and the photoactivatable group (warhead). In some embodiments, the physical properties of the tether (such as those above) are selected so that, upon binding of the compound to the active or allosteric sites of a target RNA, the modifying moiety selectively reacts with a an available functionality of the target RNA such as a purine C8 carbon or 2'-OH group of the target RNA proximal to the active site or allosteric sites, or reacts with a proximal amino acid of a RBP.

Click-Ready Groups

A variety of bioorthogonal reaction partners (e.g., $R^{CG}$ in Formulae I-VIII or $R^2$ in Formulae above) may be used in the present invention to couple a compound described herein with a pull-down moiety. The term "bioorthogonal chemistry" or "bioorthogonal reaction," as used herein, refers to any chemical reaction that can take place in living systems without interfering with native biochemical processes. Accordingly, a "bioorthogonal reaction partner" is a chemical moiety capable of undergoing a bioorthogonal reaction with an appropriate reaction partner to couple a compound described herein to a pull-down moiety. In some embodiments, a bioorthogonal reaction partner is covalently attached to the chemical modifying moiety or the tethering group. In some embodiments, the bioorthogonal reaction partner is selected from a click-ready group or a group capable of undergoing a nitrone/cyclooctyne reaction, oxime/hydrazone formation, a tetrazine ligation, an isocyanide-based click reaction, or a quadricyclane ligation.

In some embodiments, the bioorthogonal reaction partner is a click-ready group. The term "click-ready group" refers to a chemical moiety capable of undergoing a click reaction, such as an azide or alkyne.

Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition and the Diels-Alder cycloaddition are two such reactions.

Such click reactions (i.e., dipolar cycloadditions) are associated with a high activation energy and therefore require heat or a catalyst. Indeed, use of a copper catalyst is routinely employed in click reactions. However, in certain instances where click chemistry is particularly useful (e.g., in bioconjugation reactions), the presence of copper can be detrimental (See Wolbers, F. et al.; Electrophoresis 2006, 27, 5073). Accordingly, methods of performing dipolar cycloaddition reactions were developed without the use of metal catalysis. Such "metal free" click reactions utilize activated moieties in order to facilitate cycloaddition. Therefore, the present invention provides click-ready groups suitable for metal-free click chemistry.

Certain metal-free click moieties are known in the literature. Examples include 4-dibenzocyclooctynol (DIBO) (from Ning et al; *Angew Chem Int Ed,* 2008, 47, 2253); gem-difluorinated cyclooctynes (DIFO or DFO) (from Codelli, et al.; *J. Am. Chem. Soc.* 2008, 130, 11486-11493.); biarylazacyclooctynone (BARAC) (from Jewett et al.; *J. Am. Chem. Soc.* 2010, 132, 3688.); or bicyclononyne (BCN) (From Dommerholt, et al.; *Angew Chem Int Ed,* 2010, 49, 9422-9425).

As used herein, the phrase "a moiety suitable for metal-free click chemistry" refers to a functional group capable of dipolar cycloaddition without use of a metal catalyst. Such moieties include an activated alkyne (such as a strained cyclooctyne), an oxime (such as a nitrile oxide precursor), or oxanorbornadiene, for coupling to an azide to form a cycloaddition product (e.g., triazole or isoxazole).

Thus, in certain embodiments, the click-ready group is selected from an azide, an alkyne, 4-dibenzocyclooctynol (DIBO) gem-difluorinated cyclooctynes (DIFO or DFO), biarylazacyclooctynone (BARAC), bicyclononyne (BCN), a strained cyclooctyne, an oxime, or oxanorbornadiene.

In some embodiments, the click-ready group is selected from those shown in FIG. 9.

Pull-Down Groups

A number of pull-down groups ($R^{PD}$ in, for example, Formulae I-VIII above) may be used in the present invention. In some embodiments, pull-down groups contain a bioorthogonal reaction partner that reacts with a click-ready group to attach the pull-down group to the rest of the compound, as well as an appropriate functional group or affinity group such as a hapten (e.g., biotin) or a radiolabel allowing for selective isolation or detection of the pulled-down compound. For example, use of avidin or streptavidin to interact with a pull-down group would allow isolation of only those RNAs that had been covalently modified, as explained in further detail below.

In some embodiments, a pull-down group is covalently attached to a disclosed compound as described above and in formulae described herein, before binding to a target RNA and before irradiation to activate the photoactivatable group. In other embodiments, a pull-down group is attached to a compound or RNA conjugate after the photoactivatable group has been irradiated and covalent modification of a target RNA has taken place. In some embodiments, such attachment is achieved by a bioorthogoal reaction between a click-ready group on the compound or RNA conjugate and an appropriate reaction partner that is part of the pull-down group. Accordingly, in some embodiments, the pull-down group comprises a click-ready group attached via a tether (as described elsewhere herein) to an affinity group or bioorthogonal functional group. In some embodiments, the affinity group or bioorthogonal functional group is a hapten (e.g., biotin) or a radiolabel such as $^{125}I$, $^{14}C$, $^{32}P$, or $^{3}H$.

3. General Methods of Providing the Present Compounds

The compounds of this invention may be prepared or isolated in general by synthetic and/or semi-synthetic methods known to those skilled in the art for analogous compounds and by methods described in detail in the Examples and Figures, herein.

In the schemes and chemical reactions depicted in the detailed description, Examples, and Figures, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyl oxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry," $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification and Figures.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit or modulate a target RNA, or a mutant thereof, in a biological sample or in a patient. In certain embodiments, the amount of compound in compositions of this invention is such that is effective to measurably inhibit or modulate a target RNA, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulation of a target RNA to retreat an RNA-mediated disease or condition.

The activity of a compound utilized in this invention to modulate a target RNA may be assayed in vitro, in vivo or in a cell line. In vitro assays include assays that determine modulation of the target RNA. Alternate in vitro assays quantitate the ability of the compound to bind to the target RNA. Detailed conditions for assaying a compound utilized in this invention to modulate a target RNA are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are modulators of a target RNA and are therefore useful for treating one or more disorders associated with or affected by (e.g., downstream of) the target RNA. Thus, in certain embodiments, the present invention provides a method for treating an RNA-mediated disorder comprising the step of administering to a patient in need thereof a compound of the present invention, or pharmaceutically acceptable composition thereof.

As used herein, the terms "RNA-mediated" disorders, diseases, and/or conditions as used herein means any disease or other deleterious condition in which RNA, such as an overexpressed, underexpressed, mutant, misfolded, pathogenic, or ongogenic RNA, is known to play a role. Accordingly, another embodiment of the present invention relates to treating or lessening the severity of one or more diseases in which RNA, such as an overexpressed, underexpressed, mutant, misfolded, pathogenic, or ongogenic RNA, is known to play a role.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by modulating a target RNA. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Cancers includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Inflammatory Disorders and Diseases

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Metabolic Disease

In some embodiments the invention provides a method of treating a metabolic disease. In some embodiments the metabolic disease is selected from Type 1 diabetes, Type 2 diabetes, metabolic syndrome or obesity.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient," as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating the activity of a target RNA in a biological sample comprising the step of contacting said biological sample with a compound of this invention, or a composition comprising said compound.

According to another embodiment, the invention relates to a method of modulating the activity of a target RNA in a biological sample comprising the step of contacting said biological sample with a compound of this invention, or a composition comprising said compound. In certain embodiments, the invention relates to a method of irreversibly inhibiting the activity of a target RNA in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, cerebrospinal fluid, or other body fluids or extracts thereof.

Another embodiment of the present invention relates to a method of modulating the activity of a target RNA in a patient comprising the step of administering to said patient a compound of the present invention, or a composition comprising said compound.

According to another embodiment, the invention relates to a method of inhibiting the activity of a target RNA in a patient comprising the step of administering to said patient a compound of the present invention, or a composition comprising said compound. According to certain embodiments, the invention relates to a method of irreversibly inhibiting the activity of a target RNA in a patient comprising the step of administering to said patient a compound of the present invention, or a composition comprising said compound. In other embodiments, the present invention provides a method for treating a disorder mediated by a target RNA in a patient in need thereof, comprising the step of administering to said patient a compound according to the present invention or pharmaceutically acceptable composition thereof. Such disorders are described in detail herein.

EXEMPLIFICATION

As depicted in the Examples below, exemplary compounds are prepared according to the following general procedures and used in biological assays and other procedures described generally herein. It will be appreciated that, although the general methods depict the synthesis of certain compounds of the present invention, the following general methods, and other methods known to one of ordinary skill in the art, can be applied to all compounds and subclasses and species of each of these compounds, as described herein. Similarly, assays and other analyses can be adapted according to the knowledge of one of ordinary skill in the art.

Example 1: Application of Photoprobes to Locate and Quantify Sites of Modifications in RNA As discussed above, a variety of RNA molecules play important regulatory roles in cells. RNA secondary and tertiary structures are critical for these regulatory activities. Various tools are available for determining RNA structure. One of the most effective methods is SHAPE (selective 2'-hydroxyl acylation and primer extension). This methodology takes advantage of the characteristic that the ribose group in all RNAs has a 2'-hydroxyl whose reactivity is affected by local nucleotide flexibility and accessability to solvent. This 2'-hydroxyl is reactive in regions of the RNA that are single-stranded and flexible, but is unreactive at nucleotides that are base-paired. In other words, SHAPE reactivity is inversely proportional to the probability that a nucleotide is base paired within an RNA secondary structure. Reagents that chemically modify the RNA at this 2'-hydroxyl can be used as probes to discern RNA structure. SHAPE reagents include small-molecules such as 1-methyl-7-nitroisatoic anhydride (1M7) and benzoyl cyanide (BzCN) that react with the 2'-hydroxyl group of flexible nucleotides to form a 2'-O-adduct. Other acylation electrophiles such as 2-methylnicotinic acid imidazolide (NAI) and 2-methyl-3-furoic acid imidazolide (FAI) can be utilized.

One useful aspect of the present invention is the tethering of a RNA-binding small molecule ligand to a photoprobe. This links the photoactivation-mediated covalent modification event with the ligand binding event such that the photoprobe is most likely to react with a portion of the RNA that is proximal (e.g., near in space) to the binding site of the ligand. Thus, the modification pattern on the RNA will be decisively altered because the activity of the photoactivatable agent will be constrained to nucleotides proximal to ligand binding pockets on the RNA. Thus, one can infer the existence and the location of ligand binding pockets from the altered reactivity pattern, as revealed in appropriate analytical methods such as sequencing.

The SHAPE-MaP approach exploits conditions that cause reverse transcriptase to misread SHAPE-modified nucleotides and incorporate a nucleotide non-complementary to the original sequence into the newly synthesized cDNA. The positions and relative frequencies of SHAPE adducts are recorded as mutations in the cDNA primary sequence. In a SHAPE-MaP experiment, the RNA is treated with a SHAPE reagent or treated with solvent only, and the RNA is modified. RNA from each experimental condition is reverse-transcribed, and the resulting cDNAs are then sequenced. Reactive positions are identified by subtracting data for the treated sample from data obtained for the untreated sample and by normalizing to data for a denatured (unfolded) control RNA.

SHAPE-MaP can be performed and analyzed according to detailed published methods (Martin et al., *RNA* 2012; 18:77-87; McGuinness et al., *J. Am. Chem. Soc.* 2012; 134:6617-6624; Siegfried et al., *Nature Methods* 2014; 11:959-965; Lavender et al., *PLoS Comput. Biol.* 2015; 11(5)e1004230; McGuinness et al., *Proc. Natl. Acad. Sci. USA* 2015; 112:2425-2430). The SHAPE-MaP sequence data can be analyzed using ShapeFinder (Vasa et al., RNA 2008; 14:1979-1990) or ShapeMapper (Siegfried et al., *Nature Methods* 2014; 11:959-965) or other software. Each of the foregoing publications is hereby incorporated by reference.

PEARL-seq (Proximity-Enhanced Activation via RNA Ligation-sequencing) departs from SHAPE and SHAPE-MaP in that it uses a tether to link the acylation event to a ligand binding event, thus decisively altering the acylation pattern, which is observed as 'mutations' in the sequencing, because only riboses proximal to ligand binding pockets will be acylated. From this one infers the existence of small-molecule binding sites on the targeted RNA as well as the location of those ligand binding sites across the transcriptome. Those RNA ligand/tether/warhead constructs ('hooks') that also bear a click functional group can be pulled down by clicking to a clickable biotin and then complexing with streptavidin on beads. This click/pull-down protocol enables sequencing of only those RNAs that have been covalently modified by a 'hook'. SHAPE-MaP & RING-MaP protocols carried out separately on the targeted RNAs enable the building of structural models of targeted RNAs as a framework that will enhance the interpretation of "covalent affinity transcriptomics" sequence data. Success is measured by bioactivities of free ligands in cells.

Libraries for use in the present invention will contain small molecules ("RNA ligands") tethered to electrophilic warheads that selectively form covalent bonds with nucleotides proximal to the binding site in the target RNA. The library's diversity encompasses variation in RNA ligand structure, tether structure, and warhead structure.

The RNA ligands are designed based on hypotheses about the structural determinant of RNA affinity and then synthesized and attached to the tether and warhead. As an example, Lau and coworkers used SELEX (systematic evolution of ligands by exponential enrichment) to evolve a short RNA sequence termed Aptamer-21 as a high-affinity RNA aptamer ($K_d$=50 nM) against a heteroaryldihydropyrimidine structure, compound 1b (I-1 herein) below:

I-1

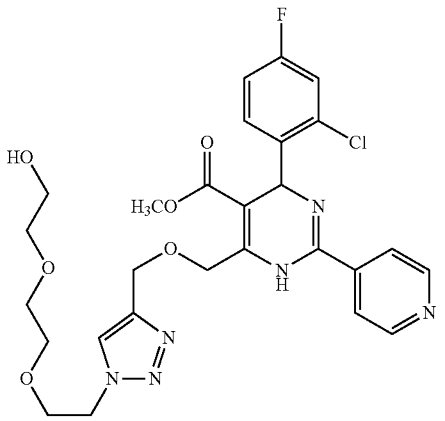

(compound 1b in Lau et al.)

(Lau, J. L.; Baksh, M. M.; Fiedler, J. D.; Brown, S. D.; Kussrow, A.; Bornhop, D. J.; Ordoukhanian, P.; Finn, M. G. *ACS Nano,* 2011, 5, 7722-7729; for more information on SELEX, see also, e.g., a) S. E. Osborne, A. D. Ellington, *Chem. Rev.* 1997, 97, 349-370; b) L. Gold, D. Brown, Y. Y. He, T. Shtatland, B. S. Singer, Y. Wu, *Proc. Natl. Acad. Sci.*

*USA* 1997, 94, 59-64; c) L. Gold, B. Polisky, O. Uhlenbeck, M. Yarus, *Annu. Rev. Biochem.* 1995, 64, 763-797.) This structure was chosen as a representative drug-like molecule with no cross-reactivity with mammalian or bacterial cells. The authors also embedded Aptamer 21, its weaker-binding variants, and a known aptamer against theophylline in a longer RNA sequence that was encapsidated inside a virus-like particle by an expression technique. These nucleoprotein particles were shown by backscattering interferometry to bind to the small-molecule ligands with affinities similar to those of the free (nonencapsidated) aptamers. Compound I-1 is water-soluble, nontoxic, and sufficiently dissimilar in structure to native biological molecules to minimize off-target binding. It features a 1,4-triazole linkage installed with copper-catalyzed azide-alkyne cycloaddition (CuAAC) chemistry, which enables convenient connection of the ligand to other molecules of interest. Other HAP variants described herein are expected to have similarly advantageous properties. Furthermore, use of the Aptamer 21 RNA as a starting point offers the advantage of a well-characterized RNA of known structure and whose binding mode with I-1 can be verified by reference to the original publication. Aptamer 21 has the following sequence: GGGUAGGCCAGGCAGCCAACUAGCGAGAGC-UUAAAUCUCUGAGCCCGAGAGGGU UCAGUGCUGCUUAUGUGGACGGCU (SEQ. ID:25).

Alternatively, the RNA ligands are selected from commercially available sources based on their similarity to known RNA ligands or complementarity to RNA binding pockets, purchased, and subjected to further synthesis to attach to the tether and warhead. Examples include but are not limited to: tetracycline antibiotics, aminoglycoside antibiotics, theophylline and similar structures (e.g., xanthines), ribocil and similar structures, linezolid and similar structures. In a third and complementary approach, libraries of RNA ligands are prepared using combinatorial chemistry techniques. Specifically, the tethers of choice are affixed to polymers that support organic synthesis, and through a series of synthetic chemistry steps, compounds are made in a one-bead-one-compound format. These steps lead to the incorporation in the final RNA ligand a wide range of fragments and reactants connected by a wide range of functional groups. Those compounds are released and the final off-bead step is attachment of the RNA warhead.

As a key element of the library's functional outcome, for each RNA ligand and RNA warhead, a number of structurally diverse tethers are incorporated in order to optimize tether length, tether flexibility, and the ability to tolerate additional functionality (in particular, click functional groups). Specific tethers that are explored include oligoethylene glycols containing one to six ethylene units, oligopeptides that are highly flexible (e.g., oligoglycines or oligo-N-methylglycines containing one to six amino acids) or more rigid (e.g., oligoprolines or oligo-4-hydroxyprolines containing one to six amino acids). Incorporation of click functional groups into the oligoethylene glycol tethers requires insertion of an amino acid, bearing a clickable functional group, at either the RNA ligand or the RNA warhead end of the tether. Incorporation of click functional groups into the oligopeptides tethers simply requires replacing any one of the amino acid residues with an amino acid bearing the clickable functional group.

The RNA warheads are selected from known or modified photoactivatable functional groups. Additional warheads will be identified by (1) synthetic modifications to the aforementioned warheads to establish the structure/activity relationship for RNA warheads as well as (2) screening commercially available photoactivatable groups.

Click functional groups are selected from the standard 'toolkit' of published click reagents and reactants. The present work focuses on azides, alkynes (both terminal and strained), dienes, tetrazines, and dienophiles.

Further details of the SHAPE, SHAPE-MaP, and PEARL-seq methods, including alternate reagents, conditions, and data analysis are described in WO 2017/136450, WO 2015/054247, US 2014/0154673, U.S. Pat. Nos. 7,745,614, and 8,313,424, each of which is hereby incorporated by reference in its entirety.

Example 2: Preparation of CPNQ Analogues and Other Quinoline-Based Ligands

Exemplary small molecule ligands based on CPNQ and other quinoline scaffolds may be prepared based on the synthetic schemes shown in WO2017/136450, which is hereby incorporated by reference in its entirety.

Example 3: Synthesis of Exemplary Photoprobe Compounds

General: Unless otherwise noted, all reactions were conducted under an $N_2$ atmosphere. All solvents and reagents were used as received without further purification. Compound 1 was synthesized as previously described in Lau, J. L.; Baksh, M. M.; Fiedler, J. D.; Brown, S. D.; Kussrow, A.; Bornhop, D. J.; Ordoukhanian, P.; Finn, M. G. *ACS Nano,* 2011, 5, 7722-7729. 3-azido-5-(azidomethyl)benzoic acid was prepared as previously described in Yoshida, S.; Misawa, Y.; Hosoya, T. *Eur. J. Org. Chem.,* 2014, 19, 3991-3995. Rotary evaporation was performed under 30 torr with a bath temperature below 40° C. Analytical LC-MS data were obtained on a Waters Acquity UPLC system equipped with an Acquity BEH 1.7 μm $C_{18}$ column (2.1×50 mm) and an elution gradient of 90:10 A:B to 40:60 A:B over 2.3 min, where A=0.1% formic acid in water and B=0.1% formic acid in acetonitrile and with a flow rate of 0.80 mL $min^{-1}$. Column chromatography was performed on a Teledyne Isco Combiflash Rf+ system using pre-packed RediSep Rf+ Gold silica gel (Teledyne Isco) or 40-60 μm spherical $C_{18}$ silica gel columns (Agela). NMR spectra were obtained on a Bruker 400 MHz spectrometer; chemical shifts are referenced to the residual mono-$^{1}$H-isotopomer of the solvent: $CHD_2OD$=3.31 ppm; $CD_3SOCD_2H$=2.49 ppm; $CHCl_3$=7.26 ppm.

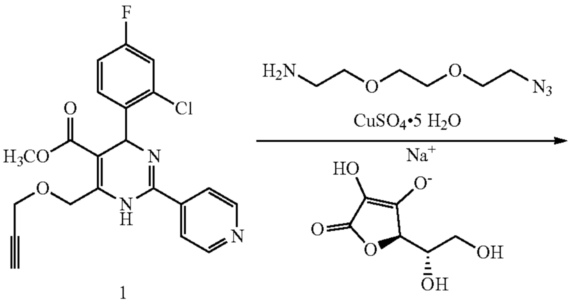

1

-continued

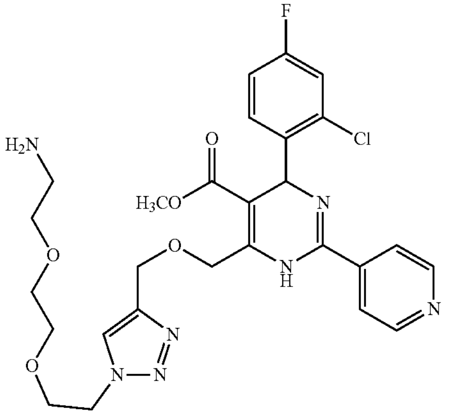

2

Compound 2: To a solution of MeOH (4 mL) and $H_2O$ (1 mL) at room temperature was added 1 (100 mg, 242 μmol, 1 eq.), 2-[2-(2-azidoethoxy)ethoxy]ethylamine (42 mg, 242 μmol, 1.0 eq.), $CuSO_4 \cdot 5H_2O$ (60 mg, 242 μmol, 1.0 eq.) and sodium ascorbate (96 mg, 483 μmol, 2.0 eq.). The mixture was stirred at 20° C. for 0.5 h. The mixture was diluted with a saturated aqueous solution of $NaHCO_3$ (30 mL), then the mixture was extracted with EtOAc (3×50 mL). The combined extracts were washed with saturated aqueous NaCl solution, then were dried over $Na_2SO_4$. The solids were filtered and the filtrate was concentrated under reduced pressure to afford the crude product as a yellow solid. The residue was purified by preparatory HPLC using a Phenomenex Synergi $C_{18}$ column (150×25×10 μm), eluting with a gradient of 10-30% $CH_3CN$ in water containing 0.05% HCl to afford 2 as yellow solid (HCl salt, 65 mg, 43% yield). LCMS: $t_R$: 1.749 min; (M+H)=588.2. $^1H$ NMR (400 MHz, METHANOL-$d_4$) ppm=9.12 (br s, 2H), 8.21 (br d, J=17.1 Hz, 3H), 7.76 (dd, J=6.0, 8.7 Hz, 1H), 7.42 (dd, J=2.4, 8.6 Hz, 1H), 7.26 (dt, J=2.6, 8.3 Hz, 1H), 6.42 (s, 1H), 5.02-4.93 (m, 2H), 4.84 (s, 2H), 4.65 (t, J=5.0 Hz, 2H), 3.94 (t, J=5.0 Hz, 2H), 3.75-3.55 (m, 9H), 3.10 (t, J=4.8 Hz, 2H).

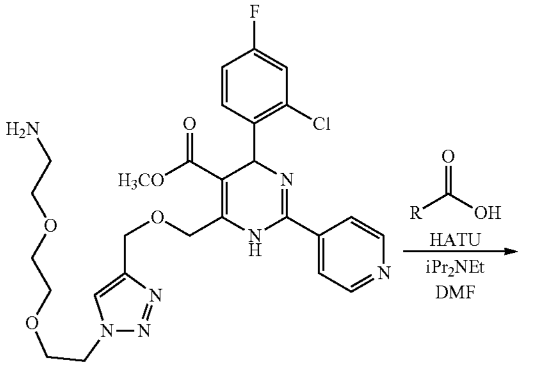

2

-continued

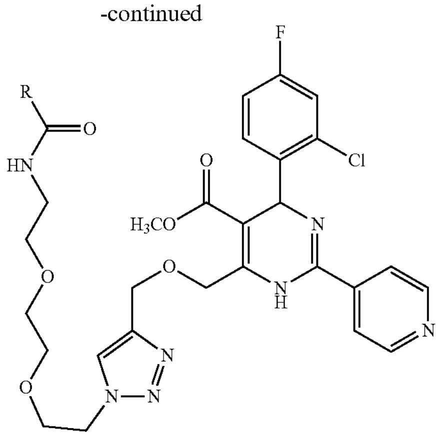

General procedure A—HATU-mediated acid-amine coupling reactions: To a stirring solution of carboxylic acid (1.2 eq.) in DMF (0.05 M) at room temperature was added HATU (2.0 eq.), N,N-diisopropylethylamine (4.0 eq.), and primary amine (1 eq.). The resulting solution was incubated at room temperature for 2-16 h, then the reaction mixture was loaded directly onto a pre-packed $C_{18}$-silica gel column for purification. Fractions containing the desired product were combined, frozen at −78° C. (acetone/$CO_2$), and lyophilized to afford the final photoprobe compounds as solids.

3

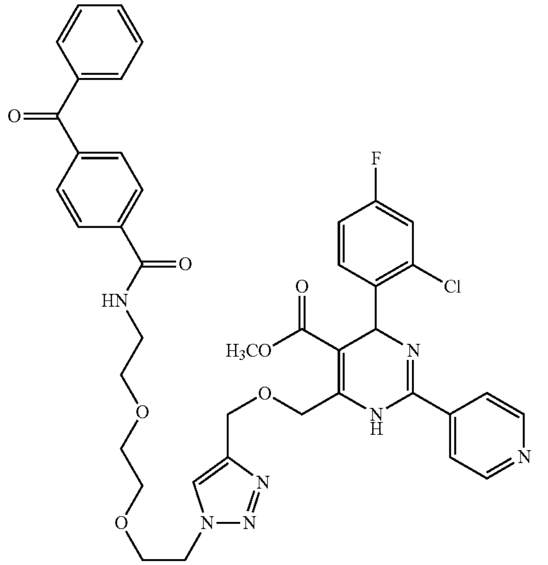

Compound 3: Compound 3 was prepared according to General Procedure A above from 2 (30 mg, 51 μmol) and 4-benzoylbenzoic acid. The crude product mixture was purified by reverse-phase chromatography over $C_{18}$-silica gel, eluting with 0-100% $CH_3CN$ in water containing 0.1% formic acid. Probe 3 was isolated as a light tan solid (formate salt, 39 mg, 83% yield). LC-MS: $t_R$: 1.49 min; $[M+H]^+$ 796.2.

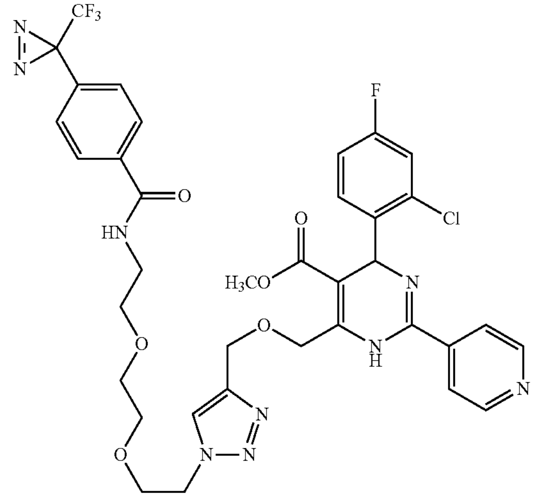

Compound 4: Compound 4 was prepared according to General Procedure A above from 2 (30 mg, 51 μmol) and 4-[3-(trifluoromethyl)-3H-diazirin-3-yl]benzoic acid. The crude product mixture was purified by reverse-phase chromatography over $C_{18}$-silica gel, eluting with 0-100% $CH_3CN$ in water containing 0.1% formic acid. Compound 4 was isolated as a bright yellow solid (formate salt, 19 mg, 44% yield). LC-MS: $t_R$: 1.56 min; $[M+H]^+$ 800.2.

5

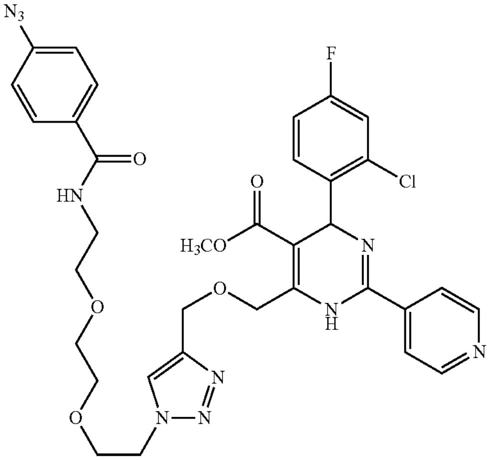

Compound 5: Compound 5 was prepared according to General Procedure A above from 2 (50 mg, 85 μmol) and 4-azidobenzoic acid (as a 0.2 M solution in methyl tert-butyl ether). After stirring at room temperature for 3 h, the crude product mixture was partially concentrated to remove methyl tert-butyl ether, then the resulting product solution (in DMF) was purified by reverse-phase chromatography over $C_{18}$-silica gel, eluting with 0-100% $CH_3CN$ in water containing 0.1% formic acid. Compound 5 was isolated as a bright yellow solid (formate salt, 32 mg, 49% yield). LC-MS: $t_R$: 1.45 min; $[M+H]^+$ 733.2.

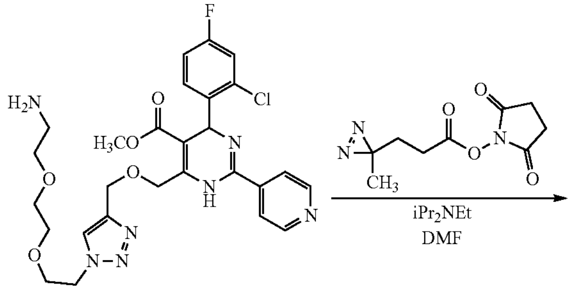

2

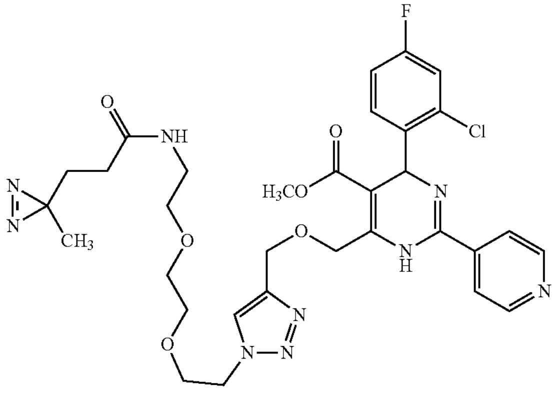

6

Compound 6: To a stirring solution of 2 (30 mg, 51 μmol, 1 eq.) in DMF (2.0 mL) at room temperature was added N,N-diisopropylethylamine (27 μL, 153 μmol, 3.0 eq.) and 2,5-dioxopyrrolidin-1-yl 3-(3-methyl-3H-diazirin-3-yl)propanoate (12 mg, 54 μmol, 1.05 eq.). The resulting bright yellow reaction mixture was allowed to stir at room temperature for 2 h, then was purified immediately by flash column chromatography over $C_{18}$-silica gel, eluting with 0-60% $CH_3CN$ in water containing 0.1% formic acid. Fractions containing the desired product were concentrated under reduced pressure to remove $CH_3CN$, then were frozen at −78° C. and lyophilized to afford the desired product 6 as a bright yellow solid (formate salt, 16.0 mg, 42% yield). LC-MS: $t_R$: 1.40 min; $[M+H]^+$ 698.3.

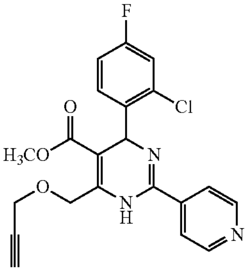

1

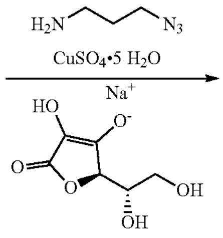

-continued

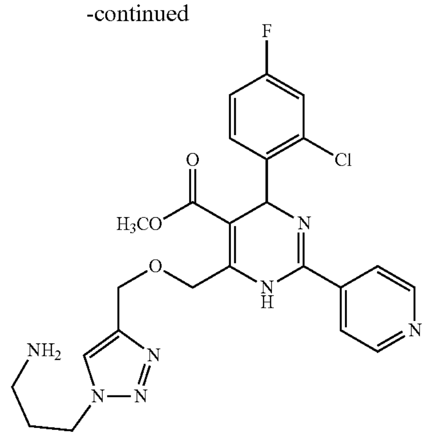

7

Compound 7: To a stirring suspension of 1 (321 mg, 0.78 mmol, 1 eq.) in t-BuOH (4.0 mL) and water (4.0 mL) was added 3-azidopropylamine (93 mg, 0.93 mmol, 1.2 eq.) and $CuSO_4 \cdot 5H_2O$ (15 mg, 62 μmol, 0.08 eq.). To the resulting suspension was added a solution of sodium ascorbate (46 mg, 0.23 mmol, 0.30 eq.) in water (1.0 mL). The resulting suspension was allowed to stir vigorously at room temperature for 2 h, then was concentrated under reduced pressure to remove t-BuOH. The crude product solution that remained was directly purified by flash column chromatography over $C_{18}$-silica gel, eluting with 0-30% $CH_3CN$ in water containing 0.1% $NH_3$. Fractions containing the desired product were frozen at −78° C. and lyophilized to afford compound 7 as a bright yellow solid (305 mg, 77% yield). LCMS: $t_R$: 1.19 min; $[M+H]^+$ 514.2.

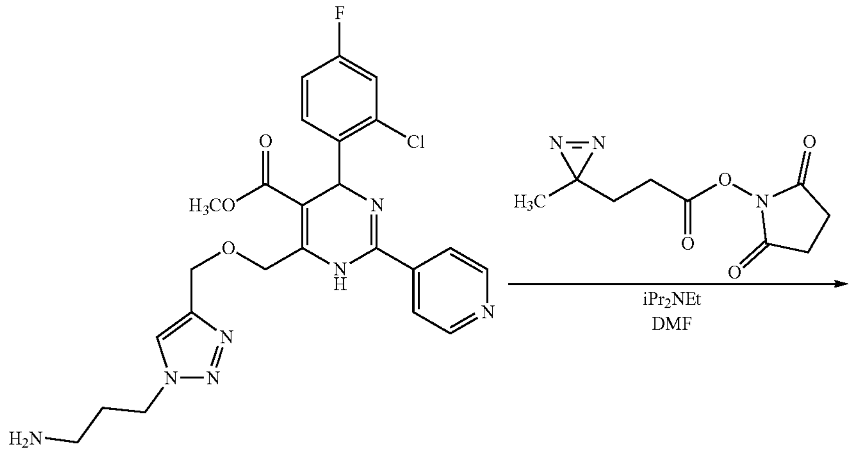

7

-continued

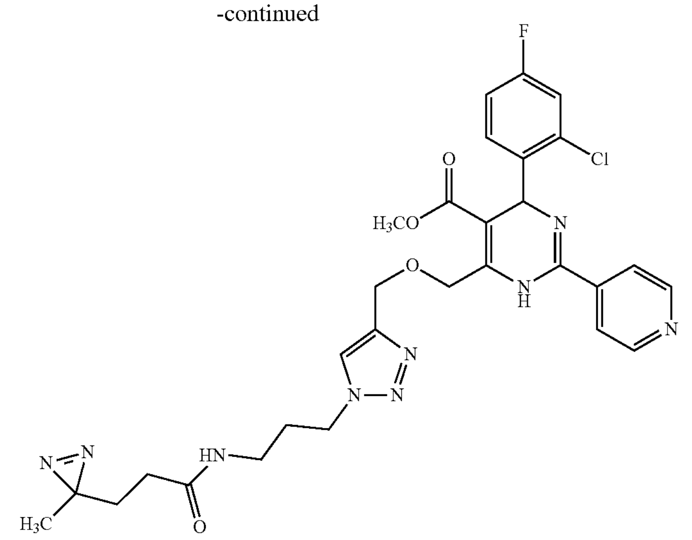

8

Compound 8: To a stirring solution of 7 (30 mg, 58 μmol, 1 eq.) in DMF (2.0 mL) at room temperature was added N,N-diisopropylethylamine (41 μL, 233 μmol, 4.0 eq.) and 2,5-dioxopyrrolidin-1-yl 3-(3-methyl-3H-diazirin-3-yl)propanoate (14 mg, 64 μmol, 1.10 eq.). The resulting bright yellow reaction mixture was allowed to stir at room temperature for 2 h, then was purified immediately by flash column chromatography over $C_{18}$-silica gel, eluting with 0-100% $CH_3CN$ in water containing 0.1% formic acid. Fractions containing the desired product were concentrated under reduced pressure to remove $CH_3CN$, then were frozen at −78° C. and lyophilized to afford the desired product as a bright yellow solid (formate salt, 17.0 mg, 44% yield). LC-MS: $t_R$: 1.40 min; $[M+H]^+$ 624.2.

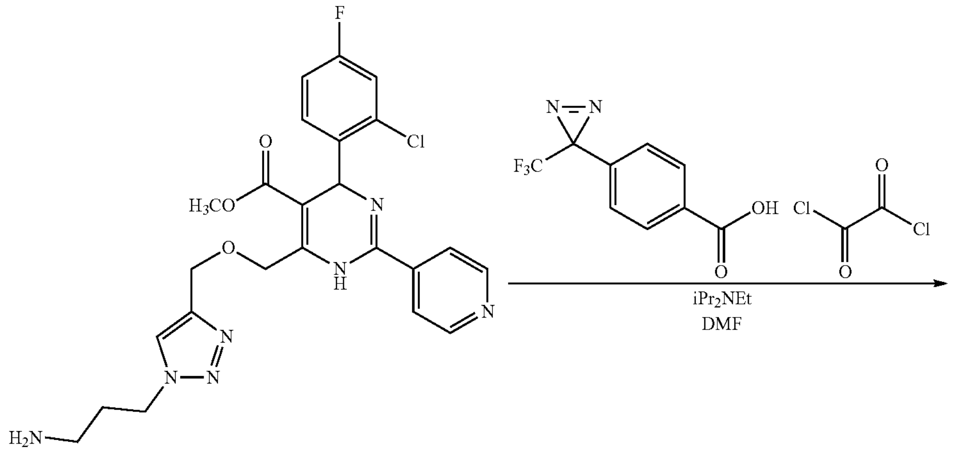

7

-continued

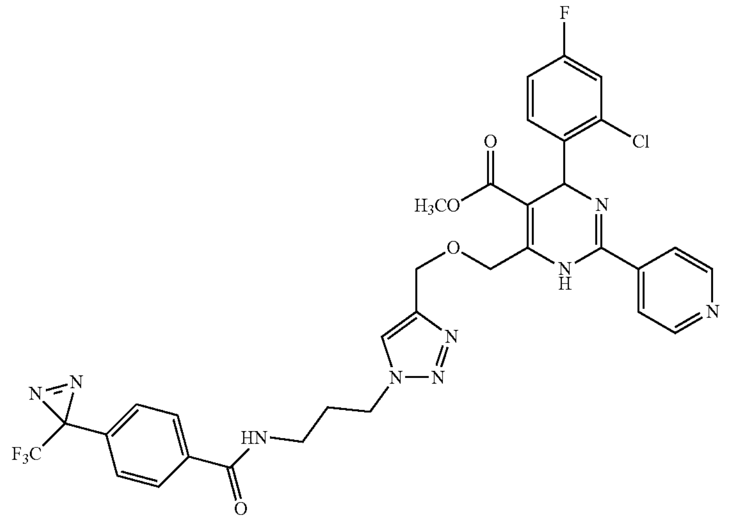

9

Compound 9: To a stirring suspension of 4-[3-(trifluoromethyl)-3H-diazirin-3-yl]benzoic acid (27 mg, 116 μmol, 1.2 eq.) in $CH_2Cl_2$ (2.0 mL) at room temperature was added DMF (ca. 10 μL) and a 2.0 M solution of oxalyl chloride in $CH_2Cl_2$ (49 μL, 98 μmol, 1.0 eq.). The resulting clear, colorless mixture was allowed to stir at room temperature for 1 h, then 7 (50 mg, 97 μmol, 1 eq.) and N,N-diisopropylethylamine (68 μL, 0.39 mmol, 4.0 eq.) were added. The mixture was allowed to stir at room temperature for 3 h, then was concentrated under reduced pressure. The crude product was purified by reverse-phase flash column chromatography on $C_{18}$-silica gel, eluting with 0-100% $CH_3CN$ in water containing 0.1% formic acid. Fractions containing the desired product were combined and partially evaporated, then were frozen at −78° C. and lyophilized to afford the desired product as a yellow solid (formate salt, 32 mg, 47% yield). LC-MS: $t_R$: 1.57 min; $[M+H]^+$ 726.0.

General Procedure B—Three component coupling of an amino acid, carboxylic acid NHS ester, and an amine: To a suspension of amino acid (1 eq.) in DMF (2.0 mL) at room temperature was added N,N-diisopropylethylamine (4.0 eq.) and carboxylic acid N-hydroxysuccinimidyl ester (1.05 eq.). The resulting suspension was allowed to stir at room temperature for 12-48 h. Once formation of the amide was complete (as determined by LC-MS analysis), 1-[Bis(dimethylamino)methylene]-triazolo[4,5-b]pyridinium 3-oxid hexafluorophosphate (HATU) (2.0 eq.) and amine (1.2 eq.) were added and the resulting bright yellow mixture was allowed to stir at room temperature for 3 h. The mixture was directly purified by column chromatography over $C_{18}$ silica gel. Fractions containing the desired product were combined and partially evaporated to remove $CH_3CN$, then were frozen at −78° C. and lyophilized to afford the desired products as solids.

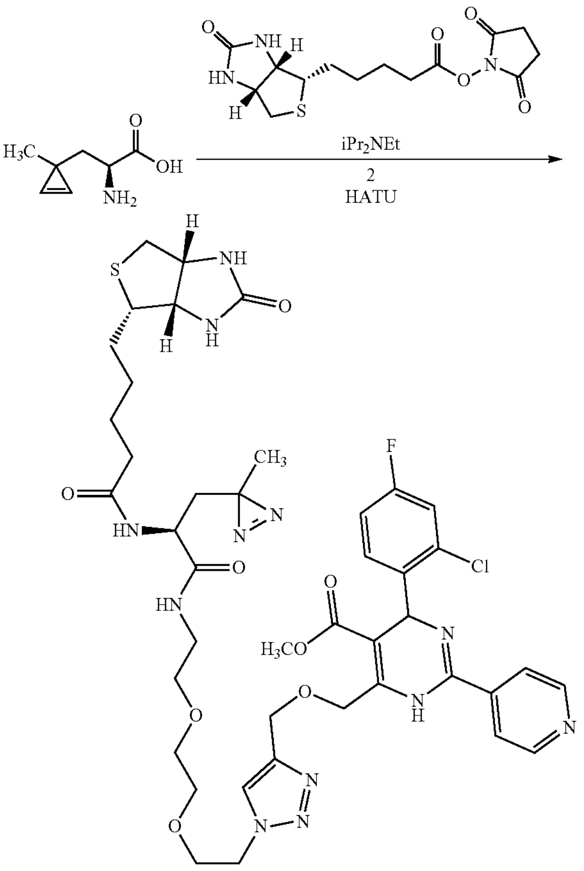

10

Compound 10: Compound 10 was prepared according to General Procedure B above from L-photoleucine (25 mg, 0.17 mmol, 1 eq.), biotin N-hydroxysuccinimidyl ester (62 mg, 0.18 mmol, 1.05 eq.), and 2 (122 mg, 0.21 mmol, 1.2 eq.). The mixture was directly purified by column chromatography over $C_{18}$ silica gel, eluting with 0-100% $CH_3CN$ in water containing 0.1% formic acid. Fractions containing the desired product were combined and partially evaporated to remove $CH_3CN$, then were frozen at −78° C. and lyophilized to afford the desired product as a yellow solid (formate salt, 97 mg, 57% yield). LC-MS: $t_R$: 1.35 min; $[M+H]^+$ 939.3.

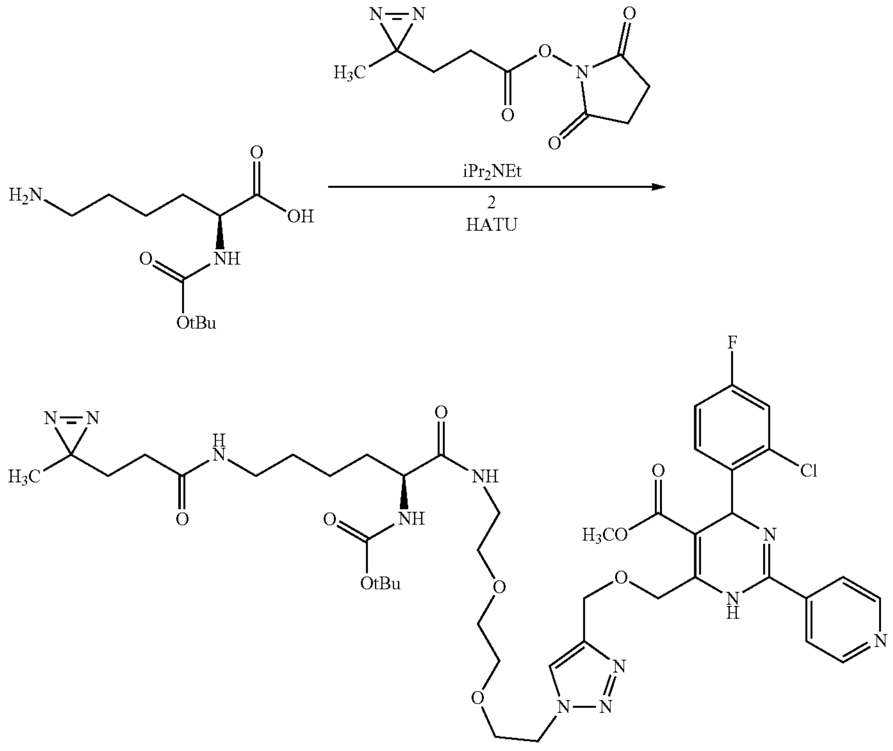

11

Compound 11: Compound 11 was prepared according to General Procedure B above from $N^{\alpha}$-tert-butoxycarbonyl-L-lysine (50 mg, 0.20 mmol, 1 eq.), 2,5-dioxopyrrolidin-1-yl 3-(3-methyl-3H-diazirin-3-yl)propanoate (48 mg, 0.21 mmol, 1.05 eq.), and 2 (142 mg, 0.24 mmol, 1.2 eq.). The mixture was directly purified by column chromatography over $C_{18}$ silica gel, eluting with 0-50% $CH_3CN$ in water containing 0.1% formic acid. Fractions containing the desired product were combined and partially evaporated to remove $CH_3CN$, then were frozen at −78° C. and lyophilized to afford the desired product as a yellow solid (formate salt, 120 mg, 61% yield). LC-MS: $t_R$: 1.46 min; $[M+H]^+$ 926.4.

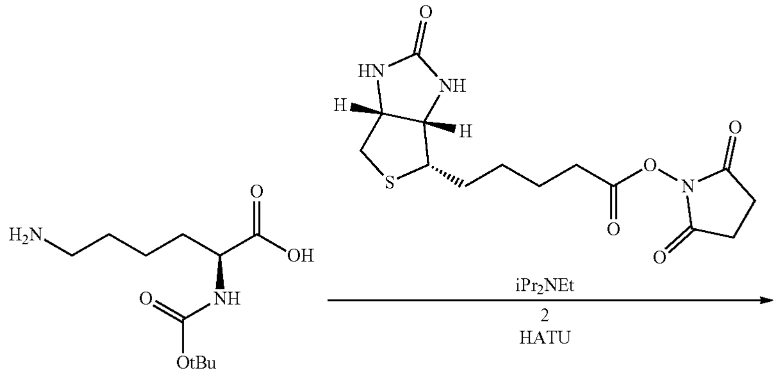

-continued

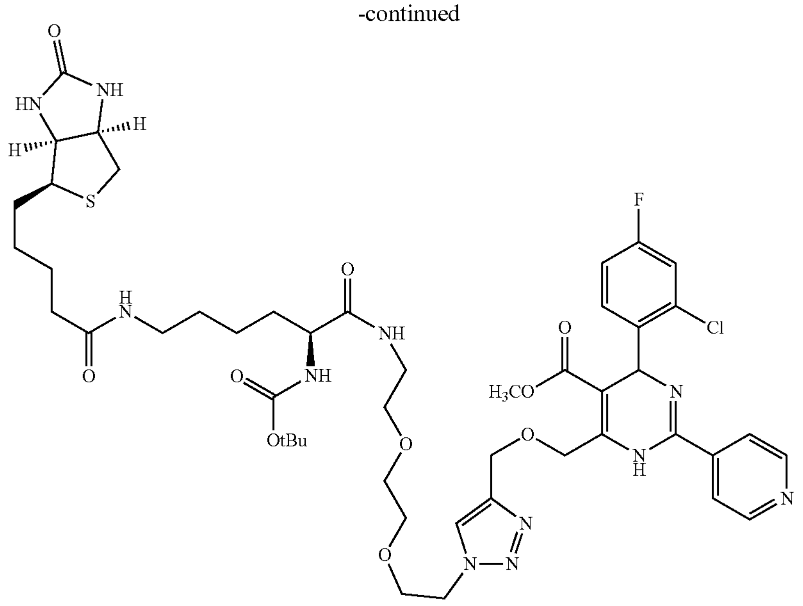

12

Compound 12: Compound 12 was prepared according to General Procedure B above from $N^{\alpha}$-tert-butoxycarbonyl-L-lysine (50 mg, 0.20 mmol, 1 eq.), biotin N-hydroxysuccinimidyl ester (72 mg, 0.21 mmol, 1.05 eq.), and 2 (142 mg, 0.24 mmol, 1.2 eq.). The mixture was directly purified by column chromatography over $C_{18}$ silica gel, eluting with 0-50% $CH_3CN$ in water containing 0.1% formic acid. Fractions containing the desired product were combined and partially evaporated to remove $CH_3CN$, then were frozen at −78° C. and lyophilized to afford the desired product as a yellow solid (formate salt, 105 mg, 48% yield). LC-MS: $t_R$: 1.38 min; $[M+H]^+$ 1042.4.

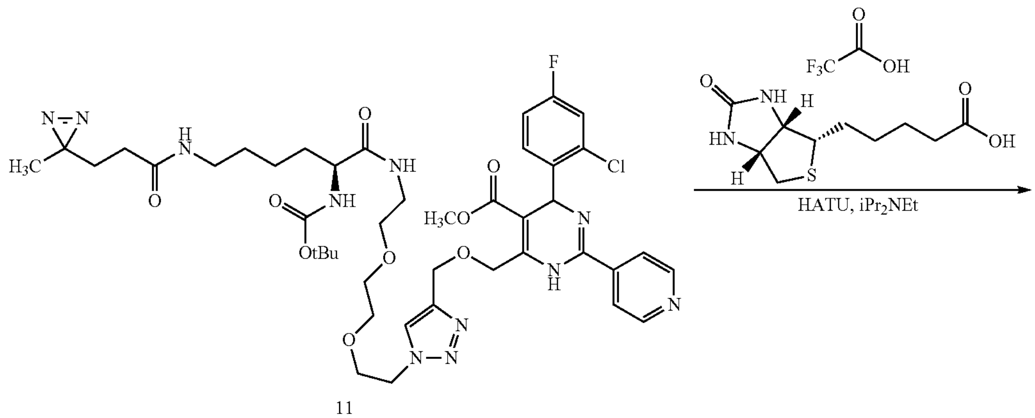

11

-continued

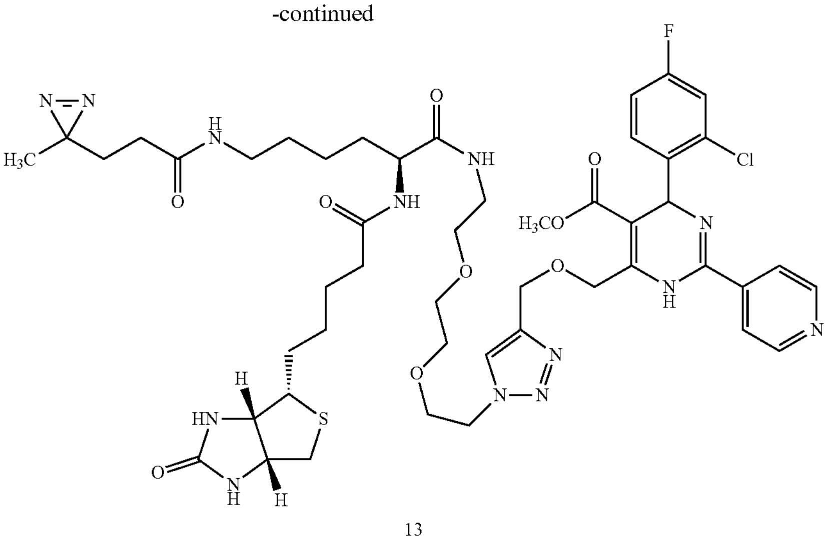

13

Compound 13: A stirring solution of 11 (40 mg, 41 μmol, 1 eq.) in $CH_2Cl_2$ (1.0 mL) at 0° C. was treated dropwise with neat trifluoroacetic acid (250 μL). The resulting mixture was allowed to warm to room temperature, then was allowed to stir at room temperature for 15 min. The mixture was concentrated to dryness under reduced pressure to afford the crude primary amine. The crude amine was resuspended in DMF (1.0 mL), then was treated with N,N-diisopropylethylamine (72 μL, 0.41 mmol, 10.0 eq.), biotin, (15 mg, 62 μmol, 1.5 eq.), and HATU (31 mg, 82 μmol, 2.0 eq.). The resulting bright yellow mixture was maintained at room temperature for 2 h, then was immediately loaded onto a $C_{18}$-silica gel column, eluting with 0-70% $CH_3CN$ in water containing 0.1% formic acid). Fractions containing the desired product were combined and partially evaporated under reduced pressure to remove $CH_3CN$, then were frozen and lyophilized to afford the desired product as a yellow solid (formate salt, 27 mg, 60% yield). LC-MS: $t_R$: 1.38 min; $[M+H]^+$ 1052.4.

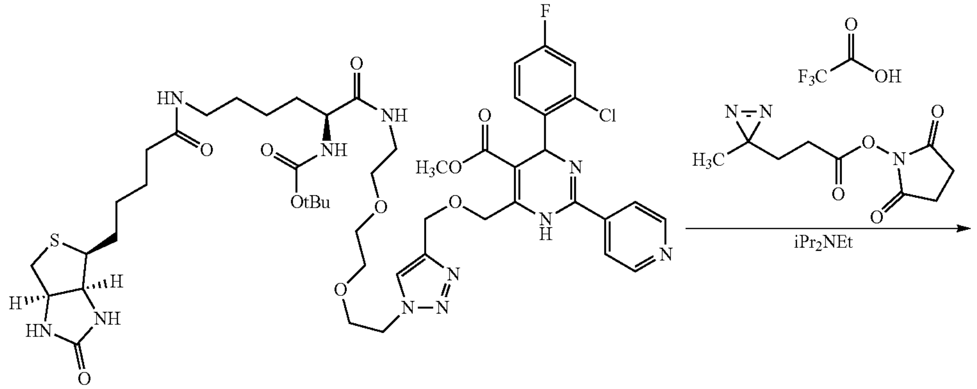

12

-continued

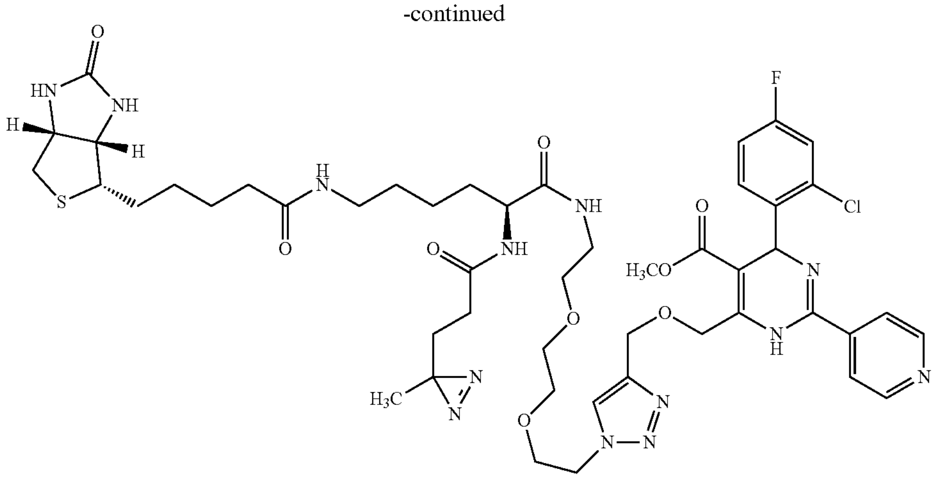

14

Compound 14: A stirring solution of 12 (40 mg, 37 μmol, 1 eq.) in $CH_2Cl_2$ (1.0 mL) at 0° C. was treated dropwise with neat trifluoroacetic acid (250 The resulting mixture was allowed to warm to room temperature, then was allowed to stir at room temperature for 55 min. The mixture was concentrated to dryness under reduced pressure to afford the crude primary amine. The crude amine was resuspended in DMF (1.0 mL), then was treated with N,N-diisopropylethylamine (64 μL, 0.37 mmol, 10.0 eq.), and 2,5-dioxopyrrolidin-1-yl 3-(3-methyl-3H-diazirin-3-yl)propanoate (10 mg, 44 μmol, 1.2 eq.). The resulting bright yellow mixture was maintained at room temperature for 16 h, then was immediately loaded onto a $C_{18}$-silica gel column, eluting with 0-70% $CH_3CN$ in water containing 0.1% formic acid). Fractions containing the desired product were combined and partially evaporated under reduced pressure to remove $CH_3CN$, then were frozen and lyophilized to afford the desired product as a yellow solid (formate salt, 22 mg, 54% yield). LC-MS: $t_R$: 1.37 min; $[M+H]^+$ 1052.4.

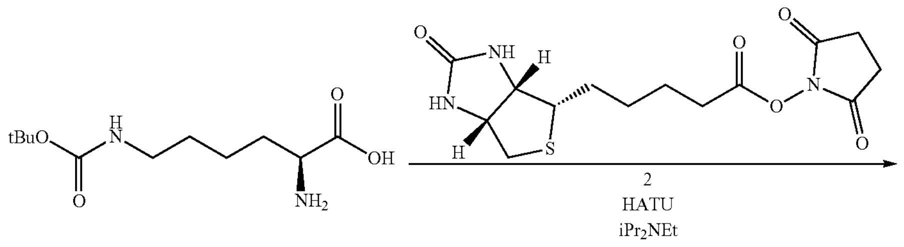

-continued

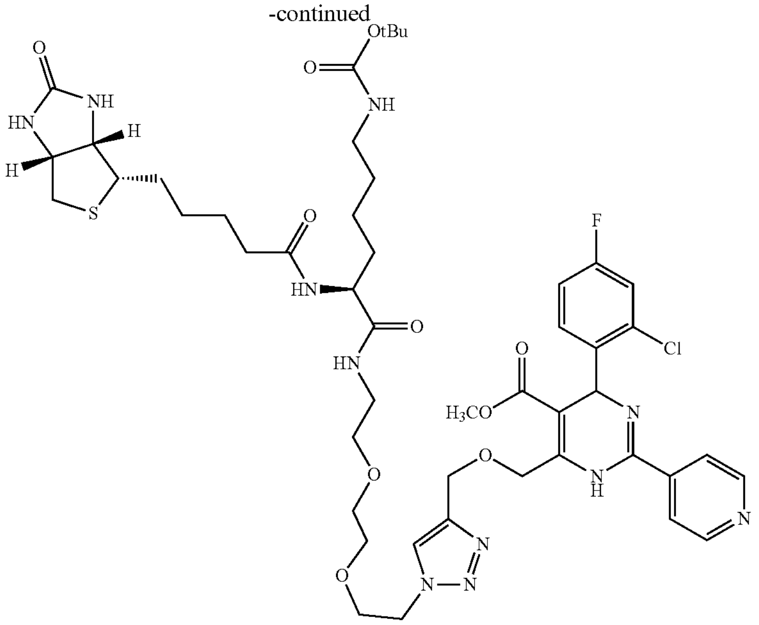

15

Compound 15: Compound 15 was prepared according to General Procedure B above using N∈-tert-butoxycarbonyl-L-lysine (175 mg, 0.71 mmol, 1 eq.), biotin N-hydroxysuccinimidyl ester (252 mg, 0.74 mmol, 1.05 eq.), and 2 (500 mg, 0.85 mmol, 1.2 eq.). Following completion of the reaction (as determined by LC-MS analysis), the reaction mixture was diluted with EtOAc (150 mL) and was washed with 4×40 mL portions of water. The organic phase was dried over $Na_2SO_4$, the solids filtered, and the filtrate was concentrated to afford the crude product as a yellow gum. The crude product was triturated once with diethyl ether: pentane (1:1, 10 mL), then the resulting solid was dissolved in methanol (5 mL) and was cooled to −50° C. Diethyl ether (20 mL) was added, then the resulting solid was collected by filtration to afford 15 as a yellow solid (380 mg, 43% yield). LC-MS: $t_R$:1.40 min; $[M+H]^+$ 1042.1.

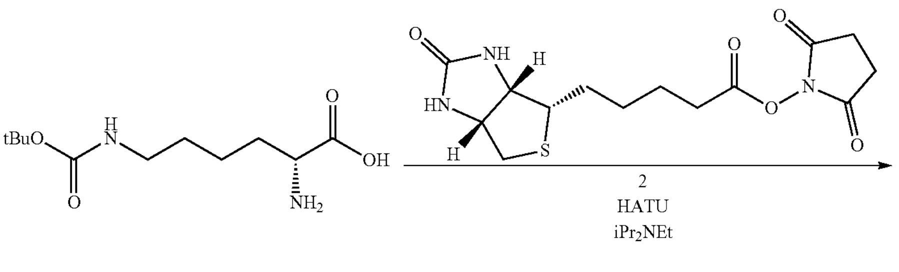

-continued
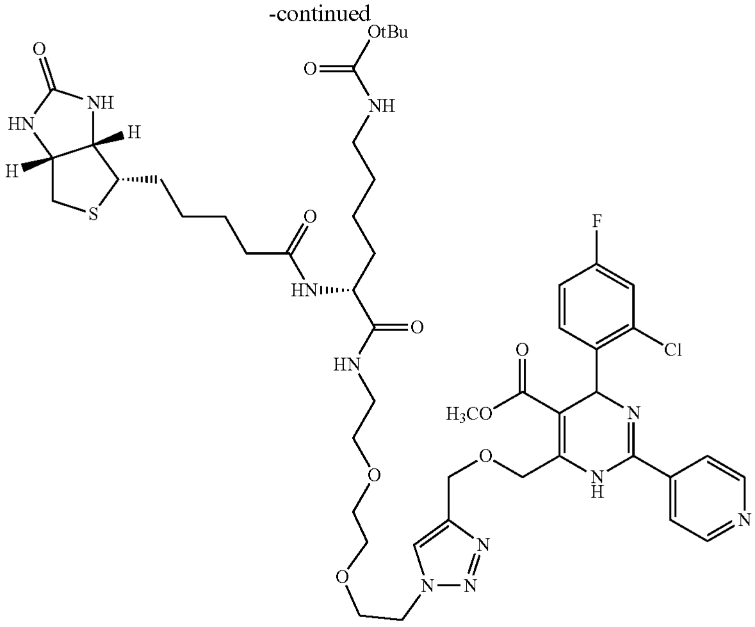
16
Compound 16: Compound 16 was prepared analogously to compound 15, with the exception that $N^{\epsilon}$-tert-butoxycarbonyl-D-lysine (900 mg, 1.90 mmol, 1 eq.) was used in place of $N^{\epsilon}$-tert-butoxycarbonyl-L-lysine as the starting amino acid. Compound 16 was obtained as a yellow solid (1.03 g, 52% yield). LC-MS: $t_R$: 1.40 min; [M+H]P 1042.1.
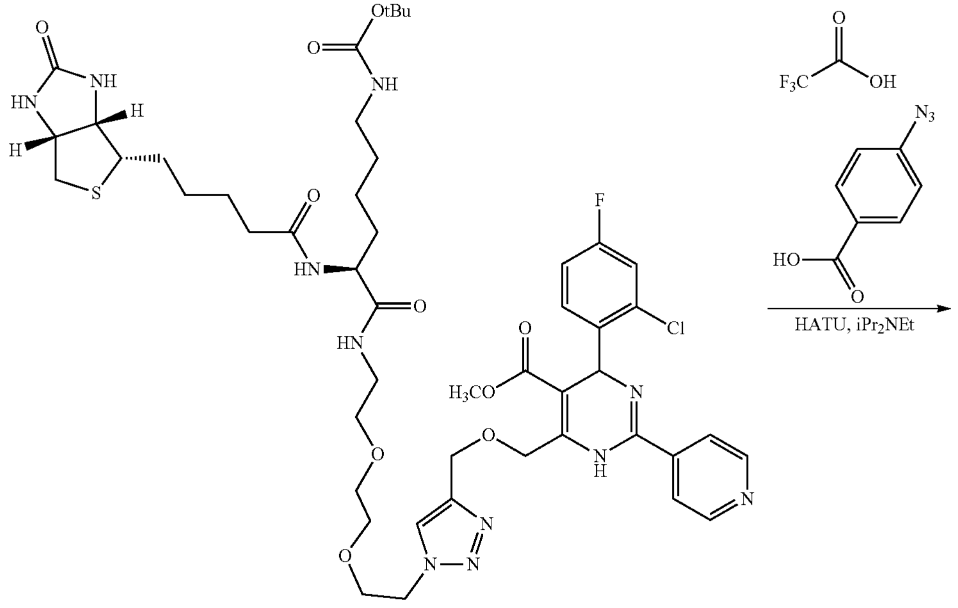
15

-continued

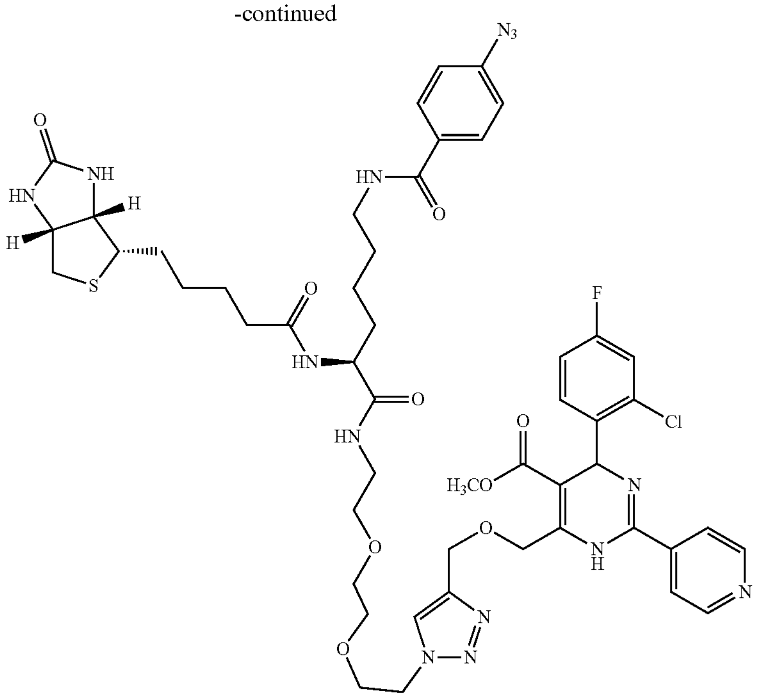

17

Compound 17: A solution of 15 (55 mg, 53 μmol, 1 eq.) in $CH_2Cl_2$ (1.0 mL) at 0° C. was treated with trifluoroacetic acid (0.25 mL). The resulting mixture was allowed to warm to room temperature over 15 minutes. After this time the mixture was concentrated to dryness under reduced pressure. The resulting crude amine was dissolved in DMF (2.0 mL), then was treated with a 0.2 M solution of 4-azidobenzoic acid in methyl tert-butyl ether (0.53 mL, 0.11 mmol, 2.0 eq.), HATU (40 mg, 0.11 mmol, 2.0 eq.), and N,N-diisopropylethylamine (37 μL, 0.21 mmol, 4.0 eq.). The resulting mixture was allowed to stir at room temperature overnight, then was partially concentrated to remove methyl tert-butyl ether. The resulting product solution (in DMF) was directly purified by column chromatography over $C_{18}$-silica gel, eluting with 0-100% $CH_3CN$ in water containing 0.1% formic acid. Fractions containing the desired product were combined and partially evaporated to remove $CH_3CN$, then were frozen at −78° C. and lyophilized to afford 17 as a yellow solid (formate salt, 35 mg, 58% yield). LC-MS: $t_R$: 1.41 min; $[M+H]^+$ 1087.4.

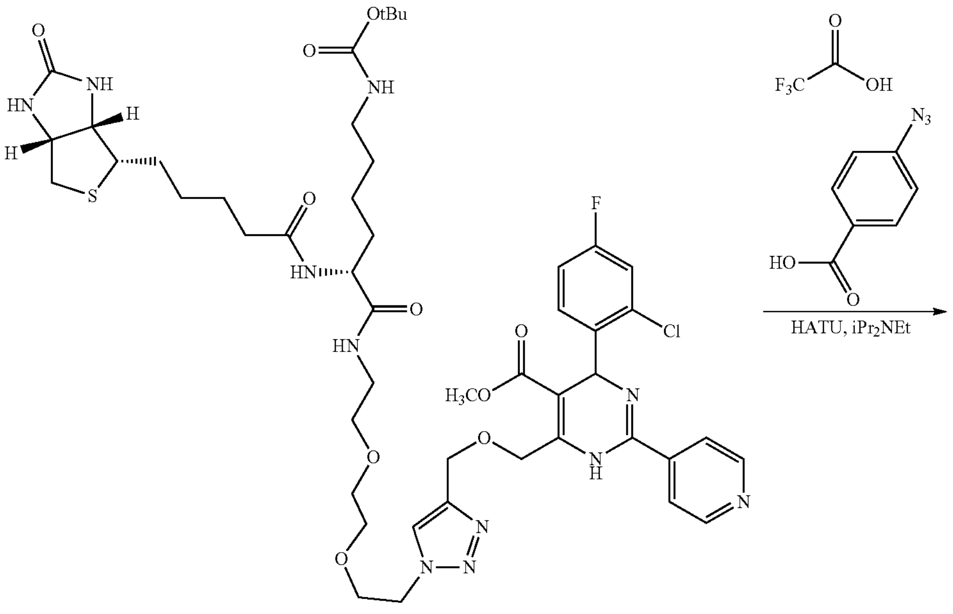

16

-continued

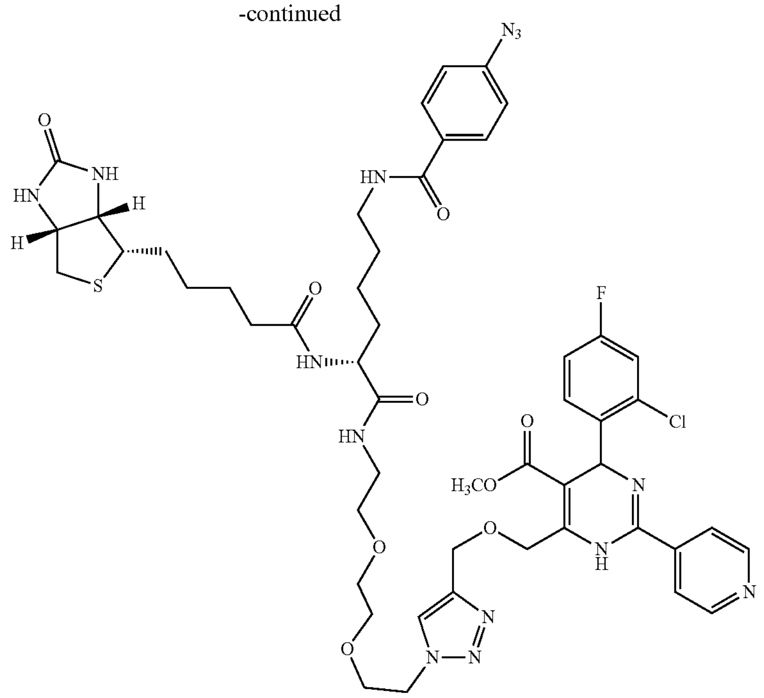

18

Compound 18: A solution of 16 (55 mg, 53 μmol, 1 eq.) in $CH_2Cl_2$ (1.0 mL) at 0° C. was treated with trifluoroacetic acid (0.25 mL). The resulting mixture was allowed to warm to room temperature over 15 minutes. After this time the mixture was concentrated to dryness under reduced pressure. The resulting crude amine was dissolved in DMF (2.0 mL), then was treated with a 0.2 M solution of 4-azidobenzoic acid in methyl tert-butyl ether (0.53 mL, 0.11 mmol, 2.0 eq.), HATU (40 mg, 0.11 mmol, 2.0 eq.), and N,N-diisopropylethylamine (37 μL, 0.21 mmol, 4.0 eq.). The resulting mixture was allowed to stir at room temperature overnight, then was partially concentrated to remove methyl tert-butyl ether. The resulting product solution (in DMF) was directly purified by column chromatography over $C_{18}$-silica gel, eluting with 0-100% $CH_3CN$ in water containing 0.1% formic acid. Fractions containing the desired product were combined and partially evaporated to remove $CH_3CN$, then were frozen at −78° C. and lyophilized to afford 18 as a yellow solid (formate salt, 38 mg, 63% yield). LC-MS: $t_R$: 1.41 min; $[M+H]^+$ 1087.4.

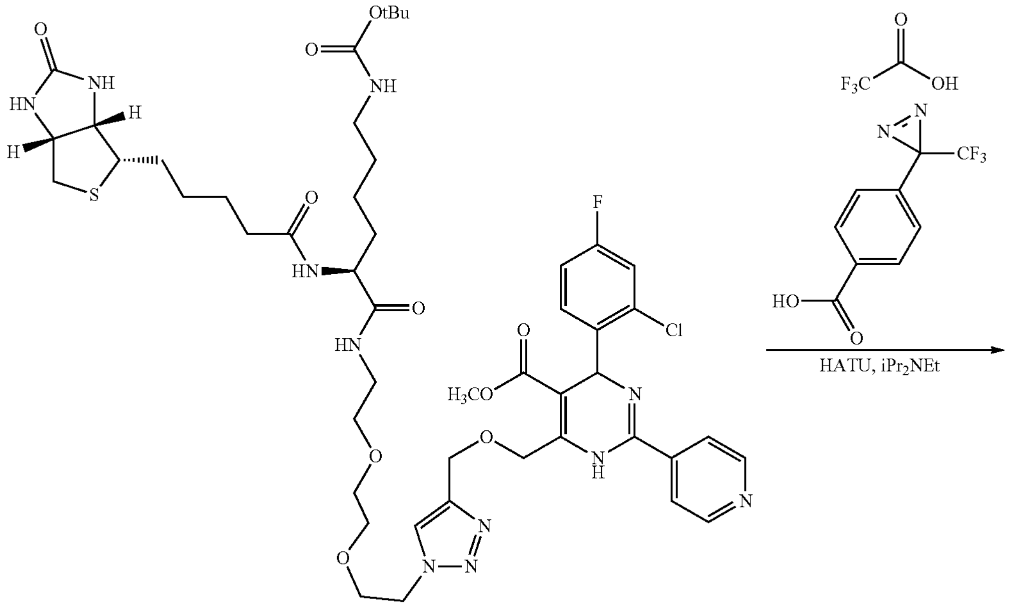

15

-continued

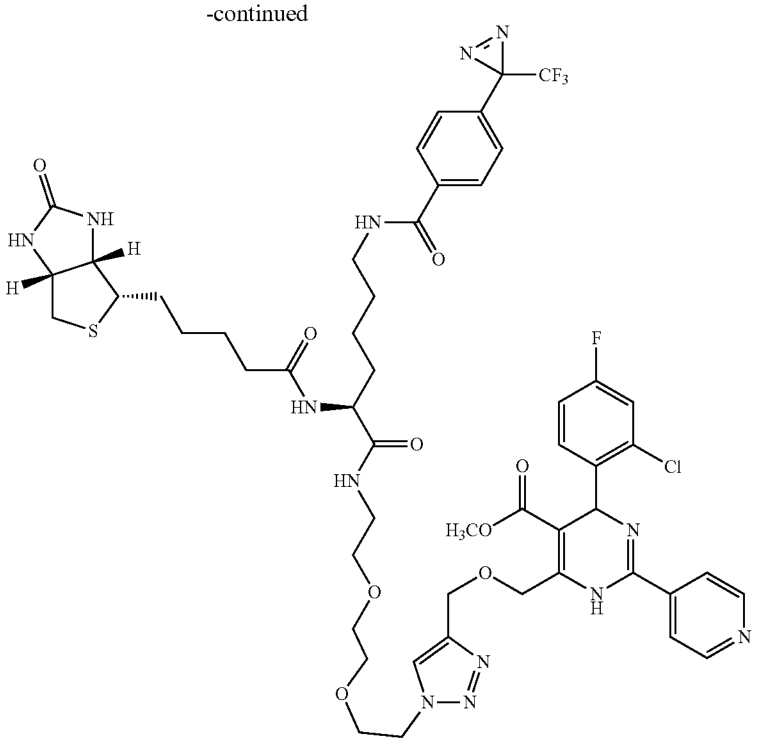

19

Compound 19: A solution of 15 (55 mg, 53 μmol, 1 eq.) in $CH_2Cl_2$ (1.0 mL) at 0° C. was treated with trifluoroacetic acid (0.25 mL). The resulting mixture was allowed to warm to room temperature over 15 minutes. After this time the mixture was concentrated to dryness under reduced pressure. The resulting crude amine was dissolved in DMF (2.0 mL), then was treated with 4-[3-(trifluoromethyl)-3H-diazirin-3-yl]benzoic acid (24 mg, 0.11 mmol, 2.0 eq.), HATU (40 mg, 0.11 mmol, 2.0 eq.), and N,N-diisopropylethylamine (37 μL, 0.21 mmol, 4.0 eq.). The resulting mixture was allowed to stir at room temperature overnight, then the resulting product solution (in DMF) was directly purified by column chromatography over $C_{18}$-silica gel, eluting with 0-100% $CH_3CN$ in water containing 0.1% formic acid. Fractions containing the desired product were combined and partially evaporated to remove $CH_3CN$, then were frozen at −78° C. and lyophilized to afford 19 as a yellow solid (formate salt, 15 mg, 24% yield). LC-MS: $t_R$: 1.48 min; $[M+H]^+$ 1155.6.

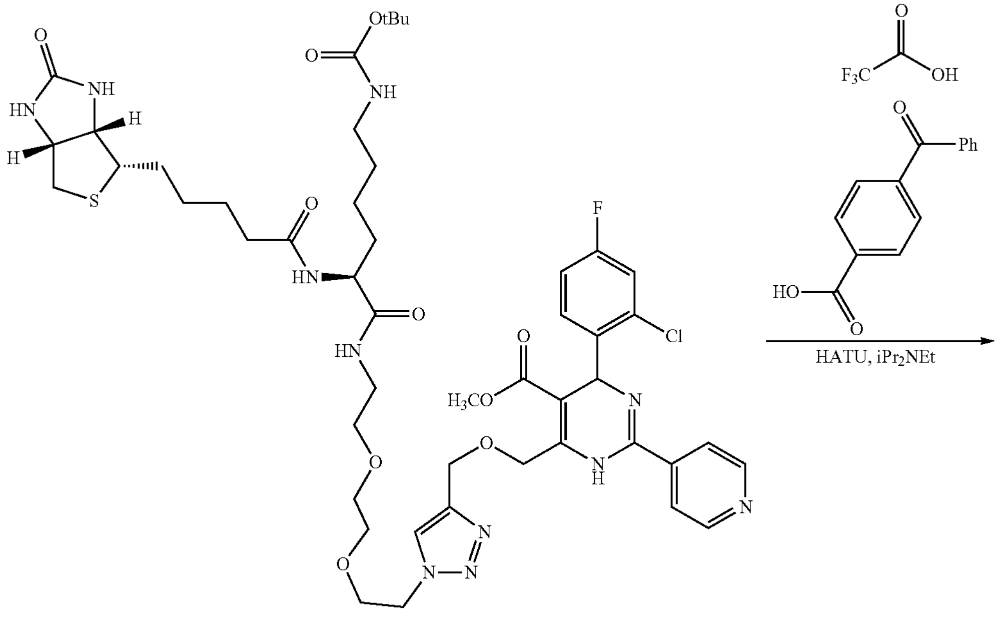

15

-continued

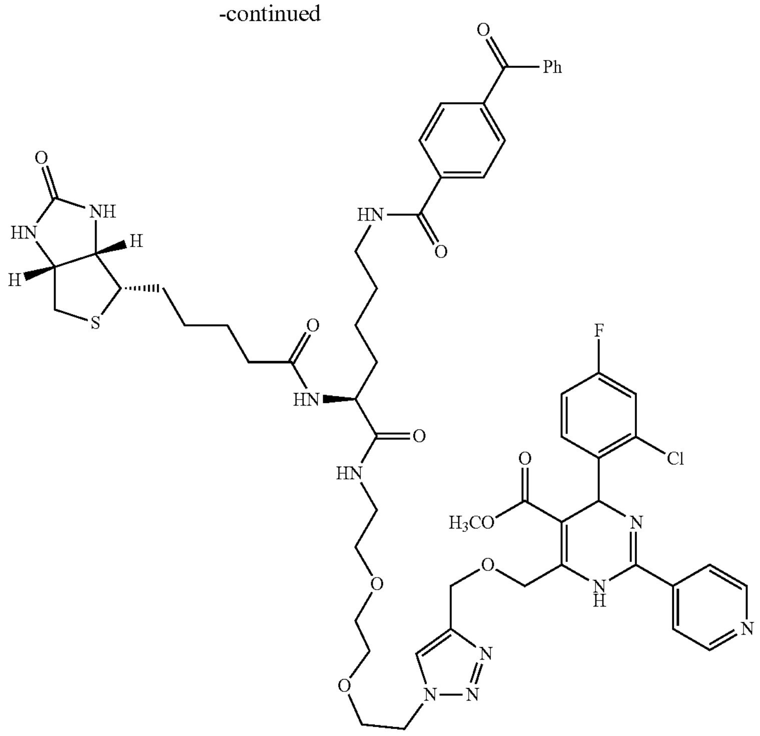

20

Compound 20: A solution of 15 (55 mg, 53 μmol, 1 eq.) in $CH_2Cl_2$ (1.0 mL) at 0° C. was treated with trifluoroacetic acid (0.25 mL). The resulting mixture was allowed to warm to room temperature over 15 minutes. After this time the mixture was concentrated to dryness under reduced pressure. The resulting crude amine was dissolved in DMF (2.0 mL), then was treated with a 4-benzoylbenzoic acid (24 mg, 0.11 mmol, 2.0 eq.), HATU (40 mg, 0.11 mmol, 2.0 eq.), and N,N-diisopropylethylamine (37 μL, 0.21 mmol, 4.0 eq.). The resulting mixture was allowed to stir at room temperature overnight, then the resulting product solution (in DMF) was directly purified by column chromatography over $C_{18}$-silica gel, eluting with 0-100% $CH_3CN$ in water containing 0.1% formic acid. Fractions containing the desired product were combined and partially evaporated to remove $CH_3CN$, then were frozen at −78° C. and lyophilized to afford 20 as a yellow solid (formate salt, 32 mg, 52% yield). LC-MS: $t_R$: 1.43 min; $[M+H]^+$ 1151.7.

21

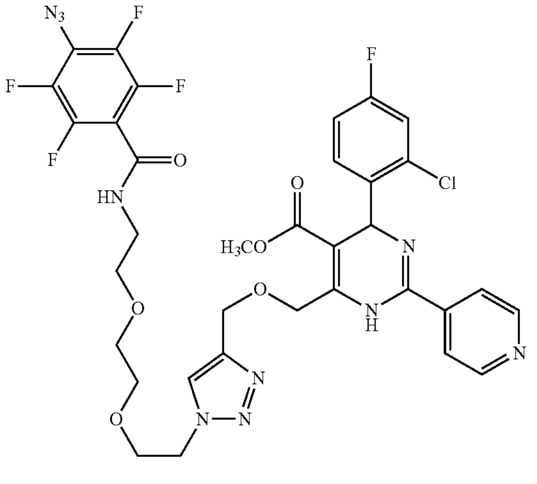

Compound 21: Compound 21 was prepared according to General Procedure A above from 2 (37 mg, 63 μmol) and 4-azido-2,3,5,6-tetrafluorobenzoic acid. After stirring at room temperature for 3 h, the crude product mixture was purified by reverse-phase chromatography over $C_{18}$-silica gel, eluting with 0-100% $CH_3CN$ in water containing 0.1% formic acid. Compound 21 was isolated as a bright yellow solid (formate salt, 26 mg, 52% yield). LC-MS: $t_R$: 1.51 min; $[M+H]^+$ 806.6.

22

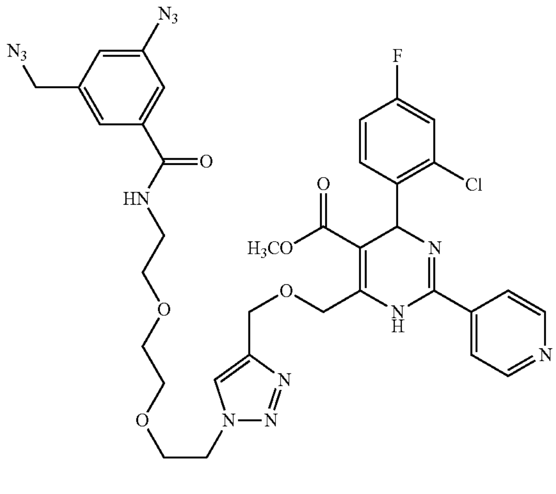

Compound 22: Compound 22 was prepared according to General Procedure A above from 2 (37 mg, 63 μmol) and 3-azido-5-(azidomethyl)benzoic acid. After stirring at room temperature for 3 h, the crude product mixture was purified by reverse-phase chromatography over $C_{18}$-silica gel, eluting with 0-100% $CH_3CN$ in water containing 0.1% formic acid. Compound 22 was isolated as a bright yellow solid (formate salt, 26 mg, 52% yield). LC-MS: $t_R$: 1.51 min; $[M+H]^+$ 789.5.

Example 4: SFC Separation of I-1 (ARK-139) Enantiomers and Determination of Absolute Stereochemistry of Active Isomer Racemic I-1 (ARK-139) was subjected to SFC chiral separation (ChiralPak AD column, isocratic elution of 70% A/30% B, phase A for supercritical $CO_2$, phase B for MeOH, total flowrate of 60 g/min, cycle time 3 min), and two peaks were separated and collected.

I-1a

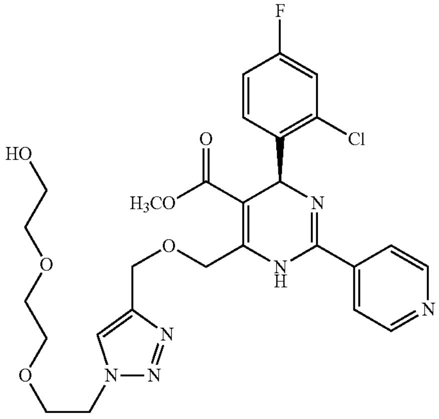

(S-enantiomer) ARK-702

-continued

I-1b

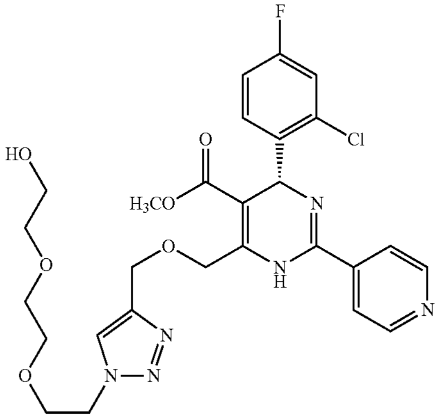

(R-enantiomer) ARK-701

Separation of the two enantiomers of I-1 allows preparation of non-racemic versions of each of the compounds of Table 5 and Example 3 and other HAP compounds disclosed herein.

In some embodiments, the present invention accordingly provides such compounds that are enantioenriched at the HAP stereocenter.

(R)-methyl 4-(2-chloro-4-fluorophenyl)-6-(((1-(2-(2-(2-hydroxyethoxy)ethoxy)ethyl)-1H-1,2,3-triazol-4-yl)methoxy)methyl)-2-(pyridin-4-yl)-1,4-dihydropyrimidine-5-carboxylate (I-1b above). Yellow oil. $^1$H NMR: (400 MHz, $CDCl_3$) δ 8.68 (q, J=1.6, 3.2 Hz, 2H), 8.54 (br s, 1H), 7.87 (s, 1H), 7.70 (q, J=1.6, 3.2 Hz, 2H), 7.31 (dd, J=6.0, 2.4 Hz, 1H), 7.13 (dd, J=2.4, 6.0 Hz, 1H), 6.95-6.90 (dt, J=4.2, 8.4 Hz, 1H), 6.21 (s, 1H), 4.98 (d, J=1.0, 2H), 4.83 (s, 2H), 4.59 (t, J=4.8 Hz, 2H), 3.90 (t, J=4.8 Hz, 2H), 3.71 (t, J=4.8 Hz, 2H), 3.65-3.60 (m, 7H), 3.56 (t, t, J=4.8 Hz, 1H), 2.70 (br s, 1H). LCMS, calcd $C_{27}H_{30}ClFN_6O_6$ (M+H)=589.02, found=589.4. Retention time in chiral LCMS: 1.74 min, Optical rotation: $[\alpha]_D^{25}$+57.4 (c 0.7, MeOH).

(S)-methyl 4-(2-chloro-4-fluorophenyl)-6-(((1-(2-(2-(2-hydroxyethoxy)ethoxy)ethyl)-1H-1,2,3-triazol-4-yl)methoxy)methyl)-2-(pyridin-4-yl)-1,4-dihydropyrimidine-5-carboxylate (I-1a above). Yellow oil. $^1$H NMR: (400 MHz, $CDCl_3$) δ 8.68 (q, J=1.6, 3.2 Hz, 2H), 8.54 (br s, 1H), 7.87 (s, 1H), 7.70 (q, J=1.6, 3.2 Hz, 2H), 7.31 (dd, J=6.0, 2.4 Hz, 1H), 7.13 (dd, J=2.4, 6.0 Hz, 1H), 6.95-6.90 (dt, J=4.2, 8.4 Hz, 1H), 6.21 (s, 1H), 4.98 (s, 2H), 4.83 (s, 2H), 4.59 (t, J=4.8 Hz, 2H), 3.90 (t, J=4.8 Hz, 2H), 3.71 (t, J=4.8 Hz, 2H), 3.65-3.60 (m, 7H), 3.56 (t, t, J=4.8 Hz, 1H), 2.62 (br s, 1H). LCMS, calcd $C_{27}H_{30}ClFN_6O_6$ (M+H)=589.02, found=589.4. Retention time in chiral LCMS: 1.93 min, Optical rotation: $[\alpha]_D^{25}$−60.7 (c 0.7, MeOH).

| SFC Separation Conditions | |
|---|---|
| Instrument | Waters 80Q SFC |
| Column | ChiralPak AD column, 250 × 25 mm I.D., 10 um particle size; |
| Mobile Phase | Phase A for Supercritical $CO_2$ Phase B for Methanol (neutral)) |
| Isocratic elution | 30% Phase B (70% Phase A) |
| Total flow rate | 60 g/min |
| Cycle time | 3 min |
| Back Pressure | 100 bar to keep the $CO_2$ in Supercritical flow |
| Detector | UV 220 nm |

-continued
| SFC Separation Conditions | |
|---|---|
| Sample preparation | Material (about 80 mg) was dissolved in 25 mL MeOH |
| Injection | 1 mL |
Further experiments (SPR) showed that ARK-702 (I-1a) did not bind at 10 uM to Aptamer 21. On the other hand, ARK-701 (I-1b) did bind and is therefore the sole active isomer. Absolute stereochemistry was determined as shown below and using SFC to confirm.
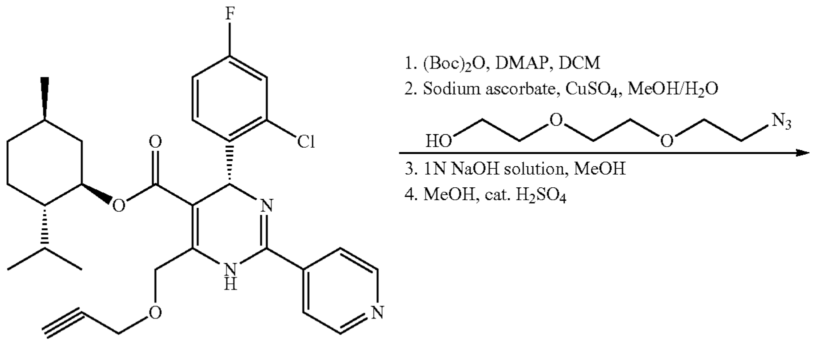
5a
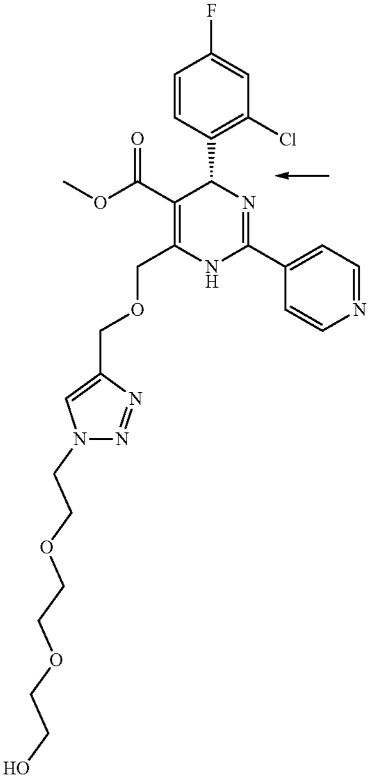
9a -continued

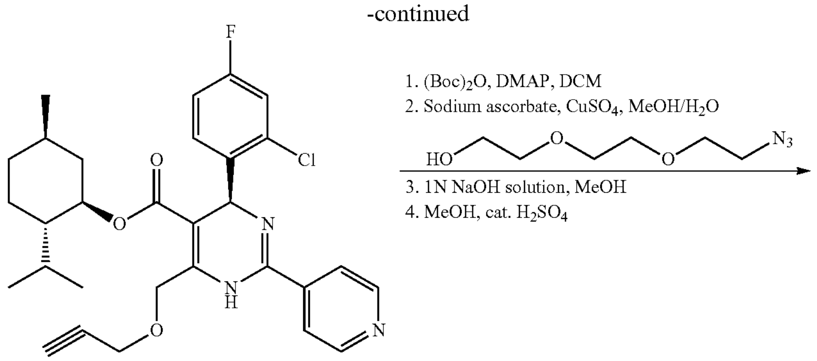

5b

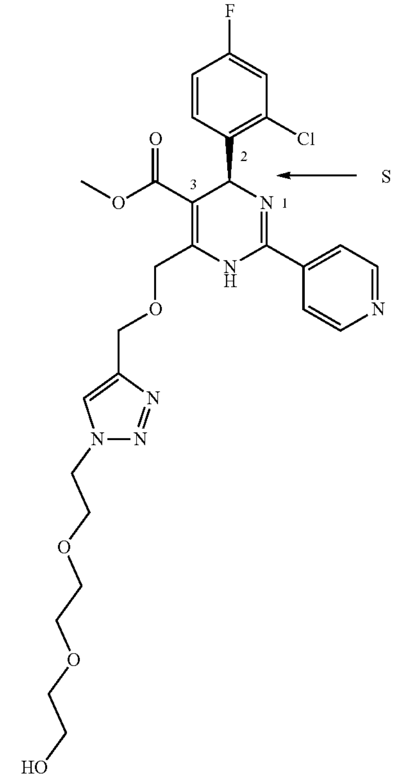

9b
Optical rotation: $[\alpha]_D^{25}$-27.9
c = 1 mg/1 ml MeOH

Example 5: Procedure for SEC/MS Analyses

Online SEC-LCMS has been used to study the binding to Aptamer 21 RNA against I-1 (ARK-139).

The RNA concentration was 1 μM and the ligand concentration ranged from 0.1 to 10 μM in an appropriate buffer (TRIS-HCl 20 mM pH 8.0, $MgCl_2$ 3 mM, KCl 100 mM).

The RNA/ligand mixtures were incubated at room temperature for 20 minutes in a 96-well plate format, then this plate was loaded into an autosampler linked to the chromatography system fitted with a reusable SEC column for rapid separation of target/ligand complexes from unbound components. RNA/ligand complexes in SEC eluent were monitored by UV detection, and an automated valving system directed the RNA peak to a reverse phase chromatography column for dissociation, desalting, and elution of any ligands into an ESI-MS system for identification.

All liquid chromatographic components were HP1200 modules. The mass spectrometer was the Waters LCT premier instrument operated in positive electrospray (ES+) TOF-MS mode. The mass range acquired was 80-1000 m/z in 0.25 s. The SEC column was 50×4.6 mm polyhydroxyethyl column. The SEC mobile phase was 50 mM phosphate buffer with 200 mM NaCl, pH=7.0. The LC column was a 2.1×50 mm C18 Phenomenex column. The gradient LC mobile phase A was 0.1% formic acid in water and B was acetonitrile/water with 0.1% formic acid. The run time was 7.9 min.

For more information on SEC/LCMS, see, e.g., Blom, K. F. et al., *J. Comb. Chem.* 1999, 1, 82-90.

Results

Binding of I-1 to Aptamer 21 was measured. SEC/LCMS conditions for this experiment were: [I-1]=5 uM, [RNA]=1 uM, Buffer=Tris-HCl 20 mM, KCl 100 mM, 3 mM $MgCl_2$.

TABLE 6

Binding of I-1 to Aptamer 21

| ARK-000139 conc (μM) | Peak area SEC-LCMS | Peak area LCMS | % of binding |
|---|---|---|---|
| 0.1 | 26.81 | 36.99 | 72.5 |
| 0.5 | 75.34 | 206.33 | 36.5 |
| 1 | 151.55 | 451.51 | 33.6 |
| 3 | 372.39 | 1665.87 | 22.4 |
| 10 | 471.84 | 5305.54 | 8.9 |

The experiment was duplicated and showed good reproducibility between the 2 experiments. The start of saturation was between 1 and 3 μM. SEC/LCMS was also used to measure I-1 binding to Aptamer 21-E. Consistent with SPR data and the published literature, I-1 does not bind Aptamer 21-E. SEC/LCMS represents a promising homogeneous method for assessing affinity.

Example 6: PEARL-seq Photoprobe Assay

General Methods

Sequences

The following sequences were employed in the assays described herein.

TABLE 7

Nucleic Acid Sequences

| Name | Sequence |
|---|---|
| PEARLv2_RT | CTTTCCCTACACGACGCTCTTCCGATCTTAGATCATTGATGG TGCCTACAG (SEQ ID NO: 26) |
| PEARLv2_2nd_adapter | AGATCGGAAGAGCACACGTCTGAACTCCAGTCAC (SEQ ID NO: 27) |
| PEARLv2_for_pri (where <index> refers to the 6 bp Illumina index) | CAAGCAGAAGACGGCATACGAGAT <index> GTGACTGGAGTTCAGACGTGTGCTC (SEQ ID NO: 28) |
| PEARLv2_rev_pri | AATGATACGGCGACCACCGAGATCTACACTCTTTCCCTACACGACGCTCTTCCG ATCT (SEQ ID NO: 29) |
| PEARLv3_1st_linker (where rN refers to a random mixture of the A, G, C and U RNA residues) | /5Phos/rArUrArUrArGrGrNrNrNrNrNrNrArGrArUrCrGrGrArArGrArGrCrArCrArCrGrUr CrUrGrArArCrUrC/3SpC3/ (SEQ ID NO: 30) |
| PEARLv3_2nd_adapter | /5Phos/AGATCGGAAGAGCGTCGTGTAGGGAAAGAGTGT/3SpC3/(SEQ ID NO: 31) |
| PEARLv3_RT | GAGTTCAGACGTGTGCTCTTCCGATCT (SEQ ID NO: 32) |
| PEARLv3_for_pri (where <i5> refers to the 6 bp Illumina i5 index) | AATGATACGGCGACCACCGAGATCTACAC <i5> ACACTCTTTCCCTACACGAC (SEQ ID NO: 33) |
| PEARLv3_rev_pri (where <i7> refers to the 6 bp Illumina i7 index) | CAAGCAGAAGACGGCATACGAGAT <i7> GTGACTGGAGTTCAGACGTGTGCTC (SEQ ID NO: 34) |

TABLE 8

| Illumina Index Sequences | |
|---|---|
| Index ID | Sequence |
| 1 | CGTGAT |
| 2 | ACATCG |
| 3 | GCCTAA |
| 4 | TGGTCA |
| 5 | CACTGT |
| 6 | ATTGGC |
| 7 | GATCTG |
| 8 | TCAAGT |
| 9 | CTGATC |
| 10 | AAGCTA |
| 11 | GTAGCC |
| 12 | TACAAG |
| 13 | TTGACT |
| 14 | GGAACT |
| 15 | TGACAT |
| 16 | GGACGG |
| 18 | GCGGAC |
| 19 | TTTCAC |
| 20 | GGCCAC |
| 21 | CGAAAC |
| 22 | CGTACG |
| 23 | CCACTC |
| 25 | ATCAGT |
| 27 | AGGAAT |

Folding RNA

A solution of RNA at 2 to 5 μM in nuclease-free water was heated to 95° C. for 3 min and then cooled on ice for 2 min. This solution was diluted with ½ volume of 3×RNA folding buffer (60 mM TrisHCl pH 8, 300 mM KCl, 9 mM $MgCl_2$) and incubated at 37° C. for 20 min. Folding was carried out immediately before use of the RNA in each experiment. In cases where a mixture of RNA molecules was used in vitro the RNAs were folded separately and then combined prior to the probing experiment.

Reverse Transcription Drop-Off Gel Assay

Cross-Linking

Folded RNA (1 μM) was incubated with the photoaffinity probe (10 μM) in total 25 μL of buffer (20 mM TrisHCl pH 8, 100 mM KCl, 3 mM $MgCl_2$) with 2.5% DMSO for 30 min at 37° C. to allow binding to come to equilibrium. The sample was then irradiated with long wave UV light (~365 nm) for 30 min in a UV crosslinker (Fisher Scientific).

Reverse Transcription

A 3.75 μL aliquot of 10 μM reverse transcription primer was added to the cross-linked RNA sample, which was then incubated for 5 min at 65° C. and then cooled on ice. The sample was then diluted to a final volume of 60 μL and final buffer concentration of 1× Protoscript-II buffer (New England Biolabs), 0.5 mM dNTPs, 10 mM DTT, 0.4 U/μL RNase Inhibitor (New England Biolabs), and 10 U/μL Protoscript-II (New England Biolabs). The reaction was incubated at 45° C. for 2 h, 65° C. for 20 min, and then 4° C.

Isolation of cDNA

The RNA was hydrolyzed by the addition of 4.8 μL of 2.5 M NaOH and heating at 95° C. for 5 min. The reaction was quenched by the addition of 0.9 μL of acetic acid. The cDNA was precipitated by the addition of 6.6 μL of 3 M sodium acetate pH 5 and 181 μL ethanol, cooling to −80° C. for 1 h, and then centrifuging at 20,500×g at 4° C. for 30 min. The cDNA pellet was washed twice with 500 μL of 70% ethanol and then air dried for 5 min.

Polyacrylamide Gel Analysis

The cDNA pellet was resuspended in 12 μL of 1×TBE-urea sample loading buffer (Bio-Rad) and heated to 95° C. for 5 min. The sample was then run on a pre-cast 8.6×6.7 cm TBE-urea 10% PAGE gel (Bio-Rad) at 120 V until the lower bromophenol blue dye reached the bottom of the gel. The gel was stained with 1×SYBR-gold (Invitrogen) in 1×TBE buffer at room temperature for 20 min covered from light. The gel fluorescence was imaged on an Azure c600 instrument.

LC-MS Analysis of Cross-Linked RNA

Generating Cross-Linked RNA

Folded RNA (1.33 μM) was incubated with or without the photoaffinity probe (20 μM) in total 100 μL of buffer (20 mM TrisHCl pH 8, 100 mM KCl, 3 mM $MgCl_2$) with 2% DMSO for 30 min at 37° C. to allow binding to come to equilibrium. The sample was then irradiated with long wave UV light (~365 nm) for 30 min in a UV crosslinker (Fisher Scientific).

The RNA was then precipitated by adding 10 μL of 3 M sodium acetate pH 5 and 275 μL ethanol, cooling to −80° C. for 1 h, and then centrifuging at 20,500×g at 4° C. for 30 min. The RNA pellet was washed with 500 μL of 70% ethanol, air dried for 5 min, and then resuspended in 120 μL of water.

LC-MS Analysis

50 μL of RNA sample was injected onto Clarity 2.6 μm Oligo X-T column (50*2.1 mm, 60° C.), and the gradient and flowrate were as follows: 95% A/5% B to 75% A/25% B over 5 min, flowrate: 400 μL/min; 75% A/25% B to 30% A/70% B over 1 min, flowrate: 400 μL/min; 100% D over 1 min, flowrate: 500 μL/min; 95% A/5% B over 2 min, flowrate: 500 μL/min (A: 1% HFIPA (hexafluoroisopropyl alcohol), 0.1% DIEA (diisopropylethylamine), 1 μM EDTA (ethylenediamine tetraacetic acid) in $H_2O$; B: 0.075% HFIPA, 0.0375% DIEA, 1 μM EDTA in 65/35 MeCN/$H_2O$; D: 40/40/20% MeOH/MeCN/$H_2O$); The LCMS instrument was a Thermo Finnigan LTQ, and ProMass deconvolution software coupled with Xcaliber were used for all data processing.

Next Generation Sequencing Analysis of ARK-547 Cross-Linked RNA

Generating Crosslinked RNA

A 9.5 μL sample of folded RNA (2.6 μM) in buffer (20 mM TrisHCl pH 8, 100 mM KCl, 3 mM $MgCl_2$) was added to a 0.5 μL aliquot of 1 mM ARK-547 in DMSO. The reaction was incubated for 10 min at 37° C., irradiated with long wave UV light (~365 nm) for 30 min in a UV crosslinker (Fisher Scientific), and then kept on ice.

Linker Ligation

The samples of cross-linked RNA were diluted to a final volume of 20 μL and final reaction conditions of 1×T4 RNA ligase buffer (New England Biolabs), 5 U/μL T4 RNA ligase 2, truncated KQ (New England Biolabs), 16.5% PEG-8000, and 0.5 μM universal miRNA cloning linker (New England Biolabs). The reaction was incubated in a thermal cycler for 2.5 h cycling between 5 min at 16° C. and 3 min at 25° C. The RNA was then purified using Agencourt AMPure XP beads (Beckman Coulter) using the standard protocol from the manufacturer. The RNA was eluted with 20 μL of nuclease-free water.

Reverse Transcription

A 10 μL aliquot of the eluted RNA sample was mixed with a 1 μL aliquot of 2 μM PEARLv2_RT primer, heated to 65° C. for 5 min, and then cooled on ice. An 8 μL sample of 2.5× mutagenic reverse transcription buffer (125 mM TrisHCl pH 8, 187.5 mM KCl, 25 mM DTT, 1.25 mM dNTPs) was added to the sample and it was heated to 42° C. for 2 min, followed by addition of 1 μL of SuperScript II enzyme (Thermo), and then incubation at 42° C. for 3 h and 70° C. for 15 min.

To remove excess primer, the sample was mixed with 4.5 μL of ExoSAP-IT, incubated at 37° C. for 15 min, and then quenched with 1 μL of 0.5 M EDTA pH 8. The RNA was then degraded by adding 2.08 μL of 2.5 M NaOH, incubating at 95° C. for 5 min, and quenching with 3.25 μL of 10% acetic acid. The remaining cDNA was purified by Agencourt AMPure XP beads (Beckman Coulter) using the standard protocol from the manufacturer and eluted in 30 μL of nuclease-free water. The concentration was determined by absorbance at 260 nm.

Second Adaptor Ligation

Second adaptor ligation was carried out using the CircLigase ssDNA ligase system (Epicentre). A 0.8 pmol aliquot of purified cDNA was brought to a final volume of 20 μL and final concentration of 83.5 μM PEARLv2_2nd_adapter oligo, 1× CircLigase buffer, 50 μM ATP, 2.5 mM $MnCl_2$, and 5 U/μL enzyme. The reaction was incubated at 60° C. for 2 h and then 80° C. for 10 min. The adaptor-ligated cDNA was purified by Agencourt AMPure XP beads (Beckman Coulter) using the standard protocol from the manufacturer and eluted in 30 μL of nuclease-free water.

Polymerase Chain Reaction

The adaptor-ligated cDNA was PCR amplified using Q5 high-fidelity DNA polymerase (New England Biolabs) to install the Illumina adaptor sequences. A 5 μL aliquot of the adaptor-ligated cDNA was brought to a final volume of 50 μL and final concentration of 0.2 μM PEARLv2_for_pri primer, 0.2 μM PEARLv2_rev_pri primer, and 1× Q5 master mix. The polymerase chain reaction was carried out with heating to 98° C. for 30 seconds; 5 cycles of 98° C. for 10 seconds, 60° C. for 30 seconds, and 72° C. for 30 seconds; 15 cycles of 98° C. for 10 seconds, and 72° C. for 30 seconds; 72° C. for 2 min. A different Illumina barcode was installed in each PCR product via the forward primer. PCR products were purified using Agencourt AMPure XP beads (Beckman Coulter) using the standard protocol from the manufacturer and eluted in 30 μL of nuclease-free water.

Next Generation Sequencing

The concentrations of different PCR products were measured using the Denovix dsDNA fluorescence quantitation kit (Denovix) and multiplexed at equal concentrations with a 20% PhiX spike-in. Sequencing was performed on an Illumina MiSeq with 150 bp paired-end reads using the standard manufacturer protocol.

Capture of Aptamer 21 from a Defined Mixture of RNAs

Generating Crosslinked RNA

A sample of folded RNA was prepared containing 1 μM each of Myc HP PA, Aptamer 21, FMN, MYC_3WJ-HP_N3G, and PreQ1 RNAs in folding buffer (20 mM TrisHCl pH 8, 100 mM KCl, 3 mM $MgCl_2$). A 95 μL sample of this solution was added to a 5 μL aliquot of 0.2 mM ARK-670 (probe) or ARK-139 (control) in DMSO. The reaction was incubated for 30 min at 37° C., irradiated with long wave UV light (~365 nm) for 30 min in a UV crosslinker (Fisher Scientific), and then cooled on ice. The excess probe and buffer was then removed by passing the sample through an Illustra MicroSpin G-25 spin column (GE Healthcare) according to the manufacturer's protocol.

Avidin Bead Capture

For each treatment, a 75 μL aliquot of the crosslinked RNA was mixed with 0.75 μL of 10% Tween-20 and 0.45 μL of 0.5 M EDTA pH 8 solution. A 50 μL aliquot of MyOne Streptavidin C1 Dynabead slurry (Thermo) was captured on a magnet, washed twice with 50 μL of 1× bind/wash buffer (20 mM TrisHCl pH 7, 100 mM KCl, 0.1% Tween-20), and then resuspended in 50 μL of the crosslinked RNA sample. The bead suspension was rotated at room temperature for 60 min and then washed twice with 100 μL of 1× bind/wash solution. To elute the bound RNA, the beads were resuspended in 50 μL of elution buffer (95% formamide, 20 mM EDTA), heated to 95° C. for 5 min, and then the supernatant was removed. The RNA was ethanol precipitated by adding 50 μL of water, 2 uL of 5 mg/mL glycogen, 10 μL 3 M NaOAc pH 5, and 250 μL ethanol, incubating at −80° C. for 1 h, centrifuging at 20,000 g for 30 min, washing the pellet twice with 500 μL of 70% ethanol, air drying the pellet, and then resuspending the pellet in 16 μL of nuclease-free water.

Linker Ligation

The samples of bead-eluted RNA were diluted to a final volume of 20 μL and final reaction conditions of 1×T4 RNA ligase buffer (New England Biolabs), 5 U/μL T4 RNA ligase 2, truncated KQ (New England Biolabs), 16.5% PEG-8000, and 0.5 μM universal miRNA cloning linker (New England Biolabs). The reaction was incubated in a thermal cycler for 2.5 h cycling between 5 min at 16° C. and 3 min at 25° C. The RNA was then purified using Agencourt AMPure XP beads (Beckman Coulter) using the standard protocol from the manufacturer. The RNA was eluted with 11 μL of nuclease-free water.

Reverse Transcription with SuperScript III

To the 11 μL RNA sample from linker ligation was added 1 μL of 2 μM PEARLv2_RT primer and 1 μL of 10 mM dNTP mix. The sample was heated to 65° C. for 5 min and then cooled on ice for 1 min. The sample was then mixed with 4 μL of 5× first-strand buffer (Thermo), 1 of 0.1 M DTT, 1 μL of RNaseOUT (Thermo), and 1 μL of SuperScript III enzyme (Thermo). The reaction was incubated at 55° C. for 45 min, 70° C. for 15 min, and then cooled to 4° C.

To remove excess primer, the sample was mixed with 4.5 μL of ExoSAP-IT, incubated at 37° C. for 15 min, and then quenched with 1 μL of 0.5 M EDTA pH 8. The RNA was then degraded by adding 2.08 μL of 2.5 M NaOH, incubating at 95° C. for 5 min, and quenching with 3.25 μL of 10% acetic acid. The remaining cDNA was purified by Agencourt AMPure XP beads (Beckman Coulter) using the standard protocol from the manufacturer and eluted in 15 μL of nuclease-free water. The concentration was determined by absorbance at 260 nm.

Second Adapter Ligation

Second adaptor ligation was carried out using the CircLigase ssDNA ligase system (Epicentre). A 0.8 pmol aliquot of purified cDNA was brought to a final volume of 20 μL and final concentration of 83.5 μM PEARLv2_2nd_adapter oligo, 1× CircLigase buffer, 50 μM ATP, 2.5 mM $MnCl_2$, and 5 U/μL enzyme. The reaction was incubated at 60° C. for 2 h and then 80° C. for 10 min. The adaptor-ligated cDNA was purified by Agencourt AMPure XP beads (Beckman Coulter) using the standard protocol from the manufacturer and eluted in 30 μL of nuclease-free water.

Polymerase Chain Reaction

The adaptor-ligated cDNA was PCR amplified using Q5 high-fidelity DNA polymerase (New England Biolabs) to install the Illumina adaptor sequences. A 5 μL aliquot of the adaptor-ligated cDNA was brought to a final volume of 50 μL and final concentration of 0.2 μM PEARLv2_for_pri primer, 0.2 μM PEARLv2_rev_pri primer, and 1×Q5 master mix. The polymerase chain reaction was carried out with heating to 98° C. for 30 seconds; 5 cycles of 98° C. for 10 seconds, 60° C. for 30 seconds, and 72° C. for 30 seconds; 15 cycles of 98° C. for 10 seconds, and 72° C. for 30 seconds; 72° C. for 2 min. A different Illumina barcode was installed in each PCR product via the forward primer. PCR products were purified using Agencourt AMPure XP beads (Beckman Coulter) using the standard protocol from the manufacturer and eluted in 30 μL of nuclease-free water.

Next Generation Sequencing

The concentrations of different PCR products were measured using the Denovix dsDNA fluorescence quantitation kit (Denovix) and multiplexed at equal concentrations with a 20% PhiX spike-in. Sequencing was performed on an Illumina MiSeq with 150 bp paired-end reads using the standard manufacturer protocol.

Capture of Aptamer 21 with Click-Biotinylated Probes

Generating Crosslinked and Click-Biotinylated RNA

A 50 μL sample of 1 μM folded Aptamer 21 or Aptamer 21-E solution in folding buffer (20 mM TrisHCl pH 8, 100 mM KCl, 3 mM $MgCl_2$) was added to a 0.5 μL aliquot of 0.5 mM ARK-729, ARK-2058, ARK-816, or ARK-2059 in DMSO or a DMSO-only control. The solution was incubated at 37° C. for 1 h and then irradiated with long wave UV light (~365 nm) for 30 min in a UV crosslinker (Fisher Scientific). To this solution was added 0.5 μL of 10 mM DBCO-biotin (Click Chemistry Tools, cat. #A105) and 2 μL of 0.5 M EDTA pH 8 and then the solution was incubated at 65° C. for 2 h. The RNA was ethanol precipitated by adding 35 μL of water, 2 uL of 5 mg/mL glycogen, 10 μL 3 M NaOAc pH 5, and 250 μL ethanol, incubating at −80° C. for 1 h, centrifuging at 20000×g for 30 min, washing the pellet twice with 500 μL of 70% ethanol, and then air drying the pellet.

Streptavidin Bead Capture

The RNA pellet was redissolved in 50 μL of 1× bind/wash buffer (20 mM TrisHCl pH 7, 100 mM KCl, 0.1% Tween-20). A 50 μL aliquot of MyOne Streptavidin C1 Dynabead slurry (Thermo) was captured on a magnet, washed twice with 50 μL of 1× bind/wash buffer, and then resuspended in 50 μL of the crosslinked RNA sample. The bead suspension was rotated at room temperature for 30 min and then washed twice with 100 μL of 1× bind/wash solution.

On-Bead Dephosphorylation

The magnetic beads with captured RNA were resuspended in a 50 μL solution containing 1× FastAP buffer and 0.08 U/μL FastAP enzyme (Thermo) and the slurry was incubated at 37° C. for 15 min with 1200 rpm agitation. A 150 μL solution of 1×PNK buffer, 1 mM DTT, and 0.25 U/μL T4 PNK (New England Biolabs) was then added to the mixture and the slurry was incubated at 37° C. for 20 min with 1200 rpm agitation. The beads were then washed three times with 400 μL of 1× bind/wash solution.

First Linker Ligation

The beads were washed twice with 400 μL of linker wash buffer (50 mM TrisHCl pH 8, 5 mM $MgCl_2$) and then resuspended in a 27.5 μL ligation reaction mixture containing 2 μM of the PEARLv3_1st_linker oligo, 1×RNA Ligase 1 buffer, 1 mM ATP, 2.9% DMSO, 16% PEG8000, and 2.7 U/μL RNA Ligase 1 (New England Biolabs, cat #M0437). The slurry was incubated at 22° C. for 75 min with 1200 rpm agitation and then the beads were washed twice with 100 μL of 1× bind/wash buffer.

Reverse Transcription

The beads were washed twice with 200 μL of 1× first-strand buffer (Thermo) and then resuspended in a solution containing 14.75 μL water, 1.25 μL of 10 mM dNTPs, and 0.25 μL of 10 μM PEARLv3_RT oligo. The slurry was heated to 65° C. for 5 min, chilled on ice, and then a solution containing 5 μL of 5× first-strand buffer (Thermo), 1.25 μL of 100 mM DTT, 1.25 μL of RNaseOUT (Thermo), and 1.25 μL of SuperScript III (Thermo) was added. The slurry was mixed, incubated at 50° C. for 50 min, heated to 85° C. for 5 min, and then chilled on ice.

To elute the cDNA, the 2.5 μL of 2.5 M sodium hydroxide was added to the slurry and it was heated to 95° C. for 5 min, chilled on ice, and then 3.6 μL of a 1.74 M solution of acetic acid was added to quench the pH. The supernatant was removed from the beads, brought to a final volume of 50 μL with nuclease-free water, and then purified using Agencourt AMPure XP beads (Beckman Coulter) using the standard protocol from the manufacturer and eluted in 15 μL of nuclease-free water.

Second Adapter Ligation

A 14 μL aliquot of the AMPure-eluted cDNA was brought to 20 μL reaction mixture with a final concentration of 1× CircLigase buffer, 80 nM PEARLv3_2nd_adapter oligo, 50 μM ATP, 2.5 mM $MnCl_2$, and 5 U/μL CircLigase ssDNA ligase (EpiCentre) and incubated at 60° C. for 2 h and then 80° C. for 10 min. The ligated cDNA was purified using Agencourt AMPure XP beads (Beckman Coulter) using the standard protocol from the manufacturer and eluted in 25 μL of nuclease-free water.

Polymerase Chain Reaction

The adaptor-ligated cDNA was PCR amplified using Q5 high-fidelity DNA polymerase (New England Biolabs) to install the Illumina adaptor sequences. A 5 μL aliquot of the adaptor-ligated cDNA was brought to a final volume of 50 μL and final concentration of 0.2 μM PEARLv3_for_pri primer, 0.2 μM PEARLv3_rev_pri primer, and 1× Q5 master mix. The polymerase chain reaction was carried out with heating to 98° C. for 30 seconds; 5 cycles of 98° C. for 10 seconds, 60° C. for 30 seconds, and 72° C. for 30 seconds; 15 cycles of 98° C. for 10 seconds, and 72° C. for 30 seconds; 72° C. for 2 min. A different Illumina barcode was installed in each PCR product via the forward primer. PCR products were purified using Agencourt AMPure XP beads (Beckman Coulter) using the standard protocol from the manufacturer and eluted in 30 μL of nuclease-free water.

Next Generation Sequencing

The concentrations of different PCR products were measured using the Denovix dsDNA fluorescence quantitation kit (Denovix) and multiplexed at equal concentrations with a 20% PhiX spike-in. Sequencing was performed on an Illumina MiSeq with 150 bp paired-end reads using the standard manufacturer protocol.

Capture of Aptamer 21 from PolyA+ RNA Extract

Isolation of PolyA+ RNA from Cells

Total RNA was extracted from a pellet of $5\times10^6$ HepG2 cells using the ReliaPrep mini-prep kit (Promega) according to the manufacturer's standard protocol. The polyA+ RNA fraction was isolated from 50 μL sample of total RNA at 454 ng/μL using the magnetic mRNA isolation kit (New England Biolabs, cat #S1550) according to the manufacturer's standard protocol using 450 μL of lysis buffer and 100 μL of beads.

Generating Crosslinked and Click-Biotinylated RNA

A sample of folded aptamer 21 RNA was spiked into a sample of polyA+ RNA extract at a final concentration of 1 nM aptamer 21 and 3 ng/μL polyA+ RNA. A 50 μL sample of this RNA mixture was then added to a 0.5 μL aliquot of 100 μM ARK-816 or ARK-2059 in DMSO or a DMSO control and the mixture was incubated for 20 min at 37° C. The solution was then diluted with 50 μL of 1× folding buffer and then irradiated with long wave UV light (~365 nm) for 30 min in a UV crosslinker (Fisher Scientific). To this solution was added 1 μL of 5 mM DBCO-biotin (Click Chemistry Tools, cat. #A105) and 1 μL of 0.5 M EDTA pH 8 and then the solution was incubated at 65° C. for 2 h. The RNA was ethanol precipitated by adding 35 μL of water, 2 uL of 5 mg/mL glycogen, 10 μL 3 M NaOAc pH 5, and 250 μL ethanol, incubating at −80° C. for 1 h, centrifuging at 20,000 g for 30 min, washing the pellet twice with 500 μL of 70% ethanol, and then air drying the pellet.

Fragment RNA

RNA samples were fragmented using the Ambion fragmentation kit (Thermo). RNA pellets were resuspended in 50 μL of 1× fragmentation buffer, incubated at 70° C. for 15 min, and then quenched by the addition of 5 μL of stop solution. The sample was then ethanol precipitated by adding 50 μL water, 10 μL 3 M NaOAc pH 5, 2 μL 5 mg/mL glycogen and 280 μL ethanol, incubating for 1 h at −80° C., centrifuging at 20,000 g for 30 min, washing the pellet twice with 500 μL of 70% ethanol, and then air drying the pellet.

Avidin Bead Enrichment and Sequencing Library Preparation

Avidin bead capture, dephosphorylation, first linker ligation, reverse transcription, second adapter ligation, and polymerase chain reaction were performed as per the "Capture of Aptamer 21 with Click-Biotinylated Probes" section above.

Size Selection of Sequencing Library

To remove primer dimer and size select the sequencing library, the PCR product was run on a 3% agarose gel with 1×SYBR-gold. The region from 275 to 400 bp was cut out and the DNA was extracted using the Zymoclean Gel DNA Recovery Kit (Zymo Research) according to the manufacturer's suggested protocol and eluted into 12 μL of nuclease-free water.

Next Generation Sequencing

Sequencing was performed on a single Illumina HiSeq 4000 lane with 150 bp paired-end reads using the standard manufacturer protocol.

PEARL-seq Informatics

Genome References

All analyses were referenced to the GRCh38 human genome assembly and GENCODE release 28 transcript annotations, with Aptamer 21 added (AGGGGTAGGCCAGGCAGCCAACTAGCGAGAGCT-TAAATCTCTGAGCCCGAGAGGG TTCAGTGCTGCT-TATGTGGACGGCTTGAT; SEQ. ID:25).

Read Stitching

To ensure that only high-quality, concordant read pairs were used to define mutations and reverse transcriptase stalls, reads were first stitched with Paired-End reAd mergeR (PEAR) (https://dx.doi.org/10.1093%2Fbioinformatics %2Fbtt593), requiring a minimum assembled length of at least 10 nucleotides (nt).

Single-Transcript Read Alignment (SHAPEware)

For all SHAPEware analysis, reads were adapter-trimmed aligned as previously described (https://bitbucket.org/arrakistx/shapeware/src) using Trimmomatic (http://dx.doi.org/10.1093/bioinformatics/btu170) and bwa-mem (https://arxiv.org/abs/1303.3997), respectively.

SHAPE Reactivity Calculation (SHAPEware)

Mutations (substitutions, insertions, and deletions) were tabulated using bam-readcount (https://github.com/genome/bam-readcount). Mutations were then filtered to retain only those that can be unambiguously linked to a given transcript position (ambiguous mutations could arise from multiple positions). SHAPE reactivities were defined based upon the excess of mutations in SHAPE reagent-treated sample compared to untreated sample, normalized to an unfolded control:

$$\text{Reactivity} = \frac{Mut_{treated} - Mut_{untreated}}{Mut_{denatured}}.$$

Reactivities were then further normalized within each transcript as described in Deigan et al. (PNAS Jan. 6, 2009, 106 (1) 97-102).

Transcriptome-Wide Read Alignment (PEARL-Seq)

Stitched reads were then processed with Cutadapt (http://dx.doi.org/10.14806/ej.17.1.200) with at least 5-nts of overlap and a maximum of 20% mismatches to simultaneously 1) define a unique 6-nt unique molecular identifier (UMI) in the correct adapter context (ATATAGGN$_6$AGATCGG) (SEQ. ID:35) and 2) trim away adapters to allow more precise definition of fragment termini. UMIs were appended to read names, and reads were mapped the against the genome and transcriptome references (plus Aptamer 21) using the STAR aligner (http://dx.doi.org/10.1093/bioinformatics/bts635) with at most 10% mismatches. Groups of reads with identical or near-identical UMIs were then collapsed using the Directional Adjacency methods of UMI-tools (http://dx.doi.org/10.1101/gr.209601.116) with default parameters. As a result, PCR duplicates were removed from the data to avoid potential artifacts that might introduce bias or variance.

Definition of RT Stall Sites

Sites of interaction between probe and transcripts were defined by reverse transcriptase (RT) stalling sites. RT stalling sites were defined based upon the mapped position of the 5' end of a trimmed read. For short defined transcripts such as Aptamer 21, high-confidence RT stall sites were defined from reads with 3' ends mapping to the precise transcript end. The frequency of high-confidence stall sites are plotted for each position in Aptamer 21.

Peakcalling (PEARL-Seq)

True sites of small molecule-transcript interaction were defined based upon significant enrichment of stall sites in a PEARL-seq probe compared to a warhead-only control. These peaks are expected to be quite narrow based upon the single-nucleotide resolution of RT stall sites. Thus, we developed a peakcalling method optimized to detect these narrow peaks and thus identify sites enriched for RT sites in probe when compared to a warhead-only control. Briefly, uniquely mapping reads were trimmed to retain their 5' most nucleotide only. These 5' ends were then counted across 10-nt bins throughout the whole genome using Deeptools (http://dx.doi.org/10.1093/nar/gkw257) combined with custom scripts. Each bin with detectable read 5' ends was tested for significant enrichment with the Empirical Analysis of Digital Gene Expression Data in R (edgeR) pipeline (https:// doi.org/doi:10.18129/B9.bioc.edgeR), using Benjamini-Hochberg multiple hypothesis correction. Peaks with both positive enrichment in probe over control and an FDR <0.01 were considered to contain probe-induced RT stalling events corresponding to probe-transcript interactions.

Example 7: Surface Plasmon Resonance Assay for Aptamer 21

Surface plasmon resonance (SPR) may be used to screen ligands and hook and click constructs for binding to a target RNA of interest. SPR is especially useful for monitoring biomolecular interactions in real time. Typically, target species and unrelated control are immobilized to a sensor chip, then analytes (compounds/fragments) are flowed over the surface. Binding of the compound to target species results in increase of SPR signal (association phase). Washing away bound compound with buffer results in a decrease of SPR signal (dissociation phase). Fitting of sensorgrams recorded at different compound concentrations is performed to an appropriate interaction model. The method allows extraction of kinetic parameters ($k_a$, $k_d \rightarrow K_D$). Requirements/limitations include that the $k_a/k_d$ values be in reasonable ranges; and the target size must not be too large (<100 kDa). It is an excellent method to screen fragments and profile or validate hits. BC4000 may be used for primary screening (up to 4,000 data pts/week). Biacore T200 is suitable for hit profiling and validation.

Aptamer evolution for codeine binding has been achieved and the aptamer's binding constant determined by use of SPR. Win, N. M. et al., *Nucleic Acids Research* 2006, 34(19), 5670-5682. See, e.g., Chang, A. L. et al., *Anal. Chem.* 2014, 86, 3273-3278.

In the PEARL-seq context, SPR allows monitoring binding of "hooks" to DNA/RNA aptamers. The target species is immobilized to sensor chip, analytes (i.e. hooks) are flowed over surface (association phase), DNA/RNA aptamer is flowed over surface (plateau phase), competitor compound is washed over surface (dissociation phase), thus yielding binding data.

Sensor Chip Surface Preparation

Experiments were performed on a MASS-2 (Sierra Sensors) at 25° C. A high capacity amine chip was equilibrated with PBS. The chip was conditioned with alternating injections of 10 mM HCl and 10 mM NaOH in 1 M NaCl. The carboxymethylated dextran of the surface of the amine chip was activated for 7 minutes at a flow rate of 10 µL/min using a 1:1 volume ratio of 0.4 M 1-ethyl-3-(3-dimethylaminopropyl) carbodiimide (Sierra) and 0.1 M N-hydroxysuccinimide (Sierra). Neutravidin (70 µg/mL, Thermofisher) was injected over the activated surface for 10 minutes at a flow rate of 10 µl/min. Excess activated groups were blocked by an injection of 1 M ethanolamine, pH 8.5 (Sierra) for 7 minutes at a flow rate of 10 µl/min. A final injection of 10 mM NaOH in 1 M NaCl for 7 minutes at 10 µl/min was used to remove any unbound material to the chip. The immobilization reaction typically yielded approximately 12,000 resonance units (RU) of neutravidin. At least one spot in a channel was not injected with RNA and was used as a background control. Unrelated RNA was also used as a background control.

RNA Preparation

A 1 µM sample of biotin-aptamer 21 was prepared in RNAse free water, heated to 95° C. for 3 minutes, cooled on ice for 4 minutes, diluted with an equal volume 2× folding buffer (40 mM Tris-HCl, pH 8.0, 6 mM $MgCl_2$, 200 mM KCl), and incubated at 37° C. for 30 minutes. The final concentration of RNA was 0.5 µM.

RNA Surface Capture

The MASS-2 was primed 2 times with 20 mM Tris-HCl, pH 8.0, 3 mM $MgCl_2$, 100 mM KCl (Capture Buffer). RNA was injected over the neutravidin surface for 7 minutes at a flow rate of 10 µl/min. Capture levels typically reached approximately 3500-4500 of resonance units of aptamer 21.

Compound Testing

Compounds were diluted 2-fold in 100% DMSO at a starting concentration of 500 µM. Dilutions of 1:100, compound to buffer resulted in compound solutions in 20 mM Tris-HCl, pH 8.0, 3 mM $MgCl_2$, 100 mM KCl, 1% DMSO.

The MASS-2 was primed 2 times with 20 mM Tris-HCl, pH 8.0, 3 mM $MgCl_2$, 100 mM KCl, 1% DMSO (running buffer). Prior to testing compounds 3 injections of running buffer were used to equilibrate the sensor surface. Injections of DMSO correction solutions ranging from 0.6%-1.8% DMSO were injected over the surface for 30 µl at a flow rate of 30 µl/min to generate a DMSO correction curve for data analysis. Compound (120 µL) was injected over the RNA surface at a flow rate of 10 µl/min with a dissociation time of 240 sec.

Data Analysis

Data processing and analysis were done using Sierra Analyzer Software (Sierra Sensors). A double-referencing method was performed to process all datasets and a DMSO correction curve was applied to account for any differences in bulk refractive index changes between samples and running buffer. Double-referenced data were fit to a 1:1 binding model for kinetic analysis. The calculated $K_D$ was ~0.8 nM under these conditions.

Example 8: Preparation of $PreQ_1$ RNA Photoprobe

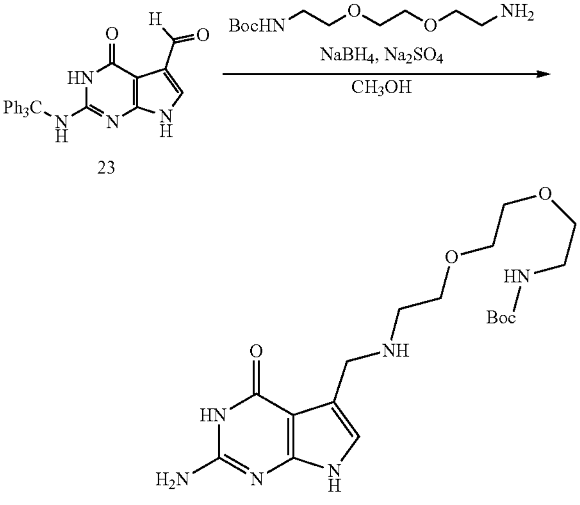

23

24

Use of the $PreQ_1$ riboswitch and preparation of small molecule ligands for it are described in Roth, A. et al., *Nature Structural & Molecular Biology* 2007, 14(4), 308-317, which is hereby incorporated by reference.

Compound 24: To a suspension of 23 (500 mg, 1.19 mmol, 1 eq,) and tert-butyl (2-(2-(2-aminoethoxy)ethoxy)ethyl)carbamate (354 mg, 1.43 mmol, 1.2 eq.) in methanol (14.0 mL) was added sodium sulfate (14 mg, 0.09 mmol, 0.08 eq.) at room temperature. The resulting suspension was stirred at room temperature for 2 h. Sodium borohydride (135 mg, 3.57 mmol, 3.0 eq.) was then added in small portions to the reaction mixture, then stirring at room temperature was maintained for and additional 4 h. The reaction mixture was diluted with ethyl acetate (250 mL), then was washed with sequential 50 mL portions of water (three times) and sat. aq. NaCl solution. The product solution was dried over $Na_2SO_4$, filtered, and the filtrate concentrated under reduced pressure. The obtained crude material was purified by reverse phase chromatography using $C_{18}$-silica gel (42-45% $CH_3CN$ in 10 mM $NH_4HCO_3$ in water) to afford 24 as an off-white solid (302 mg, 39% yield). $^1H$ NMR (400 MHz, DMSO-$d_6$, δ): 10.61 (s, 1H), 10.32 (br s, 1H), 7.38 (s, 1H), 7.31-7.28 (m, 12H), 7.24-7.19 (m, 3H), 6.82 (t, J=5.6 Hz, 1H), 6.31 (d, J=2 Hz, 1H), 3.56 (s, 2H), 3.46-3.35 (m, 11H), 3.08-3.03 (m, 2H), 1.36 (s, 9H). MS (ESI-MS): m/z calc. for $C_{37}H_{44}N_6O_5[MH]^+$ 653.34; found 653.14.

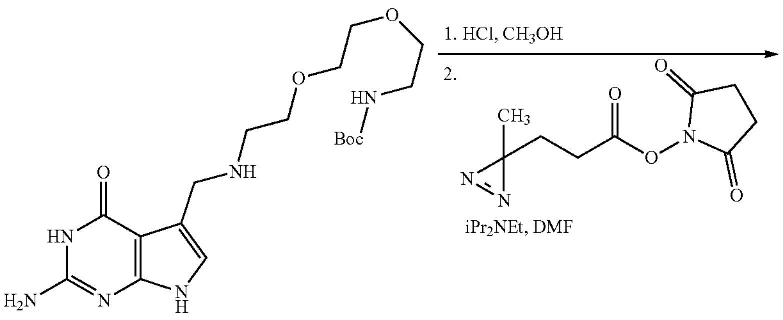

24

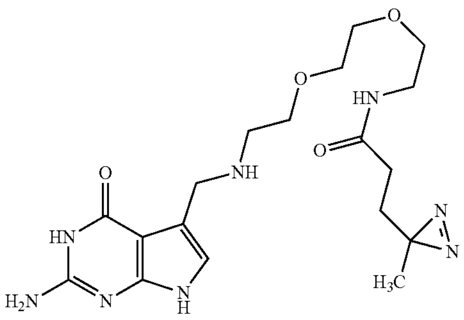

25

Compound 25 (I-23): A stirring solution of 24 (21 mg, 32 μmol, 1 eq.) in $CH_3OH$ (1.0 mL) at room temperature was treated dropwise with a 1.25 M $CH_3OH$ solution of HCl 583 μL, 0.73 mmol, 23 eq.). The resulting mixture was allowed to stir at room temperature for 24 h, then the precipitated solids were collected by filtration. The resulting crude solid was triturated with sequential 10 mL portions of pentane (twice) and diethyl ether (twice) to afford the intermediate primary amine as a white solid. The primary amine (10 mg, 32 μmol, 1 eq.) was resuspended in DMF (1.0 mL), then was treated with N,N-diisopropylethylamine (22 μL, 0.13 mmol, 4.0 eq.), and 2,5-dioxopyrrolidin-1-yl 3-(3-methyl-3H-diazirin-3-yl)propanoate (7.6 mg, 34 μmol, 1.05 eq.). The resulting mixture was maintained at room temperature for 16 h, then was immediately loaded onto a $C_{18}$-silica gel column, eluting with 0-70% $CH_3CN$ in water containing 0.1% formic acid). Fractions containing the desired product were combined and partially evaporated under reduced pressure to remove $CH_3CN$, then were frozen and lyophilized to afford the desired product I-23 as a white solid (formate salt, 9 mg, 60% yield).

Example 9: Synthesis of Additional Exemplary Photoprobe Compounds

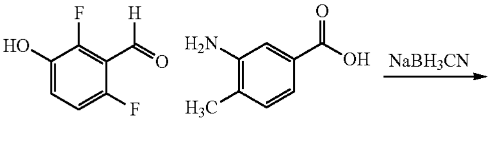

-continued

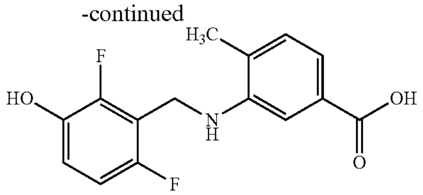

26

Compound 26: To a solution of 3-amino-4-methylbenzoic acid (4.00 g, 26.5 mmol, 1 eq.) in acetic acid (80 mL) was added 2,6-difluoro-3-hydroxybenzaldehyde (5.01 g, 31.7 mmol, 1.2 eq.) at 0° C. The reaction was slowly warmed to room temperature and stirred at room temperature for 3 h. The reaction mixture was again cooled to 0° C. $NaCNBH_3$ (3.32 g, 52.9 mmol, 2.0 eq.) was added, in small portions. The reaction mixture was allowed to warm to room temperature, then was stirred at room temperature for 16 h. The resulting reaction mixture was poured into ice-cold water (500 mL). The resulting precipitate was collected by filtration and washed with water (3×25 mL). The obtained solid was dried under high vacuum to afford 26 as a white solid (6.00 g, 62% yield). $^1H$ NMR (400 MHz, DMSO-$d_6$) δ 12.48 (br s, 1H), 9.74 (s, 1H), 7.22 (d, J=1.2 Hz, 1H), 7.13 (dd, J=7.6, 1.6 Hz, 1H), 7.05 (d, J=8.0 Hz, 1H), 6.86-6.83 (m, 2H), 5.38 (t, J=5.6 Hz, 1H), 4.36 (d, J=5.2 Hz, 2H), 2.11 (s, 3H). MS (ESI-MS): m/z calcd for $C_{15}H_{13}F_2NO_3^+$=294.09, found 294.16.

27

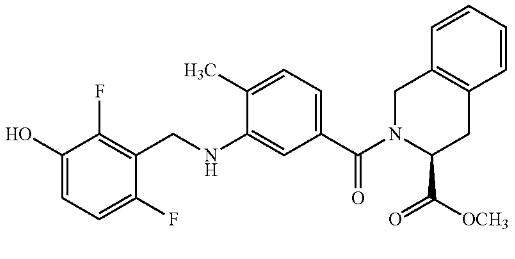

Compound 27: Compound 27 was synthesized according to General Procedure A from 26 (2.00 g, 6.82 mmol) and methyl (S)-1,2,3,4-tetrahydroisoquinoline-3-carboxylate hydrochloride in DMF (20 mL) at room temperature. Following stirring at room temperature for 3 h, the reaction mixture was diluted with water and the resulting solids collected by filtration. The crude product was purified by flash column chromatography over silica gel (40% EtOAc/hexanes) to afford 27 as a light pink solid (1.60 g, 34% yield). MS (ESI-MS): m/z calcd for $C_{26}H_{24}F_2N_2O_4^+$=467.17, found 467.22.

28

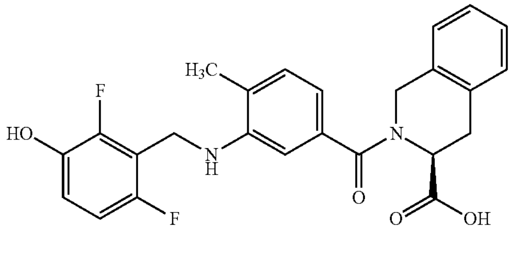

Compound 28: To a stirred solution of 27 (1.60 g, 3.93 mmol, 1 eq.) in THF:MeOH:Water (4:2:1, 11.2 mL) was added $LiOH \cdot H_2O$ (0.43 g, 10.3 mmol, 3.0 eq.) at room temperature. The reaction mixture was stirred at room temperature for 3 h, then was evaporated under vacuum. The obtained crude material was diluted with water and washed with diethyl ether. The aqueous layer was separated, acidified using 1N HCl and extracted with ethyl acetate (4×100 mL). The combined organic layer was washed with brine solution (150 mL), dried over $Na_2SO_4$, filtered and concentrated under reduced pressure. The obtained crude material was purified by column chromatography over silica gel (7% MeOH/DCM) to afford 28 as an off-white solid (1.55 g, 100% yield). $^1H$ NMR (400 MHz, DMSO-$d_6$) δ 12.79 (br s, 1H), 9.76 (s, 1H), 7.26-7.13 (m, 3H), 7.07-7.03 (m, 1H), 6.96-6.78 (m, 3H), 6.63 (d, J=8.8 Hz, 1H), 6.58-6.52 (m, 1H), 5.39-5.38 (m, 1H), 5.13-4.42 (m, 3H), 4.32-4.30 (m, 2H), 3.18-3.11 (m, 2H), 2.10 (d, J=8.4 Hz, 3H). MS (ESI-MS): m/z calcd for $C_{25}H_{22}F_2N_2O_4^+$=453.16, found 453.27.

29

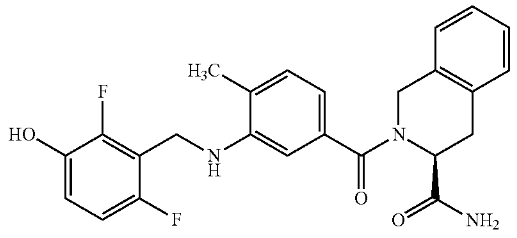

Compound 29: Compound 29 (ARK-852) was synthesized according to General Procedure A from 26 (100 mg, 351 μmol) and (S)-1,2,3,4-tetrahydroisoquinoline-3-carboxamide in DMF (2 mL) at room temperature. The resulting dark mixture was allowed to stir at room temperature for 60 minutes, then was purified by reverse-phase flash column chromatography over $C_{18}$ silica gel ($C_{18}$-silica gel, eluting with 0-100% acetonitrile in water containing 0.1% formic acid) to afford 29 as an off-white solid (formate salt, 21 mg, 12% yield). MS (ESI-MS): $t_R$=1.54 min; m/z calcd for $C_{30}H_{27}F_2N_3O_3^+$=498.1, found 520.1 ([M+Na]$^+$).

30

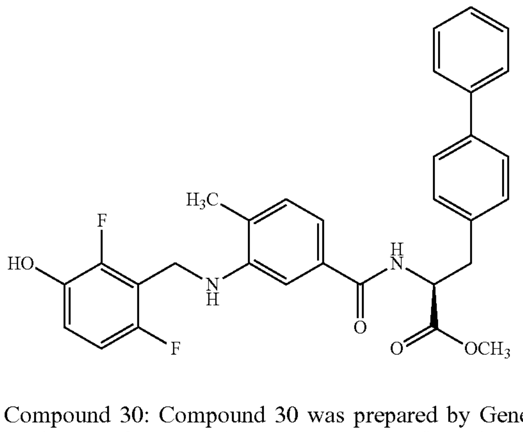

Compound 30: Compound 30 was prepared by General Procedure A from 26 (3.00 g, 10.2 mmol) and (S)-4-phenylphenylalanine methyl ester hydrochloride. After stirring at room temperature for 4 h, the reaction mixture was poured into ice-cold water (250 mL). The resulting solids were collected by filtration and purified by column chromatography over silica gel (30% EtOAc/hexanes) to afford 30 as a white solid (4.20 g, 77% yield). MS (ESI-MS): m/z calcd for $C_{31}H_{28}F_2N_2O_4^+$=531.04, found 531.27.

31

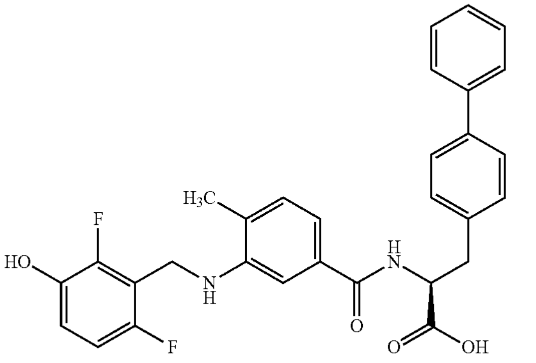

Compound 31: Compound 31 was prepared analogously to 28 above from 30 (4.20 g, 7.91 mmol). The crude product was purified by column chromatography over silica gel (7% MeOH in $CH_2Cl_2$) to afford 31 as a white solid (1.70 g, 42% yield). $^1H$ NMR (400 MHz, DMSO-$d_6$) δ 12.77 (br s, 1H), 9.76 (s, 1H), 8.42 (s, 1H), 7.60-7.54 (m, 4H), 7.40-7.33 (m, 5H), 7.08-7.01 (m, 3H), 6.86-6.84 (m, 2H), 5.21-5.19 (m, 1H), 4.56 (s, 1H), 4.33 (s, 2H), 3.18-3.10 (m, 2H), 2.07 (s, 3H). MS (ESI-MS): m/z calcd for $C_{30}H_{26}F_2N_2O_4^+$517.19, found 517.07.

32

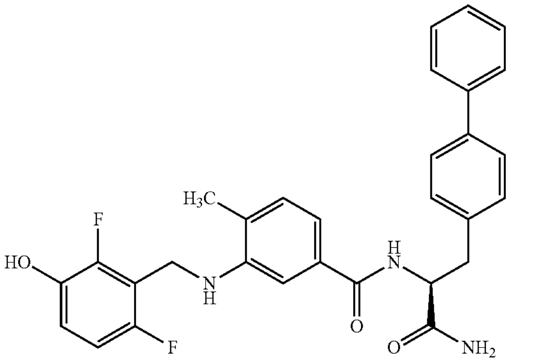

Compound 32: Compound 32 (ARK-850) was synthesized according to General Procedure A from 26 (100 mg, 351 μmol) and (S)-4-phenylphenylalaninamide in DMF (2 mL) at room temperature. The resulting dark mixture was allowed to stir at room temperature for 30 minutes, then was partitioned between sat. aq. $NaHCO_3$ solution (30 mL) and ethyl acetate (30 mL). The aqueous phase was extracted with 30 mL EtOAc, then the combined extracts were washed with 30 mL water and 30 mL sat. aq. NaCl solution. The product solution was dried over $MgSO_4$, filtered, and concentrated to afford the crude product as a brown oil. The crude product was purified by reverse-phase flash column chromatography over $C_{18}$ silica gel (0-100% $CH_3CN$ in water containing 0.1% formic acid). Fractions containing 32 were combined and partially evaporated to remove $CH_3CN$, then the resulting suspension was partitioned between sat. aq. $NaHCO_3$ solution (30 mL) and EtOAc (30 mL). The aqueous phase was extracted with 30 mL EtOAc, then the combined extracts were washed with 30 mL water and 30 mL sat. aq. NaCl solution. The product solution was dried over $MgSO_4$, filtered, and concentrated to afford 32 as an off-white foam (62 mg, 40% yield). MS (ESI-MS): $t_R$=1.67 min; m/z calcd for $C_{30}H_{27}F_2N_3O_3^+$=516.1, found 499.1 ($[M+H-NH_3]^+$.

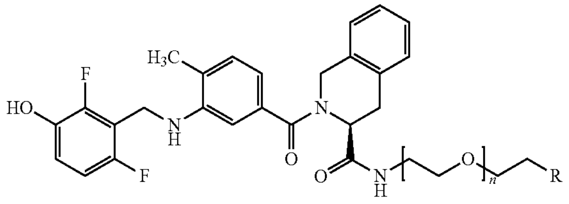

33: n = 1, R = $CO_2tBu$
34: n = 2, R = $CO_2tBu$
35: n = 4, R = $CO_2tBu$
36: n = 1; R = NHBoc
37: n = 2; R = NHBoc
38: n = 4, R = NHBoc

Compound 33: Compound 33 was synthesized according to General Procedure A from 28 (30 mg, 66 μmol) and $NH_2$-$PEG_1$-$CO_2{}^tBu$. The reaction mixture was stirred at room temperature for 1 h, then was purified by column chromatography ($C_{18}$ silica gel, eluting with 0-100% $CH_3CN$ in water containing 0.1% formic acid) to afford 33 as a colorless film (40 mg, 98% yield). MS (ESI-MS): m/z calcd for $C_{34}H_{40}F_2N_3O_6^+$=624.3, found 624.3.

Compound 34: Compound 34 was synthesized according to General Procedure A from 28 (30 mg, 66 μmol) and $NH_2$-$PEG_2$-$CO_2{}^tBu$. The reaction mixture was stirred at room temperature for 1 h, then was purified by column chromatography ($C_{18}$ silica gel, eluting with 0-100% $CH_3CN$ in water containing 0.1% formic acid) to afford 34 as a colorless film (41 mg, 93% yield). MS (ESI-MS): m/z calcd for $C_{36}H_{44}F_2N_3O_7^+$=668.3, found 668.3.

Compound 35: Compound 35 was synthesized according to General Procedure A from 28 (30 mg, 66 μmol) and $NH_2$-$PEG_4$-$CO_2{}^tBu$. The reaction mixture was stirred at room temperature for 1 h, then was purified by column chromatography ($C_{18}$ silica gel, eluting with 0-100% $CH_3CN$ in water containing 0.1% formic acid) to afford 35 as a colorless film (47 mg, 94% yield). MS (ESI-MS): m/z calcd for $C_{44}H_{52}F_2N_3O_9^+$=756.4, found 756.4.

Compound 36: Compound 36 was synthesized according to General Procedure A from 28 (30 mg, 66 μmol) and $NH_2$-$PEG_1$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 36 as a colorless film (35 mg, 82% yield). MS (ESI-MS): m/z calcd for $C_{34}H_{41}F_2N_4O_6^+$=639.3, found 639.3.

Compound 37: Compound 37 was synthesized according to General Procedure A from 28 (100 mg, 221 μmol) and $NH_2$-$PEG_2$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 37 as a colorless film (126 mg, 84% yield). MS (ESI-MS): m/z calcd for $C_{36}H_{45}F_2N_4O_7^+$=683.3, found 683.3.

Compound 38: Compound 33 was synthesized according to General Procedure A from 28 (30 mg, 66 μmol) and $NH_2$-$PEG_4$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 38 as a colorless film (37 mg, 72% yield). MS (ESI-MS): m/z calcd for $C_{44}H_{53}F_2N_4O_9^+$=771.4, found 771.4.

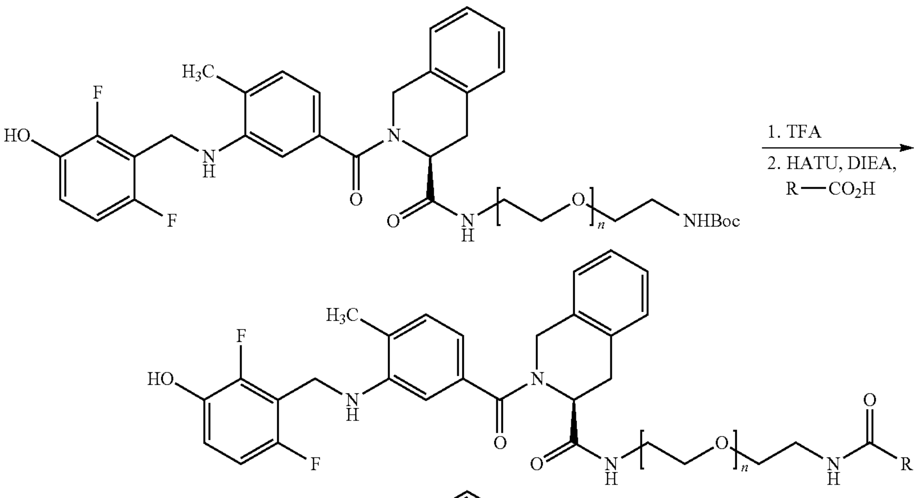

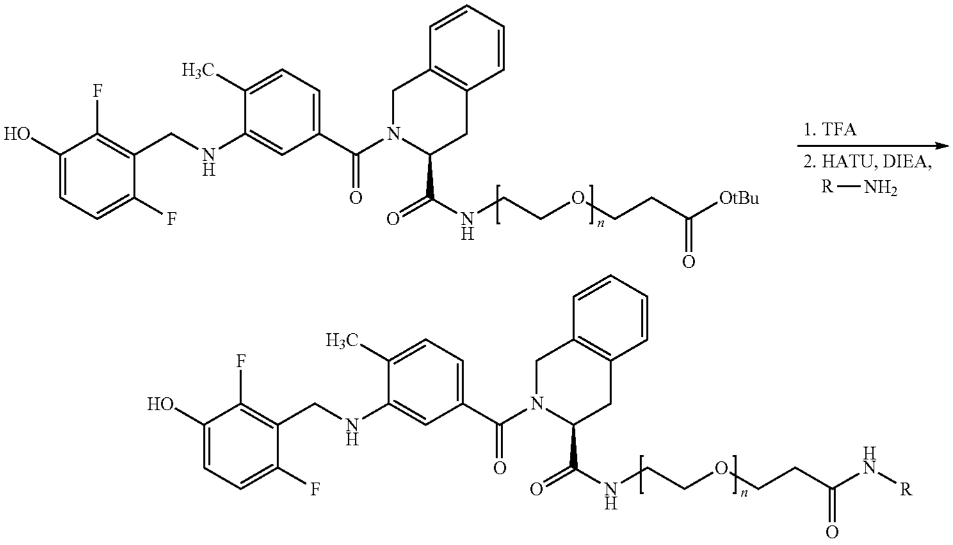

General Procedure C—Synthesis of Photoprobes from Boc- or tert-butyl ester-Protected Ligands: The Boc- or tert-butyl ester-protected ligand (1 eq.) was treated with neat trifluoroacetic acid (2 mL). The mixture was allowed to stir at room temperature for 5 minutes, then was concentrated to dryness under reduced pressure. The residue was then resuspended in DMF (2 mL), then was treated with DIEA (10 eq.), HATU (2.0 eq.) and the photoreactive warhead (as an free amine, amine hydrochloride, or carboxylic acid). The resulting mixtures were stirred at room temperature until LC-MS analysis indicated that the reaction was complete, then the photoprobes were purified by reverse-phase flash column chromatography. Fractions containing the desired products were combined and concentrated to remove $CH_3CN$, then were frozen and lyophilized to afford the final photoprobes as white solids.

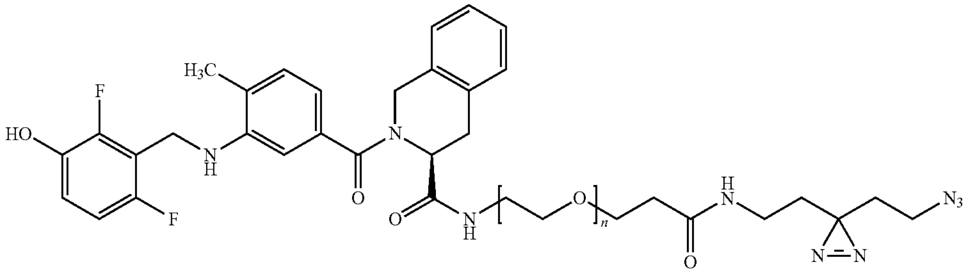

39 (I-24): n = 1
40 (I-25): n = 2
41 (I-26): n = 4

Compound 39: Compound 39 (I-24) was synthesized according to General Procedure C from 33 (33 mg, 53 μmol) and 2-(3-(2-azidoethyl)-3H-diazirin-3-yl)ethan-1-amine. See Pan, S.; Jang, S.; Wang, D.; Liew, S.; Li, Z.; Lee, J.; Yao, S. Q. *Angew. Chem. Int. Ed.,* 2017, 39, 11816-11821. After stirring at room temperature for 1 h, the mixture was purified by flash column chromatography over $C_{18}$ silica gel to afford 39 as a white solid (17 mg, 46% yield). MS (ESI-MS): m/z calcd for $C_{35}H_{40}F_2N_9O_5^+$=704.3, found 704.3.

Compound 40: Compound 40 (I-25) was synthesized according to General Procedure C from 34 (22 mg, 33 μmol) and 2-(3-(2-azidoethyl)-3H-diazirin-3-yl)ethan-1-amine. After stirring at room temperature for 1 h, the mixture was purified by flash column chromatography over $C_{18}$ silica gel to afford 40 as a white solid (15 mg, 62% yield). MS (ESI-MS): m/z calcd for $C_{37}H_{44}F_2N_9O_6^+$=748.3, found 748.3.

Compound 41: Compound 41 (I-26) was synthesized according to General Procedure C from 35 (32 mg, 43 μmol) and 2-(3-(2-azidoethyl)-3H-diazirin-3-yl)ethan-1-amine. After stirring at room temperature for 1 h, the mixture was purified by flash column chromatography over $C_{18}$ silica gel to afford 41 as a white solid (16 mg, 45% yield). MS (ESI-MS): m/z calcd for $C_{41}H_{52}F_2N_9O_8^+$=836.4, found 836.4.

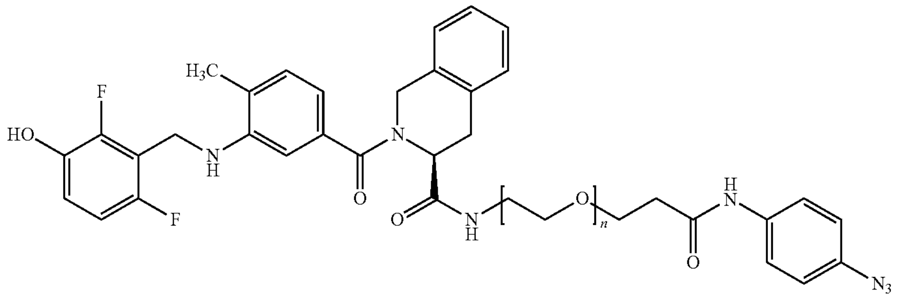

42 (I-27): n = 1
43 (I-28): n = 2
44 (I-29): n = 4

Compound 42: Compound 42 (I-27) was synthesized according to General Procedure C from 33 (33 mg, 53 μmol) and 4-azidoaniline hydrochloride. After stirring at room temperature for 1 h, the mixture was purified by flash column chromatography over $C_{18}$ silica gel to afford 42 as a white solid (14 mg, 39% yield). MS (ESI-MS): m/z calcd for $C_{36}H_{36}F_2N_7O_5^+$=684.3, found 684.3.

Compound 43: Compound 43 (I-28) was synthesized according to General Procedure C from 34 (22 mg, 33 μmol) and 4-azidoaniline hydrochloride. After stirring at room temperature for 1 h, the mixture was purified by flash column chromatography over $C_{18}$ silica gel to afford 43 as a white solid (11 mg, 43% yield). MS (ESI-MS): m/z calcd for $C_{38}H_{40}F_2N_7O_6^+$=728.4, found 728.4.

Compound 44: Compound 44 (I-29) was synthesized according to General Procedure C from 35 (32 mg, 43 μmol) and 4-azidoaniline hydrochloride. After stirring at room temperature for 1 h, the mixture was purified by flash column chromatography over $C_{18}$ silica gel to afford 44 as a white solid (17 mg, 49% yield). MS (ESI-MS): m/z calcd for $C_{42}H_{48}F_2N_7O_8^+$=816.4, found 816.4.

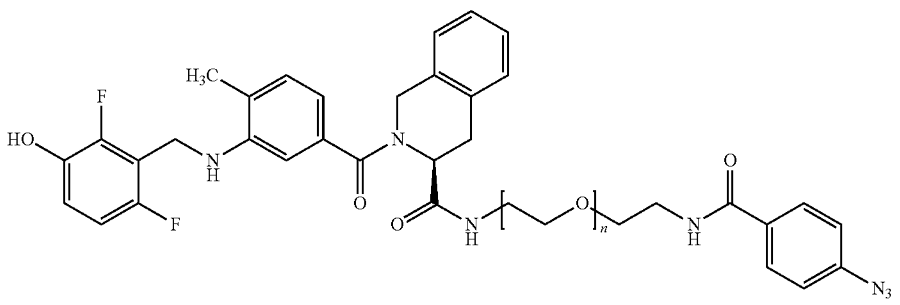

45 (I-30): n = 1
46 (I-31): n = 2
47 (I-32): n = 4

Compound 45: Compound 45 (I-30) was synthesized according to General Procedure C from 36 (11 mg, 17 μmol) and 4-azidobenzoic acid. After stirring at room temperature for 1 h, the mixture was purified by flash column chromatography over $C_{18}$ silica gel to afford 45 as a white solid (10 mg, 85% yield). MS (ESI-MS): m/z calcd for $C_{36}H_{36}F_2N_7O_5^+$=684.3, found 684.3.

Compound 46: Compound 46 (I-31) was synthesized according to General Procedure C from 37 (14 mg, 21 μmol) and 4-azidobenzoic acid. After stirring at room temperature for 1 h, the mixture was purified by flash column chromatography over $C_{18}$ silica gel to afford 46 as a white solid (11 mg, 71% yield). MS (ESI-MS): m/z calcd for $C_{38}H_{40}F_2N_7O_6^+$=728.4, found 728.4.

Compound 47: Compound 47 (I-32) was synthesized according to General Procedure C from 38 (21 mg, 27 μmol) and 4-azidobenzoic acid. After stirring at room temperature for 1 h, the mixture was purified by flash column chromatography over $C_{18}$ silica gel to afford 47 as a white solid (12 mg, 54% yield). MS (ESI-MS): m/z calcd for $C_{42}H_{48}F_2N_7O_8^+$=816.4, found 816.4.

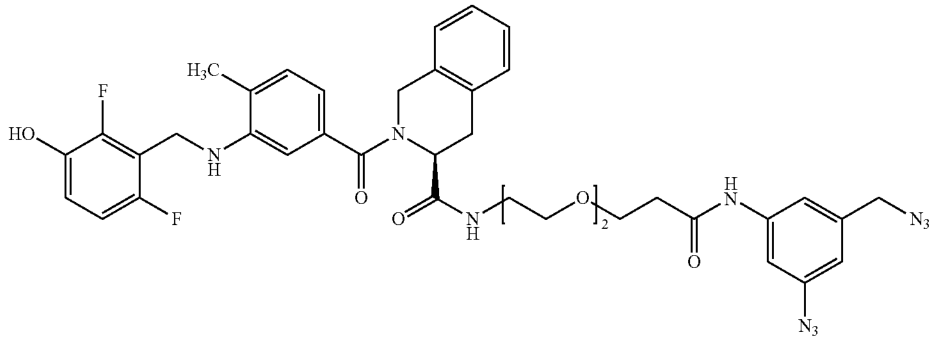

48
I-33

Compound 48: Compound 48 (I-33) was synthesized according to General Procedure C from 37 (126 mg, 184 μmol) and 3-azido-5-(azidomethyl)benzoic acid. After stirring at room temperature for 16 h, the mixture was purified by flash column chromatography over $C_{18}$ silica gel to afford 48 as a white solid (26 mg, 18% yield). MS (ESI-MS): m/z calcd for $C_{39}H_{41}F_2N_{10}O_6^+$=783.4, found 783.4.

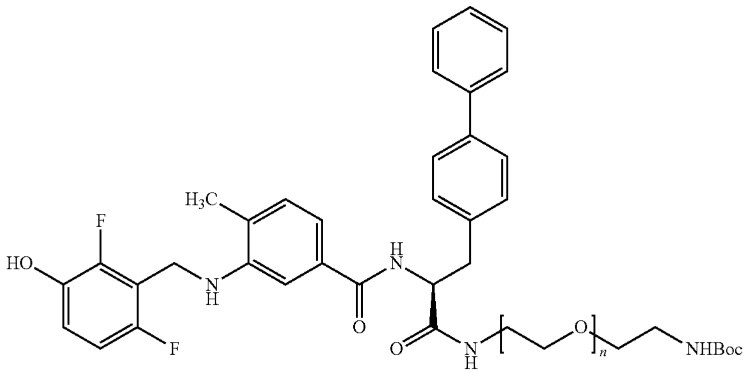

49: n = 1
50: n = 2
51: n = 4

Compound 49: Compound 49 was synthesized according to General Procedure A from 31 (30 mg, 58 μmol) and $NH_2$-$PEG_1$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 49 as a colorless film (27 mg, 65% yield). MS (ESI-MS): m/z calcd for $C_{39}H_{45}F_2N_4O_6^+$=703.3, found 703.3.

Compound 50: Compound 50 was synthesized according to General Procedure A from 31 (30 mg, 58 μmol) and $NH_2$-$PEG_2$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 50 as a colorless film (31 mg, 69% yield). MS (ESI-MS): m/z calcd for $C_{41}H_{49}F_2N_4O_7^+$=747.3, found 747.3.

Compound 51: Compound 51 was synthesized according to General Procedure A from 31 (30 mg, 58 μmol) and $NH_2$-$PEG_4$-NHBoc. The reaction mixture was stirred at room temperature for 1 h, then was purified by column chromatography ($C_{18}$ silica gel, eluting with 0-100% $CH_3CN$ in water containing 0.1% formic acid) to afford 51 as a colorless film (41 mg, 84% yield). MS (ESI-MS): m/z calcd for $C_{45}H_{57}F_2N_4O_9^+$=835.3, found 835.3.

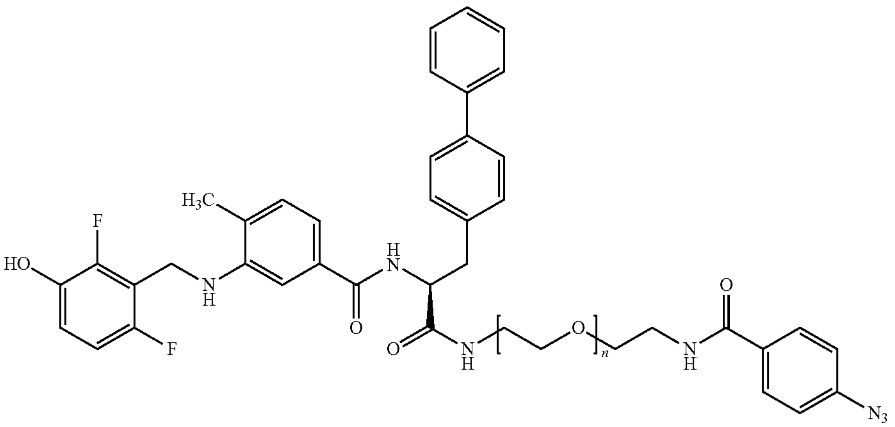

52 (I-34): n = 1
53 (I-35): n = 2
54 (I-36): n = 4

Compound 52: Compound 52 (I-34) was synthesized according to General Procedure C from 49 (25 mg, 36 μmol) and 4-azidobenzoic acid. After stirring at room temperature for 1 h, the mixture was purified by flash column chromatography over $C_{18}$ silica gel to afford 52 as a white solid (9 mg, 34% yield). MS (ESI-MS): m/z calcd for $C_{41}H_{40}F_2N_7O_5^+$=748.3, found 748.3.

Compound 53: Compound 53 (I-35) was synthesized according to General Procedure C from 50 (30 mg, 40 μmol) and 4-azidobenzoic acid. After stirring at room temperature for 1 h, the mixture was purified by flash column chromatography over $C_{18}$ silica gel to afford 53 as a white solid (6 mg, 19% yield). MS (ESI-MS): m/z calcd for $C_{43}H_{44}F_2N_7O_6^+$=792.3, found 792.3.

Compound 54: Compound 54 (I-36) was synthesized according to General Procedure C from 51 (31 mg, 37 μmol) and 4-azidobenzoic acid. After stirring at room temperature for 1 h, the mixture was purified by flash column chromatography over $C_{18}$ silica gel to afford 54 as a white solid (23 mg, 71% yield). MS (ESI-MS): m/z calcd for $C_{47}H_{52}F_2N_7O_8^+$=880.4, found 880.4.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of determining the three-dimensional structure, binding site of a ligand of interest, or accessibility of a nucleotide in a target nucleic acid, comprising: contacting the target nucleic acid with a compound of Formula I or a pharmaceutically acceptable salt thereof; irradiating the compound; determining whether covalent modification of a nucleotide of the nucleic acid has occurred; and optionally deriving the pattern of nucleotide modification, the three-dimensional structure, ligand binding site, or other structural information about the nucleic acid; wherein the compound of Formula I is of the following structure:

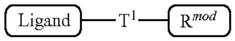

I or a pharmaceutically acceptable salt thereof; wherein:

Ligand is a small molecule RNA binder selected from the group consisting of a heteroaryldihydropyrimidine (HAP), a macrolide, an alkaloid, an aminoglycoside, a tetracycline, a SMN2 ligand, a pleuromutilin, theophylline or an analogue thereof, ribocil or an analogue thereof, a substituted anthracene, a substituted triptycene, an oxazolidinone, and CPNQ or an analogue thereof; wherein Ligand may be optionally substituted with one or more substituents;

$T^1$ is a bivalent tethering group selected from a $C_{1-20}$ bivalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2$N(R)—, —(R)N$SO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

wherein each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from the group consisting of nitrogen, oxygen, and sulfur, an optionally substituted 5-6 membered monocyclic heteroaromatic ring having 1-4 heteroatoms independently selected from the group consisting of nitrogen, oxygen, and sulfur, an optionally substituted 8-10 membered bicyclic or bridged bicyclic saturated or partially unsaturated heterocyclic ring having 1-5 heteroatoms independently selected from the group consisting of nitrogen, oxygen, and sulfur, or an optionally substituted 8-10 membered bicyclic or bridged bicyclic heteroaromatic ring having 1-5 heteroatoms independently selected from the group consisting of nitrogen, oxygen, and sulfur;

each R is independently hydrogen or an optionally substituted group selected from the group consisting of $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from the group consisting of nitrogen, oxygen, and sulfur, a 5-6 membered monocyclic heteroaromatic ring having 1-4 heteroatoms independently selected from the group consisting of nitrogen, oxygen, and sulfur, and an 8-10 membered bicyclic heteroaromatic ring having 1-5 heteroatoms independently selected from the group consisting of nitrogen, oxygen, and sulfur; and $R^{mod}$ is a the group consisting of

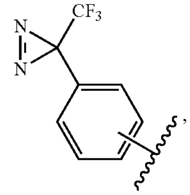,
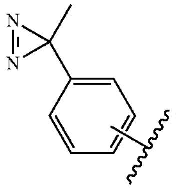,
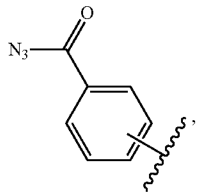,
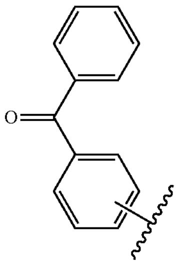,
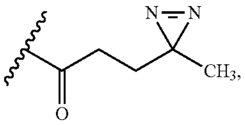
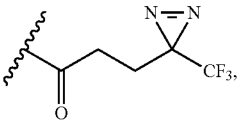
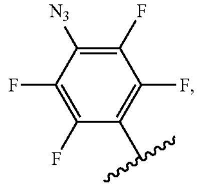
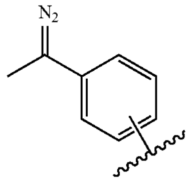,
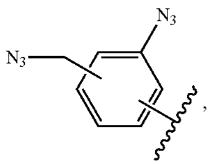,
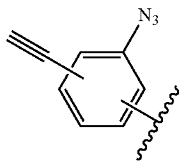,
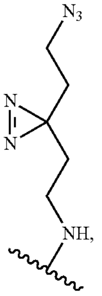
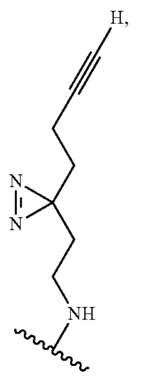
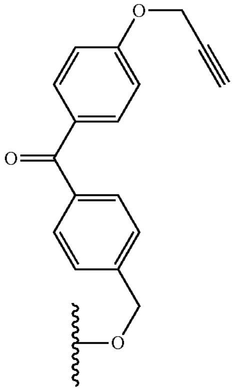, and -continued

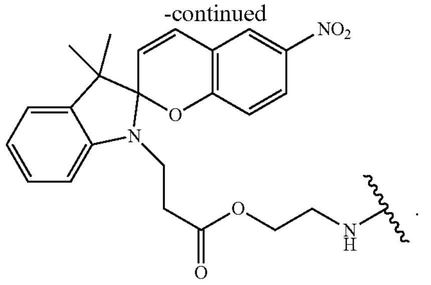

2. The method of claim 1, wherein Ligand is selected from the group consisting of an optionally substituted heteroaryl-dihydropyrimidine (HAP), erythromycin, azithromycin, berberine, palmatine, a paromomycin, a neomycin, a kanamycin, doxycycline, oxytetracycline, pleuromutilin, theophylline or an analogue thereof, ribocil or an analogue thereof, LMI070 (NVS-SM1), a substituted triptycene, linezolid, tedizolid, and CPNQ or an analogue thereof; wherein Ligand may be optionally substituted with 1, 2, 3, or 4 substituents.

3. The method of claim 1, wherein $T^1$ is selected from a $C_{1-10}$ bivalent straight or branched hydrocarbon chain wherein 1, 2, 3, 4, or 5 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, $—SO_2—$, $—SO_2N(R)—$, $—(R)NSO_2—$, —C(S)—, —C(S)O—, —OC(S)—, —C(S)N(R)—, —(R)NC(S)—, —(R)NC(S)N(R)—, or -Cy-; and 1, 2, 3, 4, or 5, of the methylene units of the chain are independently and optionally replaced with $—OCH_2CH_2—$.

4. The method of claim 1, wherein $R^{mod}$ is selected from the group consisting of

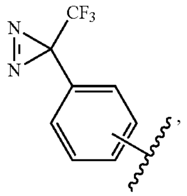

,

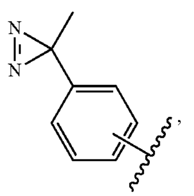

,

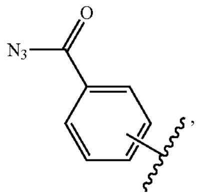

,

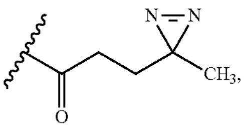

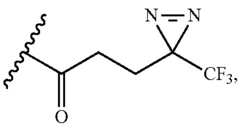

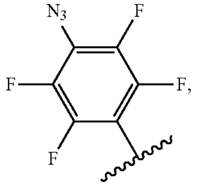

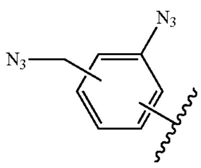

,

-continued

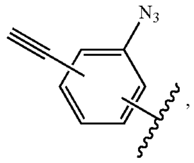

,

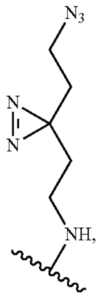

and

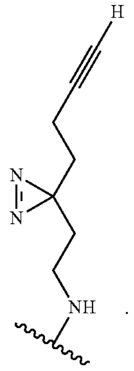

.

5. The method of claim 1, wherein $R^{mod}$ is

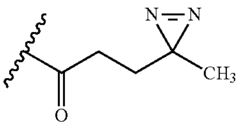

or

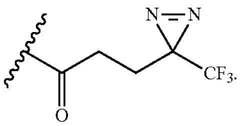

6. The method of claim 1, wherein the method determines the binding site of a ligand of interest.

7. The method of claim 1, wherein the method comprises the step of deriving the pattern of nucleotide modification, the three-dimensional structure, ligand binding site, or other structural information about the nucleic acid.

8. A method of determining the three-dimensional structure, binding site of a ligand of interest, or accessibility of a nucleotide in a target nucleic acid, comprising: contacting the target nucleic acid with a of Formula II or a pharmaceutically acceptable salt thereof; irradiating the compound; determining whether covalent modification of a nucleotide of the nucleic acid has occurred; and optionally deriving the pattern of nucleotide modification, the three-dimensional structure, ligand binding site, or other structural information about the nucleic acid;

wherein the of Formula II is of the following structure:

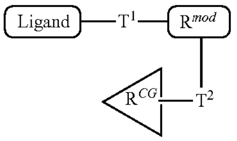

II or a pharmaceutically acceptable salt thereof; wherein:

Ligand is a small molecule RNA binder selected from the group consisting of a heteroaryldihydropyrimidine (HAP), a macrolide, an alkaloid, an aminoglycoside, a tetracycline, a SMN2 ligand, a pleuromutilin, theophylline, ribocil, a substituted anthracene, a substituted triptycene, an oxazolidinone, and CPNQ; wherein Ligand may be optionally substituted with one or more substituents;

$T^1$ is a bivalent tethering group selected from a $C_{1-20}$ bivalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2$—, —$SO_2N(R)$—, —$(R)NSO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

wherein each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from the group consisting of nitrogen, oxygen, and sulfur, an optionally substituted 5-6 membered monocyclic heteroaromatic ring having 1-4 heteroatoms independently selected from the group consisting of nitrogen, oxygen, and sulfur, an optionally substituted 8-10 membered bicyclic or bridged bicyclic saturated or partially unsaturated heterocyclic ring having 1-5 heteroatoms independently selected from the group consisting of nitrogen, oxygen, and sulfur, or an optionally substituted 8-10 membered bicyclic or bridged bicyclic heteroaromatic ring having 1-5 heteroatoms independently selected from the group consisting of nitrogen, oxygen, and sulfur;

each R is independently hydrogen or an optionally substituted group selected from the group consisting of $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from the group consisting of nitrogen, oxygen, and sulfur, a 5-6 membered monocyclic heteroaromatic ring having 1-4 heteroatoms independently selected from the group consisting of nitrogen, oxygen, and sulfur, and, or an 8-10 membered bicyclic heteroaromatic ring having 1-5 heteroatoms independently selected from the group consisting of nitrogen, oxygen, and sulfur;

$T^2$ is a covalent bond or a bivalent tethering group selected from a $C_{1-20}$ bivalent straight or branched hydrocarbon chain wherein 1, 2, 3, 4, 5, 6, 7, 8, 9, or 10 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —$SO_2N(R)$—, —$(R)NSO_2$—, —C(S)—, —C(S)O—, —OC(S)—, —C(S)N(R)—, —(R)NC(S)—, —(R)NC(S)N(R)—, or -Cy-; and 1-20 of the methylene units of the chain are independently and optionally replaced with —$OCH_2CH_2$—;

$R^{CG}$ is a click-ready group selected from the group consisting of an azide, an alkyne, 4-dibenzocyclooctynol (DIBO) gem-difluorinated cyclooctynes (DIFO or DFO), biarylazacyclooctynone (BARAC), bicyclononyne (BCN), a strained cyclooctyne, an oxime, and oxanorbornadiene; or a pull-down group selected from the group consisting of a hapten, a $^{14}C$, a $^{32}P$, and a $^{3}H$ radiolabel; and $R^{mod}$ is a photoactivatable group selected from the group consisting of

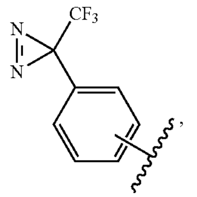 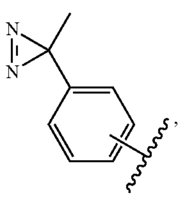 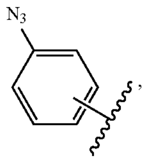

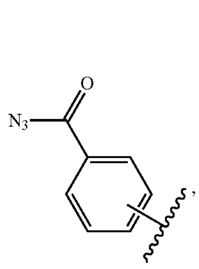 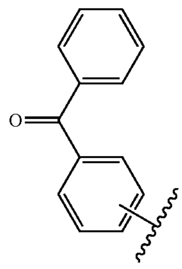

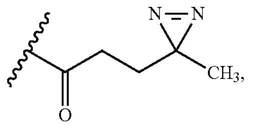 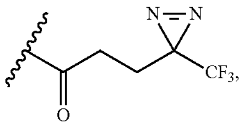

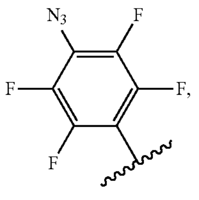 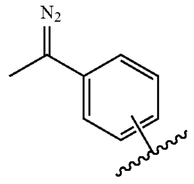 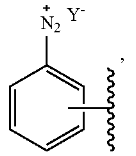

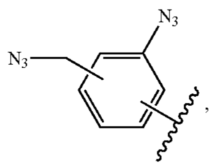 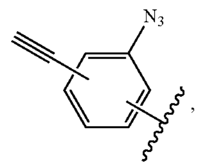 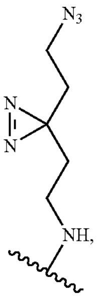

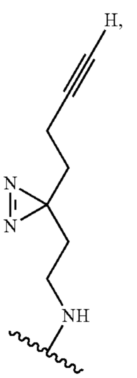 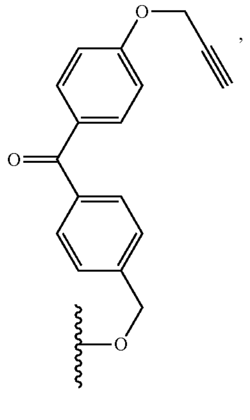, and

-continued

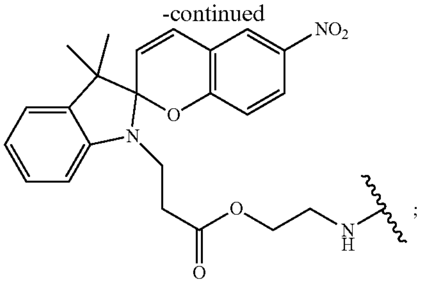

wherein $Y^-$ is a pharmaceutically acceptable anion.

9. The method of claim 8, wherein Ligand is selected from the group consisting of an optionally substituted heteroaryldihydropyrimidine (HAP), erythromycin, azithromycin, berberine, palmatine, a paromomycin, a neomycin, a kanamycin, doxycycline, oxytetracycline, pleuromutilin, theophylline, ribocil, LMI070 (NVS-SM1), a substituted triptycene, linezolid, tedizolid, and CPNQ; wherein Ligand may be optionally substituted with 1, 2, 3, or 4 substituents.

10. The method of claim 8, wherein $T^1$ is selected from a $C_{1-10}$ bivalent straight or branched hydrocarbon chain wherein 1, 2, 3, 4, or 5 methylene units of the chain are independently and optionally replaced with a natural or non-natural amino acid, —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, $—SO_2—$, $—SO_2N(R)—$, $—(R)NSO_2—$, —C(S)—, —C(S)O—, —OC(S)—, —C(S)N(R)—, —(R)NC(S)—, —(R)NC(S)N(R)—, or -Cy-; and 1, 2, 3, 4, or 5, of the methylene units of the chain are independently and optionally replaced with $—OCH_2CH_2—$.

11. The method of claim 8, wherein $R^{mod}$ is selected from the group consisting of

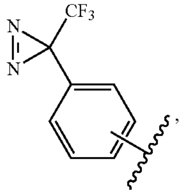

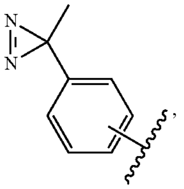

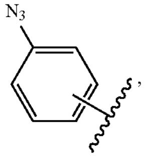

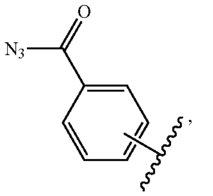

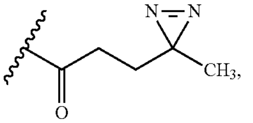

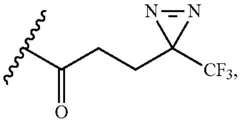

-continued

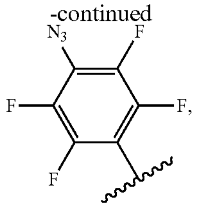

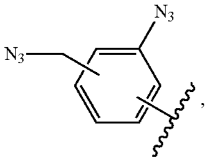

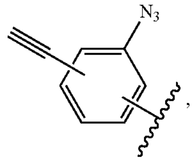

and

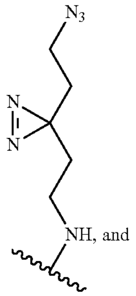

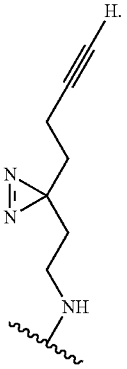

12. The method of claim 8, wherein $R^{mod}$ is

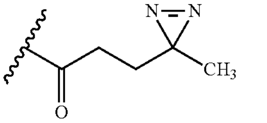

or

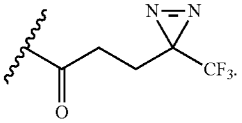

13. The method of claim 8, wherein $R^{CG}$ is an azide, an alkyne, 4-dibenzocyclooctynol (DIBO) gem-difluorinated cyclooctynes (DIFO or DFO), biarylazacyclooctynone (BARAC), bicyclononyne (BCN), or biotin.

14. The method of claim 8, wherein $R^{CG}$ is an azide or an alkyne.

15. The method of claim 8, wherein the method determines the binding site of a ligand of interest.

16. The method of claim 8, wherein the method comprises the step of deriving the pattern of nucleotide modification, the three-dimensional structure, ligand binding site, or other structural information about the nucleic acid.

* * * * *

SEQUENCE LISTING

```
Sequence total quantity: 35
SEQ ID NO: 1             moltype = DNA  length = 105
FEATURE                  Location/Qualifiers
misc_feature             1..105
                         note = Description of Artificial Sequence: Synthetic
                          polynucleotide
misc_difference          1..105
                         note = This sequence may encompass 6-35 'cag' repeating
                          units
source                   1..105
                         mol_type = other DNA
                         organism = synthetic construct
SEQUENCE: 1
cagcagcagc agcagcagca gcagcagcag cagcagcagc agcagcagca gcagcagcag  60
cagcagcagc agcagcagca gcagcagcag cagcagcagc agcag                  105

SEQ ID NO: 2             moltype = DNA  length = 108
FEATURE                  Location/Qualifiers
misc_feature             1..108
                         note = Description of Artificial Sequence: Synthetic
                          polynucleotide
misc_difference          1..108
                         note = This sequence may encompass 9-36 'cag' repeating
                          units
source                   1..108
                         mol_type = other DNA
                         organism = synthetic construct
SEQUENCE: 2
cagcagcagc agcagcagca gcagcagcag cagcagcagc agcagcagca gcagcagcag  60
cagcagcagc agcagcagca gcagcagcag cagcagcagc agcagcag               108

SEQ ID NO: 3             moltype = DNA  length = 96
FEATURE                  Location/Qualifiers
misc_feature             1..96
                         note = Description of Artificial Sequence: Synthetic
                          oligonucleotide
misc_difference          1..96
                         note = This sequence may encompass 14-32 'cag' repeating
                          units
source                   1..96
                         mol_type = other DNA
                         organism = synthetic construct
SEQUENCE: 3
cagcagcagc agcagcagca gcagcagcag cagcagcagc agcagcagca gcagcagcag  60
cagcagcagc agcagcagca gcagcagcag cagcag                            96

SEQ ID NO: 4             moltype = DNA  length = 120
FEATURE                  Location/Qualifiers
misc_feature             1..120
                         note = Description of Artificial Sequence: Synthetic
                          polynucleotide
misc_difference          1..120
                         note = This sequence may encompass 12-40 'cag' repeating
                          units
source                   1..120
                         mol_type = other DNA
                         organism = synthetic construct
SEQUENCE: 4
cagcagcagc agcagcagca gcagcagcag cagcagcagc agcagcagca gcagcagcag  60
cagcagcagc agcagcagca gcagcagcag cagcagcagc agcagcagca gcagcagcag  120

SEQ ID NO: 5             moltype = DNA  length = 54
FEATURE                  Location/Qualifiers
misc_feature             1..54
                         note = Description of Artificial Sequence: Synthetic
                          oligonucleotide
misc_difference          1..54
                         note = This sequence may encompass 4-18 'cag' repeating
                          units
source                   1..54
                         mol_type = other DNA
                         organism = synthetic construct
SEQUENCE: 5
cagcagcagc agcagcagca gcagcagcag cagcagcagc agcagcagca gcag        54

SEQ ID NO: 6             moltype = DNA  length = 51
FEATURE                  Location/Qualifiers
misc_feature             1..51
```

-continued

```
                       note = Description of Artificial Sequence: Synthetic
                        oligonucleotide
misc_difference        1..51
                       note = This sequence may encompass 7-17 'cag' repeating
                        units
source                 1..51
                       mol_type = other DNA
                       organism = synthetic construct
SEQUENCE: 6
cagcagcagc agcagcagca gcagcagcag cagcagcagc agcagcagca g           51

SEQ ID NO: 7           moltype = DNA  length = 126
FEATURE                Location/Qualifiers
misc_feature           1..126
                       note = Description of Artificial Sequence: Synthetic
                        polynucleotide
misc_difference        1..126
                       note = This sequence may encompass 25-42 'cag' repeating
                        units
source                 1..126
                       mol_type = other DNA
                       organism = synthetic construct
SEQUENCE: 7
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcag                                                             126

SEQ ID NO: 8           moltype = DNA  length = 750
FEATURE                Location/Qualifiers
misc_feature           1..750
                       note = Description of Artificial Sequence: Synthetic
                        polynucleotide
misc_difference        1..750
                       note = This sequence may encompass 36-250 'cag' repeating
                        units
source                 1..750
                       mol_type = other DNA
                       organism = synthetic construct
SEQUENCE: 8
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca gcagcagcag  240
cagcagcagc agcagcagca gcagcagcag cagcagcagc agcagcagca gcagcagcag  300
cagcagcagc agcagcagca gcagcagcag cagcagcagc agcagcagca gcagcagcag  360
cagcagcagc agcagcagca gcagcagcag cagcagcagc agcagcagca gcagcagcag  420
cagcagcagc agcagcagca gcagcagcag cagcagcagc agcagcagca gcagcagcag  480
cagcagcagc agcagcagca gcagcagcag cagcagcagc agcagcagca gcagcagcag  540
cagcagcagc agcagcagca gcagcagcag cagcagcagc agcagcagca gcagcagcag  600
cagcagcagc agcagcagca gcagcagcag cagcagcagc agcagcagca gcagcagcag  660
cagcagcagc agcagcagca gcagcagcag cagcagcagc agcagcagca gcagcagcag  720
cagcagcagc agcagcagca gcagcagcag                                   750

SEQ ID NO: 9           moltype = DNA  length = 264
FEATURE                Location/Qualifiers
misc_feature           1..264
                       note = Description of Artificial Sequence: Synthetic
                        polynucleotide
misc_difference        1..264
                       note = This sequence may encompass 49-88 'cag' repeating
                        units
source                 1..264
                       mol_type = other DNA
                       organism = synthetic construct
SEQUENCE: 9
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca gcagcagcag  240
cagcagcagc agcagcagca gcag                                         264

SEQ ID NO: 10          moltype = DNA  length = 186
FEATURE                Location/Qualifiers
misc_feature           1..186
                       note = Description of Artificial Sequence: Synthetic
                        polynucleotide
misc_difference        1..186
                       note = This sequence may encompass 38-62 'cag' repeating
                        units
```

```
source                  1..186
                        mol_type = other DNA
                        organism = synthetic construct
SEQUENCE: 10
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcag                                                             186

SEQ ID NO: 11           moltype = DNA  length = 231
FEATURE                 Location/Qualifiers
misc_feature            1..231
                        note = Description of Artificial Sequence: Synthetic
                         polynucleotide
misc_difference         1..231
                        note = This sequence may encompass 33-77 'cag' repeating
                         units
source                  1..231
                        mol_type = other DNA
                        organism = synthetic construct
SEQUENCE: 11
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca g           231

SEQ ID NO: 12           moltype = DNA  length = 258
FEATURE                 Location/Qualifiers
misc_feature            1..258
                        note = Description of Artificial Sequence: Synthetic
                         polynucleotide
misc_difference         1..258
                        note = This sequence may encompass 55-86 'cag' repeating
                         units
source                  1..258
                        mol_type = other DNA
                        organism = synthetic construct
SEQUENCE: 12
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca gcagcagcag  240
cagcagcagc agcagcag                                                258

SEQ ID NO: 13           moltype = DNA  length = 90
FEATURE                 Location/Qualifiers
misc_feature            1..90
                        note = Description of Artificial Sequence: Synthetic
                         oligonucleotide
misc_difference         1..90
                        note = This sequence may encompass 21-30 'cag' repeating
                         units
source                  1..90
                        mol_type = other DNA
                        organism = synthetic construct
SEQUENCE: 13
cagcagcagc agcagcagca gcagcagcag cagcagcagc agcagcagca gcagcagcag  60
cagcagcagc agcagcagca gcagcagcag                                   90

SEQ ID NO: 14           moltype = DNA  length = 360
FEATURE                 Location/Qualifiers
misc_feature            1..360
                        note = Description of Artificial Sequence: Synthetic
                         polynucleotide
misc_difference         1..360
                        note = This sequence may encompass 38-120 'cag' repeating
                         units
source                  1..360
                        mol_type = other DNA
                        organism = synthetic construct
SEQUENCE: 14
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca gcagcagcag  240
cagcagcagc agcagcagca gcagcagcag cagcagcagc agcagcagca gcagcagcag  300
cagcagcagc agcagcagca gcagcagcag cagcagcagc agcagcagca gcagcagcag  360

SEQ ID NO: 15           moltype = DNA  length = 189
```

-continued

```
FEATURE                 Location/Qualifiers
misc_feature            1..189
                        note = Description of Artificial Sequence: Synthetic
                         polynucleotide
misc_difference         1..189
                        note = This sequence may encompass 47-63 'cag' repeating
                         units
source                  1..189
                        mol_type = other DNA
                        organism = synthetic construct
SEQUENCE: 15
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcag                                                          189

SEQ ID NO: 16           moltype = DNA  length = 159
FEATURE                 Location/Qualifiers
misc_feature            1..159
                        note = Description of Artificial Sequence: Synthetic
                         polynucleotide
misc_difference         1..159
                        note = This sequence may encompass 6-53 'cgg' repeating
                         units
source                  1..159
                        mol_type = other DNA
                        organism = synthetic construct
SEQUENCE: 16
cggcggcggc ggcggcggcg gcggcggcgg cggcggcggc ggcggcggcg gcggcggcgg  60
cggcggcggc ggcggcggcg gcggcggcgg cggcggcggc ggcggcggcg gcggcggcgg  120
cggcggcggc ggcggcggcg gcggcggcgg cggcggcgg                         159

SEQ ID NO: 17           moltype = DNA  length = 111
FEATURE                 Location/Qualifiers
misc_feature            1..111
                        note = Description of Artificial Sequence: Synthetic
                         polynucleotide
misc_difference         1..111
                        note = This sequence may encompass 5-37 'ctg' repeating
                         units
source                  1..111
                        mol_type = other DNA
                        organism = synthetic construct
SEQUENCE: 17
ctgctgctgc tgctgctgct gctgctgctg ctgctgctgc tgctgctgct gctgctgctg  60
ctgctgctgc tgctgctgct gctgctgctg ctgctgctgc tgctgctgct g           111

SEQ ID NO: 18           moltype = DNA  length = 102
FEATURE                 Location/Qualifiers
misc_feature            1..102
                        note = Description of Artificial Sequence: Synthetic
                         polynucleotide
misc_difference         1..102
                        note = This sequence may encompass 7-34 'gaa' repeating
                         units
source                  1..102
                        mol_type = other DNA
                        organism = synthetic construct
SEQUENCE: 18
gaagaagaag aagaagaaga agaagaagaa gaagaagaag aagaagaaga agaagaagaa  60
gaagaagaag aagaagaaga agaagaagaa gaagaagaag aa                     102

SEQ ID NO: 19           moltype = DNA  length = 111
FEATURE                 Location/Qualifiers
misc_feature            1..111
                        note = Description of Artificial Sequence: Synthetic
                         polynucleotide
misc_difference         1..111
                        note = This sequence may encompass 16-37 'ctg' repeating
                         units
source                  1..111
                        mol_type = other DNA
                        organism = synthetic construct
SEQUENCE: 19
ctgctgctgc tgctgctgct gctgctgctg ctgctgctgc tgctgctgct gctgctgctg  60
ctgctgctgc tgctgctgct gctgctgctg ctgctgctgc tgctgctgct g           111

SEQ ID NO: 20           moltype = DNA  length = 160
FEATURE                 Location/Qualifiers
```

-continued

```
misc_feature            1..160
                        note = Description of Artificial Sequence: Synthetic
                         polynucleotide
misc_difference         1..160
                        note = This sequence may encompass 9-32 'attct' repeating
                         units
source                  1..160
                        mol_type = other DNA
                        organism = synthetic construct
SEQUENCE: 20
attctattct attctattct attctattct attctattct attctattct attctattct  60
attctattct attctattct attctattct attctattct attctattct attctattct  120
attctattct attctattct attctattct attctattct                        160

SEQ ID NO: 21           moltype = DNA  length = 84
FEATURE                 Location/Qualifiers
misc_feature            1..84
                        note = Description of Artificial Sequence: Synthetic
                         oligonucleotide
misc_difference         1..84
                        note = This sequence may encompass 7-28 'cag' repeating
                         units
source                  1..84
                        mol_type = other DNA
                        organism = synthetic construct
SEQUENCE: 21
cagcagcagc agcagcagca gcagcagcag cagcagcagc agcagcagca gcagcagcag  60
cagcagcagc agcagcagca gcag                                         84

SEQ ID NO: 22           moltype = DNA  length = 750
FEATURE                 Location/Qualifiers
misc_feature            1..750
                        note = Description of Artificial Sequence: Synthetic
                         polynucleotide
misc_difference         1..750
                        note = This sequence may encompass 110-250 'ctg' repeating
                         units
source                  1..750
                        mol_type = other DNA
                        organism = synthetic construct
SEQUENCE: 22
ctgctgctgc tgctgctgct gctgctgctg ctgctgctgc tgctgctgct gctgctgctg  60
ctgctgctgc tgctgctgct gctgctgctg ctgctgctgc tgctgctgct gctgctgctg  120
ctgctgctgc tgctgctgct gctgctgctg ctgctgctgc tgctgctgct gctgctgctg  180
ctgctgctgc tgctgctgct gctgctgctg ctgctgctgc tgctgctgct gctgctgctg  240
ctgctgctgc tgctgctgct gctgctgctg ctgctgctgc tgctgctgct gctgctgctg  300
ctgctgctgc tgctgctgct gctgctgctg ctgctgctgc tgctgctgct gctgctgctg  360
ctgctgctgc tgctgctgct gctgctgctg ctgctgctgc tgctgctgct gctgctgctg  420
ctgctgctgc tgctgctgct gctgctgctg ctgctgctgc tgctgctgct gctgctgctg  480
ctgctgctgc tgctgctgct gctgctgctg ctgctgctgc tgctgctgct gctgctgctg  540
ctgctgctgc tgctgctgct gctgctgctg ctgctgctgc tgctgctgct gctgctgctg  600
ctgctgctgc tgctgctgct gctgctgctg ctgctgctgc tgctgctgct gctgctgctg  660
ctgctgctgc tgctgctgct gctgctgctg ctgctgctgc tgctgctgct gctgctgctg  720
ctgctgctgc tgctgctgct gctgctgctg                                   750

SEQ ID NO: 23           moltype = DNA  length = 22500
FEATURE                 Location/Qualifiers
misc_feature            1..22500
                        note = Description of Artificial Sequence: Synthetic
                         polynucleotide
misc_difference         1..22500
                        note = This sequence may encompass 800-4500 'attct'
                         repeating units
source                  1..22500
                        mol_type = other DNA
                        organism = synthetic construct
SEQUENCE: 23
attctattct attctattct attctattct attctattct attctattct attctattct  60
attctattct attctattct attctattct attctattct attctattct attctattct  120
attctattct attctattct attctattct attctattct attctattct attctattct  180
attctattct attctattct attctattct attctattct attctattct attctattct  240
attctattct attctattct attctattct attctattct attctattct attctattct  300
attctattct attctattct attctattct attctattct attctattct attctattct  360
attctattct attctattct attctattct attctattct attctattct attctattct  420
attctattct attctattct attctattct attctattct attctattct attctattct  480
attctattct attctattct attctattct attctattct attctattct attctattct  540
attctattct attctattct attctattct attctattct attctattct attctattct  600
attctattct attctattct attctattct attctattct attctattct attctattct  660
attctattct attctattct attctattct attctattct attctattct attctattct  720
```

-continued attctattct attctattct attctattct attctattct attctattct attctattct 780
attctattct attctattct attctattct attctattct attctattct attctattct 840
attctattct attctattct attctattct attctattct attctattct attctattct 900
attctattct attctattct attctattct attctattct attctattct attctattct 960
attctattct attctattct attctattct attctattct attctattct attctattct 1020
attctattct attctattct attctattct attctattct attctattct attctattct 1080
attctattct attctattct attctattct attctattct attctattct attctattct 1140
attctattct attctattct attctattct attctattct attctattct attctattct 1200
attctattct attctattct attctattct attctattct attctattct attctattct 1260
attctattct attctattct attctattct attctattct attctattct attctattct 1320
attctattct attctattct attctattct attctattct attctattct attctattct 1380
attctattct attctattct attctattct attctattct attctattct attctattct 1440
attctattct attctattct attctattct attctattct attctattct attctattct 1500
attctattct attctattct attctattct attctattct attctattct attctattct 1560
attctattct attctattct attctattct attctattct attctattct attctattct 1620
attctattct attctattct attctattct attctattct attctattct attctattct 1680
attctattct attctattct attctattct attctattct attctattct attctattct 1740
attctattct attctattct attctattct attctattct attctattct attctattct 1800
attctattct attctattct attctattct attctattct attctattct attctattct 1860
attctattct attctattct attctattct attctattct attctattct attctattct 1920
attctattct attctattct attctattct attctattct attctattct attctattct 1980
attctattct attctattct attctattct attctattct attctattct attctattct 2040
attctattct attctattct attctattct attctattct attctattct attctattct 2100
attctattct attctattct attctattct attctattct attctattct attctattct 2160
attctattct attctattct attctattct attctattct attctattct attctattct 2220
attctattct attctattct attctattct attctattct attctattct attctattct 2280
attctattct attctattct attctattct attctattct attctattct attctattct 2340
attctattct attctattct attctattct attctattct attctattct attctattct 2400
attctattct attctattct attctattct attctattct attctattct attctattct 2460
attctattct attctattct attctattct attctattct attctattct attctattct 2520
attctattct attctattct attctattct attctattct attctattct attctattct 2580
attctattct attctattct attctattct attctattct attctattct attctattct 2640
attctattct attctattct attctattct attctattct attctattct attctattct 2700
attctattct attctattct attctattct attctattct attctattct attctattct 2760
attctattct attctattct attctattct attctattct attctattct attctattct 2820
attctattct attctattct attctattct attctattct attctattct attctattct 2880
attctattct attctattct attctattct attctattct attctattct attctattct 2940
attctattct attctattct attctattct attctattct attctattct attctattct 3000
attctattct attctattct attctattct attctattct attctattct attctattct 3060
attctattct attctattct attctattct attctattct attctattct attctattct 3120
attctattct attctattct attctattct attctattct attctattct attctattct 3180
attctattct attctattct attctattct attctattct attctattct attctattct 3240
attctattct attctattct attctattct attctattct attctattct attctattct 3300
attctattct attctattct attctattct attctattct attctattct attctattct 3360
attctattct attctattct attctattct attctattct attctattct attctattct 3420
attctattct attctattct attctattct attctattct attctattct attctattct 3480
attctattct attctattct attctattct attctattct attctattct attctattct 3540
attctattct attctattct attctattct attctattct attctattct attctattct 3600
attctattct attctattct attctattct attctattct attctattct attctattct 3660
attctattct attctattct attctattct attctattct attctattct attctattct 3720
attctattct attctattct attctattct attctattct attctattct attctattct 3780
attctattct attctattct attctattct attctattct attctattct attctattct 3840
attctattct attctattct attctattct attctattct attctattct attctattct 3900
attctattct attctattct attctattct attctattct attctattct attctattct 3960
attctattct attctattct attctattct attctattct attctattct attctattct 4020
attctattct attctattct attctattct attctattct attctattct attctattct 4080
attctattct attctattct attctattct attctattct attctattct attctattct 4140
attctattct attctattct attctattct attctattct attctattct attctattct 4200
attctattct attctattct attctattct attctattct attctattct attctattct 4260
attctattct attctattct attctattct attctattct attctattct attctattct 4320
attctattct attctattct attctattct attctattct attctattct attctattct 4380
attctattct attctattct attctattct attctattct attctattct attctattct 4440
attctattct attctattct attctattct attctattct attctattct attctattct 4500
attctattct attctattct attctattct attctattct attctattct attctattct 4560
attctattct attctattct attctattct attctattct attctattct attctattct 4620
attctattct attctattct attctattct attctattct attctattct attctattct 4680
attctattct attctattct attctattct attctattct attctattct attctattct 4740
attctattct attctattct attctattct attctattct attctattct attctattct 4800
attctattct attctattct attctattct attctattct attctattct attctattct 4860
attctattct attctattct attctattct attctattct attctattct attctattct 4920
attctattct attctattct attctattct attctattct attctattct attctattct 4980
attctattct attctattct attctattct attctattct attctattct attctattct 5040
attctattct attctattct attctattct attctattct attctattct attctattct 5100
attctattct attctattct attctattct attctattct attctattct attctattct 5160
attctattct attctattct attctattct attctattct attctattct attctattct 5220
attctattct attctattct attctattct attctattct attctattct attctattct 5280
attctattct attctattct attctattct attctattct attctattct attctattct 5340
attctattct attctattct attctattct attctattct attctattct attctattct 5400
attctattct attctattct attctattct attctattct attctattct attctattct 5460

-continued attctattct attctattct attctattct attctattct attctattct attctattct 5520
attctattct attctattct attctattct attctattct attctattct attctattct 5580
attctattct attctattct attctattct attctattct attctattct attctattct 5640
attctattct attctattct attctattct attctattct attctattct attctattct 5700
attctattct attctattct attctattct attctattct attctattct attctattct 5760
attctattct attctattct attctattct attctattct attctattct attctattct 5820
attctattct attctattct attctattct attctattct attctattct attctattct 5880
attctattct attctattct attctattct attctattct attctattct attctattct 5940
attctattct attctattct attctattct attctattct attctattct attctattct 6000
attctattct attctattct attctattct attctattct attctattct attctattct 6060
attctattct attctattct attctattct attctattct attctattct attctattct 6120
attctattct attctattct attctattct attctattct attctattct attctattct 6180
attctattct attctattct attctattct attctattct attctattct attctattct 6240
attctattct attctattct attctattct attctattct attctattct attctattct 6300
attctattct attctattct attctattct attctattct attctattct attctattct 6360
attctattct attctattct attctattct attctattct attctattct attctattct 6420
attctattct attctattct attctattct attctattct attctattct attctattct 6480
attctattct attctattct attctattct attctattct attctattct attctattct 6540
attctattct attctattct attctattct attctattct attctattct attctattct 6600
attctattct attctattct attctattct attctattct attctattct attctattct 6660
attctattct attctattct attctattct attctattct attctattct attctattct 6720
attctattct attctattct attctattct attctattct attctattct attctattct 6780
attctattct attctattct attctattct attctattct attctattct attctattct 6840
attctattct attctattct attctattct attctattct attctattct attctattct 6900
attctattct attctattct attctattct attctattct attctattct attctattct 6960
attctattct attctattct attctattct attctattct attctattct attctattct 7020
attctattct attctattct attctattct attctattct attctattct attctattct 7080
attctattct attctattct attctattct attctattct attctattct attctattct 7140
attctattct attctattct attctattct attctattct attctattct attctattct 7200
attctattct attctattct attctattct attctattct attctattct attctattct 7260
attctattct attctattct attctattct attctattct attctattct attctattct 7320
attctattct attctattct attctattct attctattct attctattct attctattct 7380
attctattct attctattct attctattct attctattct attctattct attctattct 7440
attctattct attctattct attctattct attctattct attctattct attctattct 7500
attctattct attctattct attctattct attctattct attctattct attctattct 7560
attctattct attctattct attctattct attctattct attctattct attctattct 7620
attctattct attctattct attctattct attctattct attctattct attctattct 7680
attctattct attctattct attctattct attctattct attctattct attctattct 7740
attctattct attctattct attctattct attctattct attctattct attctattct 7800
attctattct attctattct attctattct attctattct attctattct attctattct 7860
attctattct attctattct attctattct attctattct attctattct attctattct 7920
attctattct attctattct attctattct attctattct attctattct attctattct 7980
attctattct attctattct attctattct attctattct attctattct attctattct 8040
attctattct attctattct attctattct attctattct attctattct attctattct 8100
attctattct attctattct attctattct attctattct attctattct attctattct 8160
attctattct attctattct attctattct attctattct attctattct attctattct 8220
attctattct attctattct attctattct attctattct attctattct attctattct 8280
attctattct attctattct attctattct attctattct attctattct attctattct 8340
attctattct attctattct attctattct attctattct attctattct attctattct 8400
attctattct attctattct attctattct attctattct attctattct attctattct 8460
attctattct attctattct attctattct attctattct attctattct attctattct 8520
attctattct attctattct attctattct attctattct attctattct attctattct 8580
attctattct attctattct attctattct attctattct attctattct attctattct 8640
attctattct attctattct attctattct attctattct attctattct attctattct 8700
attctattct attctattct attctattct attctattct attctattct attctattct 8760
attctattct attctattct attctattct attctattct attctattct attctattct 8820
attctattct attctattct attctattct attctattct attctattct attctattct 8880
attctattct attctattct attctattct attctattct attctattct attctattct 8940
attctattct attctattct attctattct attctattct attctattct attctattct 9000
attctattct attctattct attctattct attctattct attctattct attctattct 9060
attctattct attctattct attctattct attctattct attctattct attctattct 9120
attctattct attctattct attctattct attctattct attctattct attctattct 9180
attctattct attctattct attctattct attctattct attctattct attctattct 9240
attctattct attctattct attctattct attctattct attctattct attctattct 9300
attctattct attctattct attctattct attctattct attctattct attctattct 9360
attctattct attctattct attctattct attctattct attctattct attctattct 9420
attctattct attctattct attctattct attctattct attctattct attctattct 9480
attctattct attctattct attctattct attctattct attctattct attctattct 9540
attctattct attctattct attctattct attctattct attctattct attctattct 9600
attctattct attctattct attctattct attctattct attctattct attctattct 9660
attctattct attctattct attctattct attctattct attctattct attctattct 9720
attctattct attctattct attctattct attctattct attctattct attctattct 9780
attctattct attctattct attctattct attctattct attctattct attctattct 9840
attctattct attctattct attctattct attctattct attctattct attctattct 9900
attctattct attctattct attctattct attctattct attctattct attctattct 9960
attctattct attctattct attctattct attctattct attctattct attctattct 10020
attctattct attctattct attctattct attctattct attctattct attctattct 10080
attctattct attctattct attctattct attctattct attctattct attctattct 10140
attctattct attctattct attctattct attctattct attctattct attctattct 10200

-continued attctattct attctattct attctattct attctattct attctattct attctattct 10260
attctattct attctattct attctattct attctattct attctattct attctattct 10320
attctattct attctattct attctattct attctattct attctattct attctattct 10380
attctattct attctattct attctattct attctattct attctattct attctattct 10440
attctattct attctattct attctattct attctattct attctattct attctattct 10500
attctattct attctattct attctattct attctattct attctattct attctattct 10560
attctattct attctattct attctattct attctattct attctattct attctattct 10620
attctattct attctattct attctattct attctattct attctattct attctattct 10680
attctattct attctattct attctattct attctattct attctattct attctattct 10740
attctattct attctattct attctattct attctattct attctattct attctattct 10800
attctattct attctattct attctattct attctattct attctattct attctattct 10860
attctattct attctattct attctattct attctattct attctattct attctattct 10920
attctattct attctattct attctattct attctattct attctattct attctattct 10980
attctattct attctattct attctattct attctattct attctattct attctattct 11040
attctattct attctattct attctattct attctattct attctattct attctattct 11100
attctattct attctattct attctattct attctattct attctattct attctattct 11160
attctattct attctattct attctattct attctattct attctattct attctattct 11220
attctattct attctattct attctattct attctattct attctattct attctattct 11280
attctattct attctattct attctattct attctattct attctattct attctattct 11340
attctattct attctattct attctattct attctattct attctattct attctattct 11400
attctattct attctattct attctattct attctattct attctattct attctattct 11460
attctattct attctattct attctattct attctattct attctattct attctattct 11520
attctattct attctattct attctattct attctattct attctattct attctattct 11580
attctattct attctattct attctattct attctattct attctattct attctattct 11640
attctattct attctattct attctattct attctattct attctattct attctattct 11700
attctattct attctattct attctattct attctattct attctattct attctattct 11760
attctattct attctattct attctattct attctattct attctattct attctattct 11820
attctattct attctattct attctattct attctattct attctattct attctattct 11880
attctattct attctattct attctattct attctattct attctattct attctattct 11940
attctattct attctattct attctattct attctattct attctattct attctattct 12000
attctattct attctattct attctattct attctattct attctattct attctattct 12060
attctattct attctattct attctattct attctattct attctattct attctattct 12120
attctattct attctattct attctattct attctattct attctattct attctattct 12180
attctattct attctattct attctattct attctattct attctattct attctattct 12240
attctattct attctattct attctattct attctattct attctattct attctattct 12300
attctattct attctattct attctattct attctattct attctattct attctattct 12360
attctattct attctattct attctattct attctattct attctattct attctattct 12420
attctattct attctattct attctattct attctattct attctattct attctattct 12480
attctattct attctattct attctattct attctattct attctattct attctattct 12540
attctattct attctattct attctattct attctattct attctattct attctattct 12600
attctattct attctattct attctattct attctattct attctattct attctattct 12660
attctattct attctattct attctattct attctattct attctattct attctattct 12720
attctattct attctattct attctattct attctattct attctattct attctattct 12780
attctattct attctattct attctattct attctattct attctattct attctattct 12840
attctattct attctattct attctattct attctattct attctattct attctattct 12900
attctattct attctattct attctattct attctattct attctattct attctattct 12960
attctattct attctattct attctattct attctattct attctattct attctattct 13020
attctattct attctattct attctattct attctattct attctattct attctattct 13080
attctattct attctattct attctattct attctattct attctattct attctattct 13140
attctattct attctattct attctattct attctattct attctattct attctattct 13200
attctattct attctattct attctattct attctattct attctattct attctattct 13260
attctattct attctattct attctattct attctattct attctattct attctattct 13320
attctattct attctattct attctattct attctattct attctattct attctattct 13380
attctattct attctattct attctattct attctattct attctattct attctattct 13440
attctattct attctattct attctattct attctattct attctattct attctattct 13500
attctattct attctattct attctattct attctattct attctattct attctattct 13560
attctattct attctattct attctattct attctattct attctattct attctattct 13620
attctattct attctattct attctattct attctattct attctattct attctattct 13680
attctattct attctattct attctattct attctattct attctattct attctattct 13740
attctattct attctattct attctattct attctattct attctattct attctattct 13800
attctattct attctattct attctattct attctattct attctattct attctattct 13860
attctattct attctattct attctattct attctattct attctattct attctattct 13920
attctattct attctattct attctattct attctattct attctattct attctattct 13980
attctattct attctattct attctattct attctattct attctattct attctattct 14040
attctattct attctattct attctattct attctattct attctattct attctattct 14100
attctattct attctattct attctattct attctattct attctattct attctattct 14160
attctattct attctattct attctattct attctattct attctattct attctattct 14220
attctattct attctattct attctattct attctattct attctattct attctattct 14280
attctattct attctattct attctattct attctattct attctattct attctattct 14340
attctattct attctattct attctattct attctattct attctattct attctattct 14400
attctattct attctattct attctattct attctattct attctattct attctattct 14460
attctattct attctattct attctattct attctattct attctattct attctattct 14520
attctattct attctattct attctattct attctattct attctattct attctattct 14580
attctattct attctattct attctattct attctattct attctattct attctattct 14640
attctattct attctattct attctattct attctattct attctattct attctattct 14700
attctattct attctattct attctattct attctattct attctattct attctattct 14760
attctattct attctattct attctattct attctattct attctattct attctattct 14820
attctattct attctattct attctattct attctattct attctattct attctattct 14880
attctattct attctattct attctattct attctattct attctattct attctattct 14940

-continued

```
attctattct attctattct attctattct attctattct attctattct attctattct  15000
attctattct attctattct attctattct attctattct attctattct attctattct  15060
attctattct attctattct attctattct attctattct attctattct attctattct  15120
attctattct attctattct attctattct attctattct attctattct attctattct  15180
attctattct attctattct attctattct attctattct attctattct attctattct  15240
attctattct attctattct attctattct attctattct attctattct attctattct  15300
attctattct attctattct attctattct attctattct attctattct attctattct  15360
attctattct attctattct attctattct attctattct attctattct attctattct  15420
attctattct attctattct attctattct attctattct attctattct attctattct  15480
attctattct attctattct attctattct attctattct attctattct attctattct  15540
attctattct attctattct attctattct attctattct attctattct attctattct  15600
attctattct attctattct attctattct attctattct attctattct attctattct  15660
attctattct attctattct attctattct attctattct attctattct attctattct  15720
attctattct attctattct attctattct attctattct attctattct attctattct  15780
attctattct attctattct attctattct attctattct attctattct attctattct  15840
attctattct attctattct attctattct attctattct attctattct attctattct  15900
attctattct attctattct attctattct attctattct attctattct attctattct  15960
attctattct attctattct attctattct attctattct attctattct attctattct  16020
attctattct attctattct attctattct attctattct attctattct attctattct  16080
attctattct attctattct attctattct attctattct attctattct attctattct  16140
attctattct attctattct attctattct attctattct attctattct attctattct  16200
attctattct attctattct attctattct attctattct attctattct attctattct  16260
attctattct attctattct attctattct attctattct attctattct attctattct  16320
attctattct attctattct attctattct attctattct attctattct attctattct  16380
attctattct attctattct attctattct attctattct attctattct attctattct  16440
attctattct attctattct attctattct attctattct attctattct attctattct  16500
attctattct attctattct attctattct attctattct attctattct attctattct  16560
attctattct attctattct attctattct attctattct attctattct attctattct  16620
attctattct attctattct attctattct attctattct attctattct attctattct  16680
attctattct attctattct attctattct attctattct attctattct attctattct  16740
attctattct attctattct attctattct attctattct attctattct attctattct  16800
attctattct attctattct attctattct attctattct attctattct attctattct  16860
attctattct attctattct attctattct attctattct attctattct attctattct  16920
attctattct attctattct attctattct attctattct attctattct attctattct  16980
attctattct attctattct attctattct attctattct attctattct attctattct  17040
attctattct attctattct attctattct attctattct attctattct attctattct  17100
attctattct attctattct attctattct attctattct attctattct attctattct  17160
attctattct attctattct attctattct attctattct attctattct attctattct  17220
attctattct attctattct attctattct attctattct attctattct attctattct  17280
attctattct attctattct attctattct attctattct attctattct attctattct  17340
attctattct attctattct attctattct attctattct attctattct attctattct  17400
attctattct attctattct attctattct attctattct attctattct attctattct  17460
attctattct attctattct attctattct attctattct attctattct attctattct  17520
attctattct attctattct attctattct attctattct attctattct attctattct  17580
attctattct attctattct attctattct attctattct attctattct attctattct  17640
attctattct attctattct attctattct attctattct attctattct attctattct  17700
attctattct attctattct attctattct attctattct attctattct attctattct  17760
attctattct attctattct attctattct attctattct attctattct attctattct  17820
attctattct attctattct attctattct attctattct attctattct attctattct  17880
attctattct attctattct attctattct attctattct attctattct attctattct  17940
attctattct attctattct attctattct attctattct attctattct attctattct  18000
attctattct attctattct attctattct attctattct attctattct attctattct  18060
attctattct attctattct attctattct attctattct attctattct attctattct  18120
attctattct attctattct attctattct attctattct attctattct attctattct  18180
attctattct attctattct attctattct attctattct attctattct attctattct  18240
attctattct attctattct attctattct attctattct attctattct attctattct  18300
attctattct attctattct attctattct attctattct attctattct attctattct  18360
attctattct attctattct attctattct attctattct attctattct attctattct  18420
attctattct attctattct attctattct attctattct attctattct attctattct  18480
attctattct attctattct attctattct attctattct attctattct attctattct  18540
attctattct attctattct attctattct attctattct attctattct attctattct  18600
attctattct attctattct attctattct attctattct attctattct attctattct  18660
attctattct attctattct attctattct attctattct attctattct attctattct  18720
attctattct attctattct attctattct attctattct attctattct attctattct  18780
attctattct attctattct attctattct attctattct attctattct attctattct  18840
attctattct attctattct attctattct attctattct attctattct attctattct  18900
attctattct attctattct attctattct attctattct attctattct attctattct  18960
attctattct attctattct attctattct attctattct attctattct attctattct  19020
attctattct attctattct attctattct attctattct attctattct attctattct  19080
attctattct attctattct attctattct attctattct attctattct attctattct  19140
attctattct attctattct attctattct attctattct attctattct attctattct  19200
attctattct attctattct attctattct attctattct attctattct attctattct  19260
attctattct attctattct attctattct attctattct attctattct attctattct  19320
attctattct attctattct attctattct attctattct attctattct attctattct  19380
attctattct attctattct attctattct attctattct attctattct attctattct  19440
attctattct attctattct attctattct attctattct attctattct attctattct  19500
attctattct attctattct attctattct attctattct attctattct attctattct  19560
attctattct attctattct attctattct attctattct attctattct attctattct  19620
attctattct attctattct attctattct attctattct attctattct attctattct  19680
```

```
attctattct attctattct attctattct attctattct attctattct attctattct  19740
attctattct attctattct attctattct attctattct attctattct attctattct  19800
attctattct attctattct attctattct attctattct attctattct attctattct  19860
attctattct attctattct attctattct attctattct attctattct attctattct  19920
attctattct attctattct attctattct attctattct attctattct attctattct  19980
attctattct attctattct attctattct attctattct attctattct attctattct  20040
attctattct attctattct attctattct attctattct attctattct attctattct  20100
attctattct attctattct attctattct attctattct attctattct attctattct  20160
attctattct attctattct attctattct attctattct attctattct attctattct  20220
attctattct attctattct attctattct attctattct attctattct attctattct  20280
attctattct attctattct attctattct attctattct attctattct attctattct  20340
attctattct attctattct attctattct attctattct attctattct attctattct  20400
attctattct attctattct attctattct attctattct attctattct attctattct  20460
attctattct attctattct attctattct attctattct attctattct attctattct  20520
attctattct attctattct attctattct attctattct attctattct attctattct  20580
attctattct attctattct attctattct attctattct attctattct attctattct  20640
attctattct attctattct attctattct attctattct attctattct attctattct  20700
attctattct attctattct attctattct attctattct attctattct attctattct  20760
attctattct attctattct attctattct attctattct attctattct attctattct  20820
attctattct attctattct attctattct attctattct attctattct attctattct  20880
attctattct attctattct attctattct attctattct attctattct attctattct  20940
attctattct attctattct attctattct attctattct attctattct attctattct  21000
attctattct attctattct attctattct attctattct attctattct attctattct  21060
attctattct attctattct attctattct attctattct attctattct attctattct  21120
attctattct attctattct attctattct attctattct attctattct attctattct  21180
attctattct attctattct attctattct attctattct attctattct attctattct  21240
attctattct attctattct attctattct attctattct attctattct attctattct  21300
attctattct attctattct attctattct attctattct attctattct attctattct  21360
attctattct attctattct attctattct attctattct attctattct attctattct  21420
attctattct attctattct attctattct attctattct attctattct attctattct  21480
attctattct attctattct attctattct attctattct attctattct attctattct  21540
attctattct attctattct attctattct attctattct attctattct attctattct  21600
attctattct attctattct attctattct attctattct attctattct attctattct  21660
attctattct attctattct attctattct attctattct attctattct attctattct  21720
attctattct attctattct attctattct attctattct attctattct attctattct  21780
attctattct attctattct attctattct attctattct attctattct attctattct  21840
attctattct attctattct attctattct attctattct attctattct attctattct  21900
attctattct attctattct attctattct attctattct attctattct attctattct  21960
attctattct attctattct attctattct attctattct attctattct attctattct  22020
attctattct attctattct attctattct attctattct attctattct attctattct  22080
attctattct attctattct attctattct attctattct attctattct attctattct  22140
attctattct attctattct attctattct attctattct attctattct attctattct  22200
attctattct attctattct attctattct attctattct attctattct attctattct  22260
attctattct attctattct attctattct attctattct attctattct attctattct  22320
attctattct attctattct attctattct attctattct attctattct attctattct  22380
attctattct attctattct attctattct attctattct attctattct attctattct  22440
attctattct attctattct attctattct attctattct attctattct attctattct  22500

SEQ ID NO: 24          moltype = DNA  length = 234
FEATURE                Location/Qualifiers
misc_feature           1..234
                       note = Description of Artificial Sequence: Synthetic
                        polynucleotide
misc_difference        1..234
                       note = This sequence may encompass 66-78 'cag' repeating
                        units
source                 1..234
                       mol_type = other DNA
                       organism = synthetic construct
SEQUENCE: 24
cagcagcagc agcagcagca gcagcagcag cagcagcagc agcagcagca gcagcagcag  60
cagcagcagc agcagcagca gcagcagcag cagcagcagc agcagcagca gcagcagcag  120
cagcagcagc agcagcagca gcagcagcag cagcagcagc agcagcagca gcagcagcag  180
cagcagcagc agcagcagca gcagcagcag cagcagcagc agcagcagca gcag        234

SEQ ID NO: 25          moltype = RNA  length = 78
FEATURE                Location/Qualifiers
misc_feature           1..78
                       note = Description of Artificial Sequence: Synthetic
                        polynucleotide
source                 1..78
                       mol_type = other RNA
                       organism = synthetic construct
SEQUENCE: 25
gggtaggcca ggcagccaac tagcgagagc ttaaatctct gagcccgaga gggttcagtg  60
ctgcttatgt ggacggct                                                78

SEQ ID NO: 26          moltype = DNA  length = 51
FEATURE                Location/Qualifiers
```

-continued

```
misc_feature          1..51
                      note = Description of Artificial Sequence: Synthetic
                       polynucleotide
source                1..51
                      mol_type = other DNA
                      organism = synthetic construct
SEQUENCE: 26
ctttccctac acgacgctct tccgatctta gatcattgat ggtgcctaca g           51

SEQ ID NO: 27         moltype = DNA  length = 34
FEATURE               Location/Qualifiers
misc_feature          1..34
                      note = Description of Artificial Sequence: Synthetic
                       oligonucleotide
source                1..34
                      mol_type = other DNA
                      organism = synthetic construct
SEQUENCE: 27
agatcggaag agcacacgtc tgaactccag tcac                              34

SEQ ID NO: 28         moltype = DNA  length = 55
FEATURE               Location/Qualifiers
misc_feature          1..55
                      note = Description of Artificial Sequence: Synthetic
                       oligonucleotide
misc_feature          25..30
                      note = "nnnnnn" refers to the 6 bp Illumina index
misc_difference       25..30
                      note = a, c, t, g, unknown, or other
source                1..55
                      mol_type = other DNA
                      organism = synthetic construct
SEQUENCE: 28
caagcagaag acggcatacg agatnnnnnn gtgactggag ttcagacgtg tgctc       55

SEQ ID NO: 29         moltype = DNA  length = 58
FEATURE               Location/Qualifiers
misc_feature          1..58
                      note = Description of Artificial Sequence: Synthetic
                       oligonucleotide
source                1..58
                      mol_type = other DNA
                      organism = synthetic construct
SEQUENCE: 29
aatgatacgg cgaccaccga gatctacact ctttccctac acgacgctct tccgatct    58

SEQ ID NO: 30         moltype = RNA  length = 40
FEATURE               Location/Qualifiers
misc_feature          1..40
                      note = Description of Artificial Sequence: Synthetic
                       oligonucleotide
modified_base         1
                      mod_base = OTHER
                      note = 5' phosphorylated nucleotide
misc_difference       8..13
                      note = n refers to a random mixture of A, G, C and U RNA
                       residues
modified_base         40
                      mod_base = OTHER
                      note = Nucleotide attached to 3' C3 Spacer
source                1..40
                      mol_type = other RNA
                      organism = synthetic construct
SEQUENCE: 30
atataggnnn nnnagatcgg aagagcacac gtctgaactc                        40

SEQ ID NO: 31         moltype = DNA  length = 33
FEATURE               Location/Qualifiers
misc_feature          1..33
                      note = Description of Artificial Sequence: Synthetic
                       oligonucleotide
modified_base         1
                      mod_base = OTHER
                      note = 5' phosphorylated nucleotide
modified_base         33
                      mod_base = OTHER
                      note = Nucleotide attached to 3' C3 Spacer
source                1..33
                      mol_type = other DNA
```

```
                        organism = synthetic construct
SEQUENCE: 31
agatcggaag agcgtcgtgt agggaaagag tgt                               33

SEQ ID NO: 32           moltype = DNA  length = 27
FEATURE                 Location/Qualifiers
misc_feature            1..27
                        note = Description of Artificial Sequence: Synthetic
                         oligonucleotide
source                  1..27
                        mol_type = other DNA
                        organism = synthetic construct
SEQUENCE: 32
gagttcagac gtgtgctctt ccgatct                                      27

SEQ ID NO: 33           moltype = DNA  length = 55
FEATURE                 Location/Qualifiers
misc_feature            1..55
                        note = Description of Artificial Sequence: Synthetic
                         oligonucleotide
misc_feature            30..35
                        note = "nnnnnn" refers to the 6 bp Illumina i5 index
misc_difference         30..35
                        note = a, c, t, g, unknown, or other
source                  1..55
                        mol_type = other DNA
                        organism = synthetic construct
SEQUENCE: 33
aatgatacgg cgaccaccga gatctacacn nnnnnacact ctttccctac acgac       55

SEQ ID NO: 34           moltype = DNA  length = 55
FEATURE                 Location/Qualifiers
misc_feature            1..55
                        note = Description of Artificial Sequence: Synthetic
                         oligonucleotide
misc_feature            25..30
                        note = "nnnnnn" refers to the 6 bp Illumina i7 index
misc_difference         25..30
                        note = a, c, t, g, unknown, or other
source                  1..55
                        mol_type = other DNA
                        organism = synthetic construct
SEQUENCE: 34
caagcagaag acggcatacg agatnnnnnn gtgactggag ttcagacgtg tgctc       55

SEQ ID NO: 35           moltype = DNA  length = 20
FEATURE                 Location/Qualifiers
misc_feature            1..20
                        note = Description of Artificial Sequence: Synthetic
                         polynucleotide
misc_difference         8..13
                        note = n is a, c, g, or t
source                  1..20
                        mol_type = other DNA
                        organism = synthetic construct
SEQUENCE: 35
atataggnnn nnnagatcgg                                              20
```